United States Patent
Swanson et al.

(10) Patent No.: US 10,435,476 B2
(45) Date of Patent: Oct. 8, 2019

(54) ANTIBODY THERAPEUTICS THAT BIND JAG1

(71) Applicant: Sorrento Therapeutics, Inc., San Diego, CA (US)

(72) Inventors: Barbara A. Swanson, Encinitas, CA (US); Allyson Terry, Chatsworth, CA (US); Edwige Gros, San Diego, CA (US); Heyue Zhou, San Diego, CA (US)

(73) Assignee: Sorrento Therapeutics, Inc., San Diego, CA (US)

( * ) Notice: Subject to any disclaimer, the term of this patent is extended or adjusted under 35 U.S.C. 154(b) by 228 days.

(21) Appl. No.: 15/063,006

(22) Filed: Mar. 7, 2016

(65) Prior Publication Data

US 2016/0257759 A1 Sep. 8, 2016

Related U.S. Application Data

(60) Provisional application No. 62/129,180, filed on Mar. 6, 2015.

(51) Int. Cl.
| | |
|---|---|
| *C07K 16/22* | (2006.01) |
| *C07K 16/28* | (2006.01) |
| *C07K 14/475* | (2006.01) |
| *A61K 39/395* | (2006.01) |

(52) U.S. Cl.
CPC .......... *C07K 16/2896* (2013.01); *C07K 16/22* (2013.01); *A61K 39/3955* (2013.01); *C07K 14/475* (2013.01); *C07K 2317/21* (2013.01); *C07K 2317/33* (2013.01); *C07K 2317/56* (2013.01); *C07K 2317/565* (2013.01); *C07K 2317/76* (2013.01); *C07K 2317/92* (2013.01)

(58) Field of Classification Search
CPC ........ A61K 2039/505; A61K 39/39558; A61K 39/3955; A61K 39/395; C07K 2317/76; C07K 2317/92; C07K 2317/565; C07K 2317/73; C07K 2317/56; C07K 16/22; C07K 2317/732; C07K 16/00; C07K 16/24

See application file for complete search history.

(56) References Cited

U.S. PATENT DOCUMENTS

| | | | |
|---|---|---|---|
| 2008/0160035 A1 | 7/2008 | Stevens et al. | |
| 2011/0293511 A1 | 12/2011 | Johns et al. | |
| 2014/0314749 A1 | 10/2014 | French et al. | |

OTHER PUBLICATIONS

Brorson et al. Mutational analysis of avidity and fine specificity of anti-levan antibodies. J Immunol 163: 6694-6701, 1999.*
Brummell et al. Probing the combining site of an anti-carbohydrate antibody by saturation-mutagenesis: role of the heavy-chain CDR3 residues. Biochem 32(4): 1180-1187, 1993 (abstract).*
Burks et al. In vitro scanning saturation mutagenesis of an antibody binding pocket. Proc Natl Acad Sci USA 94: 412-417, 1997.*
Colman, P.M. Effects of amino acid sequence changes on antibody-antigen interactions. Res Immunol 145: 33-36, 1994.*
Dikic et al. Notch: implications of endogenous inhibitors for therapy. Bioessays 32: 481-487, 2010.*
Jang et al. The structural basis for DNA binding by an anti-DNA autoantibody. Mol Immunol 35: 1207-1217, 1998.*
Kobayashi et al. Tryptophan H33 plays an important role in pyrimidine (6-4) pyrimidone photoproduct binding by a high-affinity antibody. Protein Engineering 12(10): 879-884, 1999.*
Li et al. The Notch ligand Jagged1 as a target for anti-tumor therapy. Frontiers Oncol vol. 4, Article 254, 2014, pp. 1-13.*
Lloyd et al. Modelling the human immune response: performance of a 10x11 human antibody repertoire against a broad panel of therapeutically relevant antigens. Protein Eng Design Selection 22(3): 159-168, 2009.*
Paul, William E., Fundamental Immunology, 3rd Edition, Raven Press, New York, Chapt. 8, pp. 292-295 (1993).*
Rudikoff et al. Single amino acid substitution altering antigen-binding specificity. Proc Natl Acad Sci USA 79: 1979-1983, 1982.*
European Patent Office, Supplementary European Search Report relating to corresponding EP Application 16762296, dated Nov. 6, 2018.
European Patent Office, Partial Search Report relating to corresponding EP Application 16762296, dated Jul. 27, 2018.
International Searching Authority, International Preliminary Report on Patentability relating to International Application No. PCT/US2016/021193, dated Aug. 26, 2016.
International Searching Authority, Written Opinion relating to International Application No. PCT/US2016/021193, dated Aug. 26, 2016.
International Searching Authority, International Search Report relating to International Application No. PCT/US2016/021193, dated Aug. 26, 2016.

* cited by examiner

Primary Examiner — Bridget E Bunner

(57) ABSTRACT

There is disclosed compositions and methods relating to or derived from anti-JAG1 antibodies. More specifically, there is disclosed fully human antibodies that bind JAG1, JAG1-binding fragments and derivatives of such antibodies, and JAG1-binding polypeptides comprising such fragments. Further still, there is disclosed nucleic acids encoding such antibodies, antibody fragments and derivatives and polypeptides, cells comprising such polynucleotides, methods of making such antibodies, antibody fragments and derivatives and polypeptides, and methods of using such antibodies, antibody fragments and derivatives and polypeptides, including methods of treating or diagnosing subjects having JAG1 related disorders or conditions. There is also disclosed a method for treating JAG1-expressing tumors, including hepatocellular carcinomas and squamous carcinomas, and non-oncology diseases selected from the group consisting of rheumatoid arthritis, experimental lung injury, atherosclerosis, chronic liver disease induced by hepatitis C virus, ischemic myocardial injury and heart failure.

5 Claims, 9 Drawing Sheets

Specification includes a Sequence Listing.

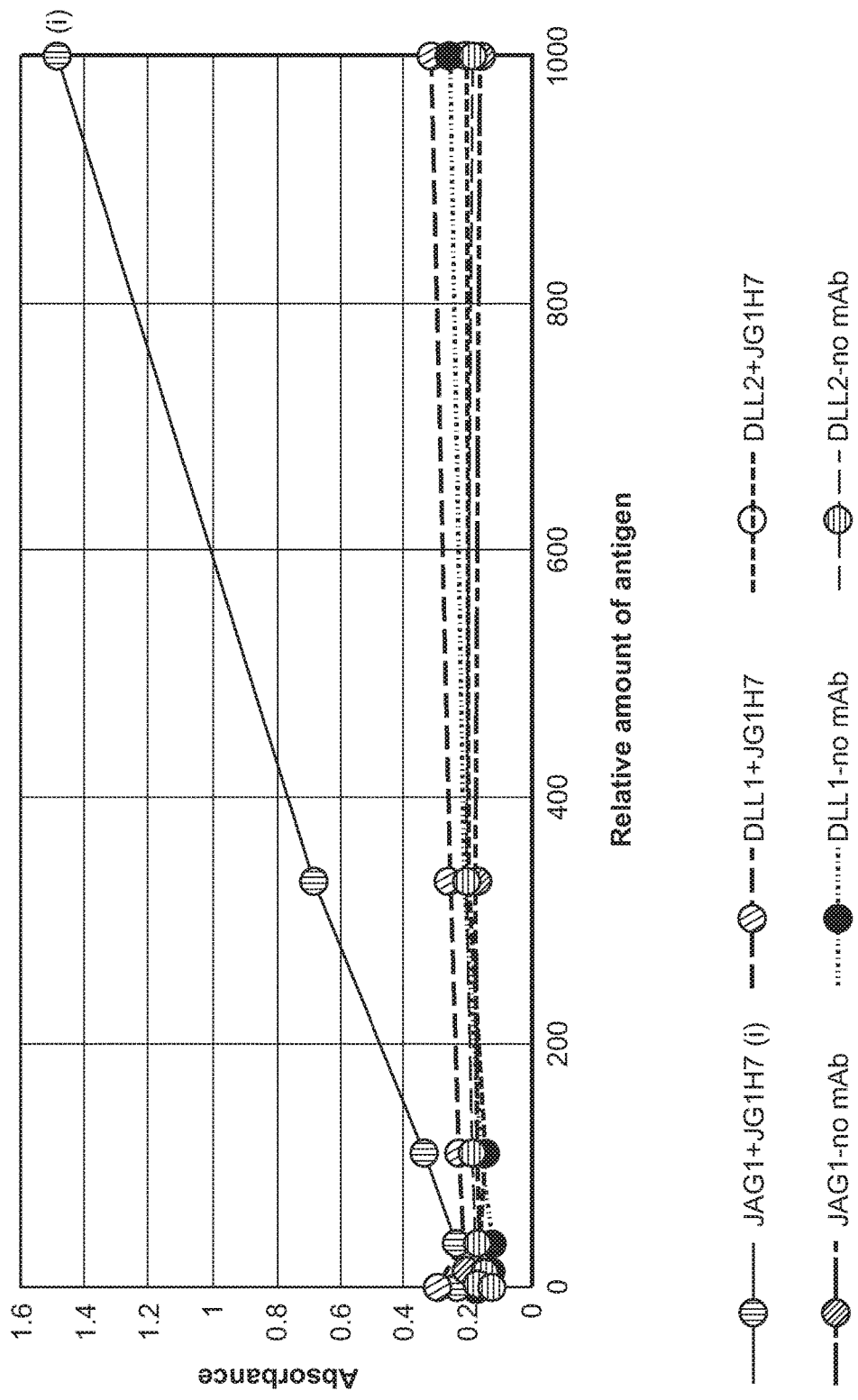

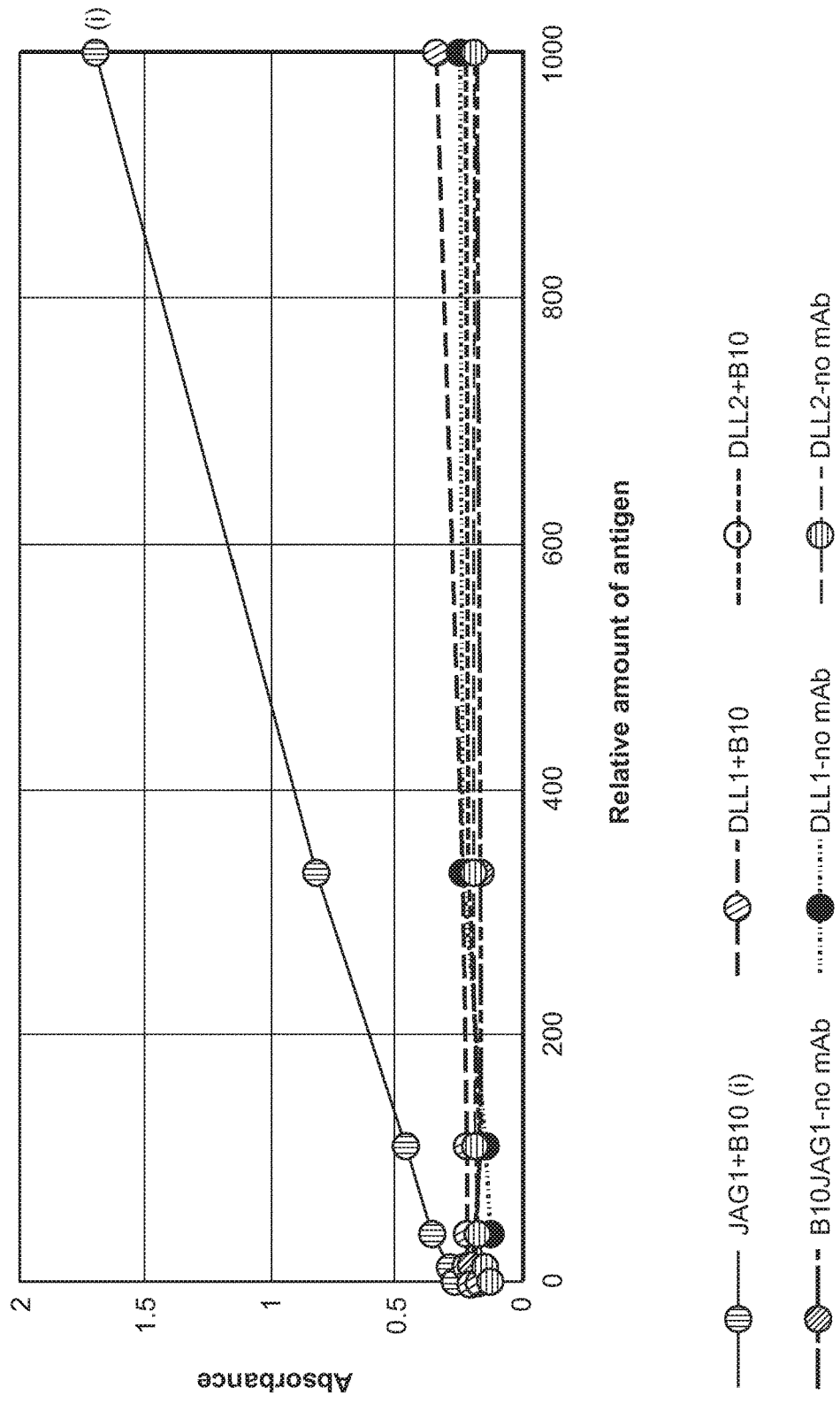

ANTIBODY THERAPEUTICS THAT BIND JAG1

RELATED APPLICATIONS

This application claims priority to U.S. Provisional Application No. 62/129,180 filed on Mar. 6, 2015, the entire contents of which are incorporated by reference in their entirety herein.

TECHNICAL FIELD

The present disclosure provides compositions and methods relating to or derived from anti-JAG1 antibodies. More specifically, the present disclosure provides fully human antibodies that bind JAG1, JAG1-antibody binding fragments and derivatives of such antibodies, and JAG1-binding polypeptides comprising such fragments. Further still, the present disclosure provides nucleic acids encoding such antibodies, antibody fragments and derivatives and polypeptides, cells comprising such polynucleotides, methods of making such antibodies, antibody fragments and derivatives and polypeptides, and methods of using such antibodies, antibody fragments and derivatives and polypeptides, including methods of treating or diagnosing subjects having JAG1 related disorders or conditions. The present disclosure further provides a method for treating Notch-signaling tumors, including breast, prostate, colorectal, lung and other solid tumors.

BACKGROUND

The Notch signaling pathway is one of several critical regulators of embryonic pattern formation, post-embryonic tissue maintenance, and stem cell biology. More specifically, Notch signaling is involved in the process of lateral inhibition between adjacent cell fates and plays an important role in cell fate determination during asymmetric cell divisions. Unregulated Notch signaling is associated with numerous human cancers where it can alter the developmental fate of tumor cells to maintain them in an undifferentiated and proliferative state (Brennan and Brown, 2003, *Breast Cancer Res.* 5:69). Thus carcinogenesis can proceed by usurping homeostatic mechanisms controlling normal development and tissue repair by stem cell populations (Beachy et al., 2004, *Nature* 432:324).

The Notch receptor was first identified in *Drosophila* mutants with haploinsufficiency resulting in notches at the wing margin, whereas loss-of-function produces an embryonic lethal "neurogenic" phenotype where cells of the epidermis switch fate to neural tissue (Moohr, 1919, *Genet.* 4:252; Poulson, 1937, *PNAS* 23:133; Poulson, 1940, *J. Exp. Zool.* 83:271). The Notch receptor is a single-pass transmembrane receptor containing numerous tandem epidermal growth factor (EGF)-like repeats and three cysteine-rich Notch/LIN-12 repeats within a large extracellular domain (Wharton et al., 1985, *Cell* 43:567; Kidd et al., 1986, *Mol. Cell. Biol.* 6:3094; reviewed in Artavanis et al., 1999, *Science* 284:770). Four mammalian Notch proteins have been identified (Notch1, Notch2, Notch3, and Notch4), and mutations in these receptors invariably result in developmental abnormalities and human pathologies including several cancers as described in detail below (Gridley, 1997, *Mol. Cell. Neurosci.* 9:103; Joutel & Tournier-Lasserve, 1998, *Semin. Cell Dev. Biol.* 9:619-25).

Notch receptors are activated by single-pass transmembrane ligands of the Delta, Serrated, Lag-2 (DSL) family. There are five known Notch ligands in mammals: Delta-like 1 (DLL1), Delta-like 3 (DLL3), Delta-like 4 (DLL4), Jagged 1 (JAG1) and Jagged 2 (JAG2) characterized by a DSL domain and tandem EGF-like repeats within the extracellular domain. The extracellular domain of the Notch receptor interacts with that of its ligands, typically on adjacent cells, resulting in two proteolytic cleavages of Notch, one extracellular cleavage mediated by an ADAM (A Disintegrin And Metallopeptidase) protease and one cleavage within the transmembrane domain mediated by gamma secretase. This latter cleavage generates the Notch intracellular domain (ICD), which then enters the nucleus where it activates the CBF1, Suppressor of Hairless [Su(H)], Lag-2 (CSL) family of transcription factors as the major downstream effectors to increase transcription of nuclear basic helix-loop-helix transcription factors of the Hairy and Enhancer of Split [E(sp1)] family (Artavanis et al., 1999, *Science* 284:770; Brennan and Brown, 2003, *Breast Cancer Res.* 5:69; Iso et al., 2003, *Arterioscler. Thromb. Vasc. Biol.* 23:543). Alternative intracellular pathways involving the cytoplasmic protein Deltex identified in *Drosophila* may also exist in mammals (Martinez et al., 2002, *Curr. Opin. Genet. Dev.* 12:524-33), and this Deltex-dependent pathway may act to suppress expression of Wnt target genes (Brennan et al., 1999, *Curr. Biol.* 9:707-710; Lawrence et al., 2001, *Curr. Biol.* 11:375-85).

Mammalian Notch receptors undergo cleavage to form the mature receptor and also following ligand binding to activate downstream signaling. A furin-like protease cleaves the Notch receptors during maturation to generate juxtamembrane heterodimers that comprise a non-covalently associated extracelluar subunit and a transmembrane subunit held together in an auto-inhibitory state. Ligand binding relieves this inhibition and induces cleavage of the Notch receptor by an ADAM-type metalloprotease and a gamma-secretase, the latter of which releases the intracellular domain (ICD) into the cytoplasm, allowing it to translocate into the nucleus to activate gene transcription. Cleavage by ADAM occurs within the non-ligand binding cleavage domain within the membrane proximal negative regulatory region.

Hematopoietic stem cells (HSCs) are the best understood stem cells in the body, and Notch signaling is implicated in their normal maintenance as well as in leukemic transformation (Kopper & Hajdu, 2004, *Pathol. Oncol. Res.* 10:69-73). HSCs are a rare population of cells that reside in a stromal niche within the adult bone marrow. These cells are characterized both by a unique gene expression profile as well as an ability to continuously give rise to more differentiated progenitor cells to reconstitute the entire hematopoietic system. Constitutive activation of Notch1 signaling in HSCs and progenitor cells establishes immortalized cell lines that generate both lymphoid and myeloid cells in vitro and in long-term reconstitution assays (Varnum-Finney et al., 2000, *Nat. Med.* 6:1278-81), and the presence of Jagged1 increases engraftment of human bone marrow cell populations enriched for HSCs (Karanu et al., 2000, *J. Exp. Med.* 192:1365-72). More recently, Notch signaling has been demonstrated in HSCs in vivo and shown to be involved in inhibiting HSC differentiation. Furthermore, Notch signaling appears to be required for Wnt-mediated HSC self-renewal (Duncan et al., 2005, *Nat. Immunol.* 6:314).

The Notch signaling pathway also plays a central role in the maintenance of neural stem cells and is implicated in their normal maintenance as well as in brain cancers (Kopper & Hajdu, 2004, *Pathol. Oncol. Res.* 10:69-73; Purow et al., 2005, *Cancer Res.* 65:2353-63; Hallahan et al., 2004, Cancer Res. 64:7794-800). Neural stem cells give rise to all neuronal and glial cells in the mammalian nervous system during development, and more recently have been identified in the adult brain (Gage, 2000, *Science* 287:1433-8). Mice deficient for Notch1; the Notch target genes Hes1, 3, and 5; and a regulator of Notch signaling presenilin1 (PS1) show decreased numbers of embryonic neural stem cells. Furthermore, adult neural stem cells are reduced in the brains of PS 1 heterozygote mice (Nakamura et al., 2000, *J. Neurosci.* 20:283-93; Hitoshi et al., 2002, *Genes Dev.* 16:846-58). The reduction in neural stem cells appears to result from their premature differentiation into neurons (Hatakeyama et al., 2004, *Dev.* 131:5539-50) suggesting that Notch signaling regulates neural stem cell differentiation and self-renewal.

Aberrant Notch signaling is implicated in a number of human cancers. The Notch1 gene in humans was first identified in a subset of T-cell acute lymphoblastic leukemias as a translocated locus resulting in activation of the Notch pathway (Ellisen et al., 1991, *Cell* 66:649-61). Constitutive activation of Notch1 signaling in T-cells in mouse models similarly generates T-cell lymphomas suggesting a causative role (Robey et al., 1996, *Cell* 87:483-92; Pear et al., 1996, *J. Exp. Med.* 183:2283-91; Yan et al., 2001, *Blood* 98:3793-9; Bellavia et al., 2000, *EMBO J.* 19:3337-48). Notch1 point mutations, insertions, and deletions producing aberrant Notch1 signaling have also been found to be frequently present in both childhood and adult T-cell acute lymphoblastic leukemia/lymphoma (Pear & Aster, 2004, *Curr. Opin. Hematol.* 11:416-33).

The frequent insertion of the mouse mammary tumor virus into both the Notch1 and Notch4 locus in mammary tumors and the resulting activated Notch protein fragments first implicated Notch signaling in breast cancer (Gallahan & Callahan, 1987, *J. Virol.* 61:66-74; Brennan & Brown, 2003, *Breast Cancer Res.* 5:69; Politi et al., 2004, *Semin. Cancer Biol.* 14:341-7). Further studies in transgenic mice have confirmed a role Notch in ductal branching during normal mammary gland development, and a constitutively active form of Notch4 in mammary epithelial cells inhibits epithelial differentiation and results in tumorigenesis (Jhappan et al., 1992, *Genes & Dev.* 6:345-5; Gallahan et al., 1996, *Cancer Res.* 56:1775-85; Smith et al., 1995, *Cell Growth Differ.* 6:563-77; Soriano et al., 2000, *Int. J. Cancer* 86:652-9; Uyttendaele et al., 1998, *Dev. Biol.* 196:204-17; Politi et al., 2004, *Semin. Cancer Biol.* 14:341-7). Evidence for a role Notch in human breast cancer is provided by data showing the expression of Notch receptors in breast carcinomas and their correlation with clinical outcome (Weijzen et al., 2002, *Nat. Med.* 8:979-86; Parr et al., 2004, *Int. J. Mol. Med.* 14:779-86). Furthermore, overexpression of the Notch pathway has been observed in cervical cancers (Zagouras et al., 1995, *PNAS* 92:6414-8), renal cell carcinomas (Rae et al., 2000, *Int. J. Cancer* 88:726-32), head and neck squamous cell carcinomas (Leethanakul et al., 2000, *Oncogene* 19:3220-4), endometrial cancers (Suzuki et al., 2000, *Int. J. Oncol.* 17:1131-9), and neuroblastomas (van Limpt et al., 2000, *Med. Pediatr. Oncol.* 35:554-8), suggestive of a potential role for Notch in the development of a number of neoplasms. Notch signaling may play a role in the maintenance of the undifferentiated state of Apc-mutant neoplastic cells of the colon (van Es & Clevers, 2005, *Trends in Mol. Med.* 11:496-502).

The Notch pathway is also involved in multiple aspects of vascular development including proliferation, migration, smooth muscle differentiation, angiogenesis and arterialvenous differentiation (Iso et al., 2003, *Arterioscler. Thromb. Vasc. Biol.* 23:543). Furthermore, DLL1-deficient and Notch2-hypomorphic mice embryos show hemorrhaging that likely results from poor development of vascular structures (Gale et al., 2004, *PNAS*, 101:15949-54; Krebs et al., 2000, *Genes Dev.* 14:1343-52; Xue et al., 1999, *Hum. Mel. Genet.* 8:723-30; Hrabe de Angelis et al., 1997, *Nature* 386:717-21; McCright et al., 2001, *Dev.* 128:491-502).

Accordingly, there is a need in the art for therapeutic antibodies that bind to Jagged-1 (JAG1) epitopes and could be used as therapeutic agents for treating Notch-signaling tumors, including breast, prostate, colorectal, lung and other solid tumors.

SUMMARY OF THE INVENTION

The invention generally provides novel antibodies and antibody fragments that bind to JAG1, e.g., human JAG1, including anti-JAG1 human antibodies.

In certain embodiments, the present disclosure provides a fully human antibody of an IgG class that binds to a JAG1 epitope with a binding affinity of at least $10^{-6}$M, which comprises a heavy chain variable domain sequence that is at least 95% identical to the amino acid sequences selected from the group consisting of SEQ ID NO. 1, SEQ ID NO. 3, SEQ ID NO. 5, SEQ ID NO. 6, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63, SEQ ID NO. 65, SEQ ID NO. 67, SEQ ID NO. 69, SEQ ID NO. 71, SEQ ID NO. 73, SEQ ID NO. 75, SEQ ID NO. 77, SEQ ID NO. 79, SEQ ID NO. 81, SEQ ID NO. 83, SEQ ID NO. 85, SEQ ID NO. 87, SEQ ID NO. 89, SEQ ID NO. 91, SEQ ID NO. 93, SEQ ID NO. 95, SEQ ID NO. 97, SEQ ID NO. 99, SEQ ID NO. 101, SEQ ID NO. 103, SEQ ID NO. 105, SEQ ID NO. 107, SEQ ID NO. 109, and combinations thereof, and comprises a light chain variable domain sequence that is at least 95% identical to the amino acid sequence consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72, SEQ ID NO. 74, SEQ ID NO. 76, SEQ ID NO. 78, SEQ ID NO. 80, SEQ ID NO. 82, SEQ ID NO. 84, SEQ ID NO. 86, SEQ ID NO. 88, SEQ ID NO. 90, SEQ ID NO. 92, SEQ ID NO. 94, SEQ ID NO. 96, SEQ ID NO. 98, SEQ ID NO. 100, SEQ ID NO. 102, SEQ ID NO. 104, SEQ ID NO. 106, SEQ ID NO. 108, SEQ ID NO. 110, and combinations thereof. In one embodiment, the fully human antibody has both a heavy chain and a light chain wherein the antibody has a heavy chain/light chain variable domain sequence selected from the group consisting SEQ ID NO. 1/SEQ ID NO. 2 (called JG1A1 herein), SEQ ID NO. 3/SEQ ID NO. 4 (called JG1A10 herein), SEQ ID NO. 5/SEQ ID NO. 6 (called JG1A12 herein), SEQ ID NO. 7/SEQ ID NO. 8 (called JG1A3 herein), SEQ ID NO. 9/SEQ ID NO. 10 (called JG1A4 herein), SEQ ID NO. 11/SEQ ID NO. 12 (called JG11A5 herein), SEQ ID NO. 13/SEQ ID NO. 14

(called JG1A6 herein), SEQ ID NO. 15/SEQ ID NO. 16 (called JG1A7 herein), SEQ ID NO. 17/SEQ ID NO. 18 (called JG1B1 herein), SEQ ID NO. 19/SEQ ID NO. 20 (called JG1B10 herein), SEQ ID NO. 21/SEQ ID NO. 22 (called JG1B11 herein), SEQ ID NO. 23/SEQ ID NO. 24 (called JG1B12 herein), SEQ ID NO. 25/SEQ ID NO. 26 (called JG1B4 herein), SEQ ID NO. 27/SEQ ID NO. 28 (called JG1B5 herein), SEQ ID NO. 29/SEQ ID NO. 30 (called JG1B6 herein), SEQ ID NO. 31/SEQ ID NO. 32 (called JG1B8 herein), SEQ ID NO. 33/SEQ ID NO. 34 (called JG1C3 herein), SEQ ID NO. 35/SEQ ID NO. 36 (called JG1C4 herein), SEQ ID NO. 37/SEQ ID NO. 38 (called JG1C5 herein), SEQ ID NO. 39/SEQ ID NO. 40 (called JG1C8 herein), SEQ ID NO. 41/SEQ ID NO. 42 (called JG1D1 herein), SEQ ID NO. 43/SEQ ID NO. 44 (called JG1D10 herein), SEQ ID NO. 45/SEQ ID NO. 46 (called JG1D11 herein), SEQ ID NO. 47/SEQ ID NO. 48 (called JG1D7 herein), SEQ ID NO. 49/SEQ ID NO. 50 (called JG1D8 herein), SEQ ID NO. 51/SEQ ID NO. 52 (called JG1E1 herein), SEQ ID NO. 53/SEQ ID NO. 54 (called JG1E11 herein), SEQ ID NO. 55/SEQ ID NO. 56 (called JG1E7 herein), SEQ ID NO. 57/SEQ ID NO. 58 (called JG1E8 herein), SEQ ID NO. 59/SEQ ID NO. 60 (called JG1F1 herein), SEQ ID NO. 61/SEQ ID NO. 62 (called JG1F10 herein), SEQ ID NO. 63/SEQ ID NO. 64 (called JG1F7 herein), SEQ ID NO. 65/SEQ ID NO. 66 (called JG1F8 herein), SEQ ID NO. 67/SEQ ID NO. 68 (called JG1G11 herein), SEQ ID NO. 69/SEQ ID NO. 70 (called JG1G5 herein), SEQ ID NO. 71/SEQ ID NO. 72 (called JG1H1 herein), SEQ ID NO. 73/SEQ ID NO. 74 (called JG1H11 herein), SEQ ID NO. 75/SEQ ID NO. 76 (called JG1H5 herein), SEQ ID NO. 77/SEQ ID NO. 78 (called JG1H7 herein), SEQ ID NO. 79/SEQ ID NO. 80 (called JH1A1 herein), SEQ ID NO. 81/SEQ ID NO. 82 (called JH1A11 herein), SEQ ID NO. 83/SEQ ID NO. 84 (called JH1A2 herein), SEQ ID NO. 85/SEQ ID NO. 86 (called JH1A4 herein), SEQ ID NO. 87/SEQ ID NO. 88 (called JH1B1 herein), SEQ ID NO. 89/SEQ ID NO. 90 (called JH1B3 herein), SEQ ID NO. 91/SEQ ID NO. 92 (called JH1B7 herein), SEQ ID NO. 93/SEQ ID NO. 94 (called JH1C10 herein), SEQ ID NO. 95/SEQ ID NO. 96 (called JH1C2 herein), SEQ ID NO. 97/SEQ ID NO. 98 (called JH1D7 herein), SEQ ID NO. 99/SEQ ID NO. 100 (called JH1E11 herein), SEQ ID NO. 101/SEQ ID NO. 102 (called JH1F3 herein), SEQ ID NO. 103/SEQ ID NO. 104 (called JH1F4 herein), SEQ ID NO. 105/SEQ ID NO. 106 (called JH1F6 herein), SEQ ID NO. 107/SEQ ID NO. 108 (called JH1H2 herein), SEQ ID NO. 109/SEQ ID NO. 110 (called JH1H7 herein), and combinations thereof.

In one embodiment, the present disclosure provides a Fab fully human antibody fragment, having a variable domain region from a heavy chain and a variable domain region from a light chain, wherein the heavy chain variable domain sequence that is at least 95% identical to the amino acid sequences selected from the group consisting of SEQ ID NO. 1, SEQ ID NO. 3, SEQ ID NO. 5, SEQ ID NO. 6, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63, SEQ ID NO. 65, SEQ ID NO. 67, SEQ ID NO. 69, SEQ ID NO. 71, SEQ ID NO. 73, SEQ ID NO. 75, SEQ ID NO. 77, SEQ ID NO. 79, SEQ ID NO. 81, SEQ ID NO. 83, SEQ ID NO. 85, SEQ ID NO. 87, SEQ ID NO. 89, SEQ ID NO. 91, SEQ ID NO. 93, SEQ ID NO. 95, SEQ ID NO. 97, SEQ ID NO. 99, SEQ ID NO. 101, SEQ ID NO. 103, SEQ ID NO. 105, SEQ ID NO. 107, SEQ ID NO. 109, and combinations thereof, and that has a light chain variable domain sequence that is at least 95% identical to the amino acid sequence consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72, SEQ ID NO. 74, SEQ ID NO. 76, SEQ ID NO. 78, SEQ ID NO. 80, SEQ ID NO. 82, SEQ ID NO. 84, SEQ ID NO. 86, SEQ ID NO. 88, SEQ ID NO. 90, SEQ ID NO. 92, SEQ ID NO. 94, SEQ ID NO. 96, SEQ ID NO. 98, SEQ ID NO. 100, SEQ ID NO. 102, SEQ ID NO. 104, SEQ ID NO. 106, SEQ ID NO. 108, SEQ ID NO. 110, and combinations thereof. In one embodiment, the fully human antibody Fab fragment comprises both a heavy chain variable domain region and a light chain variable domain region wherein the antibody has a heavy chain/light chain variable domain sequence selected from the group consisting SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28, SEQ ID NO. 29/SEQ ID NO. 30, SEQ ID NO. 31/SEQ ID NO. 32, SEQ ID NO. 33/SEQ ID NO. 34, SEQ ID NO. 35/SEQ ID NO. 36, SEQ ID NO. 37/SEQ ID NO. 38, SEQ ID NO. 39/SEQ ID NO. 40, SEQ ID NO. 41/SEQ ID NO. 42, SEQ ID NO. 43/SEQ ID NO. 44, SEQ ID NO. 45/SEQ ID NO. 46, SEQ ID NO. 47/SEQ ID NO. 48, SEQ ID NO. 49/SEQ ID NO. 50, SEQ ID NO. 51/SEQ ID NO. 52, SEQ ID NO. 53/SEQ ID NO. 54, SEQ ID NO. 55/SEQ ID NO. 56, SEQ ID NO. 57/SEQ ID NO. 58, SEQ ID NO. 59/SEQ ID NO. 60, SEQ ID NO. 61/SEQ ID NO. 62, SEQ ID NO. 63/SEQ ID NO. 64, SEQ ID NO. 65/SEQ ID NO. 66, SEQ ID NO. 67/SEQ ID NO. 68, SEQ ID NO. 69/SEQ ID NO. 70, SEQ ID NO. 71/SEQ ID NO. 72, SEQ ID NO. 73/SEQ ID NO. 74, SEQ ID NO. 75/SEQ ID NO. 76, SEQ ID NO. 77/SEQ ID NO. 78, SEQ ID NO. 79/SEQ ID NO. 80, SEQ ID NO. 81/SEQ ID NO. 82, SEQ ID NO. 83/SEQ ID NO. 84, SEQ ID NO. 85/SEQ ID NO. 86, SEQ ID NO. 87/SEQ ID NO. 88, SEQ ID NO. 89/SEQ ID NO. 90, SEQ ID NO. 91/SEQ ID NO. 92, SEQ ID NO. 93/SEQ ID NO. 94, SEQ ID NO. 95/SEQ ID NO. 96, SEQ ID NO. 97/SEQ ID NO. 98, SEQ ID NO. 99/SEQ ID NO. 100, SEQ ID NO. 101/SEQ ID NO. 102, SEQ ID NO. 103/SEQ ID NO. 104, SEQ ID NO. 105/SEQ ID NO. 106, SEQ ID NO. 107/SEQ ID NO. 108, SEQ ID NO. 109/SEQ ID NO. 110, and combinations thereof.

In one embodiment, the present disclosure provides a single chain human antibody, comprising a variable domain region from a heavy chain and a variable domain region from a light chain and a peptide linker connection the heavy chain and light chain variable domain regions, wherein the heavy chain variable domain sequence comprises a sequence that is at least 95% identical to an amino acid sequence selected from the group consisting of SEQ ID NO. 1, SEQ ID NO. 3, SEQ ID NO. 5, SEQ ID NO. 6, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63, SEQ ID NO. 65, SEQ ID NO. 67, SEQ ID NO. 69, SEQ ID NO. 71, SEQ ID NO. 73, SEQ ID NO. 75, SEQ ID NO. 77, SEQ ID NO. 79, SEQ ID NO. 81, SEQ ID NO. 83, SEQ ID NO. 85, SEQ ID NO. 87, SEQ ID NO. 89, SEQ ID NO. 91, SEQ ID NO. 93, SEQ ID NO. 95, SEQ ID NO. 97, SEQ ID NO. 99, SEQ ID NO. 101, SEQ ID NO. 103, SEQ ID NO. 105, SEQ ID NO. 107, SEQ ID NO. 109, and wherein the light chain variable domain sequence comprises a sequence that is at least 95% identical to an amino acid sequence consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72, SEQ ID NO. 74, SEQ ID NO. 76, SEQ ID NO. 78, SEQ ID NO. 80, SEQ ID NO. 82, SEQ ID NO. 84, SEQ ID NO. 86, SEQ ID NO. 88, SEQ ID NO. 90, SEQ ID NO. 92, SEQ ID NO. 94, SEQ ID NO. 96, SEQ ID NO. 98, SEQ ID NO. 100, SEQ ID NO. 102, SEQ ID NO. 104, SEQ ID NO. 106, SEQ ID NO. 108, SEQ ID NO. 110, and combinations thereof. In one embodiment, the fully human single chain antibody comprises both a heavy chain variable domain region and a light chain variable domain region, wherein the single chain fully human antibody comprises a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28, SEQ ID NO. 29/SEQ ID NO. 30, SEQ ID NO. 31/SEQ ID NO. 32, SEQ ID NO. 33/SEQ ID NO. 34, SEQ ID NO. 35/SEQ ID NO. 36, SEQ ID NO. 37/SEQ ID NO. 38, SEQ ID NO. 39/SEQ ID NO. 40, SEQ ID NO. 41/SEQ ID NO. 42, SEQ ID NO. 43/SEQ ID NO. 44, SEQ ID NO. 45/SEQ ID NO. 46, SEQ ID NO. 47/SEQ ID NO. 48, SEQ ID NO. 49/SEQ ID NO. 50, SEQ ID NO. 51/SEQ ID NO. 52, SEQ ID NO. 53/SEQ ID NO. 54, SEQ ID NO. 55/SEQ ID NO. 56, SEQ ID NO. 57/SEQ ID NO. 58, SEQ ID NO. 59/SEQ ID NO. 60, SEQ ID NO. 61/SEQ ID NO. 62, SEQ ID NO. 63/SEQ ID NO. 64, SEQ ID NO. 65/SEQ ID NO. 66, SEQ ID NO. 67/SEQ ID NO. 68, SEQ ID NO. 69/SEQ ID NO. 70, SEQ ID NO. 71/SEQ ID NO. 72, SEQ ID NO. 73/SEQ ID NO. 74, SEQ ID NO. 75/SEQ ID NO. 76, SEQ ID NO. 77/SEQ ID NO. 78, SEQ ID NO. 79/SEQ ID NO. 80, SEQ ID NO. 81/SEQ ID NO. 82, SEQ ID NO. 83/SEQ ID NO. 84, SEQ ID NO. 85/SEQ ID NO. 86, SEQ ID NO. 87/SEQ ID NO. 88, SEQ ID NO. 89/SEQ ID NO. 90, SEQ ID NO. 91/SEQ ID NO. 92, SEQ ID NO. 93/SEQ ID NO. 94, SEQ ID NO. 95/SEQ ID NO. 96, SEQ ID NO. 97/SEQ ID NO. 98, SEQ ID NO. 99/SEQ ID NO. 100, SEQ ID NO. 101/SEQ ID NO. 102, SEQ ID NO. 103/SEQ ID NO. 104, SEQ ID NO. 105/SEQ ID NO. 106, SEQ ID NO. 107/SEQ ID NO. 108, SEQ ID NO. 109/SEQ ID NO. 110, and combinations thereof.

In one embodiment, the present disclosure provides a method for treating Notch-signaling tumors, comprising administering an anti-JAG1 polypeptide, wherein the fully human antibody comprises a heavy chain variable domain sequence that is at least 95% identical to the amino acid sequences selected from the group consisting of SEQ ID NO. 1, SEQ ID NO. 3, SEQ ID NO. 5, SEQ ID NO. 6, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63, SEQ ID NO. 65, SEQ ID NO. 67, SEQ ID NO. 69, SEQ ID NO. 71, SEQ ID NO. 73, SEQ ID NO. 75, SEQ ID NO. 77, SEQ ID NO. 79, SEQ ID NO. 81, SEQ ID NO. 83, SEQ ID NO. 85, SEQ ID NO. 87, SEQ ID NO. 89, SEQ ID NO. 91, SEQ ID NO. 93, SEQ ID NO. 95, SEQ ID NO. 97, SEQ ID NO. 99, SEQ ID NO. 101, SEQ ID NO. 103, SEQ ID NO. 105, SEQ ID NO. 107, SEQ ID NO. 109, and combinations thereof, and comprises a light chain variable domain sequence that is at least 95% identical to the amino acid consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72, SEQ ID NO. 74, SEQ ID NO. 76, SEQ ID NO. 78, SEQ ID NO. 80, SEQ ID NO. 82, SEQ ID NO. 84, SEQ ID NO. 86, SEQ ID NO. 88, SEQ ID NO. 90, SEQ ID NO. 92, SEQ ID NO. 94, SEQ ID NO. 96, SEQ ID NO. 98, SEQ ID NO. 100, SEQ ID NO. 102, SEQ ID NO. 104, SEQ ID NO. 106, SEQ ID NO. 108, SEQ ID NO. 110, and combinations thereof. In one embodiment, the fully human antibody comprises both a heavy chain and a light chain wherein the antibody has a heavy chain/light chain variable domain sequence selected from the group consisting of SEQ ID NO. 1/SEQ ID NO. 2 (called JG1A1 herein), SEQ ID NO. 3/SEQ ID NO. 4 (called JG1A10 herein), SEQ ID NO. 5/SEQ ID NO. 6 (called JG1A12 herein), SEQ ID NO. 7/SEQ ID NO. 8 (called JG1A3 herein), SEQ ID NO. 9/SEQ ID NO. 10 (called JG1A4 herein), SEQ ID NO. 11/SEQ ID NO. 12 (called JG11A5 herein), SEQ ID NO. 13/SEQ ID NO. 14 (called JG1A6 herein), SEQ ID NO. 15/SEQ ID NO. 16 (called JG1A7 herein), SEQ ID NO. 17/SEQ ID NO. 18 (called JG1B1 herein), SEQ ID NO. 19/SEQ ID NO. 20 (called JG1B10 herein), SEQ ID NO. 21/SEQ ID NO. 22 (called JG1B11 herein), SEQ ID NO. 23/SEQ ID NO. 24 (called JG1B12 herein), SEQ ID NO. 25/SEQ ID NO. 26 (called JG1B4 herein), SEQ ID NO. 27/SEQ ID NO. 28 (called JG1B5 herein), SEQ ID NO. 29/SEQ ID NO. 30 (called JG1B6 herein), SEQ ID NO. 31/SEQ ID NO. 32 (called JG1B8 herein), SEQ ID NO. 33/SEQ ID NO. 34 (called JG1C3 herein), SEQ ID NO. 35/SEQ ID NO. 36 (called JG1C4 herein), SEQ ID NO. 37/SEQ ID NO. 38 (called JG1C5 herein), SEQ ID NO. 39/SEQ ID NO. 40 (called JG1C8 herein), SEQ ID NO. 41/SEQ ID NO. 42 (called JG1D1 herein), SEQ ID NO. 43/SEQ ID NO. 44 (called JG1D10 herein), SEQ ID NO. 45/SEQ ID NO. 46 (called JG1D11 herein), SEQ ID NO. 47/SEQ ID NO. 48 (called JG1D7 herein), SEQ ID NO. 49/SEQ ID NO. 50 (called JG1D8 herein), SEQ ID NO. 51/SEQ ID NO. 52 (called JG1E1 herein), SEQ ID NO. 53/SEQ ID NO. 54 (called JG1E11 herein), SEQ ID NO. 55/SEQ ID NO. 56 (called JG1E7 herein), SEQ ID NO. 57/SEQ ID NO. 58 (called JG1E8 herein), SEQ ID NO. 59/SEQ ID NO. 60 (called JG1F1 herein), SEQ ID NO. 61/SEQ ID NO. 62 (called JG1F10 herein), SEQ ID NO. 63/SEQ ID NO. 64 (called JG1F7 herein), SEQ ID NO. 65/SEQ ID NO. 66 (called JG1F8 herein), SEQ ID NO. 67/SEQ ID NO. 68 (called JG1G11 herein), SEQ ID NO. 69/SEQ ID NO. 70 (called JG1G5 herein), SEQ ID NO. 71/SEQ ID NO. 72 (called JG1H1 herein), SEQ ID NO. 73/SEQ ID NO. 74 (called JG1H11 herein), SEQ ID NO. 75/SEQ ID NO. 76 (called JG1H5 herein), SEQ ID NO. 77/SEQ ID NO. 78 (called JG1H7 herein), SEQ ID NO. 79/SEQ ID NO. 80 (called JH1A1 herein), SEQ ID NO. 81/SEQ ID NO. 82 (called JH1A11 herein), SEQ ID NO. 83/SEQ ID NO. 84 (called JH1A2 herein), SEQ ID NO. 85/SEQ ID NO. 86 (called JH1A4 herein), SEQ ID NO. 87/SEQ ID NO. 88 (called JH1B1 herein), SEQ ID NO. 89/SEQ ID NO. 90 (called JH1B3 herein), SEQ ID NO. 91/SEQ ID NO. 92 (called JH1B7 herein), SEQ ID NO. 93/SEQ ID NO. 94 (called JH1C10 herein), SEQ ID NO. 95/SEQ ID NO. 96 (called JH1C2 herein), SEQ ID NO. 97/SEQ ID NO. 98 (called JH1D7 herein), SEQ ID NO. 99/SEQ ID NO. 100 (called JH1E11 herein), SEQ ID NO. 101/SEQ ID NO. 102 (called JH1F3 herein), SEQ ID NO. 103/SEQ ID NO. 104 (called JH1F4 herein), SEQ ID NO. 105/SEQ ID NO. 106 (called JH1F6 herein), SEQ ID NO. 107/SEQ ID NO. 108 (called JH1H2 herein), SEQ ID NO. 109/SEQ ID NO. 110 (called JH1H7 herein), and combinations thereof.

In one embodiment, the present disclosure provides a method for treating Notch-signaling tumors, comprising administering a Fab fully human antibody fragment comprising a heavy chain variable domain sequence that is at least 95% identical to an amino acid sequence selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63, SEQ ID NO. 65, SEQ ID NO. 67, SEQ ID NO. 69, SEQ ID NO. 71, SEQ ID NO. 73, SEQ ID NO. 75, SEQ ID NO. 77, SEQ ID NO. 79, SEQ ID NO. 81, SEQ ID NO. 83, SEQ ID NO. 85, SEQ ID NO. 87, SEQ ID NO. 89, SEQ ID NO. 91, SEQ ID NO. 93, SEQ ID NO. 95, SEQ ID NO. 97, SEQ ID NO. 99, SEQ ID NO. 101, SEQ ID NO. 103, SEQ ID NO. 105, SEQ ID NO. 107, SEQ ID NO. 109, and combinations thereof, and comprising a light chain variable domain sequence that is at least 95% identical to an amino acid sequence selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72, SEQ ID NO. 74, SEQ ID NO. 76, SEQ ID NO. 78, SEQ ID NO. 80, SEQ ID NO. 82, SEQ ID NO. 84, SEQ ID NO. 86, SEQ ID NO. 88, SEQ ID NO. 90, SEQ ID NO. 92, SEQ ID NO. 94, SEQ ID NO. 96, SEQ ID NO. 98, SEQ ID NO. 100, SEQ ID NO. 102, SEQ ID NO. 104, SEQ ID NO. 106, SEQ ID NO. 108, SEQ ID NO. 110, and combinations thereof. In one embodiment, the fully human antibody Fab fragment comprises both a heavy chain variable domain region and a light chain variable domain region wherein the antibody comprises a heavy chain/light chain variable domain sequence selected from the group consisting of SEQ ID NO. 1/SEQ ID NO. 2 (called JG1A1 herein), SEQ ID NO. 3/SEQ ID NO. 4 (called JG1A10 herein), SEQ ID NO. 5/SEQ ID NO. 6 (called JG1A12 herein), SEQ ID NO. 7/SEQ ID NO. 8 (called JG1A3 herein), SEQ ID NO. 9/SEQ ID NO. 10 (called JG1A4 herein), SEQ ID NO. 11/SEQ ID NO. 12 (called JG11A5 herein), SEQ ID NO. 13/SEQ ID NO. 14 (called JG1A6 herein), SEQ ID NO. 15/SEQ ID NO. 16 (called JG1A7 herein), SEQ ID NO. 17/SEQ ID NO. 18 (called JG1B1 herein), SEQ ID NO. 19/SEQ ID NO. 20 (called JG1B10 herein), SEQ ID NO. 21/SEQ ID NO. 22 (called JG1B11 herein), SEQ ID NO. 23/SEQ ID NO. 24 (called JG1B12 herein), SEQ ID NO. 25/SEQ ID NO. 26 (called JG1B4 herein), SEQ ID NO. 27/SEQ ID NO. 28 (called JG1B5 herein), SEQ ID NO. 29/SEQ ID NO. 30 (called JG1B6 herein), SEQ ID NO. 31/SEQ ID NO. 32 (called JG1B8 herein), SEQ ID NO. 33/SEQ ID NO. 34 (called JG1C3 herein), SEQ ID NO. 35/SEQ ID NO. 36 (called JG1C4 herein), SEQ ID NO. 37/SEQ ID NO. 38 (called JG1C5 herein), SEQ ID NO. 39/SEQ ID NO. 40 (called JG1C8 herein), SEQ ID NO. 41/SEQ ID NO. 42 (called JG1D1 herein), SEQ ID NO. 43/SEQ ID NO. 44 (called JG1D10 herein), SEQ ID NO. 45/SEQ ID NO. 46 (called JG1D11 herein), SEQ ID NO. 47/SEQ ID NO. 48 (called JG1D7 herein), SEQ ID NO. 49/SEQ ID NO. 50 (called JG1D8 herein), SEQ ID NO. 51/SEQ ID NO. 52 (called JG1E1 herein), SEQ ID NO. 53/SEQ ID NO. 54 (called JG1E11 herein), SEQ ID NO. 55/SEQ ID NO. 56 (called JG1E7 herein), SEQ ID NO. 57/SEQ ID NO. 58 (called JG1E8 herein), SEQ ID NO. 59/SEQ ID NO. 60 (called JG1F1 herein), SEQ ID NO. 61/SEQ ID NO. 62 (called JG1F10 herein), SEQ ID NO. 63/SEQ ID NO. 64 (called JG1F7 herein), SEQ ID NO. 65/SEQ ID NO. 66 (called JG1F8 herein), SEQ ID NO. 67/SEQ ID NO. 68 (called JG1G11 herein), SEQ ID NO. 69/SEQ ID NO. 70 (called JG1G5 herein), SEQ ID NO. 71/SEQ ID NO. 72 (called JG1H1 herein), SEQ ID NO. 73/SEQ ID NO. 74 (called JG1H11 herein), SEQ ID NO. 75/SEQ ID NO. 76 (called JG1H5 herein), SEQ ID NO. 77/SEQ ID NO. 78 (called JG1H7 herein), SEQ ID NO. 79/SEQ ID NO. 80 (called JH1A1 herein), SEQ ID NO. 81/SEQ ID NO. 82 (called JH1A11 herein), SEQ ID NO. 83/SEQ ID NO. 84 (called JH1A2 herein), SEQ ID NO. 85/SEQ ID NO. 86 (called JH1A4 herein), SEQ ID NO. 87/SEQ ID NO. 88 (called JH1B1 herein), SEQ ID NO. 89/SEQ ID NO. 90 (called JH1B3 herein), SEQ ID NO. 91/SEQ ID NO. 92 (called JH1B7 herein), SEQ ID NO. 93/SEQ ID NO. 94 (called JH1C10 herein), SEQ ID NO. 95/SEQ ID NO. 96 (called JH1C2 herein), SEQ ID NO. 97/SEQ ID NO. 98 (called JH1D7 herein), SEQ ID NO. 99/SEQ ID NO. 100 (called JH1E11 herein), SEQ ID NO.

101/SEQ ID NO. 102 (called JH1F3 herein), SEQ ID NO. 103/SEQ ID NO. 104 (called JH1F4 herein), SEQ ID NO. 105/SEQ ID NO. 106 (called JH1F6 herein), SEQ ID NO. 107/SEQ ID NO. 108 (called JH1H2 herein), SEQ ID NO. 109/SEQ ID NO. 110 (called JH1H7 herein), and combinations thereof.

In one embodiment, the present disclosure provides a method for treating Notch-signaling tumors, comprising administering a single chain human antibody comprising a heavy chain variable domain sequence that is at least 95% identical to an amino acid sequence selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63, SEQ ID NO. 65, SEQ ID NO. 67, SEQ ID NO. 69, SEQ ID NO. 71, SEQ ID NO. 73, SEQ ID NO. 75, SEQ ID NO. 77, SEQ ID NO. 79, SEQ ID NO. 81, SEQ ID NO. 83, SEQ ID NO. 85, SEQ ID NO. 87, SEQ ID NO. 89, SEQ ID NO. 91, SEQ ID NO. 93, SEQ ID NO. 95, SEQ ID NO. 97, SEQ ID NO. 99, SEQ ID NO. 101, SEQ ID NO. 103, SEQ ID NO. 105, SEQ ID NO. 107, SEQ ID NO. 109, and combinations thereof, and comprising a light chain variable domain sequence that is at least 95% identical to an amino acid sequence selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72, SEQ ID NO. 74, SEQ ID NO. 76, SEQ ID NO. 78, SEQ ID NO. 80, SEQ ID NO. 82, SEQ ID NO. 84, SEQ ID NO. 86, SEQ ID NO. 88, SEQ ID NO. 90, SEQ ID NO. 92, SEQ ID NO. 94, SEQ ID NO. 96, SEQ ID NO. 98, SEQ ID NO. 100, SEQ ID NO. 102, SEQ ID NO. 104, SEQ ID NO. 106, SEQ ID NO. 108, SEQ ID NO. 110, and combinations thereof. In one embodiment, the fully human single chain antibody comprises both a heavy chain variable domain region and a light chain variable domain region, wherein the single chain fully human antibody comprises a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28, SEQ ID NO. 29/SEQ ID NO. 30, SEQ ID NO. 31/SEQ ID NO. 32, SEQ ID NO. 33/SEQ ID NO. 34, SEQ ID NO. 35/SEQ ID NO. 36, SEQ ID NO. 37/SEQ ID NO. 38, SEQ ID NO. 39/SEQ ID NO. 40, SEQ ID NO. 41/SEQ ID NO. 42, SEQ ID NO. 43/SEQ ID NO. 44, SEQ ID NO. 45/SEQ ID NO. 46, SEQ ID NO. 47/SEQ ID NO. 48, SEQ ID NO. 49/SEQ ID NO. 50, SEQ ID NO. 51/SEQ ID NO. 52, SEQ ID NO. 53/SEQ ID NO. 54, SEQ ID NO. 55/SEQ ID NO. 56, SEQ ID NO. 57/SEQ ID NO. 58, SEQ ID NO. 59/SEQ ID NO. 60, SEQ ID NO. 61/SEQ ID NO. 62, SEQ ID NO. 63/SEQ ID NO. 64, SEQ ID NO. 65/SEQ ID NO. 66, SEQ ID NO. 67/SEQ ID NO. 68, SEQ ID NO. 69/SEQ ID NO. 70, SEQ ID NO. 71/SEQ ID NO. 72, SEQ ID NO. 73/SEQ ID NO. 74, SEQ ID NO. 75/SEQ ID NO. 76, SEQ ID NO. 77/SEQ ID NO. 78, SEQ ID NO. 79/SEQ ID NO. 80, SEQ ID NO. 81/SEQ ID NO. 82, SEQ ID NO. 83/SEQ ID NO. 84, SEQ ID NO. 85/SEQ ID NO. 86, SEQ ID NO. 87/SEQ ID NO. 88, SEQ ID NO. 89/SEQ ID NO. 90, SEQ ID NO. 91/SEQ ID NO. 92, SEQ ID NO. 93/SEQ ID NO. 94, SEQ ID NO. 95/SEQ ID NO. 96, SEQ ID NO. 97/SEQ ID NO. 98, SEQ ID NO. 99/SEQ ID NO. 100, SEQ ID NO. 101/SEQ ID NO. 102, SEQ ID NO. 103/SEQ ID NO. 104, SEQ ID NO. 105/SEQ ID NO. 106, SEQ ID NO. 107/SEQ ID NO. 108, SEQ ID NO. 109/SEQ ID NO. 110, and combinations thereof.

In one embodiment, the invention provides an isolated anti-JAG1 fully human antibody of an IgG class, said antibody comprising a heavy chain variable domain sequence that is at least 95% identical to an amino acid sequence selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63, SEQ ID NO. 65, SEQ ID NO. 67, SEQ ID NO. 69, SEQ ID NO. 71, SEQ ID NO. 73, SEQ ID NO. 75, SEQ ID NO. 77, SEQ ID NO. 79, SEQ ID NO. 81, SEQ ID NO. 83, SEQ ID NO. 85, SEQ ID NO. 87, SEQ ID NO. 89, SEQ ID NO. 91, SEQ ID NO. 93, SEQ ID NO. 95, SEQ ID NO. 97, SEQ ID NO. 99, SEQ ID NO. 101, SEQ ID NO. 103, SEQ ID NO. 105, SEQ ID NO. 107, SEQ ID NO. 109, SEQ ID NO. 111, SEQ ID NO. 124, SEQ ID NO. 125, SEQ ID NO. 126, SEQ ID NO. 127, SEQ ID NO. 128, SEQ ID NO. 129, SEQ ID NO. 130, SEQ ID NO. 132, SEQ ID NO. 135, SEQ ID NO. 139 and SEQ ID NO. 142; and a light chain variable domain sequence that is at least 95% identical to an amino acid sequence selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72, SEQ ID NO. 74, SEQ ID NO. 76, SEQ ID NO. 78, SEQ ID NO. 80, SEQ ID NO. 82, SEQ ID NO. 84, SEQ ID NO. 86, SEQ ID NO. 88, SEQ ID NO. 90, SEQ ID NO. 92, SEQ ID NO. 94, SEQ ID NO. 96, SEQ ID NO. 98, SEQ ID NO. 100, SEQ ID NO. 102, SEQ ID NO. 104, SEQ ID NO. 106, SEQ ID NO. 108, SEQ ID NO. 110, SEQ ID NO. 112, SEQ ID NO. 113, SEQ ID NO. 114, SEQ ID NO. 115, SEQ ID NO. 116, SEQ ID NO. 117, SEQ ID NO. 118, SEQ ID NO. 119, SEQ ID NO. 120, SEQ ID NO. 121, SEQ ID NO. 122, SEQ ID NO. 123, SEQ ID NO. 131, SEQ ID NO. 133, SEQ ID NO. 134, SEQ ID NO. 136, SEQ ID NO. 137, SEQ ID NO. 138, SEQ ID NO. 140 and SEQ ID NO. 141.

In one embodiment, the fully human antibody comprises a heavy chain/light chain variable domain sequence selected from the group consisting of: SEQ ID NO. 1/SEQ ID NO. 2 (JG1A1), SEQ ID NO. 3/SEQ ID NO. 4 (JG1A10), SEQ ID NO. 5/SEQ ID NO. 6 (JG1A12), SEQ ID NO. 7/SEQ ID NO. 8 (JG1A3), SEQ ID NO. 9/SEQ ID NO. 10 (JG1A4), SEQ ID NO. 11/SEQ ID NO. 12 (JG11A5), SEQ ID NO. 13/SEQ ID NO. 14 (JG1A6), SEQ ID NO. 15/SEQ ID NO. 16 (JG1A7), SEQ ID NO. 17/SEQ ID NO. 18 (JG1B1), SEQ ID NO. 19/SEQ ID NO. 20 (JG1B10), SEQ ID NO. 21/SEQ ID NO. 22 (JG1B11), SEQ ID NO. 23/SEQ ID NO. 24 (JG1B12), SEQ ID NO. 25/SEQ ID NO. 26 (JG1B4), SEQ ID NO. 27/SEQ ID NO. 28 (JG1B5), SEQ ID NO. 29/SEQ ID NO. 30 (JG1B6), SEQ ID NO. 31/SEQ ID NO. 32 (JG1B8), SEQ ID NO. 33/SEQ ID NO. 34 (JG1C3), SEQ ID NO. 35/SEQ ID NO. 36 (JG1C4), SEQ ID NO. 37/SEQ ID NO. 38 (JG1C5), SEQ ID NO. 39/SEQ ID NO. 40 (JG1C8), SEQ ID NO. 41/SEQ ID NO. 42 (JG1D1), SEQ ID NO. 43/SEQ ID NO. 44 (JG1D10), SEQ ID NO. 45/SEQ ID NO. 46 (JG1D11), SEQ ID NO. 47/SEQ ID NO. 48 (JG1D7), SEQ ID NO. 49/SEQ ID NO. 50 (JG1D8), SEQ ID NO. 51/SEQ ID NO. 52 (JG1E1), SEQ ID NO. 53/SEQ ID NO. 54 (JG1E11), SEQ ID NO. 55/SEQ ID NO. 56 (JG1E7), SEQ ID NO. 57/SEQ ID NO. 58 (JG1E8), SEQ ID NO. 59/SEQ ID NO. 60 (JG1F1), SEQ ID NO. 61/SEQ ID NO. 62 (JG1F10), SEQ ID NO. 63/SEQ ID NO. 64 (JG1F7), SEQ ID NO. 65/SEQ ID NO. 66 (JG1F8), SEQ ID NO. 67/SEQ ID NO. 68 (JG1G11), SEQ ID NO. 69/SEQ ID NO. 70 (JG1G5), SEQ ID NO. 71/SEQ ID NO. 72 (JG1H1), SEQ ID NO. 73/SEQ ID NO. 74 (JG1H11), SEQ ID NO. 75/SEQ ID NO. 76 (JG1H5), SEQ ID NO. 77/SEQ ID NO. 78 (JG1H7), SEQ ID NO. 79/SEQ ID NO. 80 (JH1A1), SEQ ID NO. 81/SEQ ID NO. 82 (JH1A11), SEQ ID NO. 83/SEQ ID NO. 84 (JH1A2), SEQ ID NO. 85/SEQ ID NO. 86 (JH1A4), SEQ ID NO. 87/SEQ ID NO. 88 (JH1B1 n), SEQ ID NO. 89/SEQ ID NO. 90 (JH1B3), SEQ ID NO. 91/SEQ ID NO. 92 (JH1B7), SEQ ID NO. 93/SEQ ID NO. 94 (JH1C10), SEQ ID NO. 95/SEQ ID NO. 96 (JH1C2), SEQ ID NO. 97/SEQ ID NO. 98 (JH1D7), SEQ ID NO. 99/SEQ ID NO. 100 (JH1E11), SEQ ID NO. 101/SEQ ID NO. 102 (JH1F3), SEQ ID NO. 103/SEQ ID NO. 104 (JH1F4), SEQ ID NO. 105/SEQ ID NO. 106 (JH1F6), SEQ ID NO. 107/SEQ ID NO. 108 (JH1H2), SEQ ID NO. 109/SEQ ID NO. 110 (JH1H7), SEQ ID NO. 111/SEQ ID NO.112 (G1H73-2), SEQ ID NO. 111/SEQ ID NO.113 (JG1H7-2B2S), SEQ ID NO.111/SEQ ID NO.114 (JG1H7-2A5), SEQ ID NO. 111/SEQ ID NO.115 (JG1H73-2A7S), SEQ ID NO. 111/SEQ ID NO.116 (JG1H7-2A10S), SEQ ID NO.111/SEQ ID NO.117 (JG1H7-2A2S), SEQ ID NO. 111/SEQ ID NO.118 (JG1H73-2A9S), SEQ ID NO. 111/SEQ ID NO.119 (JG1H7-2A1S), SEQ ID NO.111/SEQ ID NO.120 (JG1H7-E11S), SEQ ID NO. 111/SEQ ID NO.121 (JG1H73-C11S), SEQ ID NO. 111/SEQ ID NO.122 (JG1H7-D10S), SEQ ID NO.111/SEQ ID NO.123 (JG1H7-2B7S), SEQ ID NO.124/SEQ ID NO.112 (JG1H7-1A8S), SEQ ID NO. 125/SEQ ID NO.112 (JG1H73-1A6S), SEQ ID NO. 126/SEQ ID NO.112 (JG1H7-1A2S), SEQ ID NO.127/SEQ ID NO.112 (JG1H7-1B1S), SEQ ID NO. 128/SEQ ID NO.112 (JG1H73-1A8S), SEQ ID NO. 129/SEQ ID NO.112 (JG1H7-5B5S), SEQ ID NO.130/SEQ ID NO.112 (JG1H7-3E5S), SEQ ID NO.127/SEQ ID NO.131 (JG1H7-G6C), SEQ ID NO. 132/SEQ ID NO.133 (JG1H73-A6C), SEQ ID NO. 132/SEQ ID NO.123 (JG1H7-E11C), SEQ ID NO.142/SEQ ID NO.123 (JG1H7-C6C), SEQ ID NO. 127/SEQ ID NO.123 (JG1H73-C9C), SEQ ID NO. 132/SEQ ID NO.134 (JG1H7-F4C), SEQ ID NO. 135/SEQ ID NO.133 (JG1H7-F2C), SEQ ID NO.132/SEQ ID NO.136 (JG1H7-F1C), SEQ ID NO.132/SEQ ID NO.137 (JG1H7-D4C), SEQ ID NO. 132/SEQ ID NO.138 (JG1H73-D5C), SEQ ID NO. 139/SEQ ID NO.123 (JG1H7-A5C), SEQ ID NO.139/SEQ ID NO.140 (JG1H7-B2C), and SEQ ID NO. 127/SEQ ID NO.141 (JG1H73-B6C).

In one embodiment, the invention features an anti-JAG1 fully human antibody Fab fragment, comprising a heavy chain variable domain comprising an amino acid sequence that is at least 95% identical to an amino acid sequence selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63, SEQ ID NO. 65, SEQ ID NO. 67, SEQ ID NO. 69, SEQ ID NO. 71, SEQ ID NO. 73, SEQ ID NO. 75, SEQ ID NO. 77, SEQ ID NO. 79, SEQ ID NO. 81, SEQ ID NO. 83, SEQ ID NO. 85, SEQ ID NO. 87, SEQ ID NO. 89, SEQ ID NO. 91, SEQ ID NO. 93, SEQ ID NO. 95, SEQ ID NO. 97, SEQ ID NO. 99, SEQ ID NO. 101, SEQ ID NO. 103, SEQ ID NO. 105, SEQ ID NO. 107, SEQ ID NO. 109, SEQ ID NO. 111, SEQ ID NO. 124, SEQ ID NO. 125, SEQ ID NO. 126, SEQ ID NO. 127, SEQ ID NO. 128, SEQ ID NO. 129, SEQ ID NO. 130, SEQ ID NO. 132, SEQ ID NO. 135, SEQ ID NO. 139 and SEQ ID NO. 142; and comprising a light chain variable domain comprising an amino acid sequence that is at least 95% identical to an amino acid sequence selected from the group consisting of: SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72, SEQ ID NO. 74, SEQ ID NO. 76, SEQ ID NO. 78, SEQ ID NO. 80, SEQ ID NO. 82, SEQ ID NO. 84, SEQ ID NO. 86, SEQ ID NO. 88, SEQ ID NO. 90, SEQ ID NO. 92, SEQ ID NO. 94, SEQ ID NO. 96, SEQ ID NO. 98, SEQ ID NO. 100, SEQ ID NO. 102, SEQ ID NO. 104, SEQ ID NO. 106, SEQ ID NO. 108, SEQ ID NO. 110, SEQ ID NO. 112, SEQ ID NO. 113, SEQ ID NO. 114, SEQ ID NO. 115, SEQ ID NO. 116, SEQ ID NO. 117, SEQ ID NO. 118, SEQ ID NO. 119, SEQ ID NO. 120, SEQ ID NO. 121, SEQ ID NO. 122, SEQ ID NO. 123, SEQ ID NO. 131, SEQ ID NO. 133, SEQ ID NO. 134, SEQ ID NO. 136, SEQ ID NO. 137, SEQ ID NO. 138, SEQ ID NO. 140 and SEQ ID NO. 141. In one embodiment, the fully human antibody Fab fragment comprises a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28, SEQ ID NO. 29/SEQ ID NO. 30, SEQ ID NO. 31/SEQ ID NO. 32, SEQ ID NO. 33/SEQ ID NO. 34, SEQ ID NO. 35/SEQ ID NO. 36, SEQ ID NO. 37/SEQ ID NO. 38, SEQ ID NO. 39/SEQ ID NO. 40, SEQ ID NO. 41/SEQ ID NO. 42, SEQ ID NO. 43/SEQ ID NO. 44, SEQ ID NO. 45/SEQ ID NO. 46, SEQ ID NO. 47/SEQ ID NO. 48, SEQ ID NO. 49/SEQ ID NO. 50, SEQ ID NO. 51/SEQ ID NO. 52, SEQ ID NO. 53/SEQ ID NO. 54, SEQ ID NO. 55/SEQ ID NO. 56, SEQ ID NO. 57/SEQ ID NO. 58, SEQ ID NO. 59/SEQ ID NO. 60, SEQ ID NO. 61/SEQ ID NO. 62, SEQ ID NO. 63/SEQ ID NO. 64, SEQ ID NO. 65/SEQ ID NO. 66, SEQ ID NO. 67/SEQ ID NO. 68, SEQ ID NO. 69/SEQ ID NO. 70, SEQ ID NO. 71/SEQ ID NO. 72, SEQ ID NO. 73/SEQ ID NO. 74, SEQ ID NO. 75/SEQ ID NO. 76, SEQ ID NO. 77/SEQ ID NO. 78, SEQ ID NO. 79/SEQ ID NO. 80, SEQ ID NO. 81/SEQ ID NO. 82, SEQ ID NO. 83/SEQ ID NO. 84, SEQ ID NO. 85/SEQ ID NO. 86, SEQ ID NO. 87/SEQ ID NO. 88, SEQ ID NO. 89/SEQ ID NO. 90, SEQ ID NO. 91/SEQ ID NO. 92, SEQ ID NO. 93/SEQ ID NO. 94, SEQ ID NO. 95/SEQ ID NO. 96, SEQ ID NO. 97/SEQ ID NO. 98, SEQ ID NO. 99/SEQ ID NO. 100, SEQ ID NO. 101/SEQ ID NO. 102, SEQ ID NO. 103/SEQ ID NO. 104, SEQ ID NO. 105/SEQ ID NO. 106, SEQ ID NO. 107/SEQ ID NO. 108, SEQ ID NO. 109/SEQ ID NO. 110, SEQ ID NO. 111/SEQ ID NO.112, SEQ ID NO. 111/SEQ ID NO.113, SEQ ID NO.111/SEQ ID NO.114, SEQ ID NO. 111/SEQ ID NO.115, SEQ ID NO. 111/SEQ ID NO.116, SEQ ID NO.111/SEQ ID NO.117, SEQ ID NO. 111/SEQ ID NO.118, SEQ ID NO. 111/SEQ ID NO.119, SEQ ID NO.111/SEQ ID NO.120, SEQ ID NO. 111/SEQ ID NO.121, SEQ ID NO. 111/SEQ ID NO.122, SEQ ID NO.111/SEQ ID NO.123, SEQ ID NO.124/SEQ ID NO.112, SEQ ID NO. 125/SEQ ID NO.112, SEQ ID NO. 126/SEQ ID NO.112, SEQ ID NO.127/SEQ ID NO.112, SEQ ID NO. 128/SEQ ID NO.112, SEQ ID NO. 129/SEQ ID NO.112, SEQ ID NO.130/SEQ ID NO.112, SEQ ID NO.127/SEQ ID NO.131, SEQ ID NO. 132/SEQ ID NO.133, SEQ ID NO. 132/SEQ ID NO.123, SEQ ID NO.142/SEQ ID NO.123, SEQ ID NO. 127/SEQ ID NO.123, SEQ ID NO. 132/SEQ ID NO.134, SEQ ID NO. 135/SEQ ID NO.133, SEQ ID NO.132/SEQ ID NO.136, SEQ ID NO.132/SEQ ID NO.137, SEQ ID NO. 132/SEQ ID NO.138, SEQ ID NO. 139/SEQ ID NO.123, SEQ ID NO.139/SEQ ID NO.140, and SEQ ID NO. 127/SEQ ID NO.141.

In one embodiment, the invention provides an anti-JAG1 single chain human antibody, comprising a heavy chain variable domain and a light chain variable domain which are connected by a peptide linker, wherein the heavy chain variable domain comprises an amino acid sequence that is at least 95% identical to an amino acid sequence selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63, SEQ ID NO. 65, SEQ ID NO. 67, SEQ ID NO. 69, SEQ ID NO. 71, SEQ ID NO. 73, SEQ ID NO. 75, SEQ ID NO. 77, SEQ ID NO. 79, SEQ ID NO. 81, SEQ ID NO. 83, SEQ ID NO. 85, SEQ ID NO. 87, SEQ ID NO. 89, SEQ ID NO. 91, SEQ ID NO. 93, SEQ ID NO. 95, SEQ ID NO. 97, SEQ ID NO. 99, SEQ ID NO. 101, SEQ ID NO. 103, SEQ ID NO. 105, SEQ ID NO. 107, SEQ ID NO. 109, SEQ ID NO. 111, SEQ ID NO. 124, SEQ ID NO. 125, SEQ ID NO. 126, SEQ ID NO. 127, SEQ ID NO. 128, SEQ ID NO. 129, SEQ ID NO. 130, SEQ ID NO. 132, SEQ ID NO. 135, SEQ ID NO. 139 and SEQ ID NO. 142; and the light chain variable domain comprises an amino acid sequence that is at least 95% identical to an amino acid sequence selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72, SEQ ID NO. 74, SEQ ID NO. 76, SEQ ID NO. 78, SEQ ID NO. 80, SEQ ID NO. 82, SEQ ID NO. 84, SEQ ID NO. 86, SEQ ID NO. 88, SEQ ID NO. 90, SEQ ID NO. 92, SEQ ID NO. 94, SEQ ID NO. 96, SEQ ID NO. 98, SEQ ID NO. 100, SEQ ID NO. 102, SEQ ID NO. 104, SEQ ID NO. 106, SEQ ID NO. 108, SEQ ID NO. 110, SEQ ID NO. 112, SEQ ID NO. 113, SEQ ID NO. 114, SEQ ID NO. 115, SEQ ID NO. 116, SEQ ID NO. 117, SEQ ID NO. 118, SEQ ID NO. 119, SEQ ID NO. 120, SEQ ID NO. 121, SEQ ID NO. 122, SEQ ID NO. 123, SEQ ID NO. 131, SEQ ID NO. 133, SEQ ID NO. 134, SEQ ID NO. 136, SEQ ID NO. 137, SEQ ID NO. 138, SEQ ID NO. 140 and SEQ ID NO. 141.

In one embodiment, the single chain fully human antibody comprises a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28, SEQ ID NO. 29/SEQ ID NO. 30, SEQ ID NO. 31/SEQ ID NO. 32, SEQ ID NO. 33/SEQ ID NO. 34, SEQ ID NO. 35/SEQ ID NO. 36, SEQ ID NO. 37/SEQ ID NO. 38, SEQ ID NO. 39/SEQ ID NO. 40, SEQ ID NO. 41/SEQ ID NO. 42, SEQ ID NO. 43/SEQ ID NO. 44, SEQ ID NO. 45/SEQ ID NO. 46, SEQ ID NO. 47/SEQ ID NO. 48, SEQ ID NO. 49/SEQ ID NO. 50, SEQ ID NO. 51/SEQ ID NO. 52, SEQ ID NO. 53/SEQ ID NO. 54, SEQ ID NO. 55/SEQ ID NO. 56, SEQ ID NO. 57/SEQ ID NO. 58, SEQ ID NO. 59/SEQ ID NO. 60, SEQ ID NO. 61/SEQ ID NO. 62, SEQ ID NO. 63/SEQ ID NO. 64, SEQ ID NO. 65/SEQ ID NO. 66, SEQ ID NO. 67/SEQ ID NO. 68, SEQ ID NO. 69/SEQ ID NO. 70, SEQ ID NO. 71/SEQ ID NO. 72, SEQ ID NO. 73/SEQ ID NO. 74, SEQ ID NO. 75/SEQ ID NO. 76, SEQ ID NO. 77/SEQ ID NO. 78, SEQ ID NO. 79/SEQ ID NO. 80, SEQ ID NO. 81/SEQ ID NO. 82, SEQ ID NO. 83/SEQ ID NO. 84, SEQ ID NO. 85/SEQ ID NO. 86, SEQ ID NO. 87/SEQ ID NO. 88, SEQ ID NO. 89/SEQ ID NO. 90, SEQ ID NO. 91/SEQ ID NO. 92, SEQ ID NO. 93/SEQ ID NO. 94, SEQ ID NO. 95/SEQ ID NO. 96, SEQ ID NO. 97/SEQ ID NO. 98, SEQ ID NO. 99/SEQ ID NO. 100, SEQ ID NO. 101/SEQ ID NO. 102, SEQ ID NO. 103/SEQ ID NO. 104, SEQ ID NO. 105/SEQ ID NO. 106, SEQ ID NO. 107/SEQ ID NO. 108, SEQ ID NO. 109/SEQ ID NO. 110, SEQ ID NO. 111/SEQ ID NO.112, SEQ ID NO. 111/SEQ ID NO.113, SEQ ID NO.111/SEQ ID NO.114, SEQ ID NO. 111/SEQ ID NO.115, SEQ ID NO.111/SEQ ID NO.116, SEQ ID NO.111/SEQ ID NO.117, SEQ ID NO. 111/SEQ ID NO.118, SEQ ID NO. 111/SEQ ID NO.119, SEQ ID NO.111/SEQ ID NO.120, SEQ ID NO. 111/SEQ ID NO.121, SEQ ID NO. 111/SEQ ID NO.122, SEQ ID NO.111/SEQ ID NO.123, SEQ ID NO.124/SEQ ID NO.112, SEQ ID NO. 125/SEQ ID NO.112, SEQ ID NO. 126/SEQ ID NO.112, SEQ ID NO.127/SEQ ID NO.112, SEQ ID NO. 128/SEQ ID NO.112, SEQ ID NO. 129/SEQ ID NO.112, SEQ ID NO.130/SEQ ID NO.112, SEQ ID NO.127/SEQ ID NO.131, SEQ ID NO. 132/SEQ ID NO.133, SEQ ID NO. 132/SEQ ID NO.123, SEQ ID NO.142/SEQ ID NO.123, SEQ ID NO. 127/SEQ ID NO.123, SEQ ID NO. 132/SEQ ID NO.134, SEQ ID NO. 135/SEQ ID NO.133, SEQ ID NO.132/SEQ ID NO.136, SEQ ID NO.132/SEQ ID NO.137, SEQ ID NO. 132/SEQ ID NO.138, SEQ ID NO. 139/SEQ ID NO.123, SEQ ID NO.139/SEQ ID NO.140, and SEQ ID NO. 127/SEQ ID NO.141.

In one embodiment, the invention provides an isolated anti-JAG1 antibody, or an antigen-binding fragment thereof, comprising a heavy chain variable domain comprising complementarity determining regions (CDRs) as set forth in a heavy chain variable domain amino acid sequence selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63, SEQ ID NO. 65, SEQ ID NO. 67, SEQ ID NO. 69, SEQ ID NO. 71, SEQ ID NO. 73, SEQ ID NO. 75, SEQ ID NO. 77, SEQ ID NO. 79, SEQ ID NO. 81, SEQ ID NO. 83, SEQ ID NO. 85, SEQ ID NO. 87, SEQ ID NO. 89, SEQ ID NO. 91, SEQ ID NO. 93, SEQ ID NO. 95, SEQ ID NO. 97, SEQ ID NO. 99, SEQ ID NO. 101, SEQ ID NO. 103, SEQ ID NO. 105, SEQ ID NO. 107, SEQ ID NO. 109, SEQ ID NO. 111, SEQ ID NO. 124, SEQ ID NO. 125, SEQ ID NO. 126, SEQ ID NO. 127, SEQ ID NO. 128, SEQ ID NO. 129, SEQ ID NO. 130, SEQ ID NO. 132, SEQ ID NO. 135, SEQ ID NO. 139 and SEQ ID NO. 142; and comprising a light chain variable domain comprising CDRs as set forth in a light chain variable region amino acid sequence selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72, SEQ ID NO. 74, SEQ ID NO. 76, SEQ ID NO. 78, SEQ ID NO. 80, SEQ ID NO. 82, SEQ ID NO. 84, SEQ ID NO. 86, SEQ ID NO. 88, SEQ ID NO. 90, SEQ ID NO. 92, SEQ ID NO. 94, SEQ ID NO. 96, SEQ ID NO. 98, SEQ ID NO. 100, SEQ ID NO. 102, SEQ ID NO. 104, SEQ ID NO. 106, SEQ ID NO. 108, SEQ ID NO. 110, SEQ ID NO. 112, SEQ ID NO. 113, SEQ ID NO. 114, SEQ ID NO. 115, SEQ ID NO. 116, SEQ ID NO. 117, SEQ ID NO. 118, SEQ ID NO. 119, SEQ ID NO. 120, SEQ ID NO. 121, SEQ ID NO. 122, SEQ ID NO. 123, SEQ ID NO. 131, SEQ ID NO. 133, SEQ ID NO. 134, SEQ ID NO. 136, SEQ ID NO. 137, SEQ ID NO. 138, SEQ ID NO. 140 and SEQ ID NO. 141.

In one embodiment, an anti-JAG1 antibody or an anti-JAG1 antibody fragment described herein may be used in a method for treating a Notch-signaling tumor in a subject in need thereof, said method comprising administering an effective amount of an anti-JAG1 antibody, or anti-JAG1 antibody fragment, to the subject in need thereof. In one embodiment, the tumor is selected from the group consisting of breast tumor, prostate, colorectal, lung, head and neck squamous cell carcinoma, T-cell acute lymphoblastic leukemia and melanoma and other solid tumors.

In one embodiment, the invention provides a method of treating cancer in a human subject in need thereof, comprising administering an effective amount of an anti-JAG1 antibody, or antigen-binding fragment thereof, disclosed herein to the subject, such that cancer is treated. In one embodiment, the cancer is associated with Notch-signaling. In one embodiment, the cancer is selected from the group consisting of breast, prostate, colorectal, lung, head and neck squamous cell carcinoma, T-cell acute lymphoblastic leukemia, melanoma, and a solid tumor.

In one embodiment, the method of the invention is for treating Notch-signaling tumors wherein the disease is selected from the group consisting of breast, prostate, colorectal, lung and other solid tumors.

In certain embodiments, the anti-JAG1 antibody, or antigen-binding fragment thereof, of the invention has a binding affinity ($K_D$) of at least $1\times10^{-6}$ M. In other embodiments, the antibody, or antigen-binding fragment thereof, of the invention has a $K_D$ of at least $1\times10^{-7}$ M. In other embodiments, the antibody, or antigen-binding fragment thereof, of the invention has a $K_D$ of at least $1\times10^{-8}$ M.

In certain embodiments, the antibody is an IgG1 isotype. In other embodiments, the antibody is an IgG4 isotype.

In certain embodiments, the antibody, or antigen-binding fragment, described herein is recombinant. In certain embodiments, the antibody, or antigen-binding fragment, described herein is a human antibody, or antigen binding fragment of an antibody.

In certain embodiments, the invention provides a pharmaceutical composition comprising an effective amount of an anti-JAG1 antibody, or antibody fragment disclosed herein, and a pharmaceutically acceptable carrier.

DESCRIPTION OF THE DRAWINGS

In FIG. 4, the designation of antibody "B10" refers to "JG1B10." The terms are used interchangeably. The designation of antibody "H7" refers to "JG1H7." The terms are used interchangeably.

FIG. 7A is a graph that shows the results of a binding ELISA of antibody JG1H7 to human JAG-1, human DLL1 and human DLL2.

FIG. 7B is a graph that shows the results of a binding ELISA of antibody JG1B10 to human JAG-1, human DLL1 and human DLL2. In FIG. 7B, B10JAG1 refers to the antibody "JG1B10."

DETAILED DESCRIPTION

Definitions

Figure 1A:
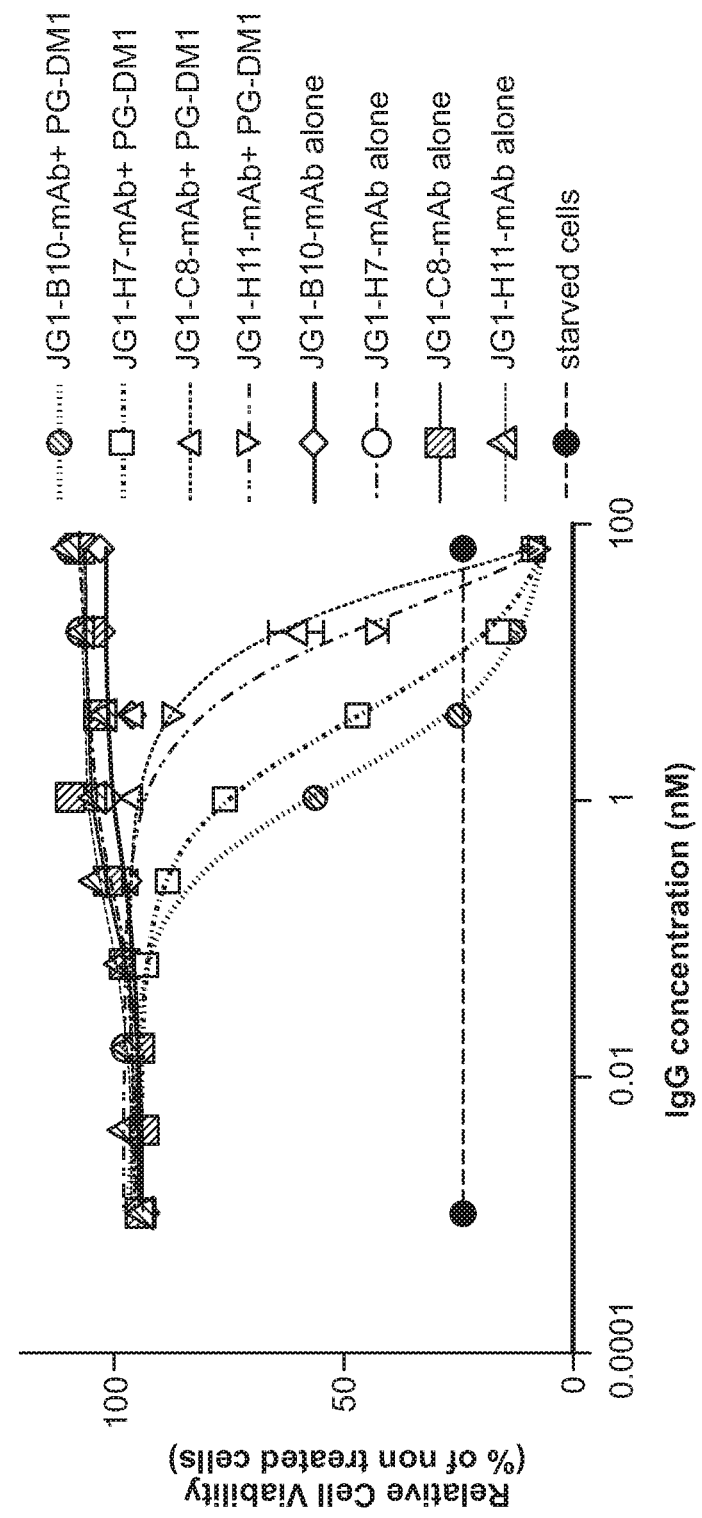
FIG. 1A is a graph that shows the cytotoxic potential of anti-JAG-1 antibodies complexed with Protein G-DM1 molecules (PG-DM1) on JAG-1-overexpressing cancer cells. Corresponding naked antibodies were used as controls.

The terms "peptide," "polypeptide" and "protein" each refers to a molecule comprising two or more amino acid residues joined to each other by peptide bonds. These terms encompass, e.g., native and artificial proteins, protein fragments and polypeptide analogs (such as muteins, variants, and fusion proteins) of a protein sequence as well as post-translationally, or otherwise covalently or non-covalently, modified proteins. A peptide, polypeptide, or protein may be monomeric or polymeric.

A "variant" of a polypeptide (for example, a variant of an antibody) comprises an amino acid sequence wherein one or more amino acid residues are inserted into, deleted from and/or substituted into the amino acid sequence relative to another polypeptide sequence. Disclosed variants include, for example, fusion proteins.

A "derivative" of a polypeptide is a polypeptide (e.g., an antibody) that has been chemically modified, e.g., via conjugation to another chemical moiety (such as, for example, polyethylene glycol or albumin, e.g., human serum albumin), phosphorylation, and glycosylation. Unless otherwise indicated, the term "antibody" includes, in addition to antibodies comprising two full-length heavy chains and two full-length light chains, derivatives, variants, fragments, and muteins thereof, examples of which are described below.

An "antigen binding protein" is a protein comprising a portion that binds to an antigen and, optionally, a scaffold or framework portion that allows the antigen binding portion to adopt a confirmation that promotes binding of the antigen binding protein to the antigen. Examples of antigen binding proteins include antibodies, antibody fragments (e.g., an antigen binding portion of an antibody), antibody derivatives, and antibody analogs. The antigen binding protein can comprise, for example, an alternative protein scaffold or artificial scaffold with grafted CDRs or CDR derivatives. Such scaffolds include, but are not limited to, antibody-derived scaffolds comprising mutations introduced to, for example, stabilize the three-dimensional structure of the antigen binding protein as well as wholly synthetic scaffolds comprising, for example, a biocompatible polymer. See, for example, Korndorfer et al., 2003, *Proteins: Structure, Function, and Bioinformatics*, Volume 53, Issue 1:121-129; Roque et al., 2004, *Biotechnol. Prog.* 20:639-654. In addition, peptide antibody mimetics ("PAMs") can be used, as well as scaffolds based on antibody mimetics utilizing fibronectin components as a scaffold.

An antigen binding protein can have, for example, the structure of an immunoglobulin. An "immunoglobulin" is a tetrameric molecule composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa or lambda light chains. Heavy chains are classified as mu, delta, gamma, alpha, or epsilon, and define the antibody's isotype as IgM, IgD, IgG, IgA, and IgE, respectively. Preferably, the anti-JAG1 antibodies disclosed herein are characterized by their variable domain region sequences in the heavy $V_H$ and light $V_L$ amino acid sequences. Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ed., 2nd ed. Raven Press, N.Y. (1989)). The variable regions of each light/heavy chain pair form the antibody binding site such that an intact immunoglobulin has two binding sites.

The variable regions of immunoglobulin chains exhibit the same general structure of relatively conserved framework regions (FR) joined by three hypervariable regions, also called complementarity determining regions or CDRs. From N-terminus to C-terminus, both light and heavy chains comprise the domains FR1, CDR1, FR2, CDR2, FR3, CDR3 and FR4. The assignment of amino acids to each domain is in accordance with the definitions of Kabat et al. in Sequences of Proteins of Immunological Interest, 5th Ed., US Dept. of Health and Human Services, PHS, NIH, NIH Publication no. 91-3242, 1991. Other numbering systems for the amino acids in immunoglobulin chains include IMGT® (international ImMunoGeneTics information system; Lefranc et al, Dev. Comp. Immunol. 29:185-203; 2005) and AHo (Honegger and Pluckthun, J. Mol. Biol. 309(3):657-670; 2001).

An "antibody" refers to an intact immunoglobulin or to an antigen binding portion thereof that competes with the intact antibody for specific binding, unless otherwise specified. In one embodiment, an antibody is an IgG and comprises four polypeptide chains including two identical heavy chains each comprising a heavy chain variable domain and heavy chain constant regions $C_{H1}$, $C_{H2}$ and $C_{H3}$, and two identical light chains each comprising a light chain variable domain and a light chain constant region ($C_L$). In certain embodiments, the antibody is an IgG4. The heavy and light chain variable domain sequences may be selected from those described herein in SEQ ID Nos: 1 to 142.

Antigen binding portions of an antibody may be produced by recombinant DNA techniques or by enzymatic or chemical cleavage of intact antibodies. Antigen binding portions include, inter alia, Fab, Fab', F(ab')2, Fv, domain antibodies (dAbs), and complementarity determining region (CDR) fragments, chimeric antibodies, diabodies, triabodies, tetrabodies, and polypeptides that contain at least a portion of an immunoglobulin that is sufficient to confer specific antigen binding to the polypeptide.

A single-chain antibody (scFv) is an antibody in which a $V_L$ and a $V_H$ region are joined via a linker (e.g., a synthetic sequence of amino acid residues) to form a continuous protein chain. The linker is long enough to allow the protein chain to fold back on itself and form a monovalent antigen binding site (see, e.g., Bird et al., 1988, *Science* 242:423-26 and Huston et al., 1988, *Proc. Natl. Acad. Sci. USA* 85:5879-83).

In certain embodiments, antibodies can be obtained from sources such as serum or plasma that contain immunoglobulins having varied antigenic specificity. If such antibodies are subjected to affinity purification, they can be enriched for a particular antigenic specificity. Such enriched preparations of antibodies usually are made of less than about 10% antibody having specific binding activity for the particular antigen. Subjecting these preparations to several rounds of affinity purification can increase the proportion of antibody having specific binding activity for the antigen. Antibodies prepared in this manner are often referred to as "monospecific."

The term "monospecific", as used herein, refers to an antibody that displays an affinity for one particular epitope. Monospecific antibody preparations can be made up of about 10%, 20%, 30%, 40%, 50%, 60%, 70%, 75%, 80%, 85%, 90%, 95%, 97%, 99%, or 99.9% antibody having specific binding activity for the particular antigen.

An "antibody fragment" or "antigen binding fragment of an antibody" comprises a portion of an intact antibody, and preferably comprises the antibody antigen binding or variable domains. Examples of an antibody fragment include a Fab, a Fab', a F(ab')2, an Fv fragment, and a linear antibody.

A Fab fragment is a monovalent fragment having the $V_L$, $V_H$, $C_L$ and $C_{H1}$ domains; a $F(ab')_2$ fragment is a bivalent fragment having two Fab fragments linked by a disulfide bridge at the hinge region; a Fd fragment has the $V_H$ and $C_{H1}$ domains; an Fv fragment has the $V_L$ and $V_H$ domains of a single arm of an antibody; and a dAb fragment has a $V_H$ domain, a $V_L$ domain, or an antigen-binding fragment of a $V_H$ or $V_L$ domain (U.S. Pat. Nos. 6,846,634; 6,696,245, US App. Pub. 20/0202512; 2004/0202995; 2004/0038291; 2004/0009507; 20 03/0039958, and Ward et al., *Nature* 341:544-546, 1989).

Diabodies are bivalent antibodies comprising two polypeptide chains, wherein each polypeptide chain comprises VH and VL domains joined by a linker that is too short to allow for pairing between two domains on the same chain, thus allowing each domain to pair with a complementary domain on another polypeptide chain (see, e.g., Holliger et al., 1993, Proc. Natl. Acad. Sci. USA 90:6444-48, and Poljak et al., 1994, Structure 2:1121-23). If the two polypeptide chains of a diabody are identical, then a diabody resulting from their pairing will have two identical antigen binding sites. Polypeptide chains having different sequences can be used to make a diabody with two different antigen binding sites. Similarly, tribodies and tetrabodies are antibodies comprising three and four polypeptide chains, respectively, and forming three and four antigen binding sites, respectively, which can be the same or different.

An antigen binding protein, such as an antibody, may have one or more binding sites. If there is more than one binding site, the binding sites may be identical to one another or may be different. For example, a naturally occurring human immunoglobulin typically has two identical binding sites, while a "bispecific" or "bifunctional" antibody has two different binding sites.

The term "human antibody" includes antibodies that have one or more variable and constant regions derived from human immunoglobulin sequences. In one embodiment, all of the variable and constant domains of the antibody are derived from human immunoglobulin sequences (referred to as "a fully human antibody"). These antibodies may be prepared in a variety of ways, examples of which are described below, including through the immunization with an antigen of interest of a mouse that is genetically modified to express antibodies derived from human heavy and/or light chain-encoding genes. In a preferred embodiment, a fully human antibody is made using recombinant methods such that the glycosylation pattern of the antibody is different than an antibody having the same sequence if it were to exist in nature.

A "humanized antibody" has a sequence that differs from the sequence of an antibody derived from a non-human species by one or more amino acid substitutions, deletions, and/or additions, such that the humanized antibody is less likely to induce an immune response, and/or induces a less severe immune response, as compared to the non-human species antibody, when it is administered to a human subject. In one embodiment, certain amino acids in the framework and constant domains of the heavy and/or light chains of the non-human species antibody are mutated to produce the humanized antibody. In another embodiment, the constant domain(s) from a human antibody are fused to the variable domain(s) of a non-human species. In another embodiment, one or more amino acid residues in one or more CDR sequences of a non-human antibody are changed to reduce the likely immunogenicity of the non-human antibody when it is administered to a human subject, wherein the changed amino acid residues either are not critical for immunospecific binding of the antibody to its antigen, or the changes to the amino acid sequence that are made are conservative changes, such that the binding of the humanized antibody to the antigen is not significantly worse than the binding of the non-human antibody to the antigen. Examples of how to make humanized antibodies may be found in U.S. Pat. Nos. 6,054,297, 5,886,152 and 5,877,293.

The term "chimeric antibody" refers to an antibody that contains one or more regions from one antibody and one or more regions from one or more other antibodies. In one embodiment, one or more of the CDRs are derived from a human anti-JAG1 antibody. In another embodiment, all of the CDRs are derived from a human anti-JAG1 antibody. In another embodiment, the CDRs from more than one human anti-JAG1 antibodies are mixed and matched in a chimeric antibody. For instance, a chimeric antibody may comprise a CDR1 from the light chain of a first human anti-PAR-2 antibody, a CDR2 and a CDR3 from the light chain of a second human anti-JAG1 antibody, and the CDRs from the heavy chain from a third anti-JAG1 antibody. Other combinations are possible.

Further, the framework regions may be derived from one of the same anti-JAG1 antibodies, from one or more different antibodies, such as a human antibody, or from a humanized antibody. In one example of a chimeric antibody, a portion of the heavy and/or light chain is identical with, homologous to, or derived from an antibody from a particular species or belonging to a particular antibody class or subclass, while the remainder of the chain(s) is/are identical with, homologous to, or derived from an antibody (-ies) from another species or belonging to another antibody class or subclass. Also included are fragments of such antibodies that exhibit the desired biological activity (i.e., the ability to specifically bind JAG1).

A "CDR grafted antibody" is an antibody comprising one or more CDRs derived from an antibody of a particular species or isotype and the framework of another antibody of the same or different species or isotype.

A "multi-specific antibody" is an antibody that recognizes more than one epitope on one or more antigens. A subclass of this type of antibody is a "bi-specific antibody" which recognizes two distinct epitopes on the same or different antigens.

An antigen binding protein "specifically binds" to an antigen (e.g., human JAG1) if it binds to the antigen with a dissociation constant of 1 nanomolar or less.

An "antigen binding domain," "antigen binding region," or "antigen binding site" is a portion of an antigen binding protein that contains amino acid residues (or other moieties) that interact with an antigen and contribute to the antigen binding protein's specificity and affinity for the antigen. For an antibody that specifically binds to its antigen, this will include at least part of at least one of its CDR domains.

The term "Fc polypeptide" includes native and mutein forms of polypeptides derived from the Fc region of an antibody. Truncated forms of such polypeptides containing the hinge region that promotes dimerization also are included. Fusion proteins comprising Fc moieties (and oligomers formed therefrom) offer the advantage of facile purification by affinity chromatography over Protein A or Protein G columns.

An "epitope" is the portion of a molecule that is bound by an antigen binding protein (e.g., by an antibody). An epitope can comprise non-contiguous portions of the molecule (e.g., in a polypeptide, amino acid residues that are not contiguous in the polypeptide's primary sequence but that, in the context of the polypeptide's tertiary and quaternary structure, are near enough to each other to be bound by an antigen binding protein).

The "percent identity" or "percent homology" of two polynucleotide or two polypeptide sequences is determined by comparing the sequences using the GAP computer program (a part of the GCG Wisconsin Package, version 10.3 (Accelrys, San Diego, Calif.)) using its default parameters.

The terms "polynucleotide," "oligonucleotide" and "nucleic acid" are used interchangeably throughout and include DNA molecules (e.g., cDNA or genomic DNA), RNA molecules (e.g., mRNA), analogs of the DNA or RNA generated using nucleotide analogs (e.g., peptide nucleic acids and non-naturally occurring nucleotide analogs), and hybrids thereof. The nucleic acid molecule can be single-stranded or double-stranded. In one embodiment, the nucleic acid molecules of the invention comprise a contiguous open reading frame encoding an antibody, or a fragment, derivative, mutein, or variant thereof.

Two single-stranded polynucleotides are "the complement" of each other if their sequences can be aligned in an anti-parallel orientation such that every nucleotide in one polynucleotide is opposite its complementary nucleotide in the other polynucleotide, without the introduction of gaps, and without unpaired nucleotides at the 5' or the 3' end of either sequence. A polynucleotide is "complementary" to another polynucleotide if the two polynucleotides can hybridize to one another under moderately stringent conditions. Thus, a polynucleotide can be complementary to another polynucleotide without being its complement.

A "vector" is a nucleic acid that can be used to introduce another nucleic acid linked to it into a cell. One type of vector is a "plasmid," which refers to a linear or circular double stranded DNA molecule into which additional nucleic acid segments can be ligated. Another type of vector is a viral vector (e.g., replication defective retroviruses, adenoviruses and adeno-associated viruses), wherein additional DNA segments can be introduced into the viral genome. Certain vectors are capable of autonomous replication in a host cell into which they are introduced (e.g., bacterial vectors comprising a bacterial origin of replication and episomal mammalian vectors). Other vectors (e.g., non-episomal mammalian vectors) are integrated into the genome of a host cell upon introduction into the host cell, and thereby are replicated along with the host genome. An "expression vector" is a type of vector that can direct the expression of a chosen polynucleotide.

A nucleotide sequence is "operably linked" to a regulatory sequence if the regulatory sequence affects the expression (e.g., the level, timing, or location of expression) of the nucleotide sequence. A "regulatory sequence" is a nucleic acid that affects the expression (e.g., the level, timing, or location of expression) of a nucleic acid to which it is operably linked. The regulatory sequence can, for example, exert its effects directly on the regulated nucleic acid, or through the action of one or more other molecules (e.g., polypeptides that bind to the regulatory sequence and/or the nucleic acid). Examples of regulatory sequences include promoters, enhancers and other expression control elements (e.g., polyadenylation signals). Further examples of regulatory sequences are described in, for example, Goeddel, 1990, Gene Expression Technology: *Methods in Enzymology* 185, Academic Press, San Diego, Calif. and Baron et al., 1995, *Nucleic Acids Res.* 23:3605-06.

A "host cell" is a cell that can be used to express a nucleic acid, e.g., a nucleic acid of the invention. A host cell can be a prokaryote, for example, *E. coli*, or it can be a eukaryote, for example, a single-celled eukaryote (e.g., a yeast or other fungus), a plant cell (e.g., a tobacco or tomato plant cell), an animal cell (e.g., a human cell, a monkey cell, a hamster cell, a rat cell, a mouse cell, or an insect cell) or a hybridoma. Examples of host cells include the COS-7 line of monkey kidney cells (ATCC CRL 1651) (see Gluzman et al., 1981, *Cell* 23:175), L cells, C127 cells, 3T3 cells (ATCC CCL 163), Chinese hamster ovary (CHO) cells or their derivatives such as Veggie CHO and related cell lines which grow in serum-free media (see Rasmussen et al., 1998, *Cytotechnology* 28:31) or CHO strain DX-B11, which is deficient in DHFR (see Urlaub et al., 1980, *Proc. Natl. Acad. Sci. USA* 77:4216-20), HeLa cells, BHK (ATCC CRL 10) cell lines, the CV1/EBNA cell line derived from the African green monkey kidney cell line CV1 (ATCC CCL 70) (see McMahan et al., 1991, *EMBO J.* 10:2821), human embryonic kidney cells such as 293, 293 EBNA or MSR 293, human epidermal A431 cells, human Colo205 cells, other transformed primate cell lines, normal diploid cells, cell strains derived from in vitro culture of primary tissue, primary explants, HL-60, U937, HaK or Jurkat cells. In one embodiment, a host cell is a mammalian host cell, but is not a human host cell. Typically, a host cell is a cultured cell that can be transformed or transfected with a polypeptide-encoding nucleic acid, which can then be expressed in the host cell. The phrase "recombinant host cell" can be used to denote a host cell that has been transformed or transfected with a nucleic acid to be expressed. A host cell also can be a cell that comprises the nucleic acid but does not express it at a desired level unless a regulatory sequence is introduced into the host cell such that it becomes operably linked with the nucleic acid. It is understood that the term host cell refers not only to the particular subject cell but also to the progeny or potential progeny of such a cell. Because certain modifications may occur in succeeding generations due to, e.g., mutation or environmental influence, such progeny may not, in fact, be identical to the parent cell, but are still included within the scope of the term as used herein.

The term "recombinant antibody" refers to an antibody that is expressed from a cell or cell line transfected with an expression vector (or possibly more than one expression vector) comprising the coding sequence of the antibody, or a portion thereof (e.g., a DNA sequence encoding a heavy chain or a light chain). In one embodiment, said coding sequence is not naturally associated with the cell. In one embodiment, a recombinant antibody has a glycosylation pattern that is different than the glycosylation pattern of an antibody having the same sequence if it were to exist in nature. In one embodiment, a recombinant antibody is expressed in a mammalian host cell which is not a human host cell. Notably, individual mammalian host cells have unique glycosylation patterns.

The term "effective amount" as used herein, refers to that amount of an antibody, or an antigen binding portion thereof that binds JAG1, which is sufficient to effect treatment of a disease associated with JAG1 signaling, as described herein, when administered to a subject. Therapeutically effective amounts of antibodies provided herein, when used alone or in combination, will vary depending upon the relative activity of the antibodies and combinations (e.g., in inhibiting cell growth) and depending upon the subject and disease condition being treated, the weight and age of the subject, the severity of the disease condition, the manner of administration and the like, which can readily be determined by one of ordinary skill in the art.

The term "isolated" refers to a protein (e.g., an antibody) that is substantially free of other cellular material. In one embodiment, an isolated antibody is substantially free of other proteins from the same species. In one embodiment, an isolated antibody is expressed by a cell from a different species and is substantially free of other proteins from the different species. A protein may be rendered substantially free of naturally associated components (or components associated with the cellular expression system used to produce the antibody) by isolation, using protein purification techniques well known in the art. In one embodiment, the antibodies, or antigen binding fragments, of the invention are isolated.

A "neutralizing antibody" or an "inhibitory antibody" is an antibody that inhibits the proteolytic activation of JAG1 when an excess of the anti-JAG1 antibody reduces the amount of activation by at least about 20% using an assay such as those described herein in the Examples. In various embodiments, the antigen binding protein reduces the amount of amount of proteolytic activation of JAG1 by at least 30%, 40%, 50%, 60%, 70%, 75%, 80%, 85%, 90%, 95%, 97%, 99%, and 99.9%.

JAG-1 Antigen Binding Proteins

The present invention pertains to JAG1 binding proteins, particularly anti-JAG1 antibodies, or antigen-binding portions thereof, that bind JAG1, and uses thereof. Various aspects of the invention relate to antibodies and antibody fragments, pharmaceutical compositions, nucleic acids, recombinant expression vectors, and host cells for making such antibodies and fragments. Methods of using the antibodies of the invention to detect human JAG1, to inhibit JAG1 activity, either in vitro or in vivo, and to prevent or treat disorders such as cancer are also encompassed by the invention. Methods of using the antibodies of the invention to detect human JAG2, to inhibit JAG2 activity, either in vitro or in vivo, and to prevent or treat disorders such as cancer are also encompassed by the invention.

As described in Table 5 below, included in the invention are novel antibody heavy and light chain variable regions that are specific to JAG1. In one embodiment, the invention provides an anti-JAG1 antibody, or an antigen-binding fragment thereof, that comprises a heavy chain having a variable domain comprising an amino acid sequence as set forth in any one of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63, SEQ ID NO. 65, SEQ ID NO. 67, SEQ ID NO. 69, SEQ ID NO. 71, SEQ ID NO. 73, SEQ ID NO. 75, SEQ ID NO. 77, SEQ ID NO. 79, SEQ ID NO. 81, SEQ ID NO. 83, SEQ ID NO. 85, SEQ ID NO. 87, SEQ ID NO. 89, SEQ ID NO. 91, SEQ ID NO. 93, SEQ ID NO. 95, SEQ ID NO. 97, SEQ ID NO. 99, SEQ ID NO. 101, SEQ ID NO. 103, SEQ ID NO. 105, SEQ ID NO. 107, SEQ ID NO. 109, SEQ ID NO. 111, SEQ ID NO. 124, SEQ ID NO. 125, SEQ ID NO. 126, SEQ ID NO. 127, SEQ ID NO. 128, SEQ ID NO. 129, SEQ ID NO. 130, SEQ ID NO. 132, SEQ ID NO. 135, SEQ ID NO. 139 and SEQ ID NO. 142. In one embodiment, the invention provides an anti-JAG1 antibody, or an antigen-binding fragment thereof, that comprises a light chain having a variable domain comprising an amino acid sequence as set forth in any one of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72, SEQ ID NO. 74, SEQ ID NO. 76, SEQ ID NO. 78, SEQ ID NO. 80, SEQ ID NO. 82, SEQ ID NO. 84, SEQ ID NO. 86, SEQ ID NO. 88, SEQ ID NO. 90, SEQ ID NO. 92, SEQ ID NO. 94, SEQ ID NO. 96, SEQ ID NO. 98, SEQ ID NO. 100, SEQ ID NO. 102, SEQ ID NO. 104, SEQ ID NO. 106, SEQ ID NO. 108, SEQ ID NO. 110, SEQ ID NO. 112, SEQ ID NO. 113, SEQ ID NO. 114, SEQ ID NO. 115, SEQ ID NO. 116, SEQ ID NO. 117, SEQ ID NO. 118, SEQ ID NO. 119, SEQ ID NO. 120, SEQ ID NO. 121, SEQ ID NO. 122, SEQ ID NO. 123, SEQ ID NO. 131, SEQ ID NO. 133, SEQ ID NO. 134, SEQ ID NO. 136, SEQ ID NO. 137, SEQ ID NO. 138, SEQ ID NO. 140 and SEQ ID NO. 141. In one embodiment, the invention provides an anti-JAG1 antibody, or an antigen-binding fragment thereof, that comprises a light chain having a variable domain comprising an amino acid sequence as set forth in any one of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72, SEQ ID NO. 74, SEQ ID NO. 76, SEQ ID NO. 78, SEQ ID NO. 80, SEQ ID NO. 82, SEQ ID NO. 84, SEQ ID NO. 86, SEQ ID NO. 88, SEQ ID NO. 90, SEQ ID NO. 92, SEQ ID NO. 94, SEQ ID NO. 96, SEQ ID NO. 98, SEQ ID NO. 100, SEQ ID NO. 102, SEQ ID NO. 104, SEQ ID NO. 106, SEQ ID NO. 108, SEQ ID NO. 110, SEQ ID NO. 112, SEQ ID NO. 113, SEQ ID NO. 114, SEQ ID NO. 115, SEQ ID NO. 116, SEQ ID NO. 117, SEQ ID NO. 118, SEQ ID NO. 119, SEQ ID NO. 120, SEQ ID NO. 121, SEQ ID NO. 122, SEQ ID NO. 123, SEQ ID NO. 131, SEQ ID NO. 133, SEQ ID NO. 134, SEQ ID NO. 136, SEQ ID NO. 137, SEQ ID NO. 138, SEQ ID NO. 140 and SEQ ID NO. 141; and a heavy chain having a variable domain comprising an amino acid sequence as set forth in any one of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63, SEQ ID NO. 65, SEQ ID NO. 67, SEQ ID NO. 69, SEQ ID NO. 71, SEQ ID NO. 73, SEQ ID NO. 75, SEQ ID NO. 77, SEQ ID NO. 79, SEQ ID NO. 81, SEQ ID NO. 83, SEQ ID NO. 85, SEQ ID NO. 87, SEQ ID NO. 89, SEQ ID NO. 91, SEQ ID NO. 93, SEQ ID NO. 95, SEQ ID NO. 97, SEQ ID NO. 99, SEQ ID NO. 101, SEQ ID NO. 103, SEQ ID NO. 105, SEQ ID NO. 107, SEQ ID NO. 109, SEQ ID NO. 111, SEQ ID NO. 124, SEQ ID NO. 125, SEQ ID NO. 126, SEQ ID NO. 127, SEQ ID NO. 128, SEQ ID NO. 129, SEQ ID NO. 130, SEQ ID NO. 132, SEQ ID NO. 135, SEQ ID NO. 139 and SEQ ID NO. 142.

Complementarity determining regions (CDRs) are known as hypervariable regions both in the light chain and the heavy chain variable domains. The more highly conserved portions of variable domains are called the framework (FR). Complementarity determining regions (CDRs) and framework regions (FR) of a given antibody may be identified using the system described by Kabat et al. supra; Lefranc et al., supra and/or Honegger and Pluckthun, supra. Also familiar to those in the art is the numbering system described in Kabat et al. (1991, NIH Publication 91-3242, National Technical Information Service, Springfield, Va.). In this regard Kabat et al. defined a numbering system for variable domain sequences that is applicable to any antibody. One of ordinary skill in the art can unambiguously assign this system of "Kabat numbering" to any variable domain amino acid sequence, without reliance on any experimental data beyond the sequence itself.

In certain embodiments, the present invention provides an anti-JAG1 antibody comprising the CDRs of a heavy and a light chain variable domain as described in Table 5 (SEQ ID Nos: 1 to 142). For example, the invention provides an anti-JAG1 antibody, or antigen-binding fragment thereof, comprising a heavy chain variable region having CDRs described in an amino acid sequence as set forth in any one of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63, SEQ ID NO. 65, SEQ ID NO. 67, SEQ ID NO. 69, SEQ ID NO. 71, SEQ ID NO. 73, SEQ ID NO. 75, SEQ ID NO. 77, SEQ ID NO. 79, SEQ ID NO. 81, SEQ ID NO. 83, SEQ ID NO. 85, SEQ ID NO. 87, SEQ ID NO. 89, SEQ ID NO. 91, SEQ ID NO. 93, SEQ ID NO. 95, SEQ ID NO. 97, SEQ ID NO. 99, SEQ ID NO. 101, SEQ ID NO. 103, SEQ ID NO. 105, SEQ ID NO. 107, SEQ ID NO. 109, SEQ ID NO. 111, SEQ ID NO. 124, SEQ ID NO. 125, SEQ ID NO. 126, SEQ ID NO. 127, SEQ ID NO. 128, SEQ ID NO. 129, SEQ ID NO. 130, SEQ ID NO. 132, SEQ ID NO. 135, SEQ ID NO. 139 and SEQ ID NO. 142. In one embodiment, the invention provides an anti-JAG1 antibody, or antigen-binding fragment thereof, comprising a light chain variable region having CDRs described in an amino acid sequence as set forth in any one of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72, SEQ ID NO. 74, SEQ ID NO. 76, SEQ ID NO. 78, SEQ ID NO. 80, SEQ ID NO. 82, SEQ ID NO. 84, SEQ ID NO. 86, SEQ ID NO. 88, SEQ ID NO. 90, SEQ ID NO. 92, SEQ ID NO. 94, SEQ ID NO. 96, SEQ ID NO. 98, SEQ ID NO. 100, SEQ ID NO. 102, SEQ ID NO. 104, SEQ ID NO. 106, SEQ ID NO. 108, SEQ ID NO. 110, SEQ ID NO. 112, SEQ ID NO. 113, SEQ ID NO. 114, SEQ ID NO. 115, SEQ ID NO. 116, SEQ ID NO. 117, SEQ ID NO. 118, SEQ ID NO. 119, SEQ ID NO. 120, SEQ ID NO. 121, SEQ ID NO. 122, SEQ ID NO. 123, SEQ ID NO. 131, SEQ ID NO. 133, SEQ ID NO. 134, SEQ ID NO. 136, SEQ ID NO. 137, SEQ ID NO. 138, SEQ ID NO. 140 and SEQ ID NO. 141. In one embodiment, the invention provides an anti-JAG1 antibody, or antigen-binding fragment thereof, comprising a light chain variable region having CDRs described in an amino acid sequence as set forth in any one of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72, SEQ ID NO. 74, SEQ ID NO. 76, SEQ ID NO. 78, SEQ ID NO. 80, SEQ ID NO. 82, SEQ ID NO. 84, SEQ ID NO. 86, SEQ ID NO. 88, SEQ ID NO. 90, SEQ ID NO. 92, SEQ ID NO. 94, SEQ ID NO. 96, SEQ ID NO. 98, SEQ ID NO. 100, SEQ ID NO. 102, SEQ ID NO. 104, SEQ ID NO. 106, SEQ ID NO. 108, SEQ ID NO. 110, SEQ ID NO. 112, SEQ ID NO. 113, SEQ ID NO. 114, SEQ ID NO. 115, SEQ ID NO. 116, SEQ ID NO. 117, SEQ ID NO. 118, SEQ ID NO. 119, SEQ ID NO. 120, SEQ ID NO. 121, SEQ ID NO. 122, SEQ ID NO. 123, SEQ ID NO. 131, SEQ ID NO. 133, SEQ ID NO. 134, SEQ ID NO. 136, SEQ ID NO. 137, SEQ ID NO. 138, SEQ ID NO. 140 and SEQ ID NO. 141; and a heavy chain variable region having CDRs described in an amino acid sequence as set forth in any one of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63, SEQ ID NO. 65, SEQ ID NO. 67, SEQ ID NO. 69, SEQ ID NO. 71, SEQ ID NO. 73, SEQ ID NO. 75, SEQ ID NO. 77, SEQ ID NO. 79, SEQ ID NO. 81, SEQ ID NO. 83, SEQ ID NO. 85, SEQ ID NO. 87, SEQ ID NO. 89, SEQ ID NO. 91, SEQ ID NO. 93, SEQ ID NO. 95, SEQ ID NO. 97, SEQ ID NO. 99, SEQ ID NO. 101, SEQ ID NO. 103, SEQ ID NO. 105, SEQ ID NO. 107, SEQ ID NO. 109, SEQ ID NO. 111, SEQ ID NO. 124, SEQ ID NO. 125, SEQ ID NO. 126, SEQ ID NO. 127, SEQ ID NO. 128, SEQ ID NO. 129, SEQ ID NO. 130, SEQ ID NO. 132, SEQ ID NO. 135, SEQ ID NO. 139 and SEQ ID NO. 142.

It should be noted that throughout, antibodies (and corresponding sequences) are referred to interchangeably with or without a "JG1" preceding the name. For example, the antibody name "JG1H7" is also referred to herein as "H7".

One or more CDRs may be incorporated into a molecule either covalently or noncovalently to make it an antigen binding protein.

An antigen binding protein may incorporate the CDR(s) as part of a larger polypeptide chain, may covalently link the CDR(s) to another polypeptide chain, or may incorporate the CDR(s) noncovalently. The CDRs permit the antigen binding protein to specifically bind to a particular antigen of interest.

In one embodiment, the present disclosure provides a fully human antibody of an IgG class that binds to a JAG1 epitope with a binding affinity of $10^{-6}$M or less, that has a heavy chain variable domain sequence that is at least 95% identical to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63, SEQ ID NO. 65, SEQ ID NO. 67, SEQ ID NO. 69, SEQ ID NO. 71, SEQ ID NO. 73, SEQ ID NO. 75, SEQ ID NO. 77, SEQ ID NO. 79, SEQ ID NO. 81, SEQ ID NO. 83, SEQ ID NO. 85, SEQ ID NO. 87, SEQ ID NO. 89, SEQ ID NO. 91, SEQ ID NO. 93, SEQ ID NO. 95, SEQ ID NO. 97, SEQ ID NO. 99, SEQ ID NO. 101, SEQ ID NO. 103, SEQ ID NO. 105, SEQ ID NO. 107, SEQ ID NO. 109, SEQ ID NO. 111, SEQ ID NO. 124, SEQ ID NO. 125, SEQ ID NO. 126, SEQ ID NO. 127, SEQ ID NO. 128, SEQ ID NO. 129, SEQ ID NO. 130, SEQ ID NO. 132, SEQ ID NO. 135, SEQ ID NO. 139, SEQ ID NO. 142, and combinations thereof, and that has a light chain variable domain sequence that is at least 95% identical to the amino acid sequence consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72, SEQ ID NO. 74, SEQ ID NO. 76, SEQ ID NO. 78, SEQ ID NO. 80, SEQ ID NO. 82, SEQ ID NO. 84, SEQ ID NO. 86, SEQ ID NO. 88, SEQ ID NO. 90, SEQ ID NO. 92, SEQ ID NO. 94, SEQ ID NO. 96, SEQ ID NO. 98, SEQ ID NO. 100, SEQ ID NO. 102, SEQ ID NO. 104, SEQ ID NO. 106, SEQ ID NO. 108, SEQ ID NO. 110, SEQ ID NO. 112, SEQ ID NO. 113, SEQ ID NO. 114, SEQ ID NO. 115, SEQ ID NO. 116, SEQ ID NO. 117, SEQ ID NO. 118, SEQ ID NO. 119, SEQ ID NO. 120, SEQ ID NO. 121, SEQ ID NO. 122, SEQ ID NO. 123, SEQ ID NO. 131, SEQ ID NO. 133, SEQ ID NO. 134, SEQ ID NO. 136, SEQ ID NO. 137, SEQ ID NO. 138, SEQ ID NO. 140, SEQ ID NO. 141, and combinations thereof.

In one embodiment, the fully human antibody has both a heavy chain and a light chain wherein the antibody has a heavy chain/light chain variable domain sequence selected from the group consisting of SEQ ID NO. 1/SEQ ID NO. 2 (called JG1A1 herein), SEQ ID NO. 3/SEQ ID NO. 4 (called JG1A10 herein), SEQ ID NO. 5/SEQ ID NO. 6 (called JG1A12 herein), SEQ ID NO. 7/SEQ ID NO. 8 (called JG1A3 herein), SEQ ID NO. 9/SEQ ID NO. 10 (called JG1A4 herein), SEQ ID NO. 11/SEQ ID NO. 12 (called JG11A5 herein), SEQ ID NO. 13/SEQ ID NO. 14 (called JG1A6 herein), SEQ ID NO. 15/SEQ ID NO. 16 (called JG1A7 herein), SEQ ID NO. 17/SEQ ID NO. 18 (called JG1B1 herein), SEQ ID NO. 19/SEQ ID NO. 20 (called JG1B10 herein), SEQ ID NO. 21/SEQ ID NO. 22 (called JG1B11 herein), SEQ ID NO. 23/SEQ ID NO. 24 (called JG1B12 herein), SEQ ID NO. 25/SEQ ID NO. 26 (called JG1B4 herein), SEQ ID NO. 27/SEQ ID NO. 28 (called JG1B5 herein), SEQ ID NO. 29/SEQ ID NO. 30 (called JG1B6 herein), SEQ ID NO. 31/SEQ ID NO. 32 (called JG1B8 herein), SEQ ID NO. 33/SEQ ID NO. 34 (called JG1C3 herein), SEQ ID NO. 35/SEQ ID NO. 36 (called JG1C4 herein), SEQ ID NO. 37/SEQ ID NO. 38 (called JG1C5 herein), SEQ ID NO. 39/SEQ ID NO. 40 (called JG1C8 herein), SEQ ID NO. 41/SEQ ID NO. 42 (called JG1D1 herein), SEQ ID NO. 43/SEQ ID NO. 44 (called JG1D10 herein), SEQ ID NO. 45/SEQ ID NO. 46 (called JG1D11 herein), SEQ ID NO. 47/SEQ ID NO. 48 (called JG1D7 herein), SEQ ID NO. 49/SEQ ID NO. 50 (called JG1D8 herein), SEQ ID NO. 51/SEQ ID NO. 52 (called JG1E1 herein), SEQ ID NO. 53/SEQ ID NO. 54 (called JG1E11 herein), SEQ ID NO. 55/SEQ ID NO. 56 (called JG1E7 herein), SEQ ID NO. 57/SEQ ID NO. 58 (called JG1E8 herein), SEQ ID NO. 59/SEQ ID NO. 60 (called JG1F1 herein), SEQ ID NO. 61/SEQ ID NO. 62 (called JG1F10 herein), SEQ ID NO. 63/SEQ ID NO. 64 (called JG1F7 herein), SEQ ID NO. 65/SEQ ID NO. 66 (called JG1F8 herein), SEQ ID NO. 67/SEQ ID NO. 68 (called JG1G11 herein), SEQ ID NO. 69/SEQ ID NO. 70 (called JG1G5 herein), SEQ ID NO. 71/SEQ ID NO. 72 (called JG1H1 herein), SEQ ID NO. 73/SEQ ID NO. 74 (called JG1H11 herein), SEQ ID NO. 75/SEQ ID NO. 76 (called JG1H5 herein), SEQ ID NO. 77/SEQ ID NO. 78 (called JG1H7 herein), SEQ ID NO. 79/SEQ ID NO. 80 (called JH1A1 herein), SEQ ID NO. 81/SEQ ID NO. 82 (called JH1A11 herein), SEQ ID NO. 83/SEQ ID NO. 84 (called JH1A2 herein), SEQ ID NO. 85/SEQ ID NO. 86 (called JH1A4 herein), SEQ ID NO. 87/SEQ ID NO. 88 (called JH1B1 herein), SEQ ID NO. 89/SEQ ID NO. 90 (called JH1B3 herein), SEQ ID NO. 91/SEQ ID NO. 92 (called JH1B7 herein), SEQ ID NO. 93/SEQ ID NO. 94 (called JH1C10 herein), SEQ ID NO. 95/SEQ ID NO. 96 (called JH1C2 herein), SEQ ID NO. 97/SEQ ID NO. 98 (called JH1D7 herein), SEQ ID NO. 99/SEQ ID NO. 100 (called JH1E11 herein), SEQ ID NO. 101/SEQ ID NO. 102 (called JH1F3 herein), SEQ ID NO. 103/SEQ ID NO. 104 (called JH1F4 herein), SEQ ID NO. 105/SEQ ID NO. 106 (called JH1F6 herein), SEQ ID NO. 107/SEQ ID NO. 108 (called JH1H2 herein), SEQ ID NO. 109/SEQ ID NO. 110 (called JH1H7 herein), SEQ ID NO. 111/SEQ ID NO.112 (called JG1H73-2 herein), SEQ ID NO. 111/SEQ ID NO.113 (called JG1H7-2B2S herein), SEQ ID NO.111/SEQ ID NO.114 (called JG1H7-2AS herein), SEQ ID NO. 111/SEQ ID NO.115 (called JG1H73-2A7S herein), SEQ ID NO. 111/SEQ ID NO.116 (called JG1H7-2A10S herein), SEQ ID NO.111/SEQ ID NO.117 (called JG1H7-2A2S herein), SEQ ID NO. 111/SEQ ID NO.118 (called JG1H73-2A9S herein), SEQ ID NO. 111/SEQ ID NO.119 (called JG1H7-2A1S herein), SEQ ID NO.111/SEQ ID NO.120 (called JG1H7-E11S herein), SEQ ID NO. 111/SEQ ID NO.121 (called JG1H73-C11S herein), SEQ ID NO. 111/SEQ ID NO.122 (called JG1H7-D10S herein), SEQ ID NO.111/SEQ ID NO.123 (called JG1H7-2B7S herein), SEQ ID NO.124/SEQ ID NO.112 (called JG1H7-1A8S herein), SEQ ID NO.

125/SEQ ID NO.112 (called JG1H73-1A6S herein), SEQ ID NO. 126/SEQ ID NO.112 (called JG1H7-1A2S herein), SEQ ID NO.127/SEQ ID NO.112 (called JG1H7-1B1S herein), SEQ ID NO. 128/SEQ ID NO.112 (called JG1H73-5A8S herein), SEQ ID NO. 129/SEQ ID NO.112 (called JG1H7-5B5S herein), SEQ ID NO.130/SEQ ID NO.112 (called JG1H7-3E5S herein), SEQ ID NO.127/SEQ ID NO.131 (called JG1H7-G6C herein), SEQ ID NO. 132/SEQ ID NO.133 (called JG1H73-A6C herein), SEQ ID NO. 132/SEQ ID NO.123 (called JG1H7-E11C herein), SEQ ID NO.142/SEQ ID NO.123 (called JG1H7-C6C herein), SEQ ID NO. 127/SEQ ID NO.123 (called JG1H73-C9C herein), SEQ ID NO. 132/SEQ ID NO.134 (called JG1H7-F4C herein), SEQ ID NO. 135/SEQ ID NO.133 (called JG1H7-F2C herein), SEQ ID NO.132/SEQ ID NO.136 (called JG1H7-F1C herein), SEQ ID NO.132/SEQ ID NO.137 (called JG1H7-D4C herein), SEQ ID NO. 132/SEQ ID NO.138 (called JG1H73-D5C herein), SEQ ID NO. 139/SEQ ID NO.123 (called JG1H7-A5C herein), SEQ ID NO.139/SEQ ID NO.140 (called JG1H7-B2C herein), SEQ ID NO. 127/SEQ ID NO.141 (called JG1H73-B6C herein), and combinations thereof.

In one embodiment, the invention provides an anti-JAG1 antibody, or an antigen-binding fragment thereof, comprising a heavy chain comprising a CDR3 domain as set forth in any one of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63, SEQ ID NO. 65, SEQ ID NO. 67, SEQ ID NO. 69, SEQ ID NO. 71, SEQ ID NO. 73, SEQ ID NO. 75, SEQ ID NO. 77, SEQ ID NO. 79, SEQ ID NO. 81, SEQ ID NO. 83, SEQ ID NO. 85, SEQ ID NO. 87, SEQ ID NO. 89, SEQ ID NO. 91, SEQ ID NO. 93, SEQ ID NO. 95, SEQ ID NO. 97, SEQ ID NO. 99, SEQ ID NO. 101, SEQ ID NO. 103, SEQ ID NO. 105, SEQ ID NO. 107, SEQ ID NO. 109, SEQ ID NO. 111, SEQ ID NO. 124, SEQ ID NO. 125, SEQ ID NO. 126, SEQ ID NO. 127, SEQ ID NO. 128, SEQ ID NO. 129, SEQ ID NO. 130, SEQ ID NO. 132, SEQ ID NO. 135, SEQ ID NO. 139 and SEQ ID NO. 142, and comprising a variable domain comprising an amino acid sequence that has at least 95%, at least 96%, at least 97%, at least 98%, or at least 99% identical to a sequence as set forth in any one of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63, SEQ ID NO. 65, SEQ ID NO. 67, SEQ ID NO. 69, SEQ ID NO. 71, SEQ ID NO. 73, SEQ ID NO. 75, SEQ ID NO. 77, SEQ ID NO. 79, SEQ ID NO. 81, SEQ ID NO. 83, SEQ ID NO. 85, SEQ ID NO. 87, SEQ ID NO. 89, SEQ ID NO. 91, SEQ ID NO. 93, SEQ ID NO. 95, SEQ ID NO. 97, SEQ ID NO. 99, SEQ ID NO. 101, SEQ ID NO. 103, SEQ ID NO. 105, SEQ ID NO. 107, SEQ ID NO. 109, SEQ ID NO. 111, SEQ ID NO. 124, SEQ ID NO. 125, SEQ ID NO. 126, SEQ ID NO. 127, SEQ ID NO. 128, SEQ ID NO. 129, SEQ ID NO. 130, SEQ ID NO. 132, SEQ ID NO. 135, SEQ ID NO. 139 and SEQ ID NO. 142. In one embodiment, the invention provides an anti-JAG1 antibody, or an antigen-binding fragment thereof, comprising a light chain comprising a CDR3 domain as set forth in any one of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72, SEQ ID NO. 74, SEQ ID NO. 76, SEQ ID NO. 78, SEQ ID NO. 80, SEQ ID NO. 82, SEQ ID NO. 84, SEQ ID NO. 86, SEQ ID NO. 88, SEQ ID NO. 90, SEQ ID NO. 92, SEQ ID NO. 94, SEQ ID NO. 96, SEQ ID NO. 98, SEQ ID NO. 100, SEQ ID NO. 102, SEQ ID NO. 104, SEQ ID NO. 106, SEQ ID NO. 108, SEQ ID NO. 110, SEQ ID NO. 112, SEQ ID NO. 113, SEQ ID NO. 114, SEQ ID NO. 115, SEQ ID NO. 116, SEQ ID NO. 117, SEQ ID NO. 118, SEQ ID NO. 119, SEQ ID NO. 120, SEQ ID NO. 121, SEQ ID NO. 122, SEQ ID NO. 123, SEQ ID NO. 131, SEQ ID NO. 133, SEQ ID NO. 134, SEQ ID NO. 136, SEQ ID NO. 137, SEQ ID NO. 138, SEQ ID NO. 140 and SEQ ID NO. 141, and having a light chain variable domain comprising an amino acid sequence that has at least 95%, at least 96%, at least 97%, at least 98%, or at least 99% identical to a sequence as set forth in any one of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72, SEQ ID NO. 74, SEQ ID NO. 76, SEQ ID NO. 78, SEQ ID NO. 80, SEQ ID NO. 82, SEQ ID NO. 84, SEQ ID NO. 86, SEQ ID NO. 88, SEQ ID NO. 90, SEQ ID NO. 92, SEQ ID NO. 94, SEQ ID NO. 96, SEQ ID NO. 98, SEQ ID NO. 100, SEQ ID NO. 102, SEQ ID NO. 104, SEQ ID NO. 106, SEQ ID NO. 108, SEQ ID NO. 110, SEQ ID NO. 112, SEQ ID NO. 113, SEQ ID NO. 114, SEQ ID NO. 115, SEQ ID NO. 116, SEQ ID NO. 117, SEQ ID NO. 118, SEQ ID NO. 119, SEQ ID NO. 120, SEQ ID NO. 121, SEQ ID NO. 122, SEQ ID NO. 123, SEQ ID NO. 131, SEQ ID NO. 133, SEQ ID NO. 134, SEQ ID NO. 136, SEQ ID NO. 137, SEQ ID NO. 138, SEQ ID NO. 140 and SEQ ID NO. 141. Thus, in certain embodiments, the CDR3 domain is held constant, while variability may be introduced into the remaining CDRs and/or framework regions of the heavy and/or light chains, while the antibody, or antigen binding fragment thereof, retains the ability to bind to JAG1 and retains the functional characteristics, e.g., binding affinity, of the parent.

In one embodiment, the substitutions made within a heavy or light chain that is at least 95% identical (or at least 96% identical, or at least 97% identical, or at least 98% identical, or at least 99% identical) are conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson (1994) Methods Mol. Biol. 24: 307-331, herein incorporated by reference. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine.

In one embodiment, the present invention is directed to an antibody, or an antigen binding fragment thereof, having the antigen binding regions of any of the antibodies described in Table 5. The antibodies of the invention, including those described in Table 5, bind to human JAG1.

In one embodiment, the present invention is directed to an antibody, or an antigen binding fragment thereof, having antigen binding regions of antibody JG1H7. In one embodiment, the invention provides an antibody, or antigen-binding fragment thereof, comprising a heavy chain variable domain sequence as set forth in SEQ ID NO: 77, and a light chain variable domain sequence as set forth in SEQ ID NO: 78. In one embodiment, the invention is directed to an antibody having a heavy chain variable domain comprising the CDRs of SEQ ID NO: 77, and a light chain variable domain comprising the CDRs of SEQ ID NO: 78. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 77, and comprises a light chain variable region having an amino acid sequence that is at least 95% identical, at least 96% identical, at least 97% identical, at least 98% identical, or at least 99% identical to the sequence set forth in SEQ ID NO: 78. The antibody may further be an IgG1 or an IgG4 isotype.

In one embodiment, the present invention is directed to an antibody, or an antigen binding fragment thereof, having antigen binding regions of antibody JG1H7.3-2 In one embodiment, the invention provides an antibody, or antigen-binding fragment thereof, comprising a heavy chain variable domain sequence as set forth in SEQ ID NO: 111, and a light chain variable domain sequence as set forth in SEQ ID NO: 112. In one embodiment, the invention is directed to an antibody having a heavy chain variable domain comprising the CDRs of SEQ ID NO: 111, and a light chain variable domain comprising the CDRs of SEQ ID NO:112. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 111, and comprises a light chain variable region having an amino acid sequence that is at least 95% identical, at least 96% identical, at least 97% identical, at least 98% identical, or at least 99% identical to the sequence set forth in SEQ ID NO: 112. The antibody may further be an IgG1 or an IgG4 isotype.

In one embodiment, the present invention is directed to an antibody, or an antigen binding fragment thereof, having antigen binding regions of antibody JG1H7-2B2S. In one embodiment, the invention provides an antibody, or antigen-binding fragment thereof, comprising a heavy chain variable domain sequence as set forth in SEQ ID NO: 111, and a light chain variable domain sequence as set forth in SEQ ID NO: 113. In one embodiment, the invention is directed to an antibody having a heavy chain variable domain comprising the CDRs of SEQ ID NO: 111, and a light chain variable domain comprising the CDRs of SEQ ID NO:113. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 111, and comprises a light chain variable region having an amino acid sequence that is at least 95% identical, at least 96% identical, at least 97% identical, at least 98% identical, or at least 99% identical to the sequence set forth in SEQ ID NO: 113. The antibody may further be an IgG1 or an IgG4 isotype.

In one embodiment, the present invention is directed to an antibody, or an antigen binding fragment thereof, having antigen binding regions of antibody JG1H7-2A3S. In one embodiment, the invention provides an antibody, or antigen-binding fragment thereof, comprising a heavy chain variable domain sequence as set forth in SEQ ID NO: 111, and a light chain variable domain sequence as set forth in SEQ ID NO: 114. In one embodiment, the invention is directed to an antibody having a heavy chain variable domain comprising the CDRs of SEQ ID NO: 111, and a light chain variable domain comprising the CDRs of SEQ ID NO:114. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 111, and comprises a light chain variable region having an amino acid sequence that is at least 95% identical, at least 96% identical, at least 97% identical, at least 98% identical, or at least 99% identical to the sequence set forth in SEQ ID NO: 114. The antibody may further be an IgG1 or an IgG4 isotype.

In one embodiment, the present invention is directed to an antibody, or an antigen binding fragment thereof, having antigen binding regions of antibody JG1H7-2A7S. In one embodiment, the invention provides an antibody, or antigen-binding fragment thereof, comprising a heavy chain variable domain sequence as set forth in SEQ ID NO: 111, and a light chain variable domain sequence as set forth in SEQ ID NO: 115. In one embodiment, the invention is directed to an antibody having a heavy chain variable domain comprising the CDRs of SEQ ID NO: 111, and a light chain variable domain comprising the CDRs of SEQ ID NO:115. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 111, and comprises a light chain variable region having an amino acid sequence that is at least 95% identical, at least 96% identical, at least 97% identical, at least 98% identical, or at least 99% identical to the sequence set forth in SEQ ID NO: 115. The antibody may further be an IgG1 or an IgG4 isotype.

In one embodiment, the present invention is directed to an antibody, or an antigen binding fragment thereof, having antigen binding regions of antibody JG1H7-2A10S. In one embodiment, the invention provides an antibody, or antigen-binding fragment thereof, comprising a heavy chain variable domain sequence as set forth in SEQ ID NO: 111, and a light chain variable domain sequence as set forth in SEQ ID NO: 116. In one embodiment, the invention is directed to an antibody having a heavy chain variable domain comprising the CDRs of SEQ ID NO: 111, and a light chain variable domain comprising the CDRs of SEQ ID NO:116. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 111, and comprises a light chain variable region having an amino acid sequence that is at least 95% identical, at least 96% identical, at least 97% identical, at least 98% identical, or at least 99% identical to the sequence set forth in SEQ ID NO: 116. The antibody may further be an IgG1 or an IgG4 isotype.

In one embodiment, the present invention is directed to an antibody, or an antigen binding fragment thereof, having antigen binding regions of antibody JG1H7-2A2S. In one embodiment, the invention provides an antibody, or antigen-binding fragment thereof, comprising a heavy chain variable domain sequence as set forth in SEQ ID NO: 111, and a light chain variable domain sequence as set forth in SEQ ID NO: 117. In one embodiment, the invention is directed to an antibody having a heavy chain variable domain comprising the CDRs of SEQ ID NO: 111, and a light chain variable domain comprising the CDRs of SEQ ID NO:117. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 111, and comprises a light chain variable region having an amino acid sequence that is at least 95% identical, at least 96% identical, at least 97% identical, at least 98% identical, or at least 99% identical to the sequence set forth in SEQ ID NO: 117. The antibody may further be an IgG1 or an IgG4 isotype.

In one embodiment, the present invention is directed to an antibody, or an antigen binding fragment thereof, having antigen binding regions of antibody JG1H7-2A9S. In one embodiment, the invention provides an antibody, or antigen-binding fragment thereof, comprising a heavy chain variable domain sequence as set forth in SEQ ID NO: 111, and a light chain variable domain sequence as set forth in SEQ ID NO: 118. In one embodiment, the invention is directed to an antibody having a heavy chain variable domain comprising the CDRs of SEQ ID NO: 111, and a light chain variable domain comprising the CDRs of SEQ ID NO:118. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 111, and comprises a light chain variable region having an amino acid sequence that is at least 95% identical, at least 96% identical, at least 97% identical, at least 98% identical, or at least 99% identical to the sequence set forth in SEQ ID NO: 118. The antibody may further be an IgG1 or an IgG4 isotype.

In one embodiment, the present invention is directed to an antibody, or an antigen binding fragment thereof, having antigen binding regions of antibody JG1H7-2A1S. In one embodiment, the invention provides an antibody, or antigen-binding fragment thereof, comprising a heavy chain variable domain sequence as set forth in SEQ ID NO: 111, and a light chain variable domain sequence as set forth in SEQ ID NO: 119. In one embodiment, the invention is directed to an antibody having a heavy chain variable domain comprising the CDRs of SEQ ID NO: 111, and a light chain variable domain comprising the CDRs of SEQ ID NO:119. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 111, and comprises a light chain variable region having an amino acid sequence that is at least 95% identical, at least 96% identical, at least 97% identical, at least 98% identical, or at least 99% identical to the sequence set forth in SEQ ID NO: 119. The antibody may further be an IgG1 or an IgG4 isotype.

In one embodiment, the present invention is directed to an antibody, or an antigen binding fragment thereof, having antigen binding regions of antibody JG1H7-E11S. In one embodiment, the invention provides an antibody, or antigen-binding fragment thereof, comprising a heavy chain variable domain sequence as set forth in SEQ ID NO: 111, and a light chain variable domain sequence as set forth in SEQ ID NO: 120. In one embodiment, the invention is directed to an antibody having a heavy chain variable domain comprising the CDRs of SEQ ID NO: 111, and a light chain variable domain comprising the CDRs of SEQ ID NO:120. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 111, and comprises a light chain variable region having an amino acid sequence that is at least 95% identical, at least 96% identical, at least 97% identical, at least 98% identical, or at least 99% identical to the sequence set forth in SEQ ID NO: 120. The antibody may further be an IgG1 or an IgG4 isotype.

In one embodiment, the present invention is directed to an antibody, or an antigen binding fragment thereof, having antigen binding regions of antibody JG1H7-C11S. In one embodiment, the invention provides an antibody, or antigen-binding fragment thereof, comprising a heavy chain variable domain sequence as set forth in SEQ ID NO: 111, and a light chain variable domain sequence as set forth in SEQ ID NO: 121. In one embodiment, the invention is directed to an antibody having a heavy chain variable domain comprising the CDRs of SEQ ID NO: 111, and a light chain variable domain comprising the CDRs of SEQ ID NO:121. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 111, and comprises a light chain variable region having an amino acid sequence that is at least 95% identical, at least 96% identical, at least 97% identical, at least 98% identical, or at least 99% identical to the sequence set forth in SEQ ID NO: 121. The antibody may further be an IgG1 or an IgG4 isotype.

In one embodiment, the present invention is directed to an antibody, or an antigen binding fragment thereof, having antigen binding regions of antibody JG1H7-D10S. In one embodiment, the invention provides an antibody, or antigen-binding fragment thereof, comprising a heavy chain variable domain sequence as set forth in SEQ ID NO: 111, and a light chain variable domain sequence as set forth in SEQ ID NO: 122. In one embodiment, the invention is directed to an antibody having a heavy chain variable domain comprising the CDRs of SEQ ID NO: 111, and a light chain variable domain comprising the CDRs of SEQ ID NO:122. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 111, and comprises a light chain variable region having an amino acid sequence that is at least 95% identical, at least 96% identical, at least 97% identical, at least 98% identical, or at least 99% identical to the sequence set forth in SEQ ID NO: 122. The antibody may further be an IgG1 or an IgG4 isotype.

In one embodiment, the present invention is directed to an antibody, or an antigen binding fragment thereof, having antigen binding regions of antibody JG1H7-2B7S. In one embodiment, the invention provides an antibody, or antigen-binding fragment thereof, comprising a heavy chain variable domain sequence as set forth in SEQ ID NO: 111, and a light chain variable domain sequence as set forth in SEQ ID NO: 123. In one embodiment, the invention is directed to an antibody having a heavy chain variable domain comprising the CDRs of SEQ ID NO: 111, and a light chain variable domain comprising the CDRs of SEQ ID NO:123. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 111, and comprises a light chain variable region having an amino acid sequence that is at least 95% identical, at least 96% identical, at least 97% identical, at least 98% identical, or at least 99% identical to the sequence set forth in SEQ ID NO: 123. The antibody may further be an IgG1 or an IgG4 isotype.

In one embodiment, the present invention is directed to an antibody, or an antigen binding fragment thereof, having antigen binding regions of antibody JG1H7-1A8S. In one embodiment, the invention provides an antibody, or antigen-binding fragment thereof, comprising a heavy chain variable domain sequence as set forth in SEQ ID NO: 124, and a light chain variable domain sequence as set forth in SEQ ID NO: 112. In one embodiment, the invention is directed to an antibody having a heavy chain variable domain comprising the CDRs of SEQ ID NO: 124, and a light chain variable domain comprising the CDRs of SEQ ID NO:112. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 124, and comprises a light chain variable region having an amino acid sequence that is at least 95% identical, at least 96% identical, at least 97% identical, at least 98% identical, or at least 99% identical to the sequence set forth in SEQ ID NO: 112. The antibody may further be an IgG1 or an IgG4 isotype.

In one embodiment, the present invention is directed to an antibody, or an antigen binding fragment thereof, having antigen binding regions of antibody JG1H7-1A6S. In one embodiment, the invention provides an antibody, or antigen-binding fragment thereof, comprising a heavy chain variable domain sequence as set forth in SEQ ID NO: 125, and a light chain variable domain sequence as set forth in SEQ ID NO: 112. In one embodiment, the invention is directed to an antibody having a heavy chain variable domain comprising the CDRs of SEQ ID NO: 125, and a light chain variable domain comprising the CDRs of SEQ ID NO:112. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 125, and comprises a light chain variable region having an amino acid sequence that is at least 95% identical, at least 96% identical, at least 97% identical, at least 98% identical, or at least 99% identical to the sequence set forth in SEQ ID NO: 112. The antibody may further be an IgG1 or an IgG4 isotype.

In one embodiment, the present invention is directed to an antibody, or an antigen binding fragment thereof, having antigen binding regions of antibody JG1H7-1A2S. In one embodiment, the invention provides an antibody, or antigen-binding fragment thereof, comprising a heavy chain variable domain sequence as set forth in SEQ ID NO: 126, and a light chain variable domain sequence as set forth in SEQ ID NO: 112. In one embodiment, the invention is directed to an antibody having a heavy chain variable domain comprising the CDRs of SEQ ID NO: 126, and a light chain variable domain comprising the CDRs of SEQ ID NO:112. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 126, and comprises a light chain variable region having an amino acid sequence that is at least 95% identical, at least 96% identical, at least 97% identical, at least 98% identical, or at least 99% identical to the sequence set forth in SEQ ID NO: 112. The antibody may further be an IgG1 or an IgG4 isotype.

In one embodiment, the present invention is directed to an antibody, or an antigen binding fragment thereof, having antigen binding regions of antibody JG1H7-1B1S. In one embodiment, the invention provides an antibody, or antigen-binding fragment thereof, comprising a heavy chain variable domain sequence as set forth in SEQ ID NO: 127, and a light chain variable domain sequence as set forth in SEQ ID NO: 112. In one embodiment, the invention is directed to an antibody having a heavy chain variable domain comprising the CDRs of SEQ ID NO: 127, and a light chain variable domain comprising the CDRs of SEQ ID NO:112. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 127, and comprises a light chain variable region having an amino acid sequence that is at least 95% identical, at least 96% identical, at least 97% identical, at least 98% identical, or at least 99% identical to the sequence set forth in SEQ ID NO: 112. The antibody may further be an IgG1 or an IgG4 isotype.

In one embodiment, the present invention is directed to an antibody, or an antigen binding fragment thereof, having antigen binding regions of antibody JG1H7-5A8S. In one embodiment, the invention provides an antibody, or antigen-binding fragment thereof, comprising a heavy chain variable domain sequence as set forth in SEQ ID NO: 128, and a light chain variable domain sequence as set forth in SEQ ID NO: 112. In one embodiment, the invention is directed to an antibody having a heavy chain variable domain comprising the CDRs of SEQ ID NO: 128, and a light chain variable domain comprising the CDRs of SEQ ID NO:112. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 128, and comprises a light chain variable region having an amino acid sequence that is at least 95% identical, at least 96% identical, at least 97% identical, at least 98% identical, or at least 99% identical to the sequence set forth in SEQ ID NO: 112. The antibody may further be an IgG1 or an IgG4 isotype.

In one embodiment, the present invention is directed to an antibody, or an antigen binding fragment thereof, having antigen binding regions of antibody JG1H7-5B5S. In one embodiment, the invention provides an antibody, or antigen-binding fragment thereof, comprising a heavy chain variable domain sequence as set forth in SEQ ID NO: 129, and a light chain variable domain sequence as set forth in SEQ ID NO: 112. In one embodiment, the invention is directed to an antibody having a heavy chain variable domain comprising the CDRs of SEQ ID NO: 129, and a light chain variable domain comprising the CDRs of SEQ ID NO:112. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 129, and comprises a light chain variable region having an amino acid sequence that is at least 95% identical, at least 96% identical, at least 97% identical, at least 98% identical, or at least 99% identical to the sequence set forth in SEQ ID NO: 112. The antibody may further be an IgG1 or an IgG4 isotype.

In one embodiment, the present invention is directed to an antibody, or an antigen binding fragment thereof, having antigen binding regions of antibody JG1H7-3E5S. In one embodiment, the invention provides an antibody, or antigen-binding fragment thereof, comprising a heavy chain variable domain sequence as set forth in SEQ ID NO: 130, and a light chain variable domain sequence as set forth in SEQ ID NO: 112. In one embodiment, the invention is directed to an antibody having a heavy chain variable domain comprising the CDRs of SEQ ID NO: 130, and a light chain variable domain comprising the CDRs of SEQ ID NO:112. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 130, and comprises a light chain variable region having an amino acid sequence that is at least 95% identical, at least 96% identical, at least 97% identical, at least 98% identical, or at least 99% identical to the sequence set forth in SEQ ID NO: 112. The antibody may further be an IgG1 or an IgG4 isotype.

In one embodiment, the present invention is directed to an antibody, or an antigen binding fragment thereof, having antigen binding regions of antibody JG1H7-G6C. In one embodiment, the invention provides an antibody, or antigen-binding fragment thereof, comprising a heavy chain variable domain sequence as set forth in SEQ ID NO: 127, and a light chain variable domain sequence as set forth in SEQ ID NO: 131. In one embodiment, the invention is directed to an antibody having a heavy chain variable domain comprising the CDRs of SEQ ID NO: 127, and a light chain variable domain comprising the CDRs of SEQ ID NO:131. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 127, and comprises a light chain variable region having an amino acid sequence that is at least 95% identical, at least 96% identical, at least 97% identical, at least 98% identical, or at least 99% identical to the sequence set forth in SEQ ID NO: 131. The antibody may further be an IgG1 or an IgG4 isotype.

In one embodiment, the present invention is directed to an antibody, or an antigen binding fragment thereof, having antigen binding regions of antibody JG1H7-A6C. In one embodiment, the invention provides an antibody, or antigen-binding fragment thereof, comprising a heavy chain variable domain sequence as set forth in SEQ ID NO: 132, and a light chain variable domain sequence as set forth in SEQ ID NO: 133. In one embodiment, the invention is directed to an antibody having a heavy chain variable domain comprising the CDRs of SEQ ID NO: 132, and a light chain variable domain comprising the CDRs of SEQ ID NO:133. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 132, and comprises a light chain variable region having an amino acid sequence that is at least 95% identical, at least 96% identical, at least 97% identical, at least 98% identical, or at least 99% identical to the sequence set forth in SEQ ID NO: 133. The antibody may further be an IgG1 or an IgG4 isotype.

In one embodiment, the present invention is directed to an antibody, or an antigen binding fragment thereof, having antigen binding regions of antibody JG1H7-E11C. In one embodiment, the invention provides an antibody, or antigen-binding fragment thereof, comprising a heavy chain variable domain sequence as set forth in SEQ ID NO: 132, and a light chain variable domain sequence as set forth in SEQ ID NO: 123. In one embodiment, the invention is directed to an antibody having a heavy chain variable domain comprising the CDRs of SEQ ID NO: 132, and a light chain variable domain comprising the CDRs of SEQ ID NO:123. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 132, and comprises a light chain variable region having an amino acid sequence that is at least 95% identical, at least 96% identical, at least 97% identical, at least 98% identical, or at least 99% identical to the sequence set forth in SEQ ID NO: 123. The antibody may further be an IgG1 or an IgG4 isotype.

In one embodiment, the present invention is directed to an antibody, or an antigen binding fragment thereof, having antigen binding regions of antibody JG1H7-C6C. In one embodiment, the invention provides an antibody, or antigen-binding fragment thereof, comprising a heavy chain variable domain sequence as set forth in SEQ ID NO: 142, and a light chain variable domain sequence as set forth in SEQ ID NO: 123. In one embodiment, the invention is directed to an antibody having a heavy chain variable domain comprising the CDRs of SEQ ID NO: 142, and a light chain variable domain comprising the CDRs of SEQ ID NO:123. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 142, and comprises a light chain variable region having an amino acid sequence that is at least 95% identical, at least 96% identical, at least 97% identical, at least 98% identical, or at least 99% identical to the sequence set forth in SEQ ID NO: 123. The antibody may further be an IgG1 or an IgG4 isotype.

In one embodiment, the present invention is directed to an antibody, or an antigen binding fragment thereof, having antigen binding regions of antibody JG1H7-C9C. In one embodiment, the invention provides an antibody, or antigen-binding fragment thereof, comprising a heavy chain variable domain sequence as set forth in SEQ ID NO: 127, and a light chain variable domain sequence as set forth in SEQ ID NO: 123. In one embodiment, the invention is directed to an antibody having a heavy chain variable domain comprising the CDRs of SEQ ID NO: 127, and a light chain variable domain comprising the CDRs of SEQ ID NO:123. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 127, and comprises a light chain variable region having an amino acid sequence that is at least 95% identical, at least 96% identical, at least 97% identical, at least 98% identical, or at least 99% identical to the sequence set forth in SEQ ID NO: 123. The antibody may further be an IgG1 or an IgG4 isotype.

In one embodiment, the present invention is directed to an antibody, or an antigen binding fragment thereof, having antigen binding regions of antibody JG1H7-F4C. In one embodiment, the invention provides an antibody, or antigen-binding fragment thereof, comprising a heavy chain variable domain sequence as set forth in SEQ ID NO: 132, and a light chain variable domain sequence as set forth in SEQ ID NO: 134. In one embodiment, the invention is directed to an antibody having a heavy chain variable domain comprising the CDRs of SEQ ID NO: 132, and a light chain variable domain comprising the CDRs of SEQ ID NO:134. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 132, and comprises a light chain variable region having an amino acid sequence that is at least 95% identical, at least 96% identical, at least 97% identical, at least 98% identical, or at least 99% identical to the sequence set forth in SEQ ID NO: 134. The antibody may further be an IgG1 or an IgG4 isotype.

In one embodiment, the present invention is directed to an antibody, or an antigen binding fragment thereof, having antigen binding regions of antibody JG1H7-F2C. In one embodiment, the invention provides an antibody, or antigen-binding fragment thereof, comprising a heavy chain variable domain sequence as set forth in SEQ ID NO: 135, and a light chain variable domain sequence as set forth in SEQ ID NO: 133. In one embodiment, the invention is directed to an antibody having a heavy chain variable domain comprising the CDRs of SEQ ID NO: 135, and a light chain variable domain comprising the CDRs of SEQ ID NO:133. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 135, and comprises a light chain variable region having an amino acid sequence that is at least 95% identical, at least 96% identical, at least 97% identical, at least 98% identical, or at least 99% identical to the sequence set forth in SEQ ID NO: 133. The antibody may further be an IgG1 or an IgG4 isotype.

In one embodiment, the present invention is directed to an antibody, or an antigen binding fragment thereof, having antigen binding regions of antibody JG1H7-F1C. In one embodiment, the invention provides an antibody, or antigen-binding fragment thereof, comprising a heavy chain variable domain sequence as set forth in SEQ ID NO: 132, and a light chain variable domain sequence as set forth in SEQ ID NO: 136. In one embodiment, the invention is directed to an antibody having a heavy chain variable domain comprising the CDRs of SEQ ID NO: 132, and a light chain variable domain comprising the CDRs of SEQ ID NO:136. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 132, and comprises a light chain variable region having an amino acid sequence that is at least 95% identical, at least 96% identical, at least 97% identical, at least 98% identical, or at least 99% identical to the sequence set forth in SEQ ID NO: 136. The antibody may further be an IgG1 or an IgG4 isotype.

In one embodiment, the present invention is directed to an antibody, or an antigen binding fragment thereof, having antigen binding regions of antibody JG1H7-D4C. In one embodiment, the invention provides an antibody, or antigen-binding fragment thereof, comprising a heavy chain variable domain sequence as set forth in SEQ ID NO: 132, and a light chain variable domain sequence as set forth in SEQ ID NO: 137. In one embodiment, the invention is directed to an antibody having a heavy chain variable domain comprising the CDRs of SEQ ID NO: 132, and a light chain variable domain comprising the CDRs of SEQ ID NO:137. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 132, and comprises a light chain variable region having an amino acid sequence that is at least 95% identical, at least 96% identical, at least 97% identical, at least 98% identical, or at least 99% identical to the sequence set forth in SEQ ID NO: 137. The antibody may further be an IgG1 or an IgG4 isotype.

In one embodiment, the present invention is directed to an antibody, or an antigen binding fragment thereof, having antigen binding regions of antibody JG1H7-D5C. In one embodiment, the invention provides an antibody, or antigen-binding fragment thereof, comprising a heavy chain variable domain sequence as set forth in SEQ ID NO: 132, and a light chain variable domain sequence as set forth in SEQ ID NO: 138. In one embodiment, the invention is directed to an antibody having a heavy chain variable domain comprising the CDRs of SEQ ID NO: 132, and a light chain variable domain comprising the CDRs of SEQ ID NO:138. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 132, and comprises a light chain variable region having an amino acid sequence that is at least 95% identical, at least 96% identical, at least 97% identical, at least 98% identical, or at least 99% identical to the sequence set forth in SEQ ID NO: 138. The antibody may further be an IgG1 or an IgG4 isotype.

In one embodiment, the present invention is directed to an antibody, or an antigen binding fragment thereof, having antigen binding regions of antibody JG1H7-A5C. In one embodiment, the invention provides an antibody, or antigen-binding fragment thereof, comprising a heavy chain variable domain sequence as set forth in SEQ ID NO: 139, and a light chain variable domain sequence as set forth in SEQ ID NO: 123. In one embodiment, the invention is directed to an antibody having a heavy chain variable domain comprising the CDRs of SEQ ID NO: 139, and a light chain variable domain comprising the CDRs of SEQ ID NO:123. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 139, and comprises a light chain variable region having an amino acid sequence that is at least 95% identical, at least 96% identical, at least 97% identical, at least 98% identical, or at least 99% identical to the sequence set forth in SEQ ID NO: 123. The antibody may further be an IgG1 or an IgG4 isotype.

In one embodiment, the present invention is directed to an antibody, or an antigen binding fragment thereof, having antigen binding regions of antibody JG1H7-B2C. In one embodiment, the invention provides an antibody, or antigen-binding fragment thereof, comprising a heavy chain variable domain sequence as set forth in SEQ ID NO: 139, and a light chain variable domain sequence as set forth in SEQ ID NO: 140. In one embodiment, the invention is directed to an antibody having a heavy chain variable domain comprising the CDRs of SEQ ID NO: 139, and a light chain variable domain comprising the CDRs of SEQ ID NO:140. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 139, and comprises a light chain variable region having an amino acid sequence that is at least 95% identical, at least 96% identical, at least 97% identical, at least 98% identical, or at least 99% identical to the sequence set forth in SEQ ID NO: 140. The antibody may further be an IgG1 or an IgG4 isotype.

In one embodiment, the present invention is directed to an antibody, or an antigen binding fragment thereof, having antigen binding regions of antibody JG1H7-B6C. In one embodiment, the invention provides an antibody, or antigen-binding fragment thereof, comprising a heavy chain variable domain sequence as set forth in SEQ ID NO: 127, and a light chain variable domain sequence as set forth in SEQ ID NO: 141. In one embodiment, the invention is directed to an antibody having a heavy chain variable domain comprising the CDRs of SEQ ID NO: 127, and a light chain variable domain comprising the CDRs of SEQ ID NO:141. In one embodiment, the invention features an isolated human antibody, or antigen-binding fragment thereof, that comprises a heavy chain variable region having an amino acid sequence that is at least 95% identical, at least 96% identical, at least 97% identical, at least 98% identical, or at least 99% identical to the sequence set forth in SEQ ID NO: 127, and comprises a light chain variable region having an amino acid sequence that is at least 95% identical, at least 96% identical, at least 97% identical, at least 98% identical, or at least 99% identical to the sequence set forth in SEQ ID NO: 141. The antibody may further be an IgG1 or an IgG4 isotype.

As described in Table 5, a number of heavy chain variable domains have amino acid sequences that are at least 95% identical to SEQ ID NO:111, including SEQ ID NO: 135 (as described for antibody JG1H7-F2C), SEQ ID NO: 142 (as described for antibody JG1H7-C6C), SEQ ID NO: 132 (as described for antibodies JG1H7-A6C, JG1H7-E11C, JG1H7-F1C, JG1H7-D4C and JG1H7-D5C), SEQ ID NO: 130 (as described for antibody JG1H7-3E5S), SEQ ID NO: 129 (as described for antibody JG1H7-5B5S), SEQ ID NO: 128 (as described for antibody JG1H7-5A8S), SEQ ID NO: 127 (as described for antibodies JG1H7-1B1S, JG1H7-G6C, JG1H7-C9C and JG1H7-B6C), SEQ ID NO: 132 (as described for antibody JG1H7-F4C), SEQ ID NO: 126 (as described for antibody JG1H7-1A2S), SEQ ID NO: 125 (as described for antibody JG1H7-1A6S), SEQ ID NO: 124 (as described for antibody JG1H7-1A8S) and SEQ ID NO: 139 (as described for antibodies JG1H7-A5C and JG1H7-B2C).

As also described in Table 5, a number of light chain variable domains have amino acid sequences that are at least 95% identical to SEQ ID NO:112, including SEQ ID NO: 140 (as described for antibody JG1H7-B2C), SEQ ID NO: 138 (as described for antibody JG1H7-D5C), SEQ ID NO: 137 (as described for antibody JG1H7-D4C), SEQ ID NO: 136 (as described for antibody JG1H7-F1C), SEQ ID NO: 134 (as described for antibody JG1H7-F4C), SEQ ID NO: 133 (as described for antibodies JG1H7-A6C and JG1H7-F2C), SEQ ID NO: 131 (as described for antibody JG1H7-G6C), SEQ ID NO: 123 (as described for antibodies JG1H7-2B7S, JG1H7-E11C, JG1H7-C6C, JG1H7-A5C and JG1H7-C9C), SEQ ID NO: 122 (as described for antibody JG1H7-D10S), SEQ ID NO: 121 (as described for antibody JG1H7-C11S), SEQ ID NO: 120 (as described for antibody JG1H7-E11S), SEQ ID NO: 119 (as described for antibody JG1H7-2A1S), SEQ ID NO: 118 (as described for antibody JG1H7-2A9S), SEQ ID NO: 117 (as described for antibody JG1H7-2A2S), SEQ ID NO: 116 (as described for antibody JG1H7-2A10S), SEQ ID NO: 115 (as described for antibody JG1H7-2A7S), SEQ ID NO: 114 (as described for antibody JG1H7-2A3S), SEQ ID NO: 141 (as described for antibody JG1H7-B6C), and SEQ ID NO: 113 (as described for antibody JG1H7-2B2S).

Antigen-binding fragments of antigen binding proteins of the invention may be produced by conventional techniques. Examples of such fragments include, but are not limited to, Fab and F(ab')2 fragments.

In certain embodiments, the present disclosure provides a Fab fully human antibody fragment, having a variable domain region from a heavy chain and a variable domain region from a light chain, wherein the heavy chain variable domain sequence that is at least 95% identical, at least 96% identical, at least 97% identical, at least 98% identical, or at least 99% identical, to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63, SEQ ID NO. 65, SEQ ID NO. 67, SEQ ID NO. 69, SEQ ID NO. 71, SEQ ID NO. 73, SEQ ID NO. 75, SEQ ID NO. 77, SEQ ID NO. 79, SEQ ID NO. 81, SEQ ID NO. 83, SEQ ID NO. 85, SEQ ID NO. 87, SEQ ID NO. 89, SEQ ID NO. 91, SEQ ID NO. 93, SEQ ID NO. 95, SEQ ID NO. 97, SEQ ID NO. 99, SEQ ID NO. 101, SEQ ID NO. 103, SEQ ID NO. 105, SEQ ID NO. 107, SEQ ID NO. 109, SEQ ID NO. 111, SEQ ID NO. 124, SEQ ID NO. 125, SEQ ID NO. 126, SEQ ID NO. 127, SEQ ID NO. 128, SEQ ID NO. 129, SEQ ID NO. 130, SEQ ID NO. 132, SEQ ID NO. 135, SEQ ID NO. 139 and SEQ ID NO. 142 and combinations thereof, and that has a light chain variable domain sequence that is at least 95% identical, at least 96% identical, at least 97% identical, at least 98% identical, or at least 99% identical, to the amino acid sequence consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72, SEQ ID NO. 74, SEQ ID NO. 76, SEQ ID NO. 78, SEQ ID NO. 80, SEQ ID NO. 82, SEQ ID NO. 84, SEQ ID NO. 86, SEQ ID NO. 88, SEQ ID NO. 90, SEQ ID NO. 92, SEQ ID NO. 94, SEQ ID NO. 96, SEQ ID NO. 98, SEQ ID NO. 100, SEQ ID NO. 102, SEQ ID NO. 104, SEQ ID NO. 106, SEQ ID NO. 108, SEQ ID NO. 110, SEQ ID NO. 112, SEQ ID NO. 113, SEQ ID NO. 114, SEQ ID NO. 115, SEQ ID NO. 116, SEQ ID NO. 117, SEQ ID NO. 118, SEQ ID NO. 119, SEQ ID NO. 120, SEQ ID NO. 121, SEQ ID NO. 122, SEQ ID NO. 123, SEQ ID NO. 131, SEQ ID NO. 133, SEQ ID NO. 134, SEQ ID NO. 136, SEQ ID NO. 137, SEQ ID NO. 138, SEQ ID NO. 140 and SEQ ID NO. 141, and combinations thereof. Preferably, the fully human antibody Fab fragment has both a heavy chain variable domain region and a light chain variable domain region wherein the antibody has a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28, SEQ ID NO. 29/SEQ ID NO. 30, SEQ ID NO. 31/SEQ ID NO. 32, SEQ ID NO. 33/SEQ ID NO. 34, SEQ ID NO. 35/SEQ ID NO. 36, SEQ ID NO. 37/SEQ ID NO. 38, SEQ ID NO. 39/SEQ ID NO. 40, SEQ ID NO. 41/SEQ ID NO. 42, SEQ ID NO. 43/SEQ ID NO. 44, SEQ ID NO. 45/SEQ ID NO. 46, SEQ ID NO. 47/SEQ ID NO. 48, SEQ ID NO. 49/SEQ ID NO. 50, SEQ ID NO. 51/SEQ ID NO. 52, SEQ ID NO. 53/SEQ ID NO. 54, SEQ ID NO. 55/SEQ ID NO. 56, SEQ ID NO. 57/SEQ ID NO. 58, SEQ ID NO. 59/SEQ ID NO. 60, SEQ ID NO. 61/SEQ ID NO. 62, SEQ ID NO. 63/SEQ ID NO. 64, SEQ ID NO. 65/SEQ ID NO. 66, SEQ ID NO. 67/SEQ ID NO. 68, SEQ ID NO. 69/SEQ ID NO. 70, SEQ ID NO. 71/SEQ ID NO. 72, SEQ ID NO. 73/SEQ ID NO. 74, SEQ ID NO. 75/SEQ ID NO. 76, SEQ ID NO. 77/SEQ ID NO. 78, SEQ ID NO. 79/SEQ ID NO. 80, SEQ ID NO. 81/SEQ ID NO. 82, SEQ ID NO. 83/SEQ ID NO. 84, SEQ ID NO. 85/SEQ ID NO. 86, SEQ ID NO. 87/SEQ ID NO. 88, SEQ ID NO. 89/SEQ ID NO. 90, SEQ ID NO. 91/SEQ ID NO. 92, SEQ ID NO. 93/SEQ ID NO. 94, SEQ ID NO. 95/SEQ ID NO. 96, SEQ ID NO. 97/SEQ ID NO. 98, SEQ ID NO. 99/SEQ ID NO. 100, SEQ ID NO. 101/SEQ ID NO. 102, SEQ ID NO. 103/SEQ ID NO. 104, SEQ ID NO. 105/SEQ ID NO. 106, SEQ ID NO. 107/SEQ ID NO. 108, SEQ ID NO. 109/SEQ ID NO. 110, SEQ ID NO. 111/SEQ ID NO.112, SEQ ID NO. 111/SEQ ID NO.113, SEQ ID NO.111/SEQ ID NO.114, SEQ ID NO. 111/SEQ ID NO.115, SEQ ID NO. 111/SEQ ID NO.116, SEQ ID NO.111/SEQ ID NO.117, SEQ ID NO. 111/SEQ ID NO.118, SEQ ID NO. 111/SEQ ID NO.119, SEQ ID NO.111/SEQ ID NO.120, SEQ ID NO. 111/SEQ ID NO.121, SEQ ID NO. 111/SEQ ID NO.122, SEQ ID NO.111/SEQ ID NO.123, SEQ ID NO.124/SEQ ID NO.112, SEQ ID NO. 125/SEQ ID NO.112, SEQ ID NO. 126/SEQ ID NO.112, SEQ ID NO.127/SEQ ID NO.112, SEQ ID NO. 128/SEQ ID NO.112, SEQ ID NO. 129/SEQ ID NO.112, SEQ ID NO.130/SEQ ID NO.112, SEQ ID NO.127/SEQ ID NO.131, SEQ ID NO. 132/SEQ ID NO.133, SEQ ID NO. 132/SEQ ID NO.123, SEQ ID NO.142/SEQ ID NO.123, SEQ ID NO. 127/SEQ ID NO.123, SEQ ID NO. 132/SEQ ID NO.134, SEQ ID NO. 135/SEQ ID NO.133, SEQ ID NO.132/SEQ ID NO.136, SEQ ID NO.132/SEQ ID NO.137, SEQ ID NO. 132/SEQ ID NO.138, SEQ ID NO. 139/SEQ ID NO.123, SEQ ID NO.139/SEQ ID NO.140, SEQ ID NO. 127/SEQ ID NO.141, and combinations thereof.

Single chain antibodies may be formed by linking heavy and light chain variable domain (Fv region) fragments via an amino acid bridge (short peptide linker), resulting in a single polypeptide chain. Such single-chain Fvs (scFvs) have been prepared by fusing DNA encoding a peptide linker between DNAs encoding the two variable domain polypeptides ($V_L$ and $V_H$). The resulting polypeptides can fold back on themselves to form antigen-binding monomers, or they can form multimers (e.g., dimers, trimers, or tetramers), depending on the length of a flexible linker between the two variable domains (Kortt et al., 1997, *Prot. Eng.* 10:423; Kortt et al., 2001, *Biomol. Eng.* 18:95-108). By combining different $V_L$ and $V_H$-comprising polypeptides, one can form multimeric scFvs that bind to different epitopes (Kriangkum et al., 2001, *Biomol. Eng.* 18:31-40). Techniques developed for the production of single chain antibodies include those described in U.S. Pat. No. 4,946,778; Bird, 1988, *Science* 242:423; Huston et al., 1988, *Proc. Natl. Acad. Sci. USA* 85:5879; Ward et al., 1989, *Nature* 334:544, de Graaf et al., 2002, *Methods Mol. Biol.* 178:379-87.

In one embodiment, the present disclosure provides a single chain human antibody, having a variable domain region from a heavy chain and a variable domain region from a light chain and a peptide linker connection the heavy chain and light chain variable domain regions, wherein the heavy chain variable domain sequence that is at least 95% identical, at least 96% identical, at least 97% identical, at least 98% identical, or at least 99% identical, to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63, SEQ ID NO. 65, SEQ ID NO. 67, SEQ ID NO. 69, SEQ ID NO. 71, SEQ ID NO. 73, SEQ ID NO. 75, SEQ ID NO. 77, SEQ ID NO. 79, SEQ ID NO. 81, SEQ ID NO. 83, SEQ ID NO. 85, SEQ ID NO. 87, SEQ ID NO. 89, SEQ ID NO. 91, SEQ ID NO. 93, SEQ ID NO. 95, SEQ ID NO. 97, SEQ ID NO. 99, SEQ ID NO. 101, SEQ ID NO. 103, SEQ ID NO. 105, SEQ ID NO. 107, SEQ ID NO. 109, SEQ ID NO. 111, SEQ ID NO. 124, SEQ ID NO. 125, SEQ ID NO. 126, SEQ ID NO. 127, SEQ ID NO. 128, SEQ ID NO. 129, SEQ ID NO. 130, SEQ ID NO. 132, SEQ ID NO. 135, SEQ ID NO. 139 and SEQ ID NO. 142, and combinations thereof, and that has a light chain variable domain sequence that is at least 95% identical, at least 96% identical, at least 97% identical, at least 98% identical, or at least 99% identical, to the amino acid sequence consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72, SEQ ID NO. 74, SEQ ID NO. 76, SEQ ID NO. 78, SEQ ID NO. 80, SEQ ID NO. 82, SEQ ID NO. 84, SEQ ID NO. 86, SEQ ID NO. 88, SEQ ID NO. 90, SEQ ID NO. 92, SEQ ID NO. 94, SEQ ID NO. 96, SEQ ID NO. 98, SEQ ID NO. 100, SEQ ID NO. 102, SEQ ID NO. 104, SEQ ID NO. 106, SEQ ID NO. 108, SEQ ID NO. 110, SEQ ID NO. 112, SEQ ID NO. 113, SEQ ID NO. 114, SEQ ID NO. 115, SEQ ID NO. 116, SEQ ID NO. 117, SEQ ID NO. 118, SEQ ID NO. 119, SEQ ID NO. 120, SEQ ID NO. 121, SEQ ID NO. 122, SEQ ID NO. 123, SEQ ID NO. 131, SEQ ID NO. 133, SEQ ID NO. 134, SEQ ID NO. 136, SEQ ID NO. 137, SEQ ID NO. 138, SEQ ID NO. 140 and SEQ ID NO. 141, and combinations thereof. In one embodiment, the fully human single chain antibody has both a heavy chain variable domain region and a light chain variable domain region, wherein the single chain fully human antibody has a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28, SEQ ID NO. 29/SEQ ID NO. 30, SEQ ID NO. 31/SEQ ID NO. 32, SEQ ID NO. 33/SEQ ID NO. 34, SEQ ID NO. 35/SEQ ID NO. 36, SEQ ID NO. 37/SEQ ID NO. 38, SEQ ID NO. 39/SEQ ID NO. 40, SEQ ID NO. 41/SEQ ID NO. 42, SEQ ID NO. 43/SEQ ID NO. 44, SEQ ID NO. 45/SEQ ID NO. 46, SEQ ID NO. 47/SEQ ID NO. 48, SEQ ID NO. 49/SEQ ID NO. 50, SEQ ID NO. 51/SEQ ID NO. 52, SEQ ID NO. 53/SEQ ID NO. 54, SEQ ID NO. 55/SEQ ID NO. 56, SEQ ID NO. 57/SEQ ID NO. 58, SEQ ID NO. 59/SEQ ID NO. 60, SEQ ID NO. 61/SEQ ID NO. 62, SEQ ID NO. 63/SEQ ID NO. 64, SEQ ID NO. 65/SEQ ID NO. 66, SEQ ID NO. 67/SEQ ID NO. 68, SEQ ID NO. 69/SEQ ID NO. 70, SEQ ID NO. 71/SEQ ID NO. 72, SEQ ID NO. 73/SEQ ID NO. 74, SEQ ID NO. 75/SEQ ID NO. 76, SEQ ID NO. 77/SEQ ID NO. 78, SEQ ID NO. 79/SEQ ID NO. 80, SEQ ID NO. 81/SEQ ID NO. 82, SEQ ID NO. 83/SEQ ID NO. 84, SEQ ID NO. 85/SEQ ID NO. 86, SEQ ID NO. 87/SEQ ID NO. 88, SEQ ID NO. 89/SEQ ID NO. 90, SEQ ID NO. 91/SEQ ID NO. 92, SEQ ID NO. 93/SEQ ID NO. 94, SEQ ID NO. 95/SEQ ID NO. 96, SEQ ID NO. 97/SEQ ID NO. 98, SEQ ID NO. 99/SEQ ID NO. 100, SEQ ID NO. 101/SEQ ID NO. 102, SEQ ID NO. 103/SEQ ID NO. 104, SEQ ID NO. 105/SEQ ID NO. 106, SEQ ID NO. 107/SEQ ID NO. 108, SEQ ID NO. 109/SEQ ID NO. 110, SEQ ID NO. 111/SEQ ID NO.112, SEQ ID NO. 111/SEQ ID NO.113, SEQ ID NO.111/SEQ ID NO.114, SEQ ID NO. 111/SEQ ID NO.115, SEQ ID NO. 111/SEQ ID NO.116, SEQ ID NO.111/SEQ ID NO.117, SEQ ID NO. 111/SEQ ID NO.118, SEQ ID NO. 111/SEQ ID NO.119, SEQ ID NO.111/SEQ ID NO.120, SEQ ID NO. 111/SEQ ID NO.121, SEQ ID NO. 111/SEQ ID NO.122, SEQ ID NO.111/SEQ ID NO.123, SEQ ID NO.124/SEQ ID NO.112, SEQ ID NO. 125/SEQ ID NO.112, SEQ ID NO. 126/SEQ ID NO.112, SEQ ID NO.127/SEQ ID NO.112, SEQ ID NO. 128/SEQ ID NO.112, SEQ ID NO. 129/SEQ ID NO.112, SEQ ID NO.130/SEQ ID NO.112, SEQ ID NO.127/SEQ ID NO.131, SEQ ID NO. 132/SEQ ID NO.133, SEQ ID NO. 132/SEQ ID NO.123, SEQ ID NO.142/SEQ ID NO.123, SEQ ID NO. 127/SEQ ID NO.123, SEQ ID NO. 132/SEQ ID NO.134, SEQ ID NO. 135/SEQ ID NO.133, SEQ ID NO.132/SEQ ID NO.136, SEQ ID NO.132/SEQ ID NO.137, SEQ ID NO. 132/SEQ ID NO.138, SEQ ID NO. 139/SEQ ID NO.123, SEQ ID NO.139/SEQ ID NO.140, SEQ ID NO. 127/SEQ ID NO.141, and combinations thereof.

Techniques are known for deriving an antibody of a different subclass or isotype from an antibody of interest, i.e., subclass switching. Thus, IgG antibodies may be derived from an IgM antibody, for example, and vice versa. Such techniques allow the preparation of new antibodies that possess the antigen-binding properties of a given antibody (the parent antibody), but also exhibit biological properties associated with an antibody isotype or subclass different from that of the parent antibody. Recombinant DNA techniques may be employed. Cloned DNA encoding particular antibody polypeptides may be employed in such procedures, e.g., DNA encoding the constant domain of an antibody of the desired isotype (Lantto et al., 2002, *Methods Mol. Biol.* 178:303-16). Moreover, if an IgG4 is desired, it may also be desired to introduce a point mutation (CPSCP→CPPCP) (SEQ ID NOS 143 and 144, respectively) in the hinge region (Bloom et al., 1997, *Protein Science* 6:407) to alleviate a tendency to form intra-H chain disulfide bonds that can lead to heterogeneity in the IgG4 antibodies. Thus, in one embodiment, the antibody of the invention is a human IgG1 antibody. Thus, in one embodiment, the antibody of the invention is a human IgG4 antibody.

The present disclosure provides a number of antibodies structurally characterized by the amino acid sequences of their variable domain regions. However, the amino acid sequences can undergo some changes while retaining their high degree of binding to their specific targets. More specifically, many amino acids in the variable domain region can be changed with conservative substitutions and it is predictable that the binding characteristics of the resulting antibody will not differ from the binding characteristics of the wild type antibody sequence. There are many amino acids in an antibody variable domain that do not directly interact with the antigen or impact antigen binding and are not critical for determining antibody structure. For example, a predicted nonessential amino acid residue in any of the disclosed antibodies is preferably replaced with another amino acid residue from the same class. Methods of identifying amino acid conservative substitutions which do not eliminate antigen binding are well-known in the art (see, e.g., Brummell et al., *Biochem.* 32: 1180-1187 (1993); Kobayashi et al. *Protein Eng.* 12(10):879-884 (1999); and Burks et al. *Proc. Natl. Acad. Sci. USA* 94:412-417 (1997)). Near et al. *Mol. Immunol.* 30:369-377, 1993 explains how to impact or not impact binding through site-directed mutagenesis. Near et al. only mutated residues that they thought had a high probability of changing antigen binding. Most had a modest or negative effect on binding affinity (Near et al. Table 3) and binding to different forms of digoxin (Near et al. Table 2).

Thus, the invention also includes, in certain embodiments, variable sequences having at least 95% identity to those sequences disclosed herein.

In certain embodiments, an antibody, or antigen-binding fragment thereof, provided herein has a dissociation constant ($K_D$) of $1 \times 10^{-6}$ M or less; $5 \times 10^{-7}$ M or less' $1 \times 10^{-7}$ M or less; $5 \times 10^{-8}$ M or less; $1 \times 10^{-8}$ M or less; $5 \times 10^{-9}$ M or less; or $1 \times 10^{-9}$ M or less. In one embodiment, the antibody, or antigen-binding fragment thereof, of the invention as a $K_D$ from $1 \times 10^{-7}$ M to $1 \times 10^{-10}$ M. In one embodiment, the antibody, or antigen-binding fragment thereof, of the invention as a $K_D$ from $1 \times 10^{-8}$ M to $1 \times 10^{-10}$ M.

Those of ordinary skill in the art will appreciate standard methods known for determining the $K_D$ of an antibody, or fragment thereof. For example, in one embodiment, $K_D$ is measured by a radiolabeled antigen binding assay (RIA). In one embodiment, an RIA is performed with the Fab version of an antibody of interest and its antigen. For example, solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881(1999)).

According to another embodiment, $K_D$ is measured using a BIACORE surface plasmon resonance assay. The term "surface plasmon resonance", as used herein, refers to an optical phenomenon that allows for the analysis of real-time interactions by detection of alterations in protein concentrations within a biosensor matrix, for example using the BIACORE system (Biacore Life Sciences division of GE Healthcare, Piscataway, N.J.).

In particular embodiments, antigen binding proteins of the present invention have a binding affinity ($K_a$) for JAG1 of at least $10^6$ M$^{-1}$. In other embodiments, the antigen binding proteins exhibit a $K_a$ of at least $10^7$ M$^{-1}$, at least $10^8$ M$^{-1}$, at least $10^9$ M$^{-1}$, or at least $10^{10}$ M$^{-1}$. In another embodiment, the antigen binding protein exhibits a $K_a$ substantially the same as that of an antibody described herein in the Examples.

In another embodiment, the present disclosure provides an antigen binding protein that has a low dissociation rate from JAG1. In one embodiment, the antigen binding protein has a $K_{off}$ of $1 \times 10^{-4}$ to $^{-1}$ sec$^{-1}$ or lower. In another embodiment, the $K_{off}$ is $5 \times 10^{-5}$ to $^{-1}$ sec$^{-1}$ or lower. In another embodiment, the $K_{off}$ is substantially the same as an antibody described herein. In another embodiment, the antigen binding protein binds to JAG1 with substantially the same $K_{off}$ as an antibody described herein.

In another aspect, the present disclosure provides an antigen binding protein that inhibits an activity of JAG1. In one embodiment, the antigen binding protein has an IC$_{50}$ of 1000 nM or lower. In another embodiment, the IC$_{50}$ is 100 nM or lower; in another embodiment, the IC$_{50}$ is 10 nM or lower. In another embodiment, the IC$_{50}$ is substantially the same as that of an antibody described herein in the Examples. In another embodiment, the antigen binding protein inhibits an activity of JAG1 with substantially the same IC$_{50}$ as an antibody described herein.

In another aspect, the present disclosure provides an antigen binding protein that binds to human JAG1 expressed on the surface of a cell and, when so bound, inhibits JAG1 signaling activity in the cell without causing a significant reduction in the amount of JAG1 on the surface of the cell. Any method for determining or estimating the amount of JAG1 on the surface and/or in the interior of the cell can be used. In other embodiments, binding of the antigen binding protein to the JAG1-expressing cell causes less than about 75%, 50%, 40%, 30%, 20%, 15%, 10%, 5%, 1%, or 0.1% of the cell-surface JAG1 to be internalized.

In another aspect, the present disclosure provides an antigen binding protein having a half-life of at least one day in vitro or in vivo (e.g., when administered to a human subject). In one embodiment, the antigen binding protein has a half-life of at least three days. In another embodiment, the antigen binding protein has a half-life of four days or longer. In another embodiment, the antigen binding protein has a half-life of eight days or longer. In another embodiment, the antigen binding protein is derivatized or modified such that it has a longer half-life as compared to the underivatized or unmodified antigen binding protein. In another embodiment, the antigen binding protein contains one or more point mutations to increase serum half life, such as described in WO2000/09560, incorporated by reference herein.

The present disclosure further provides multi-specific antigen binding proteins, for example, bispecific antigen binding protein, e.g., antigen binding protein that bind to two different epitopes of JAG1, or to an epitope of JAG1 and an epitope of another molecule, via two different antigen binding sites or regions. Moreover, bispecific antigen binding protein as disclosed herein can comprise a JAG1 binding site from one of the herein-described antibodies and a second JAG1 binding region from another of the herein-described antibodies, including those described herein by reference to other publications. Alternatively, a bispecific antigen binding protein may comprise an antigen binding site from one of the herein described antibodies and a second antigen binding site from another JAG1 antibody that is known in the art, or from an antibody that is prepared by known methods or the methods described herein.

Numerous methods of preparing bispecific antibodies are known in the art. Such methods include the use of hybrid-hybridomas as described by Milstein et al., 1983, *Nature* 305:537, and chemical coupling of antibody fragments (Brennan et al., 1985, *Science* 229:81; Glennie et al., 1987, *J. Immunol.* 139:2367; U.S. Pat. No. 6,010,902). Moreover, bispecific antibodies can be produced via recombinant means, for example by using leucine zipper moieties (i.e., from the Fos and Jun proteins, which preferentially form heterodimers; Kostelny et al., 1992, *J. Immunol.* 148:1547) or other lock and key interactive domain structures as described in U.S. Pat. No. 5,582,996. Additional useful techniques include those described in U.S. Pat. Nos. 5,959,083; and 5,807,706.

In another aspect, the antigen binding protein comprises a derivative of an antibody. The derivatized antibody can comprise any molecule or substance that imparts a desired property to the antibody, such as increased half-life in a particular use. The derivatized antibody can comprise, for example, a detectable (or labeling) moiety (e.g., a radioactive, colorimetric, antigenic or enzymatic molecule, a detectable bead (such as a magnetic or electrodense (e.g., gold) bead), or a molecule that binds to another molecule (e.g., biotin or streptavidin), a therapeutic or diagnostic moiety (e.g., a radioactive, cytotoxic, or pharmaceutically active moiety), or a molecule that increases the suitability of the antibody for a particular use (e.g., administration to a subject, such as a human subject, or other in vivo or in vitro uses). Examples of molecules that can be used to derivatize an antibody include albumin (e g, human serum albumin) and polyethylene glycol (PEG). Albumin-linked and PEGylated derivatives of antibodies can be prepared using techniques well known in the art. In one embodiment, the antibody is conjugated or otherwise linked to transthyretin (TTR) or a TTR variant. The TTR or TTR variant can be chemically modified with, for example, a chemical selected from the group consisting of dextran, poly(n-vinyl pyurrolidone), polyethylene glycols, propropylene glycol homopolymers, polypropylene oxide/ethylene oxide co-polymers, polyoxyethylated polyols and polyvinyl alcohols.

An alternative approach to antibody-targeted therapy is to utilize anti-JAG1 antibodies of the invention for delivery of cytotoxic drugs specifically to JAG1 antigen-expressing cancer cells. In one embodiment, an anti-JAG1 antibody, or fragment, of the invention is conjugated to a cytotoxic agent via a linker, to form an anti-JAG1 Antibody Drug Conjugate (ADC). Various cytotoxic drugs are known in the art which can be conjugated with any of the antibodies disclosed herein to form an ADC, including the cytotoxic drug maytansinoid. Maytansinoids, derivatives of the anti-mitotic drug maytansine, bind to microtubules in a manner similar to vinca alkaloid drugs (Issell B F et al (1978) Cancer Treat. Rev. 5:199-207; Cabanillas F et al. (1979) Cancer Treat Rep, 63:507-9. Antibody-drug conjugates (ADCs) composed of the maytansinoid DM1 linked to an anti-JAG1 antibody, as described in Example 2 below, show potent anti-tumor activity in JAG1-overexpressing tumor cell lines. Thus, in one embodiment, an anti-JAG1 antibody, or fragment thereof, of the invention is conjugated to an anti-mitotic tubulin inhibitor, e.g., maytansinoid N(2')-deacetyl-N(2')-(3-mercapto-1-oxopropyl)-maytansine (also referred to as "DM1").

Oligomers that contain one or more antigen binding proteins may be employed as JAG1 antagonists. Oligomers may be in the form of covalently-linked or non-covalently-linked dimers, trimers, or higher oligomers. Oligomers comprising two or more antigen binding protein are contemplated for use, with one example being a homodimer. Other oligomers include heterodimers, homotrimers, heterotrimers, homotetramers, heterotetramers, etc.

One embodiment is directed to oligomers comprising multiple antigen binding proteins joined via covalent or non-covalent interactions between peptide moieties fused to the antigen binding proteins. Such peptides may be peptide linkers (spacers), or peptides that have the property of promoting oligomerization. Leucine zippers and certain polypeptides derived from antibodies are among the peptides that can promote oligomerization of antigen binding proteins attached thereto, as described in more detail below.

In particular embodiments, the oligomers comprise from two to four antigen binding proteins. The antigen binding proteins of the oligomer may be in any form, such as any of the forms described above, e.g., variants or fragments. Preferably, the oligomers comprise antigen binding proteins that have JAG1 binding activity.

Another method for preparing oligomeric antigen binding proteins involves use of a leucine zipper. Leucine zipper domains are peptides that promote oligomerization of the proteins in which they are found. Leucine zippers were originally identified in several DNA-binding proteins (Landschulz et al., 1988, *Science* 240:1759), and have since been found in a variety of different proteins. Among the known leucine zippers are naturally occurring peptides and derivatives thereof that dimerize or trimerize. Examples of leucine zipper domains suitable for producing soluble oligomeric proteins are described in WO 94/10308, and the leucine zipper derived from lung surfactant protein D (SPD) described in Hoppe et al., 1994, *FEBS Letters* 344:191. The use of a modified leucine zipper that allows for stable trimerization of a heterologous protein fused thereto is described in Fanslow et al., 1994, *Semin. Immunol.* 6:267-78. In one approach, recombinant fusion proteins comprising an anti-JAG1 antibody fragment or derivative fused to a leucine zipper peptide are expressed in suitable host cells, and the soluble oligomeric anti-JAG1 antibody fragments or derivatives that form are recovered from the culture supernatant.

Antigen binding proteins directed against JAG1 can be used, for example, in assays to detect the presence of JAG1 polypeptides, either in vitro or in vivo. The antigen binding proteins also may be employed in purifying JAG1 proteins by immunoaffinity chromatography. Blocking antigen binding proteins can be used in the methods disclosed herein. Such antigen binding proteins that function as JAG1 antagonists may be employed in treating any JAG1-induced condition, including but not limited to various cancers.

Antigen binding proteins may be employed in an in vitro procedure, or administered in vivo to inhibit JAG1-induced biological activity. Disorders that would benefit (directly or indirectly) from activation of JAG1, examples of which are provided herein, thus may be treated. In one embodiment, the present invention provides a therapeutic method comprising in vivo administration of a JAG1 blocking antigen binding protein to a mammal in need thereof in an amount effective for reducing a JAG1-induced biological activity.

In certain embodiments of the invention, antigen binding proteins include fully human monoclonal antibodies that inhibit a biological activity of JAG1.

Antigen binding proteins, including antibodies and antibody fragments described herein, may be prepared by any of a number of conventional techniques. For example, they may be purified from cells that naturally express them (e.g., an antibody can be purified from a hybridoma that produces it), or produced in recombinant expression systems, using any technique known in the art. See, for example, Monoclonal Antibodies, Hybridomas: A New Dimension in Biological Analyses, Kennet et al. (eds.), Plenum Press, New York (1980); and Antibodies: A Laboratory Manual, Harlow and Land (eds.), Cold Spring Harbor Laboratory Press, Cold Spring Harbor, N.Y., (1988).

Any expression system known in the art can be used to make the recombinant polypeptides, including antibodies and antibody fragments described herein, of the invention.

In general, host cells are transformed with a recombinant expression vector that comprises DNA encoding a desired polypeptide. Among the host cells that may be employed are prokaryotes, yeast or higher eukaryotic cells. Prokaryotes include gram negative or gram positive organisms, for example *E. coli* or *bacilli*. Higher eukaryotic cells include insect cells and established cell lines of mammalian origin. Examples of suitable mammalian host cell lines include the COS-7 line of monkey kidney cells (ATCC CRL 1651) (Gluzman et al., 1981, *Cell* 23:175), L cells, 293 cells, C127 cells, 3T3 cells (ATCC CCL 163), Chinese hamster ovary (CHO) cells, HeLa cells, BHK (ATCC CRL 10) cell lines, and the CV1/EBNA cell line derived from the African green monkey kidney cell line CV1 (ATCC CCL 70) as described by McMahan et al., 1991, *EMBO J.* 10: 2821. Appropriate cloning and expression vectors for use with bacterial, fungal, yeast, and mammalian cellular hosts are described by Pouwels et al. (Cloning Vectors: A Laboratory Manual, Elsevier, N.Y., 1985).

The transformed cells can be cultured under conditions that promote expression of the polypeptide, and the polypeptide recovered by conventional protein purification procedures. One such purification procedure includes the use of affinity chromatography, e.g., over a matrix having all or a portion (e.g., the extracellular domain) of JAG1 bound thereto. Polypeptides contemplated for use herein include substantially homogeneous recombinant mammalian anti-JAG1 antibody polypeptides substantially free of contaminating endogenous materials.

Antigen binding proteins may be prepared, and screened for desired properties, by any of a number of known techniques. Certain of the techniques involve isolating a nucleic acid encoding a polypeptide chain (or portion thereof) of an antigen binding protein of interest (e.g., an anti-JAG1 antibody), and manipulating the nucleic acid through recombinant DNA technology. The nucleic acid may be fused to another nucleic acid of interest, or altered (e.g., by mutagenesis or other conventional techniques) to add, delete, or substitute one or more amino acid residues, for example.

Polypeptides of the present disclosure can be produced using any standard methods known in the art. In one example, the polypeptides are produced by recombinant DNA methods by inserting a nucleic acid sequence (a cDNA) encoding the polypeptide into a recombinant expression vector and expressing the DNA sequence under conditions promoting expression.

Nucleic acids encoding any of the various polypeptides disclosed herein may be synthesized chemically. Codon usage may be selected so as to improve expression in a cell. Such codon usage will depend on the cell type selected. Specialized codon usage patterns have been developed for *E. coli* and other bacteria, as well as mammalian cells, plant cells, yeast cells and insect cells.

General techniques for nucleic acid manipulation are described for example in Sambrook et al., *Molecular Cloning: A Laboratory Manual*, Vols. 1-3, Cold Spring Harbor Laboratory Press, 2 ed., 1989, or F. Ausubel et al., *Current Protocols in Molecular Biology* (Green Publishing and Wiley-Interscience: New York, 1987) and periodic updates, herein incorporated by reference. The DNA encoding the polypeptide is operably linked to suitable transcriptional or translational regulatory elements derived from mammalian, viral, or insect genes. Such regulatory elements include a transcriptional promoter, an optional operator sequence to control transcription, a sequence encoding suitable mRNA ribosomal binding sites, and sequences that control the termination of transcription and translation. The ability to replicate in a host, usually conferred by an origin of replication, and a selection gene to facilitate recognition of transformants is additionally incorporated.

The recombinant DNA can also include any type of protein tag sequence that may be useful for purifying the protein. Examples of protein tags include but are not limited to a histidine tag, a FLAG tag, a myc tag, an HA tag, or a GST tag. Appropriate cloning and expression vectors for use with bacterial, fungal, yeast, and mammalian cellular hosts can be found in *Cloning Vectors: A Laboratory Manual*, (Elsevier, N.Y., 1985).

The expression construct is introduced into the host cell using a method appropriate to the host cell. A variety of methods for introducing nucleic acids into host cells are known in the art, including, but not limited to, electroporation; transfection employing calcium chloride, rubidium chloride, calcium phosphate, DEAE-dextran, or other substances; microprojectile bombardment; lipofection; and infection (where the vector is an infectious agent). Suitable host cells include prokaryotes, yeast, mammalian cells, or bacterial cells.

Suitable bacteria include gram negative or gram positive organisms, for example, *E. coli* or *Bacillus* spp. Yeast, preferably from the *Saccharomyces* species, such as *S. cerevisiae*, may also be used for production of polypeptides. Various mammalian or insect cell culture systems can also be employed to express recombinant proteins. Baculovirus systems for production of heterologous proteins in insect cells are reviewed by Luckow and Summers, (*Bio/Technology*, 6:47, 1988). Examples of suitable mammalian host cell lines include endothelial cells, COS-7 monkey kidney cells, CV-1, L cells, C127, 3T3, Chinese hamster ovary (CHO), human embryonic kidney cells, HeLa, 293, 293T, and BHK cell lines. Purified polypeptides are prepared by culturing suitable host/vector systems to express the recombinant proteins. For many applications, the small size of many of the polypeptides disclosed herein would make expression in *E. coli* as the preferred method for expression. The protein is then purified from culture media or cell extracts.

Proteins can also be produced using cell-translation systems. For such purposes the nucleic acids encoding the polypeptide must be modified to allow in vitro transcription to produce mRNA and to allow cell-free translation of the mRNA in the particular cell-free system being utilized (eukaryotic such as a mammalian or yeast cell-free translation system or prokaryotic such as a bacterial cell-free translation system.

JAG1-binding polypeptides can also be produced by chemical synthesis (such as by the methods described in Solid Phase Peptide Synthesis, 2nd ed., 1984, The Pierce Chemical Co., Rockford, Ill.). Modifications to the protein can also be produced by chemical synthesis.

The polypeptides of the present disclosure can be purified by isolation/purification methods for proteins generally known in the field of protein chemistry. Non-limiting examples include extraction, recrystallization, salting out (e.g., with ammonium sulfate or sodium sulfate), centrifugation, dialysis, ultrafiltration, adsorption chromatography, ion exchange chromatography, hydrophobic chromatography, normal phase chromatography, reversed-phase chromatography, gel filtration, gel permeation chromatography, affinity chromatography, electrophoresis, countercurrent distribution or any combinations of these. After purification, polypeptides may be exchanged into different buffers and/or concentrated by any of a variety of methods known to the art, including, but not limited to, filtration and dialysis.

The purified polypeptide is preferably at least 85% pure, more preferably at least 95% pure, and most preferably at least 98% pure. Regardless of the exact numerical value of the purity, the polypeptide is sufficiently pure for use as a pharmaceutical product.

In certain embodiments, the present disclosure provides monoclonal antibodies that bind to JAG1. Monoclonal antibodies may be produced using any technique known in the art, e.g., by immortalizing spleen cells harvested from the transgenic animal after completion of the immunization schedule. The spleen cells can be immortalized using any technique known in the art, e.g., by fusing them with myeloma cells to produce hybridomas. Myeloma cells for use in hybridoma-producing fusion procedures preferably are non-antibody-producing, have high fusion efficiency, and enzyme deficiencies that render them incapable of growing in certain selective media which support the growth of only the desired fused cells (hybridomas). Examples of suitable cell lines for use in mouse fusions include Sp-20, P3-X63/Ag8, P3-X63-Ag8.653, NS1/1.Ag 4 1, Sp210-Ag14, FO, NSO/U, MPC-11, MPC11-X45-GTG 1.7 and S194/5XX0 Bul; examples of cell lines used in rat fusions include R210.RCY3, Y3-Ag 1.2.3, IR983F and 48210. Other cell lines useful for cell fusions are U-266, GM1500-GRG2, LICR-LON-HMy2 and UC729-6.

Antigen-binding fragments of antigen binding proteins of the invention may be produced by conventional techniques known in the art.

Post-Translational Modifications of Polypeptides

In certain embodiments, the binding polypeptides of the invention may further comprise post-translational modifications. Exemplary post-translational protein modifications include phosphorylation, acetylation, methylation, ADP-ribosylation, ubiquitination, glycosylation, carbonylation, sumoylation, biotinylation or addition of a polypeptide side chain or of a hydrophobic group. As a result, the modified soluble polypeptides may contain non-amino acid elements, such as lipids, poly- or mono-saccharide, and phosphates. A preferred form of glycosylation is sialylation, which conjugates one or more sialic acid moieties to the polypeptide. Sialic acid moieties improve solubility and serum half-life while also reducing the possible immunogeneticity of the protein. See Raju et al. *Biochemistry.* 2001 31; 40(30):8868-76.

In one embodiment, modified forms of the subject soluble polypeptides comprise linking the subject soluble polypeptides to nonproteinaceous polymers. In one embodiment, the polymer is polyethylene glycol ("PEG"), polypropylene glycol, or polyoxyalkylenes, in the manner as set forth in U.S. Pat. Nos. 4,640,835; 4,496,689; 4,301,144; 4,670,417; 4,791,192 or 4,179,337.

PEG is a water soluble polymer that is commercially available or can be prepared by ring-opening polymerization of ethylene glycol according to methods well known in the art (Sandler and Karo, Polymer Synthesis, Academic Press, New York, Vol. 3, pages 138-161). The term "PEG" is used broadly to encompass any polyethylene glycol molecule, without regard to size or to modification at an end of the PEG, and can be represented by the formula: $X-O(CH_2CH_2O)_n-CH_2CH_2OH$ (1), where n is 20 to 2300 and X is H or a terminal modification, e.g., a $C_{1-4}$ alkyl. In one embodiment, the PEG of the invention terminates on one end with hydroxy or methoxy, i.e., X is H or $CH_3$ ("methoxy PEG"). A PEG can contain further chemical groups which are necessary for binding reactions; which results from the chemical synthesis of the molecule; or which is a spacer for optimal distance of parts of the molecule. In addition, such a PEG can consist of one or more PEG side-chains which are linked together. PEGs with more than one PEG chain are called multiarmed or branched PEGs. Branched PEGs can be prepared, for example, by the addition of polyethylene oxide to various polyols, including glycerol, pentaerythriol, and sorbitol. For example, a four-armed branched PEG can be prepared from pentaerythriol and ethylene oxide. Branched PEG are described in, for example, EP-A 0 473 084 and U.S. Pat. No. 5,932,462. One form of PEGs includes two PEG side-chains (PEG2) linked via the primary amino groups of a lysine (Monfardini et al., *Bioconjugate Chem.* 6 (1995) 62-69).

The serum clearance rate of PEG-modified polypeptide may be decreased by about 10%, 20%, 30%, 40%, 50%, 60%, 70%, 80%, or even 90%, relative to the clearance rate of the unmodified binding polypeptide. The PEG-modified polypeptide may have a half-life ($t_{1/2}$) which is enhanced relative to the half-life of the unmodified protein. The half-life of PEG-binding polypeptide may be enhanced by at least 10%, 20%, 30%, 40%, 50%, 60%, 70%, 80%, 90%, 100%, 125%, 150%, 175%, 200%, 250%, 300%, 400% or 500%, or even by 1000% relative to the half-life of the unmodified binding polypeptide. In some embodiments, the protein half-life is determined in vitro, such as in a buffered saline solution or in serum. In other embodiments, the protein half-life is an in vivo half life, such as the half-life of the protein in the serum or other bodily fluid of an animal.

Therapeutic Methods, Formulations and Modes of Administration

The present disclosure features methods for treating Notch-signaling tumors, including breast, prostate, colorectal, lung and other solid tumors, comprising administering anti-JAG1 antibodies or antigen binding fragments of the present invention. As used herein, a "Notch-signaling tumor" or a "tumor associated with Notch signaling" refers to a tumor or malignant growth in which Notch signaling is detrimental. In one example, Notch signaling is associated with tumor growth. In other examples, Notch signaling is involved in tumor progression or metastasis. Exemplary tumors that may be treated by targeting the Notch pathway using the anti-JAG1 antibodies and antigen binding fragments of the invention, include, but are not limited to, head and neck squamous cell carcinoma (Zeng et al. 2005, Cancer Cell 8:13-23), T-cell acute lymphoblastic leukemia (Roy et al. Curr Opin Genet Dev 17: 52-59, 2007), breast cancer (Reedijk et al., Cancer Res 65: 8530-8537, 2005; Dickson et al., Mod Pathol 20: 685-693, 2007), melanoma (Pinnix and Herlyn, Pigment Cell Res 20: 458-465, 2007), lung adenocarcinoma (Chen et al., Cancer Res 67: 7954-7959, 2007), prostate (Leong et al., Differentiation Volume 76, Issue 6, July 2008, Pages 699-716) and colorectal (Guilmeau S. Adv Exp Med Biol. 2012; 727:272-88).

Any of the antibodies or antigen binding fragments disclosed herein may be used in such therapeutic methods.

The present disclosure further provides a method for treating Notch-signaling tumors, comprising administering an anti-JAG1 polypeptide selected from the group consisting of a fully human antibody of an IgG class that binds to a JAG1 epitope with a binding affinity of at least $10^{-6}$M, a Fab fully human antibody fragment, having a variable domain region from a heavy chain and a variable domain region from a light chain, a single chain human antibody, having a variable domain region from a heavy chain and a variable domain region from a light chain and a peptide linker connecting the heavy chain and light chain variable domain regions, including the heavy and light chain variable regions (and CDRs within said sequences) described in SEQ ID Nos. 1-142 (Table 5).

For example, in one embodiment, the methods disclosed herein include the use of a fully human antibody comprising a heavy chain variable domain sequence that is at least 95% identical, at least 96% identical, at least 97% identical, at least 98% identical, or at least 99% identical, to an amino acid sequence selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63, SEQ ID NO. 65, SEQ ID NO. 67, SEQ ID NO. 69, SEQ ID NO. 71, SEQ ID NO. 73, SEQ ID NO. 75, SEQ ID NO. 77, SEQ ID NO. 79, SEQ ID NO. 81, SEQ ID NO. 83, SEQ ID NO. 85, SEQ ID NO. 87, SEQ ID NO. 89, SEQ ID NO. 91, SEQ ID NO. 93, SEQ ID NO. 95, SEQ ID NO. 97, SEQ ID NO. 99, SEQ ID NO. 101, SEQ ID NO. 103, SEQ ID NO. 105, SEQ ID NO. 107, SEQ ID NO. 109, SEQ ID NO. 111, SEQ ID NO. 124, SEQ ID NO. 125, SEQ ID NO. 126, SEQ ID NO. 127, SEQ ID NO. 128, SEQ ID NO. 129, SEQ ID NO. 130, SEQ ID NO. 132, SEQ ID NO. 135, SEQ ID NO. 139 and SEQ ID NO. 142, and combinations thereof, and that has a light chain variable domain sequence that is at least 95% identical, at least 96% identical, at least 97% identical, at least 98% identical, or at least 99% identical, to an amino acid sequence selected from the group consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72, SEQ ID NO. 74, SEQ ID NO. 76, SEQ ID NO. 78, SEQ ID NO. 80, SEQ ID NO. 82, SEQ ID NO. 84, SEQ ID NO. 86, SEQ ID NO. 88, SEQ ID NO. 90, SEQ ID NO. 92, SEQ ID NO. 94, SEQ ID NO. 96, SEQ ID NO. 98, SEQ ID NO. 100, SEQ ID NO. 102, SEQ ID NO. 104, SEQ ID NO. 106, SEQ ID NO. 108, SEQ ID NO. 110, SEQ ID NO. 112, SEQ ID NO. 113, SEQ ID NO. 114, SEQ ID NO. 115, SEQ ID NO. 116, SEQ ID NO. 117, SEQ ID NO. 118, SEQ ID NO. 119, SEQ ID NO. 120, SEQ ID NO. 121, SEQ ID NO. 122, SEQ ID NO. 123, SEQ ID NO. 131, SEQ ID NO. 133, SEQ ID NO. 134, SEQ ID NO. 136, SEQ ID NO. 137, SEQ ID NO. 138, SEQ ID NO. 140 and SEQ ID NO. 141, and combinations thereof.

In one embodiment, the methods described herein include the use of a fully human Fab antibody fragment has a heavy chain variable domain sequence that is at least 95% identical, at least 96% identical, at least 97% identical, at least 98% identical, or at least 99% identical, to an amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63, SEQ ID NO. 65, SEQ ID NO. 67, SEQ ID NO. 69, SEQ ID NO. 71, SEQ ID NO. 73, SEQ ID NO. 75, SEQ ID NO. 77, SEQ ID NO. 79, SEQ ID NO. 81, SEQ ID NO. 83, SEQ ID NO. 85, SEQ ID NO. 87, SEQ ID NO. 89, SEQ ID NO. 91, SEQ ID NO. 93, SEQ ID NO. 95, SEQ ID NO. 97, SEQ ID NO. 99, SEQ ID NO. 101, SEQ ID NO. 103, SEQ ID NO. 105, SEQ ID NO. 107, SEQ ID NO. 109, SEQ ID NO. 109, SEQ ID NO. 111, SEQ ID NO. 124, SEQ ID NO. 125, SEQ ID NO. 126, SEQ ID NO. 127, SEQ ID NO. 128, SEQ ID NO. 129, SEQ ID NO. 130, SEQ ID NO. 132, SEQ ID NO. 135, SEQ ID NO. 139 and SEQ ID NO. 142 and combinations thereof, and that has the light chain variable domain sequence that is at least 95% identical to the amino acid sequence consisting SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72, SEQ ID NO. 74, SEQ ID NO. 76, SEQ ID NO. 78, SEQ ID NO. 80, SEQ ID NO. 82, SEQ ID NO. 84, SEQ ID NO. 86, SEQ ID NO. 88, SEQ ID NO. 90, SEQ ID NO. 92, SEQ ID NO. 94, SEQ ID NO. 96, SEQ ID NO. 98, SEQ ID NO. 100, SEQ ID NO. 102, SEQ ID NO. 104, SEQ ID NO. 106, SEQ ID NO. 108, SEQ ID NO. 110, SEQ ID NO. 112, SEQ ID NO. 113, SEQ ID NO. 114, SEQ ID NO. 115, SEQ ID NO. 116, SEQ ID NO. 117, SEQ ID NO. 118, SEQ ID NO. 119, SEQ ID NO. 120, SEQ ID NO. 121, SEQ ID NO. 122, SEQ ID NO. 123, SEQ ID NO. 131, SEQ ID NO. 133, SEQ ID NO. 134, SEQ ID NO. 136, SEQ ID NO. 137, SEQ ID NO. 138, SEQ ID NO. 140 and SEQ ID NO. 141, and combinations thereof.

In one embodiment, the methods described herein include the use of a single chain human antibody comprising a heavy chain variable domain sequence that is at least 95% identical, at least 96% identical, at least 97% identical, at least 98% identical, or at least 99% identical, to the amino acid sequences selected from the group consisting of SEQ ID NO. 1, SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO. 17, SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63, SEQ ID NO. 65, SEQ ID NO. 67, SEQ ID NO. 69, SEQ ID NO. 71, SEQ ID NO. 73, SEQ ID NO. 75, SEQ ID NO. 77, SEQ ID NO. 79, SEQ ID NO. 81, SEQ ID NO. 83, SEQ ID NO. 85, SEQ ID NO. 87, SEQ ID NO. 89, SEQ ID NO. 91, SEQ ID NO. 93, SEQ ID NO. 95, SEQ ID NO. 97, SEQ ID NO. 99, SEQ ID NO. 101, SEQ ID NO. 103, SEQ ID NO. 105, SEQ ID NO. 107, SEQ ID NO. 109, SEQ ID NO. 111, SEQ ID NO. 124, SEQ ID NO. 125, SEQ ID NO. 126, SEQ ID NO. 127, SEQ ID NO. 128, SEQ ID NO. 129, SEQ ID NO. 130, SEQ ID NO. 132, SEQ ID NO. 135, SEQ ID NO. 139 and SEQ ID NO. 142, and combinations thereof, and comprising a light chain variable domain sequence that is at least 95% identical, at least 96% identical, at least 97% identical, at least 98% identical, or at least 99% identical, to the amino acid sequence consisting of SEQ ID NO. 2, SEQ ID NO. 4, SEQ ID NO. 6, SEQ ID NO. 8, SEQ ID NO. 10, SEQ ID NO. 12, SEQ ID NO. 14, SEQ ID NO. 16, SEQ ID NO. 18, SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64, SEQ ID NO. 66, SEQ ID NO. 68, SEQ ID NO. 70, SEQ ID NO. 72, SEQ ID NO. 74, SEQ ID NO. 76, SEQ ID NO. 78, SEQ ID NO. 80, SEQ ID NO. 82, SEQ ID NO. 84, SEQ ID NO. 86, SEQ ID NO. 88, SEQ ID NO. 90, SEQ ID NO. 92, SEQ ID NO. 94, SEQ ID NO. 96, SEQ ID NO. 98, SEQ ID NO. 100, SEQ ID NO. 102, SEQ ID NO. 104, SEQ ID NO. 106, SEQ ID NO. 108, SEQ ID NO. 110, SEQ ID NO. 112, SEQ ID NO. 113, SEQ ID NO. 114, SEQ ID NO. 115, SEQ ID NO. 116, SEQ ID NO. 117, SEQ ID NO. 118, SEQ ID NO. 119, SEQ ID NO. 120, SEQ ID NO. 121, SEQ ID NO. 122, SEQ ID NO. 123, SEQ ID NO. 131, SEQ ID NO. 133, SEQ ID NO. 134, SEQ ID NO. 136, SEQ ID NO. 137, SEQ ID NO. 138, SEQ ID NO. 140 and SEQ ID NO. 141, and combinations thereof.

In one embodiment, the fully human antibody has both a heavy chain and a light chain wherein the antibody has a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28, SEQ ID NO. 29/SEQ ID NO. 30, SEQ ID NO. 31/SEQ ID NO. 32, SEQ ID NO. 33/SEQ ID NO. 34, SEQ ID NO. 35/SEQ ID NO. 36, SEQ ID NO. 37/SEQ ID NO. 38, SEQ ID NO. 39/SEQ ID NO. 40, SEQ ID NO. 41/SEQ ID NO. 42, SEQ ID NO. 43/SEQ ID NO. 44, SEQ ID NO. 45/SEQ ID NO. 46, SEQ ID NO. 47/SEQ ID NO. 48, SEQ ID NO. 49/SEQ ID NO. 50, SEQ ID NO. 51/SEQ ID NO. 52, SEQ ID NO. 53/SEQ ID NO. 54, SEQ ID NO. 55/SEQ ID NO. 56, SEQ ID NO. 57/SEQ ID NO. 58, SEQ ID NO. 59/SEQ ID NO. 60, SEQ ID NO. 61/SEQ ID NO. 62, SEQ ID NO. 63/SEQ ID NO. 64, SEQ ID NO. 65/SEQ ID NO. 66, SEQ ID NO. 67/SEQ ID NO. 68, SEQ ID NO. 69/SEQ ID NO. 70, SEQ ID NO. 71/SEQ ID NO. 72, SEQ ID NO. 73/SEQ ID NO. 74, SEQ ID NO. 75/SEQ ID NO. 76, SEQ ID NO. 77/SEQ ID NO. 78, SEQ ID NO. 79/SEQ ID NO. 80, SEQ ID NO. 81/SEQ ID NO. 82, SEQ ID NO. 83/SEQ ID NO. 84, SEQ ID NO. 85/SEQ ID NO. 86, SEQ ID NO. 87/SEQ ID NO. 88, SEQ ID NO. 89/SEQ ID NO. 90, SEQ ID NO. 91/SEQ ID NO. 92, SEQ ID NO. 93/SEQ ID NO. 94, SEQ ID NO. 95/SEQ ID NO. 96, SEQ ID NO. 97/SEQ ID NO. 98, SEQ ID NO. 99/SEQ ID NO. 100, SEQ ID NO. 101/SEQ ID NO. 102, SEQ ID NO. 103/SEQ ID NO. 104, SEQ ID NO. 105/SEQ ID NO. 106, SEQ ID NO. 107/SEQ ID NO. 108, SEQ ID NO. 109/SEQ ID NO. 110, SEQ ID NO. 111/SEQ ID NO.112, SEQ ID NO. 111/SEQ ID NO.113, SEQ ID NO.111/SEQ ID NO.114, SEQ ID NO. 111/SEQ ID NO.115, SEQ ID NO. 111/SEQ ID NO.116, SEQ ID NO.111/SEQ ID NO.117, SEQ ID NO. 111/SEQ ID NO.118, SEQ ID NO. 111/SEQ ID NO.119, SEQ ID NO.111/SEQ ID NO.120, SEQ ID NO. 111/SEQ ID NO.121, SEQ ID NO. 111/SEQ ID NO.122, SEQ ID NO.111/SEQ ID NO.123, SEQ ID NO.124/SEQ ID NO.112, SEQ ID NO. 125/SEQ ID NO.112, SEQ ID NO. 126/SEQ ID NO.112, SEQ ID NO.127/SEQ ID NO.112, SEQ ID NO. 128/SEQ ID NO.112, SEQ ID NO. 129/SEQ ID NO.112, SEQ ID NO.130/SEQ ID NO.112, SEQ ID NO.127/SEQ ID NO.131, SEQ ID NO. 132/SEQ ID NO.133, SEQ ID NO. 132/SEQ ID NO.123, SEQ ID NO.142/SEQ ID NO.123, SEQ ID NO. 127/SEQ ID NO.123, SEQ ID NO. 132/SEQ ID NO.134, SEQ ID NO. 135/SEQ ID NO.133, SEQ ID NO.132/SEQ ID NO.136, SEQ ID NO.132/SEQ ID NO.137, SEQ ID NO. 132/SEQ ID NO.138, SEQ ID NO. 139/SEQ ID NO.123, SEQ ID NO.139/SEQ ID NO.140, SEQ ID NO. 127/SEQ ID NO.141, and combinations thereof.

In one embodiment, the fully human antibody Fab fragment has both a heavy chain variable domain region and a light chain variable domain region wherein the antibody has a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28, SEQ ID NO. 29/SEQ ID NO. 30, SEQ ID NO. 31/SEQ ID NO. 32, SEQ ID NO. 33/SEQ ID NO. 34, SEQ ID NO. 35/SEQ ID NO. 36, SEQ ID NO. 37/SEQ ID NO. 38, SEQ ID NO. 39/SEQ ID NO. 40, SEQ ID NO. 41/SEQ ID NO. 42, SEQ ID NO. 43/SEQ ID NO. 44, SEQ ID NO. 45/SEQ ID NO. 46, SEQ ID NO. 47/SEQ ID NO. 48, SEQ ID NO. 49/SEQ ID NO. 50, SEQ ID NO. 51/SEQ ID NO. 52, SEQ ID NO. 53/SEQ ID NO. 54, SEQ ID NO. 55/SEQ ID NO. 56, SEQ ID NO. 57/SEQ ID NO. 58, SEQ ID NO. 59/SEQ ID NO. 60, SEQ ID NO. 61/SEQ ID NO. 62, SEQ ID NO. 63/SEQ ID NO. 64, SEQ ID NO. 65/SEQ ID NO. 66, SEQ ID NO. 67/SEQ ID NO. 68, SEQ ID NO. 69/SEQ ID NO. 70, SEQ ID NO. 71/SEQ ID NO. 72, SEQ ID NO. 73/SEQ ID NO. 74, SEQ ID NO. 75/SEQ ID NO. 76, SEQ ID NO. 77/SEQ ID NO. 78, SEQ ID NO. 79/SEQ ID NO. 80, SEQ ID NO. 81/SEQ ID NO. 82, SEQ ID NO. 83/SEQ ID NO. 84, SEQ ID NO. 85/SEQ ID NO. 86, SEQ ID NO. 87/SEQ ID NO. 88, SEQ ID NO. 89/SEQ ID NO. 90, SEQ ID NO. 91/SEQ ID NO. 92, SEQ ID NO. 93/SEQ ID NO. 94, SEQ ID NO. 95/SEQ ID NO. 96, SEQ ID NO. 97/SEQ ID NO. 98, SEQ ID NO. 99/SEQ ID NO. 100, SEQ ID NO. 101/SEQ ID NO. 102, SEQ ID NO. 103/SEQ ID NO. 104, SEQ ID NO. 105/SEQ ID NO. 106, SEQ ID NO. 107/SEQ ID NO. 108, SEQ ID NO. 109/SEQ ID NO. 110, SEQ ID NO. 111/SEQ ID NO.112, SEQ ID NO. 111/SEQ ID NO.113, SEQ ID NO.111/SEQ ID NO.114, SEQ ID NO. 111/SEQ ID NO.115, SEQ ID NO. 111/SEQ ID NO.116, SEQ ID NO.111/SEQ ID NO.117, SEQ ID NO. 111/SEQ ID NO.118, SEQ ID NO. 111/SEQ ID NO.119, SEQ ID NO.111/SEQ ID NO.120, SEQ ID NO. 111/SEQ ID NO.121, SEQ ID NO. 111/SEQ ID NO.122, SEQ ID NO.111/SEQ ID NO.123, SEQ ID NO.124/SEQ ID NO.112, SEQ ID NO. 125/SEQ ID NO.112, SEQ ID NO. 126/SEQ ID NO.112, SEQ ID NO.127/SEQ ID NO.112, SEQ ID NO. 128/SEQ ID NO.112, SEQ ID NO. 129/SEQ ID NO.112, SEQ ID NO.130/SEQ ID NO.112, SEQ ID NO.127/SEQ ID NO.131, SEQ ID NO. 132/SEQ ID NO.133, SEQ ID NO. 132/SEQ ID NO.123, SEQ ID NO.142/SEQ ID NO.123, SEQ ID NO. 127/SEQ ID NO.123, SEQ ID NO. 132/SEQ ID NO.134, SEQ ID NO. 135/SEQ ID NO.133, SEQ ID NO.132/SEQ ID NO.136, SEQ ID NO.132/SEQ ID NO.137, SEQ ID NO. 132/SEQ ID NO.138, SEQ ID NO. 139/SEQ ID NO.123, SEQ ID NO.139/SEQ ID NO.140, SEQ ID NO. 127/SEQ ID NO.141, and combinations thereof.

In one embodiment, the fully human single chain antibody has both a heavy chain variable domain region and a light chain variable domain region, wherein the single chain fully human antibody has a heavy chain/light chain variable domain sequence selected from the group consisting of SEQ ID NO. 1/SEQ ID NO. 2, SEQ ID NO. 3/SEQ ID NO. 4, SEQ ID NO. 5/SEQ ID NO. 6, SEQ ID NO. 7/SEQ ID NO. 8, SEQ ID NO. 9/SEQ ID NO. 10, SEQ ID NO. 11/SEQ ID NO. 12, SEQ ID NO. 13/SEQ ID NO. 14, SEQ ID NO. 15/SEQ ID NO. 16, SEQ ID NO. 17/SEQ ID NO. 18, SEQ ID NO. 19/SEQ ID NO. 20, SEQ ID NO. 21/SEQ ID NO. 22, SEQ ID NO. 23/SEQ ID NO. 24, SEQ ID NO. 25/SEQ ID NO. 26, SEQ ID NO. 27/SEQ ID NO. 28, SEQ ID NO. 29/SEQ ID NO. 30, SEQ ID NO. 31/SEQ ID NO. 32, SEQ ID NO. 33/SEQ ID NO. 34, SEQ ID NO. 35/SEQ ID NO. 36, SEQ ID NO. 37/SEQ ID NO. 38, SEQ ID NO. 39/SEQ ID NO. 40, SEQ ID NO. 41/SEQ ID NO. 42, SEQ ID NO. 43/SEQ ID NO. 44, SEQ ID NO. 45/SEQ ID NO. 46, SEQ ID NO. 47/SEQ ID NO. 48, SEQ ID NO. 49/SEQ ID NO. 50, SEQ ID NO. 51/SEQ ID NO. 52, SEQ ID NO. 53/SEQ ID NO. 54, SEQ ID NO. 55/SEQ ID NO. 56, SEQ ID NO. 57/SEQ ID NO. 58, SEQ ID NO. 59/SEQ ID NO. 60, SEQ ID NO. 61/SEQ ID NO. 62, SEQ ID NO. 63/SEQ ID NO. 64, SEQ ID NO. 65/SEQ ID NO. 66, SEQ ID NO. 67/SEQ ID NO. 68, SEQ ID NO. 69/SEQ ID NO. 70, SEQ ID NO. 71/SEQ ID NO. 72, SEQ ID NO. 73/SEQ ID NO. 74, SEQ ID NO. 75/SEQ ID NO. 76, SEQ ID NO. 77/SEQ ID NO. 78, SEQ ID NO. 79/SEQ ID NO. 80, SEQ ID NO. 81/SEQ ID NO. 82, SEQ ID NO. 83/SEQ ID NO. 84, SEQ ID NO. 85/SEQ ID NO. 86, SEQ ID NO. 87/SEQ ID NO. 88, SEQ ID NO. 89/SEQ ID NO. 90, SEQ ID NO. 91/SEQ ID NO. 92, SEQ ID NO. 93/SEQ ID NO. 94, SEQ ID NO. 95/SEQ ID NO. 96, SEQ ID NO. 97/SEQ ID NO. 98, SEQ ID NO. 99/SEQ ID NO. 100, SEQ ID NO. 101/SEQ ID NO. 102, SEQ ID NO. 103/SEQ ID NO. 104, SEQ ID NO. 105/SEQ ID NO. 106, SEQ ID NO. 107/SEQ ID NO. 108, SEQ ID NO. 109/SEQ ID NO. 110, SEQ ID NO. 111/SEQ ID NO.112, SEQ ID NO. 111/SEQ ID NO.113, SEQ ID NO.111/SEQ ID NO.114, SEQ ID NO. 111/SEQ ID NO.115, SEQ ID NO. 111/SEQ ID NO.116, SEQ ID NO.111/SEQ ID NO.117, SEQ ID NO. 111/SEQ ID NO.118, SEQ ID NO. 111/SEQ ID NO.119, SEQ ID NO.111/SEQ ID NO.120, SEQ ID NO. 111/SEQ ID NO.121, SEQ ID NO. 111/SEQ ID NO.122, SEQ ID NO.111/SEQ ID NO.123, SEQ ID NO.124/SEQ ID NO.112, SEQ ID NO. 125/SEQ ID NO.112, SEQ ID NO. 126/SEQ ID NO.112, SEQ ID NO.127/SEQ ID NO.112, SEQ ID NO. 128/SEQ ID NO.112, SEQ ID NO. 129/SEQ ID NO.112, SEQ ID NO.130/SEQ ID NO.112, SEQ ID NO.127/SEQ ID NO.131, SEQ ID NO. 132/SEQ ID NO.133, SEQ ID NO. 132/SEQ ID NO.123, SEQ ID NO.142/SEQ ID NO.123, SEQ ID NO. 127/SEQ ID NO.123, SEQ ID NO. 132/SEQ ID NO.134, SEQ ID NO. 135/SEQ ID NO.133, SEQ ID NO.132/SEQ ID NO.136, SEQ ID NO.132/SEQ ID NO.137, SEQ ID NO. 132/SEQ ID NO.138, SEQ ID NO. 139/SEQ ID NO.123, SEQ ID NO.139/SEQ ID NO.140, SEQ ID NO. 127/SEQ ID NO.141 and combinations thereof.

In one embodiment, the anti-JAG1 antibodies and antibody fragments of the invention are used to treat Notch-signaling tumors. As discussed above, any tumor or malignant growth with detrimental Notch signaling pathway activity can be treated by the anti-JAG1 antibodies and antibody fragments of the invention. For example, in one embodiment, the tumor is selected from the group consisting of breast, prostate, colorectal, lung and other solid tumors.

In one embodiment, the anti-JAG1 antibodies and antibody fragments of the invention can be administered alone or in combination with one or more additional therapies such as chemotherapy radiotherapy, immunotherapy, surgical intervention, or any combination of these. Long-term therapy is equally possible as is adjuvant therapy in the context of other treatment strategies, as described above.

In certain embodiments of such methods, one or more anti-JAG1 antibodies and antibody fragments of the invention can be administered, together (simultaneously) or at different times (sequentially). In addition, anti-JAG1 antibodies and antibody fragments of the invention can be administered with another type of compounds for treating cancer or for inhibiting angiogenesis.

In certain embodiments, the anti-JAG1 antibodies and antibody fragments of the invention can be used alone.

In certain embodiments, the anti-JAG1 antibodies and antibody fragments of the invention can be labeled or unlabeled for diagnostic purposes. Typically, diagnostic assays entail detecting the formation of a complex resulting from the binding of a binding polypeptide to JAG1. The anti-JAG1 antibodies and antibody fragments of the invention can be directly labeled, similar to antibodies. A variety of labels can be employed, including, but not limited to, radionuclides, fluorescers, enzymes, enzyme substrates, enzyme cofactors, enzyme inhibitors and ligands (e.g., biotin, haptens). Numerous appropriate immunoassays are known to the skilled artisan (see, for example, U.S. Pat. Nos. 3,817,827; 3,850,752; 3,901,654; and 4,098,876). When unlabeled, the binding polypeptides can be used in assays, such as agglutination assays. Unlabeled binding polypeptides can also be used in combination with another (one or more) suitable reagent which can be used to detect the binding polypeptide, such as a labeled antibody reactive with the binding polypeptide or other suitable reagent (e.g., labeled protein A).

Techniques and dosages for administration vary depending on the type of specific polypeptide and the specific condition being treated but can be readily determined by the skilled artisan. In general, regulatory agencies require that a protein reagent to be used as a therapeutic is formulated so as to have acceptably low levels of pyrogens. Accordingly, therapeutic formulations will generally be distinguished from other formulations in that they are substantially pyrogen free, or at least contain no more than acceptable levels of pyrogen as determined by the appropriate regulatory agency (e.g., FDA).

Therapeutic compositions of the present disclosure may be administered with a pharmaceutically acceptable diluent, carrier, or excipient, in unit dosage form. Administration may be parenteral (e.g., intravenous, subcutaneous), oral, or topical, as non-limiting examples. In addition, any gene therapy technique, using nucleic acids encoding the polypeptides of the invention, may be employed, such as naked DNA delivery, recombinant genes and vectors, cell-based delivery, including ex vivo manipulation of patients' cells, and the like.

A therapeutically effective dose refers to a dose that produces the therapeutic effects for which it is administered. The exact dose will depend on the disorder to be treated, and may be ascertained by one skilled in the art using known techniques. In general, the polypeptide is administered at about 0.01 µg/kg to about 50 mg/kg per day, preferably 0.01 mg/kg to about 30 mg/kg per day, most preferably 0.1 mg/kg to about 20 mg/kg per day. The polypeptide may be given daily (e.g., once, twice, three times, or four times daily) or preferably less frequently (e.g., weekly, every two weeks, every three weeks, monthly, or quarterly). In addition, as is known in the art, adjustments for age as well as the body weight, general health, sex, diet, time of administration, drug interaction, and the severity of the disease may be necessary.

Example 1

A screen was performed to identify human anti-human JAG1 antibodies. The heavy and light chain variable sequences from the antibodies identified in the screen are provided below in Table 5.

This example provides an analysis of the cross-reactivity of JAG1 binders to recombinant mouse JAG1. A 96-well plate was coated with 25 µl recombinant mouse JAG1/Fc (2 µg/µL in PBS) at 4° C. overnight. Washed 3 times with PBS-Tween (PBST). Added 5 µl scFv phage soup that diluted in 20 µl Casein in each well and incubated 30 min with shaking. The plate was washed 3 times with PBST, then horseradish peroxidase (HRP)-conjugated M13 (1:2000 in casein) was added, then 3,3',5,5'-Tetramethylbenzidine (TMB) was added as substrate and developed 30 min 2M $H_2SO_4$ was used to stop the reaction and the OD was read at 450 nm. The results showed that more than 80% of the JAG1 binding antibodies can also bind to murine antigen.

The binding affinity of antibody JG1H7 for human JAG1 was tested using a BiaCore assay. Specifically, anti-human Fc antibody (GE, BR-1008-39) was immobilized on a CM5 sensor chip to approximately 700 RU using standard NHS/EDC coupling methodology. Antibodies (about 10 µg/ml) were captured for 60 s at a flow rate 10 µl/min. Recombinant human JAG1/His was serially diluted in running buffer (HBS-EP). All measurements were conducted with a flow rate of 30 µL/min Surfaces were regenerated with 3M $MgCl_2$ for 60 s. A 1:1 (Langmuir) binding model was used to fit the data. The results are shown in Table 1, where the $K_D$ of antibody JG1H7 was determined to be $2.08 \times 10^{-7}$ M for human JAW.

TABLE 1

| name | ka (1/Ms) | kd (1/s) | Rmax (RU) | KA (1/M) | KD (M) | Chi2 |
|---|---|---|---|---|---|---|
| JG1H7 | 1.97E5 | 0.0411 | 85.1 | 4.8E6 | 2.08E−7 | 0.147 |

Example 2

This example illustrates in vitro data showing the assessment of anti-JAG-1 antibodies in a cytotoxicity assay using secondary antibody-drug conjugate technique ("Secondary Antibody-Drug Conjugates As Tools for ADC Discovery". Helen Mao, Poster, IBC 24th Annual, 2013). This example demonstrates the potential of anti-JAG-1 to be used as antibody drug conjugates.

JAG-1 expressing cells (Calu-6; lung cancer cells) were harvested with enzyme-free Cell Dissociation Buffer (GIBCO), seeded into white 96-Well Clear Bottom plates (1,000 cells/well in 90 µl) and allowed to adhere overnight at 37° C. Anti-human JAG1 antibodies JG1B10, JG1H7, JG1C8 and JG1H11 were pre-complexed with Protein G-DM1 (DM1; maytansinoid N(2')-deacetyl-N(2')-(3-mercapto-1-oxopropyl)-maytansine (DM1)) (Concords Biosystems) in cell culture media, at a 1:4 molar ratio. The same anti-human JAG1 antibodies JG1B10, JG1H7, JG1C8 and JG1H11 were also used as naked antibodies (not complexed) as controls. After 10 min at room temperature, serial dilutions of the antibody-ProteinG-DM1 complex (as well as the un-complexed antibody controls) were prepared in cell culture media, incubated 10 more minutes at room temperature, and added to cells (10 µl/well) in triplicate. After 6 days incubation at 37° C., cells proliferation was analyzed as follows: 100 µl of Cell Titer Glo buffer (Promega) was added to each well. Plates were incubated with shaking at room temperature for 20 min Luminescence signal was then measured on a Flexstation 3 plate reader (Molecular Device). Data were reported as relative Luminescent Units. Dose-response curves were generated in GraphPad prism, and $IC_{50}$ values were calculated using non-linear regression fit (Log (inhibitor) vs. response—Variable slope equation).

The same method was also used with normal human fibroblasts (HFF) to assess the non-specificity of cell killing of anti-JAG-1 antibodies/Protein G-DM1 complexes.

Figure 1B:
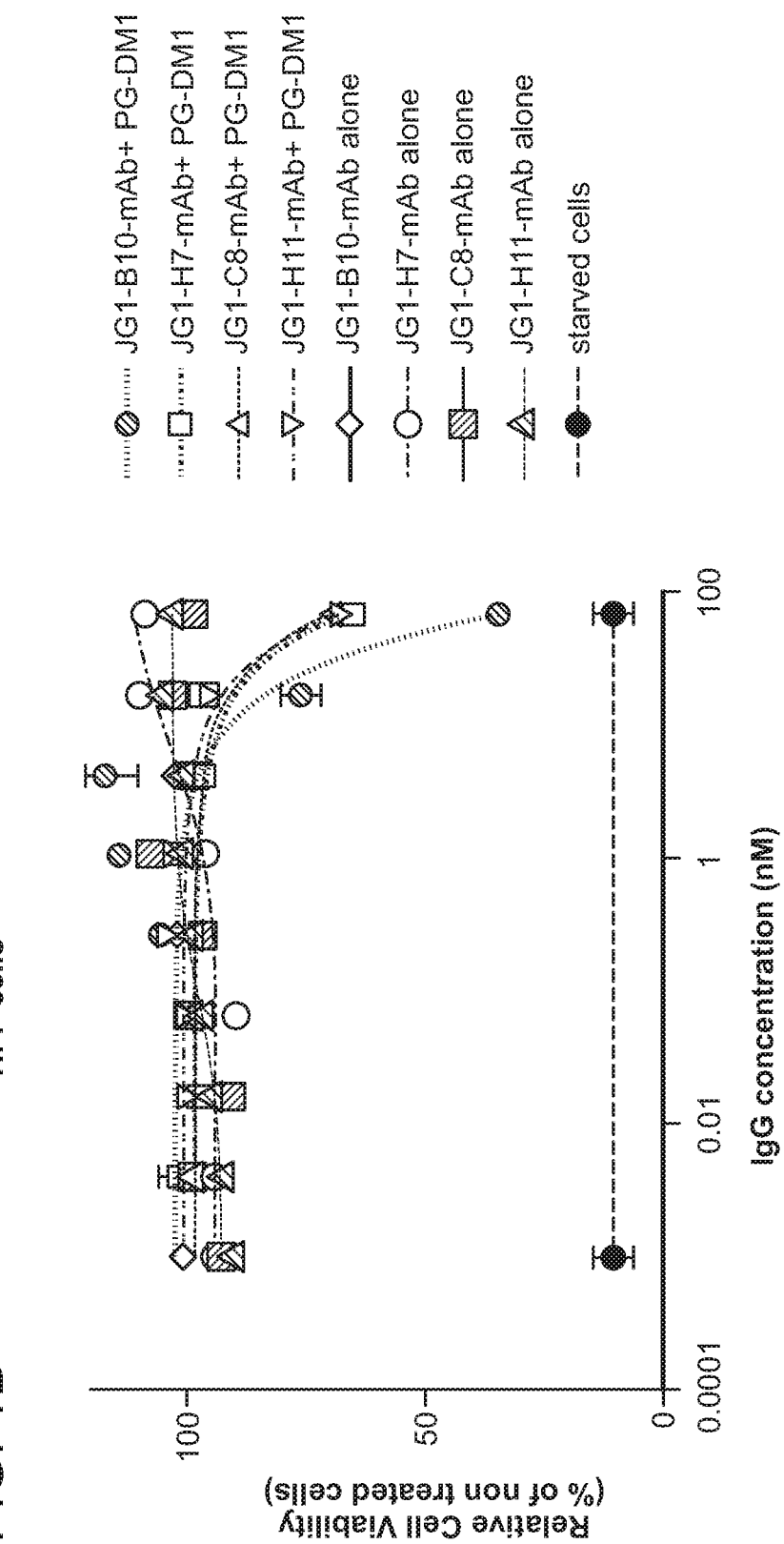
FIG. 1B illustrates the non-specific cell killing effect observed on normal human fibroblasts (HFF cells) with anti-JAG-1 antibodies complexed with Protein G-DM1 molecules. Corresponding naked antibodies were used as controls.

The results are shown in FIGS. 1A (Calu-6 cancer cells) and 1B (HFF cells), and Table 2. FIG. 1A shows that that anti-JAG-1 antibodies, especially antibodies JG1B10 and JG1H7, can induce cell killing when complexed with a cytotoxin such as DM-1, with $IC_{50}$ values of 1.35 and 3.89 nM respectively (Table 2). These data illustrate the potential of JAG-1 antibodies as antibody-drug conjugates. In FIG. 1B, data shows that very little non-specific cell killing was observed on normal HFF cells which do not overexpress JAG1, suggesting a good selectivity index for future JAG1 ADC.

TABLE 2

| | Protein G-DM1+ | | | |
|---|---|---|---|---|
| | JG1-B10 | JG1-H7 | JG1-C8 | JG1-H11 |
| IC50 (nM) | 1.35 | 3.89 | 87.26 | 26.51 |

Example 3

Figure 2:
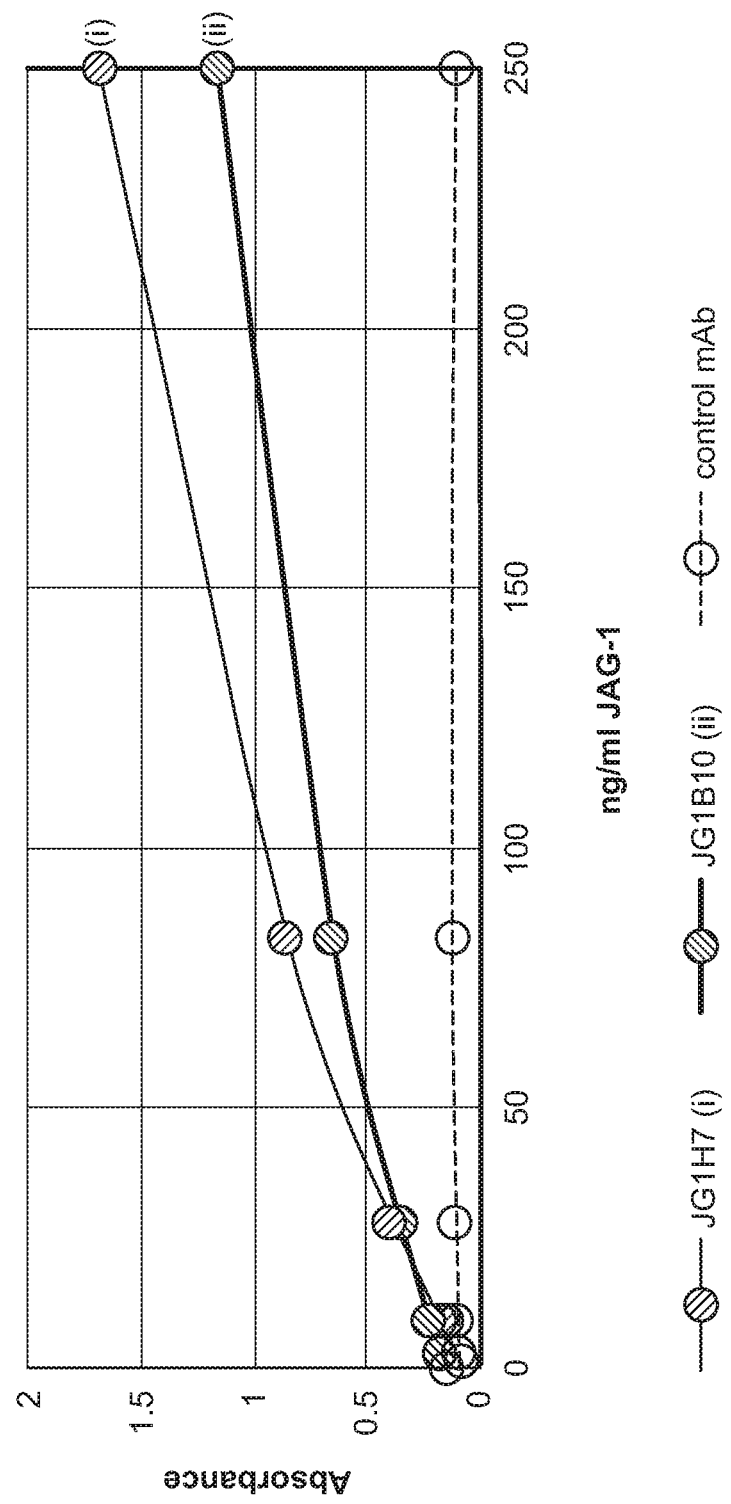
FIG. 2 is a graph that shows the results of a binding ELISA of two antibodies, JG1H7 and JG1B10, to human JAG-1.

An ELISA assay was carried out to determine antibody binding to human JAG1. A 96-well ELISA plate was coated overnight with goat anti-human lambda. The next morning the plate was blocked with casein solution for 1 hour, followed by addition of the JG1H7 and JG1B10 IgG antibodies at 0.3 µg/ml. After 1 hour, the plate was washed and serially diluted biotinylated human Jagged 1 (JAG1) was added. As a control, biotinylated JAG1 was added to wells that contained a control IgG. After an hour the plate was washed, labeled neutravidin was added and incubated for 30 minutes. The plate was washed, developed and the absorbance in each well measured by a spectrophotometer. As shown in FIG. 2, both JG1B10 (i) and JG1H7 (ii) show specific binding to human JAG1. The control antibody used was an IgG1 that does not bind to JAG-1 or JAG-2.

Figure 3:
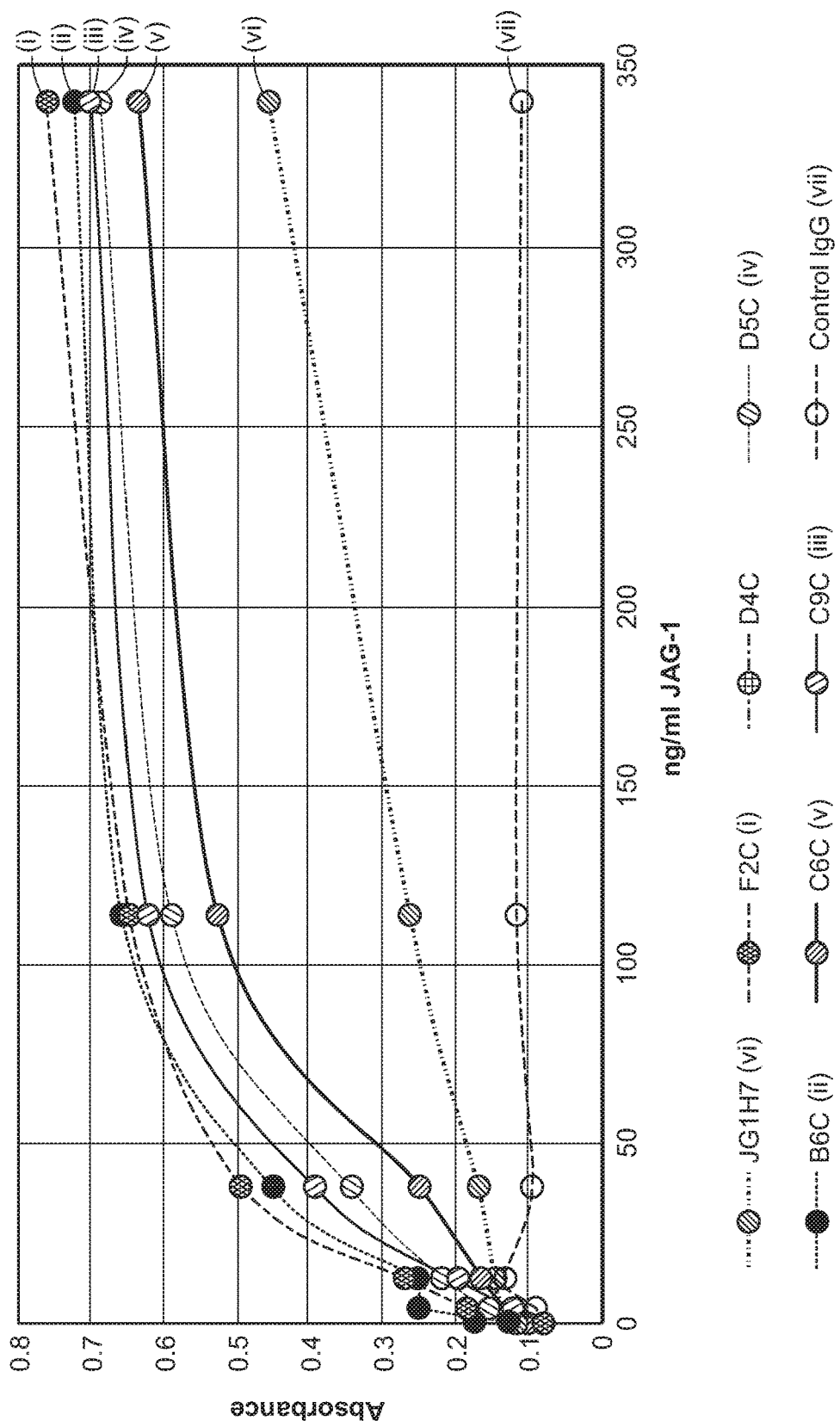
FIG. 3 is a graph that shows the results of a binding ELISA of JG1H7 and variants (F2C, D4C, D5C, B6C, C6C, C9C) to human JAG-1.

A similar protocol was used to measure binding of selected JG1H7 variants JG1H7-F2C (i), JG1H7-B6C (ii), JG1H7-C9C(iii), JG1H7-D5C (iv), JG1H7-C6C(v) and JG1H7(vi). These results are shown in FIG. 3. As shown in FIG. 3, all of the tested variants bound more JAG1 than the control antibody. The control antibody used was an IgG1 that does not bind to JAG1 or JAG2. In the results shown in FIG. 3, JG1H7-C4C almost perfectly overlays with JGH7-C9C, which is why it the line is not visible in the graph.

Figure 4:
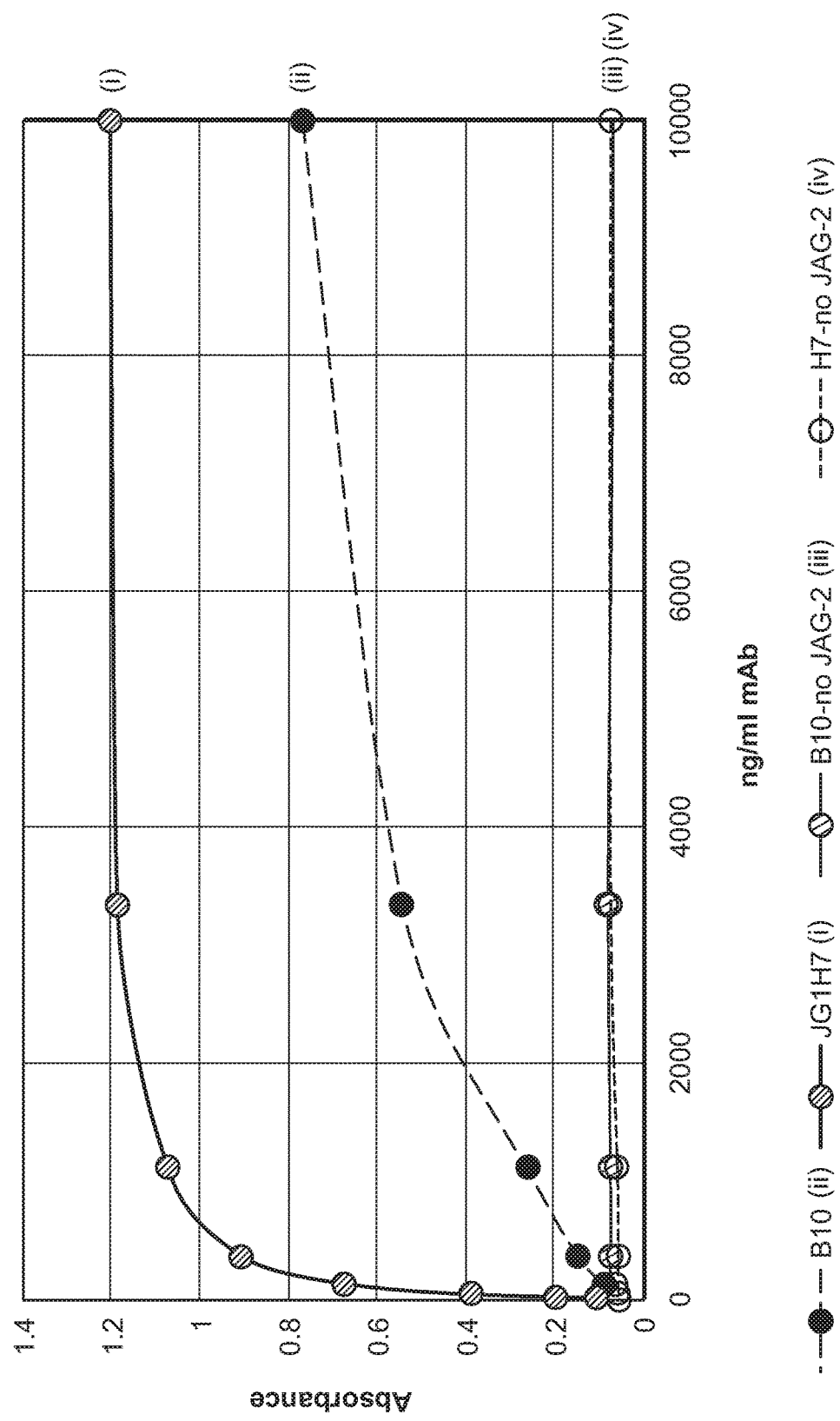
FIG. 4 is a graph that shows the results of a binding ELISA of two antibodies, JG1H7 and B10, to human JAG-2.

An ELISA assay was also carried out to determine the ability of the identified antibodies to bind to human JAG2. A 96-well ELISA plate was coated with human JAG2-Fc overnight. The next morning the plate was blocked with casein solution for 1 hour, followed by addition of serially diluted JG1H7 and JG1B10 IgG antibodies. As a control, antibodies were added to wells that were not coated with JAG2-Fc. After incubating for an hour, the plate was washed and labeled goat anti-human $F_D$ antibody was added for 30 minutes. The plate was washed, developed with substrate and the absorbance in each well measured on a spectrophotometer. As shown in FIG. 4, both JG1B10 (i) and JG1H7 (ii) show specific binding to JAG2.

Figure 5:
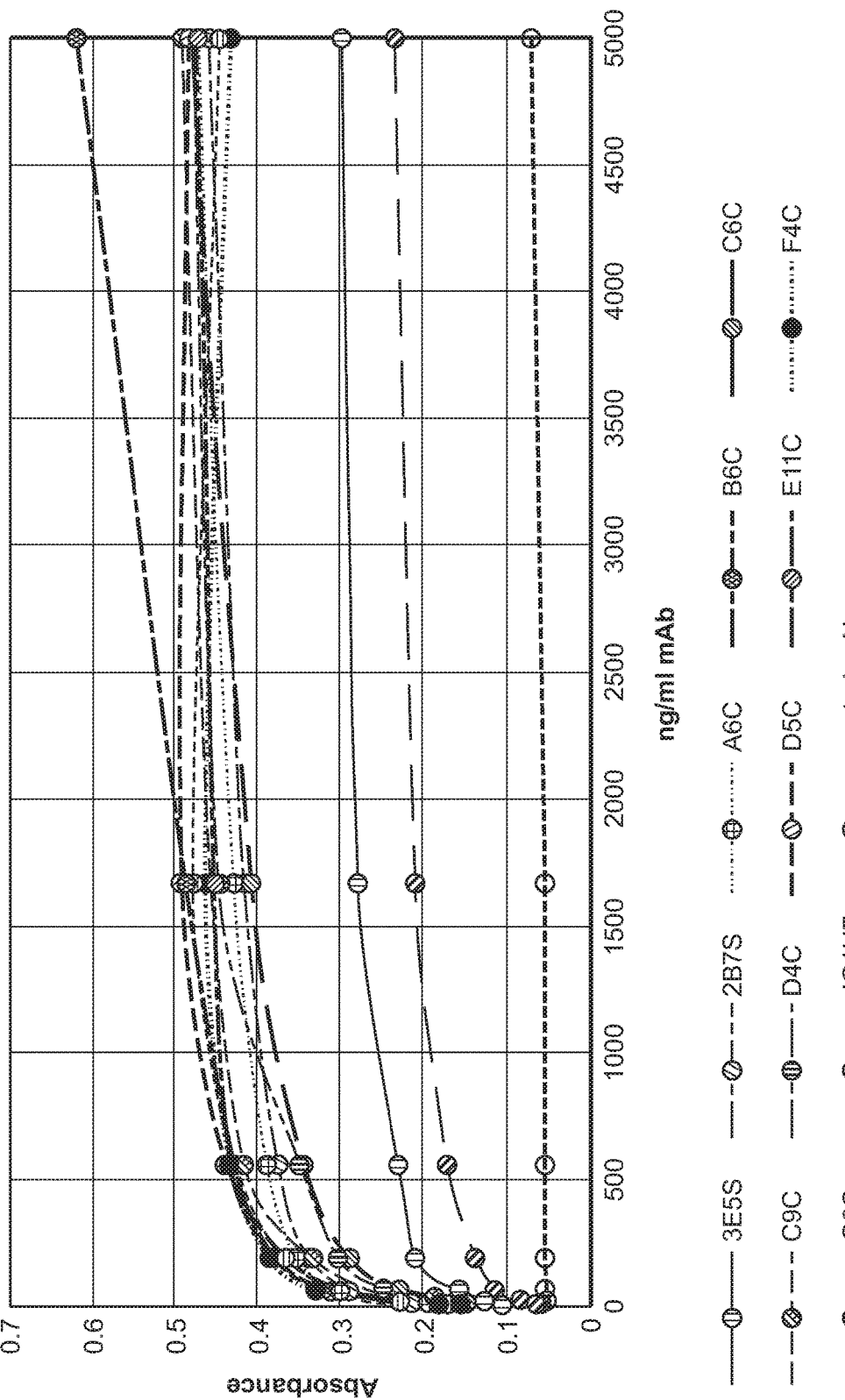
FIG. 5 is a graph that shows the results of a binding ELISA of JG1H7 and variants to human JAG-2.

A similar protocol was used in an ELISA to show binding of JG1H7 variants with JAG-2. These results are shown in FIG. 5. The control antibody used was an IgG1 that does not bind to JAG1 or JAG2. Similar to the results shown in FIG. 3, all of the tested variants showed specific binding to JAG2.

Figure 6:
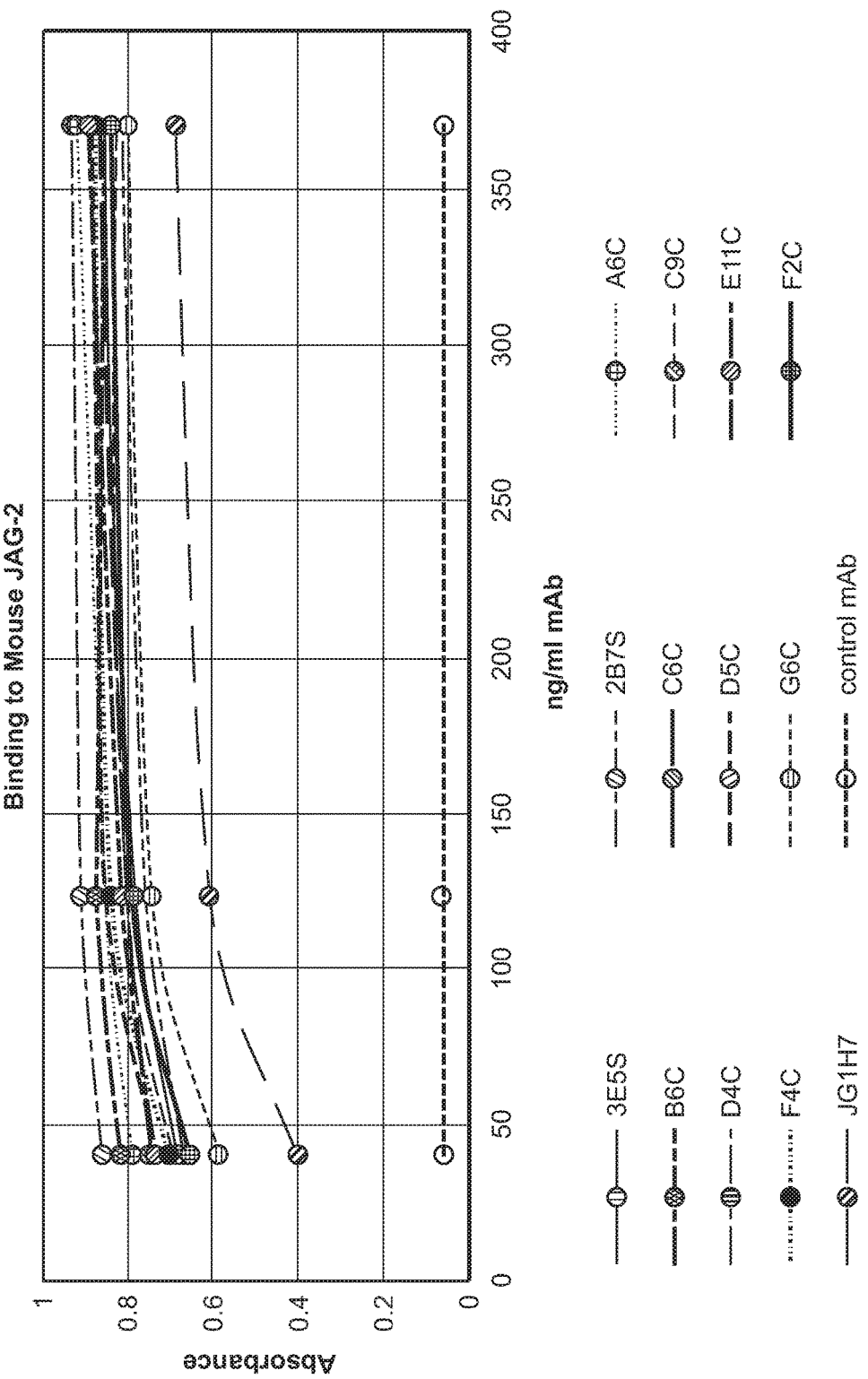
FIG. 6 is a graph that shows the results of a binding ELISA of JG1H7 and variants to murine JAG-2.

An ELISA assay was also carried out to determine the ability of the identified antibodies to bind to murine JAG2. A high-binding 96-well plate was coated overnight with 1 μg/ml recombinant mouse Jagged-2 Fc Chimera protein (R&D Systems) in PBS. The plate was then blocked with a 1:1 mixture of casein:Super Block for several hours at room temperature. Each IgG was diluted to 10 μg/ml in the blocking solution, serially diluted 3-fold and added to the 96-well plate after washing. After 2 h incubation and washing, anti-human $F_D$-HRP was added and incubated 1 hour. After washing, the plate was developed with TMB and stopped with 2M $H_2SO_4$ and the absorbance measured at 450 nm. As shown in FIG. 6, JG1H7 and the tested variants showed specific binding to murine JAG-2. The control antibody used was an IgG1 that does not bind to JAG1 or JAG2.

Finally, an ELISA assay was carried out to determine antibody cross-reactivity to delta-like 1 (DLL1) and delta-like 2 (DLL2). One ELISA plate was coated with anti-human lambda and another ELISA plate was coated with anti-human kappa overnight at 4° C. The next morning each plate was blocked with a 1:1 mixture of casein:Super Block for 2 hours at room temperature. The B10 IgG was diluted to 0.3 μg/ml in block and added to the anti-human lambda coated wells, while the JG1H7 IgG was diluted to 0.3 μg/ml in block and added to the anti-human kappa coated wells and incubated at room temperature for 3 hours. As a control, other wells were treated with only block. After washing, serially-diluted biotinylated antigen (JAG1, DLL1, DLL2) was added to a column with captured antibody and a control column with no antibody, and incubated 1 hour at room temperature. After washing, neutravidin-AP was added, incubated for 20 min at room temperature, the plate washed and developed with 1-step PNPP, and the plate analyzed in a plate reader. As shown in FIGS. 7A (JG1H7) and 7B (B10), while each antibody specifically bound to human JAG-1, little binding was observed to human DLL1 or human DLL2 under these conditions. The control antibody used was an IgG1 that does not bind to JAG1 or JAG2.

Example 4

This example describes a cellular binding assay to determine the $EC_{50}$ for certain anti-JAG1 antibodies binding to K562 cells (ATCC CCL-243), where the concentration at which 50% binding saturation ($EC_{50}$) is reached. In this example, K562 cells were resuspended in FACS Buffer (2% Fetal Bovine Serum in PBS) at $1 \times 10^6$ cells/ml. 50 μl (0.5× $10^5$ cells) were aliquoted into the wells of a 96-well plate. Plated cells were spun down and the supernatant discarded. Cells were resuspended in serially diluted concentrations of each JAG1 IgG in 30 μl FACS Buffer done in triplicate. The antibodies and cells were incubated for 1 hr at 4° C. and then washed 2× with FACS Buffer. Cells were resuspended in 50 μl goat anti-human IgG (γ-chain specific)-PE-conjugated secondary antibody (Southern Biotech #2040-09) diluted 1:750 in FACS Buffer. Cells were further incubated in the dark for 30 min at 4° C. and then washed 1× with FACS Buffer. The cells were resuspended in a final volume of 30 μl FACS Buffer and analyzed using an Intellicyt Flow Cytometer. Median fluorescence in the FL-2H channel was determined using FlowJo software and $EC_{50}$ value was determined by a variable slope non-linear regression using ForeCyte software. Table 3, below, shows the $EC_{50}$ of anti-JAG1 antibodies to human JAG1.

TABLE 3

| Name | EC50 (nM), K562 cells |
|---|---|
| JG1A7 | <1 |
| JG1H7 | 16 |
| JG1C8 | 16 |
| JG1H11 | 27 |
| JG1B10 | 32 |
| JH-F4 | 97 |

Example 5

Having identified anti-JAG1 antibody JG1H7 as a therapeutic antibody given its high affinity for human JAG1 and neutralization characteristics, variants of the JG1H7 antibody were made.

Briefly, JG1H7 was used as the parent antibody for further mutation in an effort to further improve affinity characteristics. Briefly, single amino acids within the CDRs (defined by Chothia or Kabat numbering) of JG1H7 were mutated such that each position within each CDR was mutated to all possible 20 amino acids. These variant antibodies were then screened for affinity changes relative to the parent antibody and antibodies that showed improvement in binding by ELISA were sequenced. Mutations that improved binding were included in a combinatorial library, which was then expressed and screened for further improved affinity antibodies. The light and heavy chain variable domain amino acid sequences of JG1H7 variants are described below in Table 4.

The amino acid sequences of the improved JG1H7 clones are shown below in Table 4.

TABLE 4

| Clone | Heavy Chain variable domain | Light Chain variable domain |
|---|---|---|
| JG1H7 3-2 (germline changed | EVQLVESGGGLIQPGGSLRLSCAAS AFTVSNFYMTWVRQAPGKGLEWV SVIDSGGNTYYADSVRGRFTISRDN | DIQMTQSPSSLSASVGDRVTITCRASQS ISTSLNWYQQKPGKAPKLLIYAASSLQ SGVPSRFSGSGSGTDFTLTISSLQPEDF |

TABLE 4-continued

| Clone | Heavy Chain variable domain | Light Chain variable domain |
|---|---|---|
| variant) | SKNTLFLQMNSLRAEDTAVYYCAR DLGYYYAMDVWGQGTTVTVSS SEQ ID NO: 111 | ATYYCQQSYSTPTFGQGTKLEIK SEQ ID NO: 112 |
| JG1H7-2B2 | EVQLVESGGGLIQPGGSLRLSCAAS AFTVSNFYMTWVRQAPGKGLEWV SVIDSGGNTYYADSVRGRFTISRDN SKNTLFLQMNSLRAEDTAVYYCAR DLGYYYAMDVWGQGTTVTVSS SEQ ID NO: 111 | DIQMTQSPSSLSASVGDRVTITCPASQS ISTSLNWYQQKPGKAPKLLIYAASSLQ SGVPSRFSGSGSGTDFTLTISSLQPEDF ATYYCQQSYSTPTFGQGTKLEIK SEQ ID NO: 113 |
| JG1H7-2A3 | EVQLVESGGGLIQPGGSLRLSCAAS AFTVSNFYMTWVRQAPGKGLEWV SVIDSGGNTYYADSVRGRFTISRDN SKNTLFLQMNSLRAEDTAVYYCAR DLGYYYAMDVWGQGTTVTVSS SEQ ID NO: 111 | DIQMTQSPSSLSASVGDRVTITCRASHS ISTSLNWYQQKPGKAPKLLIYAASSLQ SGVPSRFSGSGSGTDFTLTISSLQPEDF ATYYCQQSYSTPTFGQGTKLEIK SEQ ID NO: 114 |
| JG1H7-2A7 | EVQLVESGGGLIQPGGSLRLSCAAS AFTVSNFYMTWVRQAPGKGLEWV SVIDSGGNTYYADSVRGRFTISRDN SKNTLFLQMNSLRAEDTAVYYCAR DLGYYYAMDVWGQGTTVTVSS SEQ ID NO: 111 | DIQMTQSPSSLSASVGDRVTITCRASPS ISTSLNWYQQKPGKAPKLLIYAASSLQ SGVPSRFSGSGSGTDFTLTISSLQPEDF ATYYCQQSYSTPTFGQGTKLEIK SEQ ID NO: 115 |
| JG1H7-2A10S | EVQLVESGGGLIQPGGSLRLSCAAS AFTVSNFYMTWVRQAPGKGLEWV SVIDSGGNTYYADSVRGRFTISRDN SKNTLFLQMNSLRAEDTAVYYCAR DLGYYYAMDVWGQGTTVTVSS SEQ ID NO: 111 | DIQMTQSPSSLSASVGDRVTITCRASQS TSTSLNWYQQKPGKAPKLLIYAASSLQ SGVPSRFSGSGSGTDFTLTISSLQPEDF ATYYCQQSYSTPTFGQGTKLEIK SEQ ID NO: 116 |
| JG1H7-2A2 | EVQLVESGGGLIQPGGSLRLSCAAS AFTVSNFYMTWVRQAPGKGLEWV SVIDSGGNTYYADSVRGRFTISRDN SKNTLFLQMNSLRAEDTAVYYCAR DLGYYYAMDVWGQGTTVTVSS SEQ ID NO: 111 | DIQMTQSPSSLSASVGDRVTITCRASQS SSTSLNWYQQKPGKAPKLLIYAASSLQ SGVPSRFSGSGSGTDFTLTISSLQPEDF ATYYCQQSYSTPTFGQGTKLEIK SEQ ID NO: 117 |
| JG1H7-2A9 | EVQLVESGGGLIQPGGSLRLSCAAS AFTVSNFYMTWVRQAPGKGLEWV SVIDSGGNTYYADSVRGRFTISRDN SKNTLFLQMNSLRAEDTAVYYCAR DLGYYYAMDVWGQGTTVTVSS SEQ ID NO: 111 | DIQMTQSPSSLSASVGDRVTITCRASQS FSTSLNWYQQKPGKAPKLLIYAASSLQ SGVPSRFSGSGSGTDFTLTISSLQPEDF ATYYCQQSYSTPTFGQGTKLEIK SEQ ID NO:118 |
| JG1H7-2A1 | EVQLVESGGGLIQPGGSLRLSCAAS AFTVSNFYMTWVRQAPGKGLEWV SVIDSGGNTYYADSVRGRFTISRDN SKNTLFLQMNSLRAEDTAVYYCAR DLGYYYAMDVWGQGTTVTVSS SEQ ID NO: 111 | DIQMTQSPSSLSASVGDRVTITCRASQS PSTSLNWYQQKPGKAPKLLIYAASSLQ SGVPSRFSGSGSGTDFTLTISSLQPEDF ATYYCQQSYSTPTFGQGTKLEIK SEQ ID NO: 119 |
| JG1H7-E11 | EVQLVESGGGLIQPGGSLRLSCAAS AFTVSNFYMTWVRQAPGKGLEWV SVIDSGGNTYYADSVRGRFTISRDN SKNTLFLQMNSLRAEDTAVYYCAR DLGYYYAMDVWGQGTTVTVSS SEQ ID NO: 111 | DIQMTQSPSSLSASVGDRVTITCRASQS ISASLNWYQQKPGKAPKLLIYAASSLQ SGVPSRFSGSGSGTDFTLTISSLQPEDF ATYYCQQSYSTPTFGQGTKLEIK SEQ ID NO: 120 |
| JG1H7-C11 | EVQLVESGGGLIQPGGSLRLSCAAS AFTVSNFYMTWVRQAPGKGLEWV SVIDSGGNTYYADSVRGRFTISRDN SKNTLFLQMNSLRAEDTAVYYCAR DLGYYYAMDVWGQGTTVTVSS SEQ ID NO: 111 | DIQMTQSPSSLSASVGDRVTITCRASQS ISTTLNWYQQKPGKAPKLLIYAASSLQ SGVPSRFSGSGSGTDFTLTISSLQPEDF ATYYCQQSYSTPTFGQGTKLEIK SEQ ID NO: 121 |
| JG1H7-D10 | EVQLVESGGGLIQPGGSLRLSCAAS AFTVSNFYMTWVRQAPGKGLEWV SVIDSGGNTYYADSVRGRFTISRDN SKNTLFLQMNSLRAEDTAVYYCAR DLGYYYAMDVWGQGTTVTVSS SEQ ID NO: 111 | DIQMTQSPSSLSASVGDRVTITCRASQS ISTSQNWYQQKPGKAPKLLIYAASSLQ SGVPSRFSGSGSGTDFTLTISSLQPEDF ATYYCQQSYSTPTFGQGTKLEIK SEQ ID NO: 122 |
| JG1H7-2B7 | EVQLVESGGGLIQPGGSLRLSCAAS AFTVSNFYMTWVRQAPGKGLEWV SVIDSGGNTYYADSVRGRFTISRDN | DIQMTQSPSSLSASVGDRVTITCRASQS ISTSLNWYQQKPGKAPKLLIYLASSLQ SGVPSRFSGSGSGTDFTLTISSLQPEDF |

TABLE 4-continued

| Clone | Heavy Chain variable domain | Light Chain variable domain |
|---|---|---|
| | SKNTLFLQMNSLRAEDTAVYYCAR DLGYYYAMDVWGQGTTVTSS SEQ ID NO: 111 | ATYYCQQSYSTPTFGQGTKLEIK SEQ ID NO: 123 |
| JG1H7-1A8 | EVQLVESGGGLIQPGGSLRLSCAAS GFTVSNFYMTWVRQAPGKGLEWV SVIDSGGNTYYADSVRGRFTISRDN SKNTLFLQMNSLRAEDTAVYYCAR DLGYYYAMDVWGQGTTVTSS SEQ ID NO: 124 | DIQMTQSPSSLSASVGDRVTITCRASQS ISTSLNWYQQKPGKAPKLLIYAASSLQ SGVPSRFSGSGSGTDFTLTISSLQPEDF ATYYCQQSYSTPTFGQGTKLEIK SEQ ID NO: 112 |
| JG1H7-1A6 | SEVQLVESGGGLIQPGGSLRLSCAAS AFTVSNFSMTWVRQAPGKGLEWV SVIDSGGNTYYADSVRGRFTISRDN SKNTLFLQMNSLRAEDTAVYYCAR DLGYYYAMDVWGQGTTVTSS SEQ ID NO: 125 | DIQMTQSPSSLSASVGDRVTITCRASQS ISTSLNWYQQKPGKAPKLLIYAASSLQ SGVPSRFSGSGSGTDFTLTISSLQPEDF ATYYCQQSYSTPTFGQGTKLEIK SEQ ID NO: 112 |
| JG1H7-1A2 | SEVQLVESGGGLIQPGGSLRLSCAAS AFTVSNFGMTWVRQAPGKGLEWV SVIDSGGNTYYADSVRGRFTISRDN SKNTLFLQMNSLRAEDTAVYYCAR DLGYYYAMDVWGQGTTVTSS SEQ ID NO: 126 | DIQMTQSPSSLSASVGDRVTITCRASQS ISTSLNWYQQKPGKAPKLLIYAASSLQ SGVPSRFSGSGSGTDFTLTISSLQPEDF ATYYCQQSYSTPTFGQGTKLEIK SEQ ID NO: 112 |
| JG1H7-1B1 | SEVQLVESGGGLIQPGGSLRLSCAAS AFTVSNFAMTWVRQAPGKGLEWV SVIDSGGNTYYADSVRGRFTISRDN SKNTLFLQMNSLRAEDTAVYYCAR DLGYYYAMDVWGQGTTVTSS SEQ ID NO: 127 | DIQMTQSPSSLSASVGDRVTITCRASQS ISTSLNWYQQKPGKAPKLLIYAASSLQ SGVPSRFSGSGSGTDFTLTISSLQPEDF ATYYCQQSYSTPTFGQGTKLEIK SEQ ID NO: 112 |
| JG1H7-5A8 | SEVQLVESGGGLIQPGGSLRLSCAAS AFTVSNFYMTWVRQAPGKGLEWV SVIDSGGNTYYADSVRGRFTISRDN SKNTLFLQMNSLRAEDTAVYYCAR ALGYYYAMDVWGQGTTVTSS SEQ ID NO: 128 | DIQMTQSPSSLSASVGDRVTITCRASQS ISTSLNWYQQKPGKAPKLLIYAASSLQ SGVPSRFSGSGSGTDFTLTISSLQPEDF ATYYCQQSYSTPTFGQGTKLEIK SEQ ID NO: 112 |
| JG1H7-5B5 | SEVQLVESGGGLIQPGGSLRLSCAAS AFTVSNFYMTWVRQAPGKGLEWV SVIDSGGNTYYADSVRGRFTISRDN SKNTLFLQMNSLRAEDTAVYYCAR SLGYYYAMDVWGQGTTVTSS SEQ ID NO: 129 | DIQMTQSPSSLSASVGDRVTITCRASQS ISTSLNWYQQKPGKAPKLLIYAASSLQ SGVPSRFSGSGSGTDFTLTISSLQPEDF ATYYCQQSYSTPTFGQGTKLEIK SEQ ID NO: 112 |
| JG1H7-3E5 | SEVQLVESGGGLIQPGGSLRLSCAAS AFTVSNFYMTWVRQAPGKGLEWV SVIDSGGNTYYADSVRGRFTISRDN SKNTLFLQMNSLRAEDTAVYYCAR DLGYYYALDVWGQGTTVTSS SEQ ID NO: 130 | DIQMTQSPSSLSASVGDRVTITCRASQS ISTSLNWYQQKPGKAPKLLIYAASSLQ SGVPSRFSGSGSGTDFTLTISSLQPEDF ATYYCQQSYSTPTFGQGTKLEIK SEQ ID NO: 112 |
| JG1H7-G6C | EVQLVESGGGLIQPGGSLRLSCAAS AFTVSNFAMTWVRQAPGKGLEWV SVIDSGGNTYYADSVRGRFTISRDN SKNTLFLQMNSLRAEDTAVYYCAR DLGYYYAMDVWGQGTTVTSS SEQ ID NO: 127 | DIQMTQSPSSLSASVGDRVTITCRASQS ISTTQNWYQQKPGKAPKLLIYAASSLQ SGVPSRFSGSGSGTDFTLTISSLQPEDF ATYYCQQSYSTPTFGQGTKLEIK SEQ ID NO: 131 |
| JG1H7-A6C | EVQLVESGGGLIQPGGSLRLSCAAS AFTVSNFYMTWVRQAPGKGLEWV SVIDSGGNTYYADSVRGRFTISRDN SKNTLFLQMNSLRAEDTAVYYCAR SLGYYYALDVWGQGTTVTSS SEQ ID NO: 132 | DIQMTQSPSSLSASVGDRVTITCRASPS ISTSLNWYQQKPGKAPKLLIYLASSLQ SGVPSRFSGSGSGTDFTLTISSLQPEDF ATYYCQQSYSTPTFGQGTKLEIK SEQ ID NO: 133 |
| JG1H7-E11C | EVQLVESGGGLIQPGGSLRLSCAAS AFTVSNFYMTWVRQAPGKGLEWV SVIDSGGNTYYADSVRGRFTISRDN SKNTLFLQMNSLRAEDTAVYYCAR SLGYYYALDVWGQGTTVTSS SEQ ID NO: 132 | DIQMTQSPSSLSASVGDRVTITCRASQS ISTSLNWYQQKPGKAPKLLIYLASSLQ SGVPSRFSGSGSGTDFTLTISSLQPEDF ATYYCQQSYSTPTFGQGTKLEIK SEQ ID NO: 123 |
| JG1H7-C6C | EVQLVESGGGLIQPGGSLRLSCAAS AFTVSNFAMTWVRQAPGKGLEWV SVIDSGGNTYYADSVRGRFTISRDN | DIQMTQSPSSLSASVGDRVTITCRASQS ISTSLNWYQQKPGKAPKLLIYLASSLQ SGVPSRFSGSGSGTDFTLTISSLQPEDF |

TABLE 4-continued

| Clone | Heavy Chain variable domain | Light Chain variable domain |
| --- | --- | --- |
|  | SKNTLFLQMNSLRAEDTAVYYCAR DLGYYYALDVWGQGTTVTSS SEQ ID NO: 142 | ATYYCQQSYSTPTFGQGTKLEIK SEQ ID NO: 123 |
| JG1H7-C9C | EVQLVESGGGLIQPGGSLRLSCAAS AFTVSNFAMTWVRQAPGKGLEWV SVIDSGGNTYYADSVRGRFTISRDN SKNTLFLQMNSLRAEDTAVYYCAR DLGYYYAMDVWGQGTTVTSS SEQ ID NO: 127 | DIQMTQSPSSLSASVGDRVTITCRASQS ISTSLNWYQQKPGKAPKLLIYLASSLQ SGVPSRFSGSGSGTDFTLTISSLQPEDF ATYYCQQSYSTPTFGQGTKLEIK SEQ ID NO: 123 |
| JG1H7-F4C | EVQLVESGGGLIQPGGSLRLSCAAS AFTVSNFYMTWVRQAPGKGLEWV SVIDSGGNTYYADSVRGRFTISRDN SKNTLFLQMNSLRAEDTAVYYCAR SLGYYYALDVWGQGTTVTSS SEQ ID NO: 132 | DIQMTQSPSSLSASVGDRVTITCRASPS ISASLNWYQQKPGKAPKLLIYLASSLQ SGVPSRFSGSGSGTDFTLTISSLQPEDF ATYYCQQSYSTPTFGQGTKLEIK SEQ ID NO: 134 |
| JG1H7-F2C | EVQLVESGGGLIQPGGSLRLSCAAS AFTVSNFYMTWVRQAPGKGLEWV SVIDSGGNTYYADSVRGRFTISRDN SKNTLFLQMNSLRAEDTAVYYCAR ALGYYYALDVWGQGTTVTSS SEQ ID NO: 135 | DIQMTQSPSSLSASVGDRVTITCRASPS ISTSLNWYQQKPGKAPKLLIYLASSLQ SGVPSRFSGSGSGTDFTLTISSLQPEDF ATYYCQQSYSTPTFGQGTKLEIK SEQ ID NO: 133 |
| JG1H7-F1C | EVQLVESGGGLIQPGGSLRLSCAAS AFTVSNFYMTWVRQAPGKGLEWV SVIDSGGNTYYADSVRGRFTISRDN SKNTLFLQMNSLRAEDTAVYYCAR SLGYYYALDVWGQGTTVTSS SEQ ID NO: 132 | DIQMTQSPSSLSASVGDRVTITCRASQS ISASLNWYQQKPGKAPKLLIYLASSLQ SGVPSRFSGSGSGTDFTLTISSLQPEDF ATYYCQQSYSTPTFGQGTKLEIK SEQ ID NO: 136 |
| JG1H7-D4C | EVQLVESGGGLIQPGGSLRLSCAAS AFTVSNFYMTWVRQAPGKGLEWV SVIDSGGNTYYADSVRGRFTISRDN SKNTLFLQMNSLRAEDTAVYYCAR SLGYYYALDVWGQGTTVTSS SEQ ID NO: 132 | DIQMTQSPSSLSASVGDRVTITCRASQS TSASLNWYQQKPGKAPKLLIYLASSLQ SGVPSRFSGSGSGTDFTLTISSLQPEDF ATYYCQQSYSTPTFGQGTKLEIK SEQ ID NO: 137 |
| JG1H7-D5C | EVQLVESGGGLIQPGGSLRLSCAAS AFTVSNFYMTWVRQAPGKGLEWV SVIDSGGNTYYADSVRGRFTISRDN SKNTLFLQMNSLRAEDTAVYYCAR SLGYYYALDVWGQGTTVTSS SEQ ID NO: 132 | DIQMTQSPSSLSASVGDRVTITCRASQS PSTSLNWYQQKPGKAPKLLIYLASSLQ SGVPSRFSGSGSGTDFTLTISSLQPEDF ATYYCQQSYSTPTFGQGTKLEIK SEQ ID NO: 138 |
| JG1H7-A5C | EVQLVESGGGLIQPGGSLRLSCAAS AFTVSNFAMTWVRQAPGKGLEWV SVIDSGGNTYYADSVRGRFTISRDN SKNTLFLQMNSLRAEDTAVYYCAR SLGYYYALDVWGQGTTVTSS SEQ ID NO: 139 | DIQMTQSPSSLSASVGDRVTITCRASQS ISTSLNWYQQKPGKAPKLLIYLASSLQ SGVPSRFSGSGSGTDFTLTISSLQPEDF ATYYCQQSYSTPTFGQGTKLEIK SEQ ID NO: 123 |
| JG1H7-B2C | EVQLVESGGGLIQPGGSLRLSCAAS AFTVSNFAMTWVRQAPGKGLEWV SVIDSGGNTYYADSVRGRFTISRDN SKNTLFLQMNSLRAEDTAVYYCAR SLGYYYALDVWGQGTTVTSS SEQ ID NO: 139 | DIQMTQSPSSLSASVGDRVTITCRASQS PSASLNWYQQKPGKAPKLLIYLASSLQ SGVPSRFSGSGSGTDFTLTISSLQPEDF ATYYCQQSYSTPTFGQGTKLEIK SEQ ID NO: 140 |
| JG1H7-B6C | EVQLVESGGGLIQPGGSLRLSCAAS AFTVSNFAMTWVRQAPGKGLEWV SVIDSGGNTYYADSVRGRFTISRDN SKNTLFLQMNSLRAEDTAVYYCAR DLGYYYAMDVWGQGTTVTSS SEQ ID NO: 127 | DIQMTQSPSSLSASVGDRVTITCRASQS SSTSLNWYQQKPGKAPKLLIYLASSLQ SGVPSRFSGSGSGTDFTLTISSLQPEDF ATYYCQQSYSTPTFGQGTKLEIK SEQ ID NO: 141 |

TABLE 5

Anti-JAG1 Heavy and Light Variable Domain Amino Acid Sequences

| | Heavy chain variable domain sequence | Light chain variable domain sequence |
|---|---|---|
| JG1A1 | EVQLVESGAEVKKPGASVKVSCKASGYTFTSYGISWVRQAPGQGLEWMGWISAYNGNTNYAQKLQGRVTMTTDTSTSTAYMELRSLRSDDTAVYYCARGTGGDGFDYWGQGTLVTVSS SEQ ID NO. 1 | DVVMTQSPSSLSASVGDRVTITCRASQGISSWLAWYQQKPGKAPKLLIYDASSLQSGVPSRFSGSGSGTDFTLSISSLQPEDFATYYCQQANSLPLTFGGGTKVEIK SEQ ID NO. 2 |
| JG1A10 | EVQLVQSGAEVKKPGASVRVSCKASGYNFRNFDINWVRQAPGQGLEWMGWMNPSSGLTGFAPKFQGRVTLTRDTSIRTAYMEVSSLRSEDTAVYYCVRQRSGLDSWGQGTLVTVSS SEQ ID NO. 3 | QSVLTQPPSVSAAPGQKVTISCSGSSSNIGKYFVSWYQQFPGTAPKLLIYDNDQRPSGIPDRFSASKSGTSARLDITGLQTGDEADYYCGTWDSSLSAGVFGGGTKLTVL SEQ ID NO. 4 |
| JG1A12 | EVQLVQSGAEVKKPGASVRVSCKASGYTFTNYYIHWVRQAPGQGLEWMGIIIPSGGSTNYPPKFQGRVTLTRDTSTSTVYMELSSLRSEDTAVYYCVREYQGGHFDYWGQGTLVTVSS SEQ ID NO. 5 | SYELMQPHSVSESPGKTVTISCTGSSGSIASNYVQWYQQRPGSAPTTVIYEDNQRPSGVPDRFSGSIDSSSNSASLTISGLKTEDEADYYCQSYDSSIVVFGGGTKLTVL SEQ ID NO. 6 |
| JG1A3 | EVQLVESGGGLVKPGGSLRLSCAASGFTFNDYYMSWIRQAPGKGLEWVSYISRSGSTMYYADSVKGRFTISRDNAKNSLYLQMNSLRDEDTAVYYCATSVGHLEQWGQGTLVTVSS SEQ ID NO. 7 | DIQLTQSPSSLSASVGDRVTITCRATQGIGNYLAWYQQKPGKVPNLLIYAATTLQSGVPSRFSGSGSGTDFTLTISSLQPEDVASYYCQKYNSAPLTFGGGTKVEIK SEQ ID NO. 8 |
| JG1A4 | QVQLVESGGVVVQPGGSLRLSCAASGFTFDDYTMHWVRQAPGKGLEWVSLISWDGGSTYYADSVKGRFTISRDNSKNSLHLQMNSLRTEDTALYYCAKDIDEYSSSTGPDYWGQGTLVTVSS SEQ ID NO. 9 | QAVLTQPASVSESPGQSITISCTGSSSDIGGYNYVSWYQQHPGKAPKLIIYEVTKRPSGVPDRFSGSKSGNTASLTVSGLQAEDEADYYCSSYVGSNDVYVFGTGTKLTVL SEQ ID NO. 10 |
| JG1A5 | QVQLVQSGAEVQKPGASVKVSCKVSGYTLSELSIHWVRQAPGKGLEWMGGFDPEDGKIVYAQKFQDRVSMTQDTSTDTAYLQLSSLTSGDTALYYCATLAQWGDWFDRWGQGTLVTVSS SEQ ID NO. 11 | QAGLTQPPSASGTPGQRVTISCSGSSSNIGSNTVNWYQRLPGTAPKLVVYSNNQRPSGVPDRFSGSKSGTSASLVISGLQSEDEADYYCAAWDYDEEGLLFGGGTQLTVL SEQ ID NO. 12 |
| JG1A6 | QVQLVQSGAEVKKPGASVKVSCKASGNTFTSYYMHWVRQAPGQGLEWMGIISPSGDSTSYAQKFQGRVTMTKDTSTSTVSMELSSLRSEDTAVYYCARDQEGLRGSGYYGMDVWGQGTTVTVSS SEQ ID NO. 13 | QSVLTQPPSVSVAPGKTARITCGGNNIGSKSVHWYQQKPGQAPVLVIYYDSDRPSGIPERFSGSNSGNTATLTISRVEAGDEADYYCQVWDSSSDHVVFGGGTKLTVL SEQ ID NO. 14 |
| JG1A7 | QVQLVESGGGLVKPGGSLRLSCAASGFTFSDYYMSWIRQAPGKGLEWVSYISSSGSTIYYADSVKGRFTISRDNAKNSLYLQMNSLRAEDTAVYYCARVNSGYDAVDYWGQGTLVTVSS SEQ ID NO. 15 | QSALTQPPSVSGAPGQTVTISCTGSRSNIGTYDVHWYQQFAGSAPKLLIYHNNDRSSGVPDRFSGSKSGTSASLAITGLQAEDEAVYFCQSHDNVLGGVFGGGTKLTVL SEQ ID NO. 16 |
| JG1B1 | EVQLVQSGAEVKKPGSSVKVSCKASGDTFSSYGIWVRQAPGQGLEWVGRINSLLDRPDYAQNFQDRVTITADKSTSTAYMELNTLGPEDTAMYYCATEHYYESSEDPFFDFVVGQGTLVTVSS SEQ ID NO. 17 | QSVVTQPPSVSGAPGQRITISCTGSSSNIGAGYDVQWYLQFPGTAPKLLIHGSSNRPSGVPARFQGSKSGTSASLVITGLQAEDEADFYCQSFDSSLNGYVFGGGTKLTVL SEQ ID NO. 18 |
| JG1B10 | EVQLVESGGGLVQPGGSLRLSCAASGSTFSSYGMHWVRQAPGKGLEWVAVIWYDGSNKYYADSVKGRFTISRDNSKNTLYLQMNSLRAEDTAVYYCARGYNHDWGQGTLVTVSS SEQ ID NO. 19 | LPVLTQPASVSGSPGQSITISCTGTSSDVGGYNYVSWYQQHPGKAPKLMIYDVSNRPSGVSNRFSGSKSGNTASLTISGLQAEDEADYYCSSYTSSSTYVFGIGTKLTVL SEQ ID NO. 20 |
| JG1B11 | EVQLVQSGAEVKKPGASVKVSCKASGYTFTSYGISWVRQAPGQGLEWMGWISAYNGNTNYAQKLQGRVTMTTDTSTSTAYMELRSLRSDDTA | QAGLTQPHSVSESPGKTVTISCTRSSGSIASNYVQWYQQRPGSAPTTVIYEDNQRPSGVPDRFSGSIDSSSNSASLTISGLKTEDEADYYCQSYDSSNHLVVFGGGTKLT |

TABLE 5-continued

Anti-JAG1 Heavy and Light Variable Domain Amino Acid Sequences

| | Heavy chain variable domain sequence | Light chain variable domain sequence |
|---|---|---|
| | VYYCARDPYSSSWYGAEYFQHWG QGTLVTVSS SEQ ID NO. 21 | VL SEQ ID NO. 22 |
| JG1B2 | EVQLLESGGGVVQPGRPLRLSCAG SGFAFSGFAMHWVRQAPGKGLEW LAVISYDGRNNNYADSVKGRFTIS RDNSKNTLFLDMDSLRPDDTALY YCARDRSSGWYGLSDYWGQGTL VTVSS SEQ ID NO. 23 | QPVLTQPPSASGSPGQSVTISCTGTSSD VGGYNYVSWYQQHPGKAPKLMIYDV SNRPSGVSNRFSGSKSGNTASLTISGLQ AEDEADYYCSSYTSSSTYVFGTGTKLT VL SEQ ID NO. 24 |
| JG1B4 | QVQLVQSGSELKKPGASVRVSCK ASGYTFTNYYIHWVRQAPGQGLE WMGIIIPSGGSTNYPPKFQGRVTLT RDTSTSTVYMELSSLRSEDTAVYY CVREYQGGHFDYWGQGTLVTVSS SEQ ID NO. 25 | QLVLTQSHSVSESPGKTVTISCTGSSGSI ASNYVQWYQQRPGSAPTTVIYEDDLRP SGVPDRFSGSIDSSSNSASLTISGLKTED EADYYCQSYDRYNVVFGGGTKLTVL SEQ ID NO. 26 |
| JG1B5 | QVQLVQSGAEVKKPGASVKVSCK ASGNTFTSYYIHWVRQAPGQGLE WMGIISPSGDSTSYAQKFQGRVTM TKDTSTSTVSMELSSLRSEDTAVY YCARDQEGLRGSGYYGMDVWGQ GTTVTVSS SEQ ID NO. 27 | SYVLTQPPSVSVAPGKTARITCGGNNIG SKSVHWYQQKPGQAPVLVIYYDSDRP SGIPERFSGSNSGNTATLTISRVEAGDE ADYYCQVWDSSSDHVVFGGGTKLTVL SEQ ID NO. 28 |
| JG1B6 | EVQLVESGGGVVQPGRSLRLSCAA SGFPFSSYAMHWVRQAPGKGLEW VAVISYDGSNKYYADSVKGRFTIS RDNSKNTLYLQMNSLRPEDTAVY YCARDLPACSGGSCYATWGGFDY WGQGTLVTVSS SEQ ID NO. 29 | SSELTQDPAVSVALGQTLTITCQGDSLR SYYASWYQQKPGQAPLLVFYGYNSRP SEIPDRFSGSFTGDTASLTITGAQAEDE ADYYCSSMSGDLVVXGGGTKVTVL SEQ ID NO. 30 |
| JG1B8 | QMQLVQSGAEVKKPGSSVKVSCK ASGATFSSYAMSWVRQAPGQGLE WMGAVIPIFGTTNYAPKFEGRVTIT ADESTSTVYMELSSLTSEDTAVYY CARQIGEVVGGIMEDYWGQGTLV TVSS SEQ ID NO. 31 | DIVMTQSPSSLSASVGDRVTITCRASQG ITNSLAWYQQKPGKVPKLLIYAASTLQ SGVPSRFSGSGSGTDFTLTISSLQPEDV ASYYCQKYDSAPLTFGGGTKVEIK SEQ ID NO. 32 |
| JG1C3 | QMQLVQSGAEVKKPGASVKVSCK ASGNTFTSYYMHWVRQAPGQGLE WMGIISPSGDSTSYAQKFQGRVTM TKDTSTSTVSMELSSLRSEDTAVY YCARDQEGLRGSGYYGMDVWGQ GTTVTVSS SEQ ID NO. 33 | SYELMQPPSVSVAPGKTARITCGGNNI GSKSVHWYQQKPGQAPVLVIYYDSDR PSGIPERFSGSNSGNTATLTISRVEAGDE ADYYCQVWDSSSDHVVFGGGTKLTVL SEQ ID NO. 34 |
| JG1C4 | QMQLVQSGADVKKPGASVKVSCK ASGNTFTSYYMHWVRQAPGQGLE WMGIISPSGDSTSYAQKFQGRVTM TKDTSTSTVSMELSSLRSEDTAVY YCARDQEGLRGSGYYGMDVWGQ GTMVTVSS SEQ ID NO. 35 | SYELMQPPSVSVASGKTARITCGGNNI GSKSVHWYQQKPGQAPVLVVYDDSD RPSGIPERFSGSNSGNTATLTISRVEAG DEADYYCQVWDSSSDHVVFGGGTKLT VL SEQ ID NO. 36 |
| JG1C5 | EVQLLESGGGLIQPGGSLRLSCAAS GFTVSSNYMTWVRQAPGKGLEW VSVIYSGGNTFYADSVKGRFTISRD NAKNSLYLQMNSLRAEDTAVYYC AREMSGPYFDYWGQGTLVTVSS SEQ ID NO. 37 | QAVVTQPPSASGTPGQRVTISCSGSSSN IGSNPVSWYQQLPGTAPKLLIYSNNQR PSGVPDRFSGSKSGTSASLAISGLQSED EADYYCAAWDDSLNGDVIFGGGTKLT VL SEQ ID NO. 38 |
| JG1C8 | EVQLVQSGAEVKKPGSSVKVSCK ASGGTFSSYAISWVRQAPGQGLEW MGWISAYNGNTNYAQKLQGRVT MTTDTSTSTAYMELRSLRSDDTAV YYCARSRYDFWSGYYSGMDVWG QGTTVTVSS SEQ ID NO. 39 | NFMLTQPRSVSGSPGQSVTISCTGTSSD VGGYHYVSWYQQHPGKAPKLIIYDVS RRPSGVPDRFSGSKSGNTASLTVSGLQ AEDEADYYCSSYGGSNNFVFGTGTKLT VL SEQ ID NO. 40 |
| JG1D1 | QVQLVESGGGVVQPGRPLRLSCA GSGFAFSGFAMHWVRQAPGKGLE WLAVISYDGRNNNYADSVKGRFTI SRDNSKNTLFLDMDSLRPDDTALY YCARDRSSGWYGLSDYWGQGTL VTVSS SEQ ID NO. 41 | QAGLTQPASVSGSPGQSITISCTGTSSD VGRYDYVSWYQQHPGKAPKLMIYDVT KRPSGVSNRFSGSKSGNTASLTISGLQA EDEADYYCISYTTSSTYVFGTGTKVTV L SEQ ID NO. 42 |
| JG1D10 | QVQLVQSGAEVKKPGASVKVSCK ASGYTFTSYNIHWVRQAPGQRFE | EIVMTQSPATLSVSPGERATLSCRASQS VRSNLAWYQQKPGQAPRLLIYGASTR |

TABLE 5-continued

Anti-JAG1 Heavy and Light Variable Domain Amino Acid Sequences

| Heavy chain variable domain sequence | Light chain variable domain sequence |
|---|---|
| WMGWISTDNGYTEYSQKFQDRVT ITRDTSASTAYMELSSLRSEDTADY YCLSGYYFDYWGQGTLVTVSS SEQ ID NO. 43 | ATGIPDRFSGSGSGTEFTLTISSLQSEDF AVYSCQQYENWPTFGQGTKVEIK SEQ ID NO. 44 |
| JG1D11 EVQLVESGAEVKKPGASVKVSCK ASGYTFTNYYMHWVRQAPGQGLE WMGIINPSSGSTTYAQKFQGRVTM TRDTSTSTVYMELSSLRSEDRAVY YCARGQGSSGWYTFDYWGQGTL VTVSS SEQ ID NO. 45 | AIQLTQSPSSLSASVGDRVTISCQASQDI SNFLNWYQQKPGKAPKLLIYAASKLQS GVPSRFSGSGSGTDFSLTINSLQPEDFA TYYCQQTNSFPLTFGQGTKVEIK SEQ ID NO. 46 |
| JG1D7 QVQLVQSGAEVKKPGASVKVSCK ASGYTFTSYYMHWVRQAPGQGLE WMGIINPSGGSTSYAQKFQGRVTM TRDTSTSTVYMELSSLRSEDTAVY YCARDVGGEGVVDYWGQGTLVT VSS SEQ ID NO. 47 | SYELMQPPSVSVAPGQTARITCGGKNI GRKSVHWYQQKPGQAPVLVVYDDRD RPSGIPERFSGSNSGNTATLTISRVEAG DEADYYCQVWDSSTDHVVFGGGTKVT VL SEQ ID NO. 48 |
| JG1D8 QVQLVQSGAEVKKPGATVKISCK VSGYTFTDYYMHWVRQAPGQGLE WVGIINPNGDKAQYTQKLKGRVT MTRDTSTNTVYMELSSLTSEDTAV YYCTTDHNWRFDSWGQGTLVTVS S SEQ ID NO. 49 | DIQMTQSPSSLSASVGDRVTITCQASQD ISNYLNWYQQKPGKAPKLLIYDASNLE TGVPSRFSGSGSGTDFTFTISSLQPEDIA TYYCQQYTTFGQGTRLEIK SEQ ID NO. 50 |
| JG1E1 EVQLVQSGAEVKKPGASVKVSCK ASGNTFTSYYMHWVRQAPGQGLE WMGIISPSGDSTSYAQKFQGRVTM TKDTSTSTVSMELSSLRSEDTAVY YCARDQEGLRGSGYYGMDVWGQ GTMVTVSS SEQ ID NO. 51 | SYELMQPPSVSVAPGKTARITCGGNNI GSKSVHWYQQKPGQAPVLVVYDSD RPSRIPERFSGSNSGNTATLTISRVEAGD EADYYCQVWDSSSDHVVFGGGTKLTV L SEQ ID NO. 52 |
| JG1E11 QVQLVESGAEVKKPGASVKVSCK ASGYTFTSYGISWVRQAPGQGLE WMGWISAYNGNTNYAQKLQGRV TMTTDTSTSTAYMELRSLRSDDTA VYYCARTNSDYYDSSGYTNAFDI WGQGTMVTVSS SEQ ID NO. 53 | DIVMTQSPSSLSASVGDRVTITCRASQS ISRSLNWYQKKPGKAPNLLIYGASSLQ SGVPSRFSGSGSGTDFTLTISSLQPEDFA TYYCQQSYTMPISFGPGTKVDIK SEQ ID NO. 54 |
| JG1E7 QVQLVQSGAEVKKPGSSVKVSCK ASGGTFSSYAISWVRQAPGQGLEW MGGIIPIFGTANYAQKFQGRVTITA DESTSTAYMELSSLRSEDTAVYYC AGYSGSYFGKFDYWGQGTLVTVS S SEQ ID NO. 55 | QAGLTQPPSVSGAPGQRVSISCTGSDSN IGAPYDVHWYQQLPGTAPRLLIYANTK RPSGVPDRFSGWKSGTSASLAISGLQSE DEAAYYCAAWDDRLNAYIFGSGTKLT VL SEQ ID NO. 56 |
| JG1E8 QVQLVQSGAEVKKPGASVKVSCK ASGYTFTSYYMHWVRQAPGQGLE WMGIINPSGGSTSYAQKFQGRVTM TRDTSTSTVYMELSSLRSEDTAVY YCARGGDSSGDYYYGMDVWGQG TTVTVSS SEQ ID NO. 57 | QPVLTQPPSASGTPGQRVTISCSGSSSNI GTNYVNWYQQFPGTAPKQLIYSNNHR PSGVPDRFSGSKSGTSASLAISGLRSED EADYYCAAWDDSLSGWVFGVGTKLT VL SEQ ID NO. 58 |
| JG1F1 EVQLVQSGAEVKKPGASVKVSCK ASGYTFTSYYMHWVRQAPGQGLE WMGIINPSGGSTSYAQKFQGRVTM TRDTSTSTVYMELSSLRSEDTAVY YCARGYYDSSGYGVGFDYWGQG TLVTVSS SEQ ID NO. 59 | QTVVTQPPSVSAAPGQKVTISCSGSSSN IGNNYVSWYQQLPGTAPKLLIYDNNKR PSGIPDRFSGSKSGTSATLGITGLQTGD EADYYCGTWDNSLSAGVFGGGTKLTV L SEQ ID NO. 60 |
| JG1F10 EVQLVQSGVEVKKPGATVKISCKV SGYTFTDYYMHWVRQAPGQGLE WMGIINPSGGSTSYAQKFQGRVTM TRDTSTSTVYMELSSLRSEDTAVY YCARDRVDSSAWSPGADYWGQG TLVTVSS SEQ ID NO. 61 | QSVLTQPPSVSGAPGQRVTISCTGSSSNI GAGYDVHWYQQLPGTAPKLLIYDNNK RPSGIPDRFSGSKSGTSATLGITGLQTG DEADYYCGSWDASLSAAVFGGGTKLT VL SEQ ID NO. 62 |
| JG1F7 EVQLVQSGGEVKKPGASVKVSCK ASGNTFTSYYMHWVRQAPGQGLE WMGIISPSGDSTSYAQKFQGRVTM TKDTSTSTVSMELSSLRSEDTAVY YCARDQEGLRGSGYYGMDVWGQ GTTVTVSS SEQ ID NO. 63 | SYELMQPPSVSVAPGKTARITCGGNNI GSKSVHWYQQKPGQAPVLVIYYDSDR PSGIPERFSGSNSGNTATLTISRVEAGDE ADYYCQVWDSSSDHVVFGGGTQLTVL SEQ ID NO. 64 |

TABLE 5-continued

Anti-JAG1 Heavy and Light Variable Domain Amino Acid Sequences

| | Heavy chain variable domain sequence | Light chain variable domain sequence |
|---|---|---|
| JG1F8 | QITLKESGGGVVQPGRSLRLSCAA SGFTFSTYGMHWVRQAPGKGLEW VAVILNDGSQSHYADSLKGRFTISR DNSRNTLYLQMDSLRVEDTAMYY CARDDDRAANAFDVWGQGTMVT VSS SEQ ID NO. 65 | QSVLTQPPSVSAAPGQKVTISCSGSSSNI GNNYVSWYQQLPGTAPKLLIYDNNKR PSGIPDRFSGSKSGTSATLGITGLQTGD EADYYCGTWDSSLSAWVFGGGTKLTV L SEQ ID NO. 66 |
| JG1G11 | EVQLVQSGGEVKKPGASVKVSCK ASGNTFTSYYMHWVRQAPGQGLE WMGIISPSGDSTSYAQKFQGRVTM TKDTSTSTVSMELSSLRSEDTAVY YCARDQEGLRGSGYYGMDVWGQ GTTVTVSS SEQ ID NO. 67 | SYELMQPPSVSVAPGKTARITCGGNNI GSKSVHWYQQKPGQAPVLVIYYDSDR PSGIPERFSGSNSGNTATLTISRVEAGDE ADYYCQVWDSSSDHVVFGGGTQLTVL SEQ ID NO. 68 |
| JG1G5 | EVQLVESGAEVKKPGASVKVSCK ASGYTFTNYYLHWVRQAPGQGLE WVGLLNPSGGSTNYAQKFQGRVT MTTDTSTSTAYMELRSLRSDDTAV YYCARSPDDYYYGSGNYDYWGQ GTLVTVSS SEQ ID NO. 69 | QPVLTQPASVSGSPGQSITISCTGTSSDV GGYNYVSWYQQYPGKAPKLLIYDVNK RPSGVSIRFSASKSGNAASLTLSGLQAE DEADYYCSSYSSRRGVVFGGGTKLTVL SEQ ID NO. 70 |
| JG1H1 | EVQLVQSGAEVKKPGASVKVSCK ASGYTFTSYYMHWVRQAPGQGLE WMGIINPSGGSTSYAQKFQGRVTM TRDTSTSTVYMELSSLRSEDTAVY YCARDRYSSSAAGYGMDVWGQG TTVTVSS SEQ ID NO. 71 | QPVLTQPASVSGSPGQSITISCTGINSNV DGSDAVSWYQQHPGKAPKLIAFDVTQ RPSGVPDRFSASKSGKTASLTISGLQPE DEADYYCSSYTTSSTFVFGTGTKVTVL SEQ ID NO. 72 |
| JG1H11 | EVQLVESGGGVVQPGRSLRLSCAA SGFTFSSYGMHWVRQAPGKGLEW VAVISYDGSNKYYADSVKGRFTIS RDNSKNTLYLQMNSLRAEDTAVY YCAKDDWNYALDYWGQGTLVTV SS SEQ ID NO. 73 | QPVLTQPASVSGSPGQSITISCTGTRSD VGGYSYVSWYQQHPGKAPKLIYDVTK RPSGVSNRFSGSKSGNTASLTISGLQAE DEADYYCSSYTSSSTYVFGTGTKVTVL SEQ ID NO. 74 |
| JG1H5 | QVQLVESGGGLVQPGGSLRLSCAA SGFTFSSYAMSWVRQAPGKGLEW VSAISGSGGSTYYADSVKGRFTISR DNSKNTLYLQMNSLRAEDTAVYY CAKEDLAMRRGYSYGYPGYWGQ GTLVTVSS SEQ ID NO. 75 | QSVLTQPPSASGSPGQSLAISCTGTSSD VGGYNYVSWYQHHPGKAPKLIIYDVN KRPSGVPDRFSGSKSGNTASLTISGLQA EDEADYFCSSYAVNNNSPYFFGTGTKV TVL SEQ ID NO. 76 |
| JG1H7 | QVQLVQSGGGLIQPGGSLRLSCAA SAFTVSNFYMTWVRQAPGKGLEW VSVIDSGGNTYYADSVRGRFTISR DNSKNTLFLQMNSLRAEDTAVYY CARDLGYYYAMDVWGQGTTVTV SS SEQ ID NO. 77 | DIVMTQSPSSLSASVGDRVTITCRASQS ISTSLNWYQQKPGKAPKLLIYAASSLQS GVPSRFSGSGSGTDFTLTISSLQPEDFAT YYCQQSYSTPTFGQGTKLEIK SEQ ID NO. 78 |
| JH1A1 | EVQLVQSGAEVKKPGASVKVSCK ASGYTFTSYGISWVRQAPGQGLE WMGWISAYNGNTNYAQKLQGRV TMTTDTSTSTAYMELRSLRSDDTA VYYCARDLAYSSGWLDYWGQGT LVTVSS SEQ ID NO. 79 | QAGLTQPASVSGSPGQSITMSCIVSNIDI GGFHYVSWYQHRPGEAPKLLIYDVDK RPPGVSNRFSASKSGHTASLTISGLHPE DDAEYYCSSFTSRSVLFGGGTKVTVL SEQ ID NO. 80 |
| JH1A11 | QVQLVQSGAEVKKPGASVKVSCK ASGYTFTNYDISWVRQAPGQGLE WMGWISTYNGDTIYAQKLQDRVT MTTDTSTSTAYMEVRSLRSDDTAV YYCARGNDLDYWGQGTLVTVSS SEQ ID NO. 81 | QSVLTQPASVSGSPGQSITISCTETSSDV GTYNYVSWYQQHPGKAPQLIIFDVSNR PSGVSTRFSGSKSGNTASLTISGLQTED EADYYCSSYIATYTPLYVFGTGTKLTV L SEQ ID NO. 82 |
| JH1A2 | EVQLVESGAEVKKPGASVKVSCK ASGYTFTNYYMHWVRQAPGQGLE WMGIINPSDGNTSYAQKFQGRVT MTKDTSTSTVYMELSSLRSDDTAV YYCARESSSWETYFDYWGQGTLV TVSS SEQ ID NO. 83 | SYELMQPPSVSVAPGKTAKITCGGDNI GIKSVHWYQQKPGQAPILVIHHDRGRP SGIPERLSGSNSGNTATLTISRVEAGDE ADYYCQVWDGTSDHVVFGGGTKLTV L SEQ ID NO. 84 |
| JH1A4 | QVQLVQSGAEVKKPGASVKVSCK ASGYTFTGYYMHWVRQAPGQGLE WMGWINPNSGGTNYAQKFQGRV TITADESTSTAYMELSSLRSEDTAV | SSELTQDPAVSVALGQTVRITCQGDSL RSYYASWYQQKPGQAPVLVIYGKNNR PSGIPDRFSGSSSGNTASLTITGAQEDE ADYYCNSRDSSGNHPLVFGTGTKLTVL |

TABLE 5-continued

Anti-JAG1 Heavy and Light Variable Domain Amino Acid Sequences

| | Heavy chain variable domain sequence | Light chain variable domain sequence |
|---|---|---|
| | YYCAREGPEYCSGGSCYSADAFDI WGQGTMVTVSS SEQ ID NO. 85 | SEQ ID NO. 86 |
| JH1B1 | EVQLVQSGAEVRKPGASVKVSCK PSGYIFSSRYMHWVRQAPGQGLE WMGIVNPSGGSTKYAQKFQGRIT MTRDTSTRTFYMELNSLRSEDTAV YYCARHTGNHGGWYMDGFDMW GQGTMVTVSS SEQ ID NO. 87 | QAGLTQPPSVSGAPGQRVTISCSGSTSN IGSNIVNWYQQLPGTAPKLLIFNNHHRP SGVPDRFSGSKSGTSASLAISGLQSEDE ADYYCAAWDDSQNAYVFGTGTKVTV L SEQ ID NO. 88 |
| JH1B3 | EVQLVQSGAEVKKPGASVKVSCK ASGYTFTGYYMHWVRQAPGQGLE WMGWINPNSGGTNYAQKFQGRV TMTRDTSISTAYMELSRLRSDDTA VYYCAREEEGGRLGFDYWGQGTL VTVSS SEQ ID NO. 89 | NFMLTQPPSVSAAPGQRVTISCSGRSTN IGKNDVSWYQQFPGAAPKLLIYDNNKR PSGIPDRFSGSKSGTSATLGITGLQTGD EADYYCGTWDNGLGVVLFGGGTKLTV L SEQ ID NO. 90 |
| JH1B7 | EVQLVQSGAEVKKPGASVKVSCK ASGYTFTSYGISWVRQAPGQGLE WMGWISAYNGNTNYAQKLQGRV TMTTDTSTSTAYMELRSLRSDDTA VYYCARDLAYSSGWLDYWGQGT LVTVSS SEQ ID NO. 91 | QPVLTQPASVSGSPGQSITISCTGTSSDV GGYNYVSWYQQHPDKAPKLIIYDVSK RPSGVSTRFSGSKSAYTASLTISGLRAE DEADYYCSSFTNDSPVVFGGGTQLTVL SEQ ID NO. 92 |
| JH1C10 | EVQLVESGAEVKKPGASVKVSCK ASGYTFTGYYIHWVRQAPGQGLE WMGVINPSGGSTTYAEKFQGRITM TRDTSTKMLFMELSSLRSDDTAVY YCARSPGAALFDYWGQGTLVTVS S SEQ ID NO. 93 | QSVVTQPPSVSAAPGQKVTISCSGSSSN IGNNYVSWYQQVPGTAPKLLIYDNNER PSGIPDRFSGSKSGTSATLGITGLQTGD EADYYCGTWDSSLSAGVFGGGTKLTV L SEQ ID NO. 94 |
| JH1C2 | QVQLVESGGGLVKPGGSLRLSCAA SGFTFIDYSMHWVRQAPGKGLEW VSSISSSSSYIYYADSVKGRFTISRD NAKNSLYLQMNSLRAEDTAVYYC ARDGLYDSSVRDAFDIWGQGTMV TVSS SEQ ID NO. 95 | QSVLTQPRSVSGSPGQSVTISCTGTSSD VGGYNYVSWYQQHPGKAPKLMIYDV SKRPSGVPDRFSGSKSGNTASLTVSGL QAEDEADYYCSSYAGSNNLVFGGGTK VTVL SEQ ID NO. 96 |
| JH1D7 | EVQLVESGAEVKKPGASVKVSCK ASGYTFTNYYMHWVRQAPGQGLE WMGIINPSDGNTSYAQKFQGRVT MTKDTSTSTVYMELSSLRSDDTAV YYCARESSSWETYFDYWGQGTLV TVSS SEQ ID NO. 97 | SYELMQPPSVSVAPGKTARITCGGNNI GSKSVHWYQQKPGQAPVLVVYDDSD RPSGIPERFSGSNSGNTATLTISRVEAG DEADYYCQVWDSSSDHVVFGGGTKLT VL SEQ ID NO. 98 |
| JH1E11 | QVQLVQSGGGLVQSGGSLRLSCA ASGFSFRSHWMHWVRQAPGKGLE WVASISPDGTDKYYVESLQGRFTIS RDNAKNSLYLQMNSLRAEDTAVY YCARDQVEQRGVYDMDVWGQGT TVTVSS SEQ ID NO. 99 | VIWMTQSPSSLSASVGDRVTITCQATQ DINNNLNWYQHRPGEAPTLLIYGASTL QSGVPSRFSGSGFGTDFTLTISSLQPED VATYYCQKYDDDPLTFGGGTKVEIK SEQ ID NO. 100 |
| JH1F3 | QVQLVQSGAEVKKPGASVKVSCQ ASGYTFTSYDIHWVRQVPGQRLE WMGIINPSGGSTSYAQKFQGRVTM TRDTSTSTVYMELSSLRSEDTAVY YCARDGYSYGPSDYWGQGTLVTV SS SEQ ID NO. 101 | DVVMTQSPSTLSASVGDRVTITCRASQ RISSWLAWYQQKPGKAPKSLIYAASSL QSGVPSKFSGGGSGTDFTLTISSLQPED FATYYCQQYIYYPPTFGQGTRLEIK SEQ ID NO. 102 |
| JH1F4 | QVQLVQSGAEVKKPGASVKVSCK ASGYTFTSYAMHWVRHAPGQRLE WMGWINAGNGNTKYSQKFQGRV TITRDTSASTAYMELSSLRSEDTAV YYCARDLDYYYGMDVWGQGTTV TVSS SEQ ID NO. 103 | QPVLTQPPSASGTPGQRVTISCSGSSSNI GSNIVNWYQQLPGTAPKWYSNNRRP SGVPDRFSGSKSGSSASLAISGLQSEDE ADYYCAAWDATLGGLYVFGTGTKVT VL SEQ ID NO. 104 |
| JH1F6 | EVQLVQSGAEVKKPGASVKVSCK ASGYTFTSYYMHWVRQAPGQGLE WMGIINPSDGNTSYAQKFQGRVT MTKDTSTSTVYMELSSLRSEDTAV YYCARESSSWETYFDYWGQGTLV TVSS SEQ ID NO. 105 | QPVLTQPPSVSVAPGKTARITCGGNNIG SKSVHWYQQKPGQAPVLVIYYDTDRP SGIPERFSGSNSGNTATLTISRVEAGDE ADFYCQVWDSSSDHVVFGGGTKLTV SEQ ID NO. 106 |
| JH1H2 | EVQLVESGGGLVKPGGSLRLSCAA SGFTFSDYYMSWIRQAPGKGLEW | QSALTQPPSVSAAPGQKVTISCSGSSSNI ANNYVSWYQQLPGTAPKLLIYDNNKR |

TABLE 5-continued

Anti-JAG1 Heavy and Light Variable Domain Amino Acid Sequences

| | Heavy chain variable domain sequence | Light chain variable domain sequence |
|---|---|---|
| | VSYISSSSSYTNYADSVKGRFTISR DNAKNSLYLQMNSLRAEDTAVYY CAKHSSSWYGDLDYWGQGTLVT VSS SEQ ID NO. 107 | PSGIPDRFSGSKSGTSATLGITGLQTGD EADYYCGTWDGSLSAGVFGGGTKLTV L SEQ ID NO. 108 |
| JH1H7 | QMQLVQSGAEVKKPGSSVKVSCK ASGATFSSYAMSWVRQAPGQGLE WMGAVIPIFGTTNYAPKFEGRVTIT ADESTSTVYMELSSLTSEDTAVYY CARQIGEVVGGIMEDYWGQGTLV TVSS SEQ ID NO. 109 | DIVMTQSPSSLSPSIGDRVTITCRASQGI SSALAWYQQKPGKAPKLLIYHASTLQS GVPSRFSGSGSGTDFTLTISSLQPEDVA TYYCQKYNSAPLTFGGGTKVEIK SEQ ID NO. 110 |
| JG1H7 3-2 | EVQLVESGGGLIQPGGSLRLSCAA SAFTVSNFYMTWVRQAPGKGLEW VSVIDSGGNTYYADSVRGRFTISR DNSKNTLFLQMNSLRAEDTAVYY CARDLGYYYAMDVWGQGTTVTV SS SEQ ID NO: 111 | DIQMTQSPSSLSASVGDRVTITCRASQS ISTSLNWYQQKPGKAPKLLIYAASSLQS GVPSRFSGSGSGTDFTLTISSLQPEDFAT YYCQQSYSTPTFGQGTKLEIK SEQ ID NO: 112 |
| JG1H7- 2B2S | EVQLVESGGGLIQPGGSLRLSCAA SAFTVSNFYMTWVRQAPGKGLEW VSVIDSGGNTYYADSVRGRFTISR DNSKNTLFLQMNSLRAEDTAVYY CARDLGYYYAMDVWGQGTTVTV SS SEQ ID NO: 111 | DIQMTQSPSSLSASVGDRVTITCPASQSI STSLNWYQQKPGKAPKLLIYAASSLQS GVPSRFSGSGSGTDFTLTISSLQPEDFAT YYCQQSYSTPTFGQGTKLEIK SEQ ID NO: 113 |
| JG1H7- 2A3S | EVQLVESGGGLIQPGGSLRLSCAA SAFTVSNFYMTWVRQAPGKGLEW VSVIDSGGNTYYADSVRGRFTISR DNSKNTLFLQMNSLRAEDTAVYY CARDLGYYYAMDVWGQGTTVTV SS SEQ ID NO: 111 | DIQMTQSPSSLSASVGDRVTITCRASHS ISTSLNWYQQKPGKAPKLLIYAASSLQS GVPSRFSGSGSGTDFTLTISSLQPEDFAT YYCQQSYSTPTFGQGTKLEIK SEQ ID NO: 114 |
| JG1H7- 2A7S | EVQLVESGGGLIQPGGSLRLSCAA SAFTVSNFYMTWVRQAPGKGLEW VSVIDSGGNTYYADSVRGRFTISR DNSKNTLFLQMNSLRAEDTAVYY CARDLGYYYAMDVWGQGTTVTV SS SEQ ID NO: 111 | DIQMTQSPSSLSASVGDRVTITCRASPSI STSLNWYQQKPGKAPKLLIYAASSLQS GVPSRFSGSGSGTDFTLTISSLQPEDFAT YYCQQSYSTPTFGQGTKLEIK SEQ ID NO: 115 |
| JG1H7- 2A10S | EVQLVESGGGLIQPGGSLRLSCAA SAFTVSNFYMTWVRQAPGKGLEW VSVIDSGGNTYYADSVRGRFTISR DNSKNTLFLQMNSLRAEDTAVYY CARDLGYYYAMDVWGQGTTVTV SS SEQ ID NO: 111 | DIQMTQSPSSLSASVGDRVTITCRASQS TSTSLNWYQQKPGKAPKLLIYAASSLQ SGVPSRFSGSGSGTDFTLTISSLQPEDFA TYYCQQSYSTPTFGQGTKLEIK SEQ ID NO: 116 |
| JG1H7- 2A2S | EVQLVESGGGLIQPGGSLRLSCAA SAFTVSNFYMTWVRQAPGKGLEW VSVIDSGGNTYYADSVRGRFTISR DNSKNTLFLQMNSLRAEDTAVYY CARDLGYYYAMDVWGQGTTVTV SS SEQ ID NO: 111 | DIQMTQSPSSLSASVGDRVTITCRASQS SSTSLNWYQQKPGKAPKLLIYAASSLQ SGVPSRFSGSGSGTDFTLTISSLQPEDFA TYYCQQSYSTPTFGQGTKLEIK SEQ ID NO: 117 |
| JG1H7- 2A9S | EVQLVESGGGLIQPGGSLRLSCAA SAFTVSNFYMTWVRQAPGKGLEW VSVIDSGGNTYYADSVRGRFTISR DNSKNTLFLQMNSLRAEDTAVYY CARDLGYYYAMDVWGQGTTVTV SS SEQ ID NO: 111 | DIQMTQSPSSLSASVGDRVTITCRASQS FSTSLNWYQQKPGKAPKLLIYAASSLQ SGVPSRFSGSGSGTDFTLTISSLQPEDFA TYYCQQSYSTPTFGQGTKLEIK SEQ ID NO: 118 |
| JG1H7- 2A1S | EVQLVESGGGLIQPGGSLRLSCAA SAFTVSNFYMTWVRQAPGKGLEW VSVIDSGGNTYYADSVRGRFTISR DNSKNTLFLQMNSLRAEDTAVYY CARDLGYYYAMDVWGQGTTVTV SS SEQ ID NO: 111 | DIQMTQSPSSLSASVGDRVTITCRASQS PSTSLNWYQQKPGKAPKLLIYAASSLQ SGVPSRFSGSGSGTDFTLTISSLQPEDFA TYYCQQSYSTPTFGQGTKLEIK SEQ ID NO: 119 |
| JG1H7- E11S | EVQLVESGGGLIQPGGSLRLSCAA SAFTVSNFYMTWVRQAPGKGLEW VSVIDSGGNTYYADSVRGRFTISR DNSKNTLFLQMNSLRAEDTAVYY | DIQMTQSPSSLSASVGDRVTITCRASQS ISASLNWYQQKPGKAPKLLIYAASSLQ SGVPSRFSGSGSGTDFTLTISSLQPEDFA TYYCQQSYSTPTFGQGTKLEIK |

TABLE 5-continued

Anti-JAG1 Heavy and Light Variable Domain Amino Acid Sequences

| | Heavy chain variable domain sequence | Light chain variable domain sequence |
|---|---|---|
| | CARDLGYYYAMDVWGQGTTVTV SS SEQ ID NO: 111 | SEQ ID NO: 120 |
| JG1H7-C11S | EVQLVESGGGLIQPGGSLRLSCAA SAFTVSNFYMTWVRQAPGKGLEW VSVIDSGGNTYYADSVRGRFTISR DNSKNTLFLQMNSLRAEDTAVYY CARDLGYYYAMDVWGQGTTVTV SS SEQ ID NO: 111 | DIQMTQSPSSLSASVGDRVTITCRASQS ISTTLNWYQQKPGKAPKLLIYAASSLQS GVPSRFSGSGSGTDFTLTISSLQPEDFAT YYCQQSYSTPTFGQGTKLEIK SEQ ID NO: 121 |
| JG1H7-D10S | EVQLVESGGGLIQPGGSLRLSCAA SAFTVSNFYMTWVRQAPGKGLEW VSVIDSGGNTYYADSVRGRFTISR DNSKNTLFLQMNSLRAEDTAVYY CARDLGYYYAMDVWGQGTTVTV SS SEQ ID NO: 111 | DIQMTQSPSSLSASVGDRVTITCRASQS ISTSQNWYQQKPGKAPKLLIYAASSLQ SGVPSRFSGSGSGTDFTLTISSLQPEDFA TYYCQQSYSTPTFGQGTKLEIK SEQ ID NO: 122 |
| JG1H7-2B7S | EVQLVESGGGLIQPGGSLRLSCAA SAFTVSNFYMTWVRQAPGKGLEW VSVIDSGGNTYYADSVRGRFTISR DNSKNTLFLQMNSLRAEDTAVYY CARDLGYYYAMDVWGQGTTVTV SS SEQ ID NO: 111 | DIQMTQSPSSLSASVGDRVTITCRASQS ISTSLNWYQQKPGKAPKLLIYLASSLQS GVPSRFSGSGSGTDFTLTISSLQPEDFAT YYCQQSYSTPTFGQGTKLEIK SEQ ID NO: 123 |
| JG1H7-1A8S | EVQLVESGGGLIQPGGSLRLSCAA SGFTVSNFYMTWVRQAPGKGLEW VSVIDSGGNTYYADSVRGRFTISR DNSKNTLFLQMNSLRAEDTAVYY CARDLGYYYAMDVWGQGTTVTV SS SEQ ID NO: 124 | DIQMTQSPSSLSASVGDRVTITCRASQS ISTSLNWYQQKPGKAPKLLIYAASSLQS GVPSRFSGSGSGTDFTLTISSLQPEDFAT YYCQQSYSTPTFGQGTKLEIK SEQ ID NO: 112 |
| JG1H7-1A6S | EVQLVESGGGLIQPGGSLRLSCAA SAFTVSNFSMTWVRQAPGKGLEW VSVIDSGGNTYYADSVRGRFTISR DNSKNTLFLQMNSLRAEDTAVYY CARDLGYYYAMDVWGQGTTVTV SS SEQ ID NO: 125 | DIQMTQSPSSLSASVGDRVTITCRASQS ISTSLNWYQQKPGKAPKLLIYAASSLQS GVPSRFSGSGSGTDFTLTISSLQPEDFAT YYCQQSYSTPTFGQGTKLEIK SEQ ID NO: 112 |
| JG1H7-1A2S | EVQLVESGGGLIQPGGSLRLSCAA SAFTVSNFGMTWVRQAPGKGLEW VSVIDSGGNTYYADSVRGRFTISR DNSKNTLFLQMNSLRAEDTAVYY CARDLGYYYAMDVWGQGTTVTV SS SEQ ID NO: 126 | DIQMTQSPSSLSASVGDRVTITCRASQS ISTSLNWYQQKPGKAPKLLIYAASSLQS GVPSRFSGSGSGTDFTLTISSLQPEDFAT YYCQQSYSTPTFGQGTKLEIK SEQ ID NO: 112 |
| JG1H7-1B1S | EVQLVESGGGLIQPGGSLRLSCAA SAFTVSNFAMTWVRQAPGKGLEW VSVIDSGGNTYYADSVRGRFTISR DNSKNTLFLQMNSLRAEDTAVYY CARDLGYYYAMDVWGQGTTVTV SS SEQ ID NO: 127 | DIQMTQSPSSLSASVGDRVTITCRASQS ISTSLNWYQQKPGKAPKLLIYAASSLQS GVPSRFSGSGSGTDFTLTISSLQPEDFAT YYCQQSYSTPTFGQGTKLEIK SEQ ID NO: 112 |
| JG1H7-5A8S | EVQLVESGGGLIQPGGSLRLSCAA SAFTVSNFYMTWVRQAPGKGLEW VSVIDSGGNTYYADSVRGRFTISR DNSKNTLFLQMNSLRAEDTAVYY CARALGYYYAMDVWGQGTTVTV SS SEQ ID NO: 128 | DIQMTQSPSSLSASVGDRVTITCRASQS ISTSLNWYQQKPGKAPKLLIYAASSLQS GVPSRFSGSGSGTDFTLTISSLQPEDFAT YYCQQSYSTPTFGQGTKLEIK SEQ ID NO: 112 |
| JG1H7-5B5S | EVQLVESGGGLIQPGGSLRLSCAA SAFTVSNFYMTWVRQAPGKGLEW VSVIDSGGNTYYADSVRGRFTISR DNSKNTLFLQMNSLRAEDTAVYY CARSLGYYYAMDVWGQGTTVTV SS SEQ ID NO: 129 | DIQMTQSPSSLSASVGDRVTITCRASQS ISTSLNWYQQKPGKAPKLLIYAASSLQS GVPSRFSGSGSGTDFTLTISSLQPEDFAT YYCQQSYSTPTFGQGTKLEIK SEQ ID NO: 112 |
| JG1H7-3E5S | EVQLVESGGGLIQPGGSLRLSCAA SAFTVSNFYMTWVRQAPGKGLEW VSVIDSGGNTYYADSVRGRFTISR | DIQMTQSPSSLSASVGDRVTITCRASQS ISTSLNWYQQKPGKAPKLLIYAASSLQS GVPSRFSGSGSGTDFTLTISSLQPEDFAT |

TABLE 5-continued

Anti-JAG1 Heavy and Light Variable Domain Amino Acid Sequences

| | Heavy chain variable domain sequence | Light chain variable domain sequence |
|---|---|---|
| | DNSKNTLFLQMNSLRAEDTAVYY<br>CARDLGYYYALDVWGQGTTVTVS<br>S<br>SEQ ID NO: 130 | YYCQQSYSTPTFGQGTKLEIK<br>SEQ ID NO: 112 |
| JG1H7-<br>G6C | EVQLVESGGGLIQPGGSLRLSCAA<br>SAFTVSNFAMTWVRQAPGKGLEW<br>VSVIDSGGNTYYADSVRGRFTISR<br>DNSKNTLFLQMNSLRAEDTAVYY<br>CARDLGYYYAMDVWGQGTTVTV<br>SS<br>SEQ ID NO: 127 | DIQMTQSPSSLSASVGDRVTITCRASQS<br>ISTTQNWYQQKPGKAPKLLIYAASSLQ<br>SGVPSRFSGSGSGTDFTLTISSLQPEDFA<br>TYYCQQSYSTPTFGQGTKLEIK<br>SEQ ID NO: 131 |
| JG1H7-<br>A6C | EVQLVESGGGLIQPGGSLRLSCAA<br>SAFTVSNFYMTWVRQAPGKGLEW<br>VSVIDSGGNTYYADSVRGRFTISR<br>DNSKNTLFLQMNSLRAEDTAVYY<br>CARSLGYYYALDVWGQGTTVTVS<br>S<br>SEQ ID NO: 132 | DIQMTQSPSSLSASVGDRVTITCRASPSI<br>STSLNWYQQKPGKAPKLLIYLASSLQS<br>GVPSRFSGSGSGTDFTLTISSLQPEDFAT<br>YYCQQSYSTPTFGQGTKLEIK<br>SEQ ID NO: 133 |
| JG1H7-<br>E11C | EVQLVESGGGLIQPGGSLRLSCAA<br>SAFTVSNFYMTWVRQAPGKGLEW<br>VSVIDSGGNTYYADSVRGRFTISR<br>DNSKNTLFLQMNSLRAEDTAVYY<br>CARSLGYYYALDVWGQGTTVTVS<br>S<br>SEQ ID NO: 132 | DIQMTQSPSSLSASVGDRVTITCRASQS<br>ISTSLNWYQQKPGKAPKLLIYLASSLQS<br>GVPSRFSGSGSGTDFTLTISSLQPEDFAT<br>YYCQQSYSTPTFGQGTKLEIK<br>SEQ ID NO: 123 |
| JG1H7-<br>C6C | EVQLVESGGGLIQPGGSLRLSCAA<br>SAFTVSNFAMTWVRQAPGKGLEW<br>VSVIDSGGNTYYADSVRGRFTISR<br>DNSKNTLFLQMNSLRAEDTAVYY<br>CARDLGYYYALDVWGQGTTVTVS<br>S<br>SEQ ID NO: 142 | DIQMTQSPSSLSASVGDRVTITCRASQS<br>ISTSLNWYQQKPGKAPKLLIYLASSLQS<br>GVPSRFSGSGSGTDFTLTISSLQPEDFAT<br>YYCQQSYSTPTFGQGTKLEIK<br>SEQ ID NO: 123 |
| JG1H7-<br>C9C | EVQLVESGGGLIQPGGSLRLSCAA<br>SAFTVSNFAMTWVRQAPGKGLEW<br>VSVIDSGGNTYYADSVRGRFTISR<br>DNSKNTLFLQMNSLRAEDTAVYY<br>CARDLGYYYAMDVWGQGTTVTV<br>SS<br>SEQ ID NO: 127 | DIQMTQSPSSLSASVGDRVTITCRASQS<br>ISTSLNWYQQKPGKAPKLLIYLASSLQS<br>GVPSRFSGSGSGTDFTLTISSLQPEDFAT<br>YYCQQSYSTPTFGQGTKLEIK<br>SEQ ID NO: 123 |
| JG1H7-<br>F4C | EVQLVESGGGLIQPGGSLRLSCAA<br>SAFTVSNFYMTWVRQAPGKGLEW<br>VSVIDSGGNTYYADSVRGRFTISR<br>DNSKNTLFLQMNSLRAEDTAVYY<br>CARSLGYYYALDVWGQGTTVTVS<br>S<br>SEQ ID NO: 132 | DIQMTQSPSSLSASVGDRVTITCRASPSI<br>SASLNWYQQKPGKAPKLLIYLASSLQS<br>GVPSRFSGSGSGTDFTLTISSLQPEDFAT<br>YYCQQSYSTPTFGQGTKLEIK<br>SEQ ID NO: 134 |
| JG1H7-<br>F2C | EVQLVESGGGLIQPGGSLRLSCAA<br>SAFTVSNFYMTWVRQAPGKGLEW<br>VSVIDSGGNTYYADSVRGRFTISR<br>DNSKNTLFLQMNSLRAEDTAVYY<br>CARALGYYYALDVWGQGTTVTVS<br>S SEQ ID NO: 135 | DIQMTQSPSSLSASVGDRVTITCRASPSI<br>STSLNWYQQKPGKAPKLLIYLASSLQS<br>GVPSRFSGSGSGTDFTLTISSLQPEDFAT<br>YYCQQSYSTPTFGQGTKLEIK<br>SEQ ID NO: 133 |
| JG1H7-<br>F1C | EVQLVESGGGLIQPGGSLRLSCAA<br>SAFTVSNFYMTWVRQAPGKGLEW<br>VSVIDSGGNTYYADSVRGRFTISR<br>DNSKNTLFLQMNSLRAEDTAVYY<br>CARSLGYYYALDVWGQGTTVTVS<br>S<br>SEQ ID NO: 132 | DIQMTQSPSSLSASVGDRVTITCRASQS<br>ISASLNWYQQKPGKAPKLLIYLASSLQS<br>GVPSRFSGSGSGTDFTLTISSLQPEDFAT<br>YYCQQSYSTPTFGQGTKLEIK<br>SEQ ID NO: 136 |
| JG1H7-<br>D4C | EVQLVESGGGLIQPGGSLRLSCAA<br>SAFTVSNFYMTWVRQAPGKGLEW<br>VSVIDSGGNTYYADSVRGRFTISR<br>DNSKNTLFLQMNSLRAEDTAVYY<br>CARSLGYYYALDVWGQGTTVTVS<br>S<br>SEQ ID NO: 132 | DIQMTQSPSSLSASVGDRVTITCRASQS<br>TSASLNWYQQKPGKAPKLLIYLASSLQ<br>SGVPSRFSGSGSGTDFTLTISSLQPEDFA<br>TYYCQQSYSTPTFGQGTKLEIK<br>SEQ ID NO: 137 |

TABLE 5-continued

Anti-JAG1 Heavy and Light Variable Domain Amino Acid Sequences

| | Heavy chain variable domain sequence | Light chain variable domain sequence |
|---|---|---|
| JG1H7-D5C | EVQLVESGGGLIQPGGSLRLSCAASAFTVSNFYMTWVRQAPGKGLEWVSVIDSGGNTYYADSVRGRFTISRDNSKNTLFLQMNSLRAEDTAVYYCARSLGYYYALDVWGQGTTVTVSS<br>SEQ ID NO: 132 | DIQMTQSPSSLSASVGDRVTITCRASQSPSTSLNWYQQKPGKAPKLLIYLASSLQSGVPSRFSGSGSGTDFTLTISSLQPEDFATYYCQQSYSTPTFGQGTKLEIK<br>SEQ ID NO: 138 |
| JG1H7-A5C | EVQLVESGGGLIQPGGSLRLSCAASAFTVSNFAMTWVRQAPGKGLEWVSVIDSGGNTYYADSVRGRFTISRDNSKNTLFLQMNSLRAEDTAVYYCARSLGYYYALDVWGQGTTVTVSS<br>SEQ ID NO: 139 | DIQMTQSPSSLSASVGDRVTITCRASQSISTSLNWYQQKPGKAPKLLIYLASSLQSGVPSRFSGSGSGTDFTLTISSLQPEDFATYYCQQSYSTPTFGQGTKLEIK<br>SEQ ID NO: 123 |
| JG1H7-B2C | EVQLVESGGGLIQPGGSLRLSCAASAFTVSNFAMTWVRQAPGKGLEWVSVIDSGGNTYYADSVRGRFTISRDNSKNTLFLQMNSLRAEDTAVYYCARSLGYYYALDVWGQGTTVTVSS<br>SEQ ID NO: 139 | DIQMTQSPSSLSASVGDRVTITCRASQSPSASLNWYQQKPGKAPKLLIYLASSLQSGVPSRFSGSGSGTDFTLTISSLQPEDFATYYCQQSYSTPTFGQGTKLEIK<br>SEQ ID NO: 140 |
| JG1H7-B6C | EVQLVESGGGLIQPGGSLRLSCAASAFTVSNFAMTWVRQAPGKGLEWVSVIDSGGNTYYADSVRGRFTISRDNSKNTLFLQMNSLRAEDTAVYYCARDLGYYYAMDVWGQGTTVTVSS<br>SEQ ID NO: 127 | DIQMTQSPSSLSASVGDRVTITCRASQSSSTSLNWYQQKPGKAPKLLIYLASSLQSGVPSRFSGSGSGTDFTLTISSLQPEDFATYYCQQSYSTPTFGQGTKLEIK<br>SEQ ID NO: 141 |

INCORPORATION BY REFERENCE

The contents of all references, patents, pending patent applications and published patents, cited throughout this application are hereby expressly incorporated by reference.

We claim:

1. An isolated anti-JAG1 fully human antibody of an IgG class that binds to a JAG1 epitope, said antibody comprising heavy/light chain variable domain amino acid sequences selected from the group consisting of: SEQ ID NO: 77/SEQ ID NO: 78, SEQ ID NO: 111/SEQ ID NO: 112, SEQ ID NO: 111, SEQ ID NO: 113, SEQ ID NO: 111/SEQ ID NO: 114, SEQ ID NO: 111/SEQ ID NO: 115, SEQ ID NO: 111/SEQ ID NO: 116, SEQ ID NO: 111/SEQ ID NO: 117, SEQ ID NO: 111/SEQ ID NO: 118, SEQ ID NO: 111/SEQ ID NO: 119, SEQ ID NO: 111/SEQ ID NO: 120, SEQ ID NO: 111/SEQ ID NO: 121, SEQ ID NO: 111/SEQ ID NO: 122, SEQ ID NO: 111/SEQ ID NO: 123, SEQ ID NO: 124/SEQ ID NO: 112, SEQ ID NO: 125/SEQ ID NO: 112, SEQ ID NO: 126/SEQ ID NO: 112, SEQ ID NO: 127/SEQ ID NO: 112, SEQ ID NO: 128/SEQ ID NO: 112, SEQ ID NO: 129/SEQ ID NO: 112, SEQ ID NO: 130/SEQ ID NO: 112, SEQ ID NO: 127/SEQ ID NO: 131, SEQ ID NO: 132/SEQ ID NO: 133, SEQ ID NO: 132/SEQ ID NO: 123, SEQ ID NO: 142/SEQ ID NO: 123, SEQ ID NO: 127/SEQ ID NO: 123, SEQ ID NO:132/SEQ ID NO: 134, SEQ ID NO: 135/SEQ ID NO: 133, SEQ ID NO: 132/SEQ ID NO: 136, SEQ ID NO: 132/SEQ ID NO: 137, SEQ ID NO: 132/SEQ ID NO: 138, SEQ ID NO: 139/SEQ ID NO: 123, SEQ ID NO: 139/SEQ ID NO: 140, and SEQ ID NO: 127/SEQ ID NO: 141.

2. The fully human antibody of claim 1, wherein the antibody has a $K_D$ of at least $1 \times 10^{-6}$ M.

3. The fully human antibody of claim 1, wherein the antibody is a single chain antibody comprising a peptide linker connecting the heavy and light chain variable domains.

4. An anti-JAG1 fully human antibody Fab fragment, wherein the antibody Fab fragment comprises heavy/light chain variable domain amino acid sequences selected from the group consisting of: SEQ ID NO: 77/SEQ ID NO: 78, SEQ ID NO: 111/SEQ ID NO: 112, SEQ ID NO: 111, SEQ ID NO: 113, SEQ ID NO: 111/SEQ ID NO: 114, SEQ ID NO: 111/SEQ ID NO: 115, SEQ ID NO: 111/SEQ ID NO: 116, SEQ ID NO: 111/SEQ ID NO: 117, SEQ ID NO: 111/SEQ ID NO: 118, SEQ ID NO: 111/SEQ ID NO: 119, SEQ ID NO: 111/SEQ ID NO: 120, SEQ ID NO: 111/SEQ ID NO: 121, SEQ ID NO: 111/SEQ ID NO: 122, SEQ ID NO: 111/SEQ ID NO: 123, SEQ ID NO: 124/SEQ ID NO: 112, SEQ ID NO: 125/SEQ ID NO: 112, SEQ ID NO: 126/SEQ ID NO: 112, SEQ ID NO: 127/SEQ ID NO: 112, SEQ ID NO: 128/SEQ ID NO: 112, SEQ ID NO: 129/SEQ ID NO: 112, SEQ ID NO: 130/SEQ ID NO: 112, SEQ ID NO: 127/SEQ ID NO: 131, SEQ ID NO: 132/SEQ ID NO: 133, SEQ ID NO: 132/SEQ ID NO: 123, SEQ ID NO: 142/SEQ ID NO: 123, SEQ ID NO: 127/SEQ ID NO: 123, SEQ ID NO:132/SEQ ID NO: 134, SEQ ID NO: 135/SEQ ID NO: 133, SEQ ID NO: 132/SEQ ID NO: 136, SEQ ID NO: 132/SEQ ID NO: 137, SEQ ID NO: 132/SEQ ID NO: 138, SEQ ID NO: 139/SEQ ID NO: 123, SEQ ID NO: 139/SEQ ID NO: 140, and SEQ ID NO: 127/SEQ ID NO: 141.

5. The fully human antibody Fab fragment of claim 4, which has a $K_D$ of at least $1 \times 10^{-6}$ M.

* * * * *

SEQUENCE LISTING

```
<160> NUMBER OF SEQ ID NOS: 144

<210> SEQ ID NO 1
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1
```

Glu Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Leu
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Thr Gly Gly Asp Gly Phe Asp Tyr Trp Gly Gln Gly Thr
            100                 105                 110

Leu Val Thr Val Ser Ser
        115

<210> SEQ ID NO 2
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Asp Val Val Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Gln Ser Gly Val Pro Ser Arg Phe Ser Gly
50                  55                  60

Ser Gly Ser Gly Thr Asp Phe Thr Leu Ser Ile Ser Ser Leu Gln Pro
65                  70                  75                  80

Glu Asp Phe Ala Thr Tyr Tyr Cys Gln Gln Ala Asn Ser Leu Pro Leu
                85                  90                  95

Thr Phe Gly Gly Gly Thr Lys Val Glu Ile Lys
            100                 105

<210> SEQ ID NO 3
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Glu Val Gln Leu Val Gln Ser Gly Ala Glu Val Lys Lys Pro Gly Ala
1               5                   10                  15

Ser Val Arg Val Ser Cys Lys Ala Ser Gly Tyr Asn Phe Arg Asn Phe
            20                  25                  30

Asp Ile Asn Trp Val Arg Gln Ala Pro Gly Gln Gly Leu Glu Trp Met
        35                  40                  45

Gly Trp Met Asn Pro Ser Ser Gly Leu Thr Gly Phe Ala Pro Lys Phe
    50                  55                  60

Gln Gly Arg Val Thr Leu Thr Arg Asp Thr Ser Ile Arg Thr Ala Tyr
65                  70                  75                  80

Met Glu Val Ser Ser Leu Arg Ser Glu Asp Thr Ala Val Tyr Tyr Cys
                85                  90                  95

Val Arg Gln Arg Ser Gly Leu Asp Ser Trp Gly Gln Gly Thr Leu Val
            100                 105                 110

Thr Val Ser Ser
        115

<210> SEQ ID NO 4
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Gln Ser Val Leu Thr Gln Pro Pro Ser Val Ser Ala Ala Pro Gly Gln
1               5                   10                  15

Lys Val Thr Ile Ser Cys Ser Gly Ser Ser Asn Ile Gly Lys Tyr
            20                  25                  30

Phe Val Ser Trp Tyr Gln Gln Phe Pro Gly Thr Ala Pro Lys Leu Leu
        35                  40                  45

Ile Tyr Asp Asn Asp Gln Arg Pro Ser Gly Ile Pro Asp Arg Phe Ser
50                  55                  60

Ala Ser Lys Ser Gly Thr Ser Ala Arg Leu Asp Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Gly Val Phe Gly Gly Gly Thr Lys Leu Thr Val Leu
            100                 105                 110

<210> SEQ ID NO 5
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Glu Val Gln Leu Val Gln Ser Gly Ala Glu Val Lys Lys Pro Gly Ala
1               5                   10                  15

Ser Val Arg Val Ser Cys Lys Ala Ser Gly Tyr Thr Phe Thr Asn Tyr
            20                  25                  30

Tyr Ile His Trp Val Arg Gln Ala Pro Gly Gln Gly Leu Glu Trp Met
        35                  40                  45

Gly Ile Ile Ile Pro Ser Gly Gly Ser Thr Asn Tyr Pro Pro Lys Phe
50                  55                  60

Gln Gly Arg Val Thr Leu Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Val Arg Glu Tyr Gln Gly Gly His Phe Asp Tyr Trp Gly Gln Gly Thr
            100                 105                 110

Leu Val Thr Val Ser Ser
        115

<210> SEQ ID NO 6
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Ser Tyr Glu Leu Met Gln Pro His Ser Val Ser Glu Ser Pro Gly Lys
1               5                   10                  15

Thr Val Thr Ile Ser Cys Thr Gly Ser Ser Gly Ser Ile Ala Ser Asn
            20                  25                  30

Tyr Val Gln Trp Tyr Gln Gln Arg Pro Gly Ser Ala Pro Thr Thr Val
             35                  40                  45

Ile Tyr Glu Asp Asn Arg Pro Ser Gly Val Pro Asp Arg Phe Ser
 50                  55                  60

Gly Ser Ile Asp Ser Ser Asn Ser Ala Ser Leu Thr Ile Ser Gly
 65                  70                  75                  80

Leu Lys Thr Glu Asp Glu Ala Asp Tyr Tyr Cys Gln Ser Tyr Asp Ser
                 85                  90                  95

Ser Ile Val Val Phe Gly Gly Gly Thr Lys Leu Thr Val Leu
                100                 105                 110

<210> SEQ ID NO 7
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Asn Asp Tyr
                 20                  25                  30

Tyr Met Ser Trp Ile Arg Gln Ala Pro Gly Lys Gly Leu Glu Trp Val
             35                  40                  45

Ser Tyr Ile Ser Arg Ser Gly Ser Thr Met Tyr Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Asp Glu Asp Thr Ala Val Tyr Tyr Cys
                 85                  90                  95

Ala Thr Ser Val Gly His Leu Glu Gln Trp Gly Gln Gly Thr Leu Val
                100                 105                 110

Thr Val Ser Ser
        115

<210> SEQ ID NO 8
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Asp Ile Gln Leu Thr Gln Ser Pro Ser Ser Leu Ser Ala Ser Val Gly
 1               5                  10                  15

Asp Arg Val Thr Ile Thr Cys Arg Ala Thr Gln Gly Ile Gly Asn Tyr
                 20                  25                  30

Leu Ala Trp Tyr Gln Gln Lys Pro Gly Lys Val Pro Asn Leu Leu Ile
             35                  40                  45

Tyr Ala Ala Thr Thr Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Val Ala Ser Tyr Tyr Cys Gln Lys Tyr Asn Ser Ala Pro Leu
                 85                  90                  95

Thr Phe Gly Gly Gly Thr Lys Val Glu Ile Lys
            100                 105

<210> SEQ ID NO 9
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Gln Val Gln Leu Val Glu Ser Gly Gly Val Val Gln Pro Gly Gly
1               5                   10                  15

Ser Leu Arg Leu Ser Cys Ala Ala Ser Gly Phe Thr Phe Asp Asp Tyr
            20                  25                  30

Thr Met His Trp Val Arg Gln Ala Pro Gly Lys Gly Leu Glu Trp Val
        35                  40                  45

Ser Leu Ile Ser Trp Asp Gly Gly Ser Thr Tyr Tyr Ala Asp Ser Val
    50                  55                  60

Lys Gly Arg Phe Thr Ile Ser Arg Asp Asn Ser Lys Asn Ser Leu His
65                  70                  75                  80

Leu Gln Met Asn Ser Leu Arg Thr Glu Asp Thr Ala Leu Tyr Tyr Cys
                85                  90                  95

Ala Lys Asp Ile Asp Glu Tyr Ser Ser Ser Thr Gly Pro Asp Tyr Trp
            100                 105                 110

Gly Gln Gly Thr Leu Val Thr Val Ser Ser
        115                 120

<210> SEQ ID NO 10
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Gln Ala Val Leu Thr Gln Pro Ala Ser Val Ser Glu Ser Pro Gly Gln
1               5                   10                  15

Ser Ile Thr Ile Ser Cys Thr Gly Ser Ser Ser Asp Ile Gly Gly Tyr
            20                  25                  30

Asn Tyr Val Ser Trp Tyr Gln Gln His Pro Gly Lys Ala Pro Lys Leu
        35                  40                  45

Ile Ile Tyr Glu Val Thr Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Val Gly Ser
                85                  90                  95

Asn Asp Val Tyr Val Phe Gly Thr Gly Thr Lys Leu Thr Val Leu
            100                 105                 110

<210> SEQ ID NO 11
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Gln Val Gln Leu Val Gln Ser Gly Ala Glu Val Gln Lys Pro Gly Ala
1               5                   10                  15

Ser Val Lys Val Ser Cys Lys Val Ser Gly Tyr Thr Leu Ser Glu Leu
            20                  25                  30

Ser Ile His Trp Val Arg Gln Ala Pro Gly Lys Gly Leu Glu Trp Met
        35                  40                  45

Gly Gly Phe Asp Pro Glu Asp Gly Lys Ile Val Tyr Ala Gln Lys Phe
    50                  55                  60

Gln Asp Arg Val Ser Met Thr Gln Asp Thr Ser Thr Asp Thr Ala Tyr
65                  70                  75                  80

Leu Gln Leu Ser Ser Leu Thr Ser Gly Asp Thr Ala Leu Tyr Tyr Cys
                85                  90                  95

Ala Thr Leu Ala Gln Trp Gly Asp Trp Phe Asp Arg Trp Gly Gln Gly
            100                 105                 110

Thr Leu Val Thr Val Ser Ser
        115

<210> SEQ ID NO 12
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Gln Ala Gly Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Arg Leu Pro Gly Thr Ala Pro Lys Leu Val
        35                  40                  45

Val Tyr Ser Asn Asn Gln Arg Pro Ser Gly Val Pro Asp Arg Phe Ser
    50                  55                  60

Gly Ser Lys Ser Gly Thr Ser Ala Ser Leu Val Ile Ser Gly Leu Gln
65                  70                  75                  80

Ser Glu Asp Glu Ala Asp Tyr Tyr Cys Ala Ala Trp Asp Tyr Asp Glu
                85                  90                  95

Glu Gly Leu Leu Phe Gly Gly Gly Thr Gln Leu Thr Val Leu
            100                 105                 110

<210> SEQ ID NO 13
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Gln Val Gln Leu Val Gln Ser Gly Ala Glu Val Lys Lys Pro Gly Ala
1               5                   10                  15

Ser Val Lys Val Ser Cys Lys Ala Ser Gly Asn Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Ser Pro Ser Gly Asp Ser Thr Ser Tyr Ala Gln Lys Phe

```
                    50                  55                  60
Gln Gly Arg Val Thr Met Thr Lys Asp Thr Ser Thr Ser Thr Val Ser
 65                  70                  75                  80

Met Glu Leu Ser Ser Leu Arg Ser Glu Asp Thr Ala Val Tyr Tyr Cys
                    85                  90                  95

Ala Arg Asp Gln Glu Gly Leu Arg Gly Ser Gly Tyr Tyr Gly Met Asp
                100                 105                 110

Val Trp Gly Gln Gly Thr Thr Val Thr Val Ser Ser
                115                 120
```

<210> SEQ ID NO 14
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

```
Gln Ser Val Leu Thr Gln Pro Pro Ser Val Ser Val Ala Pro Gly Lys
 1               5                  10                  15

Thr Ala Arg Ile Thr Cys Gly Gly Asn Asn Ile Gly Ser Lys Ser Val
                20                  25                  30

His Trp Tyr Gln Gln Lys Pro Gly Gln Ala Pro Val Leu Val Ile Tyr
            35                  40                  45

Tyr Asp Ser Asp Arg Pro Ser Gly Ile Pro Glu Arg Phe Ser Gly Ser
         50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp Ser Ser Ser Asp His
                85                  90                  95

Val Val Phe Gly Gly Gly Thr Lys Leu Thr Val Leu
                100                 105
```

<210> SEQ ID NO 15
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

```
Gln Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asp Tyr
                20                  25                  30

Tyr Met Ser Trp Ile Arg Gln Ala Pro Gly Lys Gly Leu Glu Trp Val
            35                  40                  45

Ser Tyr Ile Ser Ser Ser Gly Ser Thr Ile Tyr Tyr Ala Asp Ser Val
         50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Arg Val Asn Ser Gly Tyr Asp Ala Val Asp Tyr Trp Gly Gln Gly
                100                 105                 110

Thr Leu Val Thr Val Ser Ser
```

<210> SEQ ID NO 16
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Gln Ser Ala Leu Thr Gln Pro Pro Ser Val Ser Gly Ala Pro Gly Gln
1               5                   10                  15

Thr Val Thr Ile Ser Cys Thr Gly Ser Arg Ser Asn Ile Gly Thr Tyr
            20                  25                  30

Asp Val His Trp Tyr Gln Gln Phe Ala Gly Ser Ala Pro Lys Leu Leu
        35                  40                  45

Ile Tyr His Asn Asn Asp Arg Ser Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ala Glu Asp Glu Ala Val Tyr Phe Cys Gln Ser His Asp Asn Val Leu
                85                  90                  95

Gly Gly Val Phe Gly Gly Gly Thr Lys Leu Thr Val Leu
            100                 105

<210> SEQ ID NO 17
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Glu Val Gln Leu Val Gln Ser Gly Ala Glu Val Lys Lys Pro Gly Ser
1               5                   10                  15

Ser Val Lys Val Ser Cys Lys Ala Ser Gly Asp Thr Phe Ser Ser Tyr
            20                  25                  30

Gly Ile Ser Trp Val Arg Gln Ala Pro Gly Gln Gly Leu Glu Trp Val
        35                  40                  45

Gly Arg Ile Asn Ser Leu Leu Asp Arg Pro Asp Tyr Ala Gln Asn Phe
    50                  55                  60

Gln Asp Arg Val Thr Ile Thr Ala Asp Lys Ser Thr Ser Thr Ala Tyr
65                  70                  75                  80

Met Glu Leu Asn Thr Leu Gly Pro Glu Asp Thr Ala Met Tyr Tyr Cys
                85                  90                  95

Ala Thr Glu His Tyr Tyr Glu Ser Ser Glu Asp Pro Phe Phe Asp Phe
            100                 105                 110

Trp Gly Gln Gly Thr Leu Val Thr Val Ser Ser
        115                 120

<210> SEQ ID NO 18
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

```
Gln Ser Val Val Thr Gln Pro Pro Ser Val Gly Ala Pro Gly Gln
1               5                   10                  15

Arg Ile Thr Ile Ser Cys Thr Gly Ser Ser Asn Ile Gly Ala Gly
                20                  25                  30

Tyr Asp Val Gln Trp Tyr Leu Gln Phe Pro Gly Thr Ala Pro Lys Leu
            35                  40                  45

Leu Ile His Gly Ser Ser Asn Arg Pro Ser Gly Val Pro Ala Arg Phe
    50                  55                  60

Gln Gly Ser Lys Ser Gly Thr Ser Ala Ser Leu Val Ile Thr Gly Leu
65                  70                  75                  80

Gln Ala Glu Asp Glu Ala Asp Phe Tyr Cys Gln Ser Phe Asp Ser Ser
                85                  90                  95

Leu Asn Gly Tyr Val Phe Gly Gly Gly Thr Lys Leu Thr Val Leu
            100                 105                 110
```

<210> SEQ ID NO 19
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Thr Phe Ser Ser Tyr
                20                  25                  30

Gly Met His Trp Val Arg Gln Ala Pro Gly Lys Gly Leu Glu Trp Val
            35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Tyr Asn His Asp Tyr Trp Gly Gln Gly Thr Leu Val Thr
            100                 105                 110

Val Ser Ser
        115
```

<210> SEQ ID NO 20
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

```
Leu Pro Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45

Met Ile Tyr Asp Val Ser Asn Arg Pro Ser Gly Val Ser Asn Arg Phe
    50                  55                  60
```

```
Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Thr Ser Ser
                 85                  90                  95

Ser Thr Tyr Val Phe Gly Ile Gly Thr Lys Leu Thr Val Leu
            100                 105                 110

<210> SEQ ID NO 21
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Pro Tyr Ser Ser Ser Trp Tyr Gly Ala Glu Tyr Phe Gln
            100                 105                 110

His Trp Gly Gln Gly Thr Leu Val Thr Val Ser Ser
        115                 120

<210> SEQ ID NO 22
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Gln Ala Gly Leu Thr Gln Pro His Ser Val Ser Glu Ser Pro Gly Lys
1               5                   10                  15

Thr Val Thr Ile Ser Cys Thr Arg Ser Ser Gly Ser Ile Ala Ser Asn
            20                  25                  30

Tyr Val Gln Trp Tyr Gln Gln Arg Pro Gly Ser Ala Pro Thr Thr Val
        35                  40                  45

Ile Tyr Glu Asp Asn Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Ser Asn His Leu Val Val Phe Gly Gly Gly Thr Lys Leu Thr Val Leu
            100                 105                 110

<210> SEQ ID NO 23
```

<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Glu Val Gln Leu Leu Glu Ser Gly Gly Gly Val Val Gln Pro Gly Arg
1               5                   10                  15

Pro Leu Arg Leu Ser Cys Ala Gly Ser Gly Phe Ala Phe Ser Gly Phe
            20                  25                  30

Ala Met His Trp Val Arg Gln Ala Pro Gly Lys Gly Leu Glu Trp Leu
        35                  40                  45

Ala Val Ile Ser Tyr Asp Gly Arg Asn Asn Tyr Ala Asp Ser Val
    50                  55                  60

Lys Gly Arg Phe Thr Ile Ser Arg Asp Asn Ser Lys Asn Thr Leu Phe
65                  70                  75                  80

Leu Asp Met Asp Ser Leu Arg Pro Asp Asp Thr Ala Leu Tyr Tyr Cys
                85                  90                  95

Ala Arg Asp Arg Ser Ser Gly Trp Tyr Gly Leu Ser Asp Tyr Trp Gly
            100                 105                 110

Gln Gly Thr Leu Val Thr Val Ser Ser
        115                 120

<210> SEQ ID NO 24
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Gln Pro Val Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Tyr Val Phe Gly Thr Gly Thr Lys Leu Thr Val Leu
            100                 105                 110

<210> SEQ ID NO 25
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Gln Val Gln Leu Val Gln Ser Gly Ser Glu Leu Lys Lys Pro Gly Ala
1               5                   10                  15

-continued

Ser Val Arg Val Ser Cys Lys Ala Ser Gly Tyr Thr Phe Thr Asn Tyr
            20                  25                  30

Tyr Ile His Trp Val Arg Gln Ala Pro Gly Gln Gly Leu Glu Trp Met
        35                  40                  45

Gly Ile Ile Ile Pro Ser Gly Gly Ser Thr Asn Tyr Pro Pro Lys Phe
    50                  55                  60

Gln Gly Arg Val Thr Leu Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Val Arg Glu Tyr Gln Gly Gly His Phe Asp Tyr Trp Gly Gln Gly Thr
            100                 105                 110

Leu Val Thr Val Ser Ser
            115

<210> SEQ ID NO 26
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Gln Leu Val Leu Thr Gln Ser His Ser Val Ser Glu Ser Pro Gly Lys
1               5                   10                  15

Thr Val Thr Ile Ser Cys Thr Gly Ser Ser Gly Ser Ile Ala Ser Asn
            20                  25                  30

Tyr Val Gln Trp Tyr Gln Gln Arg Pro Gly Ser Ala Pro Thr Thr Val
        35                  40                  45

Ile Tyr Glu Asp Asp Leu Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Arg
                85                  90                  95

Tyr Asn Val Val Phe Gly Gly Gly Thr Lys Leu Thr Val Leu
            100                 105                 110

<210> SEQ ID NO 27
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Gln Val Gln Leu Val Gln Ser Gly Ala Glu Val Lys Lys Pro Gly Ala
1               5                   10                  15

Ser Val Lys Val Ser Cys Lys Ala Ser Gly Asn Thr Phe Thr Ser Tyr
            20                  25                  30

Tyr Ile His Trp Val Arg Gln Ala Pro Gly Gln Gly Leu Glu Trp Met
        35                  40                  45

Gly Ile Ile Ser Pro Ser Gly Asp Ser Thr Ser Tyr Ala Gln Lys Phe
    50                  55                  60

Gln Gly Arg Val Thr Met Thr Lys Asp Thr Ser Thr Ser Thr Val Ser
65                  70                  75                  80

-continued

```
Met Glu Leu Ser Ser Leu Arg Ser Glu Asp Thr Ala Val Tyr Tyr Cys
                 85                  90                  95

Ala Arg Asp Gln Glu Gly Leu Arg Gly Ser Gly Tyr Tyr Gly Met Asp
            100                 105                 110

Val Trp Gly Gln Gly Thr Thr Val Thr Val Ser Ser
        115                 120

<210> SEQ ID NO 28
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Ser Tyr Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Val Val Phe Gly Gly Gly Thr Lys Leu Thr Val Leu
            100                 105

<210> SEQ ID NO 29
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Glu Val Gln Leu Val Glu Ser Gly Gly Val Val Gln Pro Gly Arg
1               5                   10                  15

Ser Leu Arg Leu Ser Cys Ala Ala Ser Gly Phe Pro Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Arg Asp Leu Pro Ala Cys Ser Gly Gly Ser Cys Tyr Ala Thr Trp
            100                 105                 110

Gly Gly Phe Asp Tyr Trp Gly Gln Gly Thr Leu Val Thr Val Ser Ser
        115                 120                 125

<210> SEQ ID NO 30
<211> LENGTH: 106
```

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (97)..(97)
<223> OTHER INFORMATION: Any amino acid

<400> SEQUENCE: 30

Ser Ser Glu Leu Thr Gln Asp Pro Ala Val Ser Val Ala Leu Gly Gln
1               5                   10                  15

Thr Leu Thr Ile Thr Cys Gln Gly Asp Ser Leu Arg Ser Tyr Tyr Ala
            20                  25                  30

Ser Trp Tyr Gln Gln Lys Pro Gly Gln Ala Pro Leu Leu Val Phe Tyr
        35                  40                  45

Gly Tyr Asn Ser Arg Pro Ser Glu Ile Pro Asp Arg Phe Ser Gly Ser
    50                  55                  60

Phe Thr Gly Asp Thr Ala Ser Leu Thr Ile Thr Gly Ala Gln Ala Glu
65                  70                  75                  80

Asp Glu Ala Asp Tyr Tyr Cys Ser Ser Met Ser Gly Asp Leu Val Val
                85                  90                  95

Xaa Gly Gly Gly Thr Lys Val Thr Val Leu
            100                 105

<210> SEQ ID NO 31
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Gln Met Gln Leu Val Gln Ser Gly Ala Glu Val Lys Lys Pro Gly Ser
1               5                   10                  15

Ser Val Lys Val Ser Cys Lys Ala Ser Gly Ala Thr Phe Ser Ser Tyr
            20                  25                  30

Ala Met Ser Trp Val Arg Gln Ala Pro Gly Gln Gly Leu Glu Trp Met
        35                  40                  45

Gly Ala Val Ile Pro Ile Phe Gly Thr Thr Asn Tyr Ala Pro Lys Phe
    50                  55                  60

Glu Gly Arg Val Thr Ile Thr Ala Asp Glu Ser Thr Ser Thr Val Tyr
65                  70                  75                  80

Met Glu Leu Ser Ser Leu Thr Ser Glu Asp Thr Ala Val Tyr Tyr Cys
                85                  90                  95

Ala Arg Gln Ile Gly Glu Val Val Gly Gly Ile Met Glu Asp Tyr Trp
            100                 105                 110

Gly Gln Gly Thr Leu Val Thr Val Ser Ser
        115                 120

<210> SEQ ID NO 32
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32
```

```
Asp Ile Val Met Thr Gln Ser Pro Ser Ser Leu Ser Ala Ser Val Gly
1               5                   10                  15

Asp Arg Val Thr Ile Thr Cys Arg Ala Ser Gln Gly Ile Thr Asn Ser
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Val Ala Ser Tyr Tyr Cys Gln Lys Tyr Asp Ser Ala Pro Leu
                85                  90                  95

Thr Phe Gly Gly Gly Thr Lys Val Glu Ile Lys
            100                 105
```

<210> SEQ ID NO 33
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

```
Gln Met Gln Leu Val Gln Ser Gly Ala Glu Val Lys Lys Pro Gly Ala
1               5                   10                  15

Ser Val Lys Val Ser Cys Lys Ala Ser Gly Asn Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Ser Pro Ser Gly Asp Ser Thr Ser Tyr Ala Gln Lys Phe
50                  55                  60

Gln Gly Arg Val Thr Met Thr Lys Asp Thr Ser Thr Ser Thr Val Ser
65                  70                  75                  80

Met Glu Leu Ser Ser Leu Arg Ser Glu Asp Thr Ala Val Tyr Tyr Cys
                85                  90                  95

Ala Arg Asp Gln Glu Gly Leu Arg Gly Ser Gly Tyr Tyr Gly Met Asp
            100                 105                 110

Val Trp Gly Gln Gly Thr Thr Val Thr Val Ser Ser
        115                 120
```

<210> SEQ ID NO 34
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

```
Ser Tyr Glu Leu Met Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
50                  55                  60
```

```
Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp Ser Ser Ser Asp His
                 85                  90                  95

Val Val Phe Gly Gly Gly Thr Lys Leu Thr Val Leu
            100                 105

<210> SEQ ID NO 35
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Gln Met Gln Leu Val Gln Ser Gly Ala Asp Val Lys Lys Pro Gly Ala
 1               5                  10                  15

Ser Val Lys Val Ser Cys Lys Ala Ser Gly Asn Thr Phe Thr Ser Tyr
             20                  25                  30

Tyr Met His Trp Val Arg Gln Ala Pro Gly Gln Gly Leu Glu Trp Met
         35                  40                  45

Gly Ile Ile Ser Pro Ser Gly Asp Ser Thr Ser Tyr Ala Gln Lys Phe
     50                  55                  60

Gln Gly Arg Val Thr Met Thr Lys Asp Thr Ser Thr Ser Thr Val Ser
 65                  70                  75                  80

Met Glu Leu Ser Ser Leu Arg Ser Glu Asp Thr Ala Val Tyr Tyr Cys
                 85                  90                  95

Ala Arg Asp Gln Glu Gly Leu Arg Gly Ser Gly Tyr Tyr Gly Met Asp
            100                 105                 110

Val Trp Gly Gln Gly Thr Met Val Thr Val Ser Ser
        115                 120

<210> SEQ ID NO 36
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Ser Tyr Glu Leu Met Gln Pro Pro Ser Val Ser Val Ala Ser Gly Lys
 1               5                  10                  15

Thr Ala Arg Ile Thr Cys Gly Gly Asn Asn Ile Gly Ser Lys Ser Val
             20                  25                  30

His Trp Tyr Gln Gln Lys Pro Gly Gln Ala Pro Val Leu Val Val Tyr
         35                  40                  45

Asp Asp Ser Asp Arg Pro Ser Gly Ile Pro Glu Arg Phe Ser Gly Ser
     50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp Ser Ser Ser Asp His
                 85                  90                  95

Val Val Phe Gly Gly Gly Thr Lys Leu Thr Val Leu
            100                 105

<210> SEQ ID NO 37
<211> LENGTH: 117
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Glu Val Gln Leu Leu Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Tyr Met Thr Trp Val Arg Gln Ala Pro Gly Lys Gly Leu Glu Trp Val
        35                  40                  45

Ser Val Ile Tyr Ser Gly Gly Asn Thr Phe Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Arg Glu Met Ser Gly Pro Tyr Phe Asp Tyr Trp Gly Gln Gly Thr Leu
            100                 105                 110

Val Thr Val Ser Ser
            115

<210> SEQ ID NO 38
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Gln Ala Val Val Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Pro Val Ser Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Asp Val Ile Phe Gly Gly Gly Thr Lys Leu Thr Val Leu
            100                 105                 110

<210> SEQ ID NO 39
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
```

```
                  20                  25                  30
Ala Ile Ser Trp Val Arg Gln Ala Pro Gly Gln Gly Leu Glu Trp Met
                 35                  40                  45
Gly Trp Ile Ser Ala Tyr Asn Gly Asn Thr Asn Tyr Ala Gln Lys Leu
             50                  55                  60
Gln Gly Arg Val Thr Met Thr Thr Asp Thr Ser Thr Ser Thr Ala Tyr
 65                  70                  75                  80
Met Glu Leu Arg Ser Leu Arg Ser Asp Asp Thr Ala Val Tyr Tyr Cys
                 85                  90                  95
Ala Arg Ser Arg Tyr Asp Phe Trp Ser Gly Tyr Tyr Ser Gly Met Asp
            100                 105                 110
Val Trp Gly Gln Gly Thr Thr Val Thr Val Ser Ser
            115                 120

<210> SEQ ID NO 40
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Asn Phe Met Leu Thr Gln Pro Arg Ser Val Ser Gly Ser Pro Gly Gln
 1               5                  10                  15
Ser Val Thr Ile Ser Cys Thr Gly Thr Ser Ser Asp Val Gly Gly Tyr
                 20                  25                  30
His Tyr Val Ser Trp Tyr Gln Gln His Pro Gly Lys Ala Pro Lys Leu
             35                  40                  45
Ile Ile Tyr Asp Val Ser Arg Arg Pro Ser Gly Val Pro Asp Arg Phe
         50                  55                  60
Ser Gly Ser Lys Ser Gly Asn Thr Ala Ser Leu Thr Val Ser Gly Leu
 65                  70                  75                  80
Gln Ala Glu Asp Glu Ala Asp Tyr Tyr Cys Ser Ser Tyr Gly Gly Ser
                 85                  90                  95
Asn Asn Phe Val Phe Gly Thr Gly Thr Lys Leu Thr Val Leu
            100                 105                 110

<210> SEQ ID NO 41
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Gln Val Gln Leu Val Glu Ser Gly Gly Gly Val Val Gln Pro Gly Arg
 1               5                  10                  15
Pro Leu Arg Leu Ser Cys Ala Gly Ser Gly Phe Ala Phe Ser Gly Phe
                 20                  25                  30
Ala Met His Trp Val Arg Gln Ala Pro Gly Lys Gly Leu Glu Trp Leu
             35                  40                  45
Ala Val Ile Ser Tyr Asp Gly Arg Asn Asn Tyr Ala Asp Ser Val
         50                  55                  60
Lys Gly Arg Phe Thr Ile Ser Arg Asp Asn Ser Lys Asn Thr Leu Phe
 65                  70                  75                  80
Leu Asp Met Asp Ser Leu Arg Pro Asp Asp Thr Ala Leu Tyr Tyr Cys
```

```
                85                  90                  95
Ala Arg Asp Arg Ser Ser Gly Trp Tyr Gly Leu Ser Asp Tyr Trp Gly
            100                 105                 110

Gln Gly Thr Leu Val Thr Val Ser Ser
        115                 120

<210> SEQ ID NO 42
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Gln Ala Gly Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Arg Tyr
            20                  25                  30

Asp Tyr Val Ser Trp Tyr Gln Gln His Pro Gly Lys Ala Pro Lys Leu
        35                  40                  45

Met Ile Tyr Asp Val Thr Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ile Ser Tyr Thr Thr Ser
                85                  90                  95

Ser Thr Tyr Val Phe Gly Thr Gly Thr Lys Val Thr Val Leu
            100                 105                 110

<210> SEQ ID NO 43
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asn Ile His Trp Val Arg Gln Ala Pro Gly Gln Arg Phe Glu Trp Met
        35                  40                  45

Gly Trp Ile Ser Thr Asp Asn Gly Tyr Thr Glu Tyr Ser Gln Lys Phe
    50                  55                  60

Gln Asp Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Asp Tyr Tyr Cys
                85                  90                  95

Leu Ser Gly Tyr Tyr Phe Asp Tyr Trp Gly Gln Gly Thr Leu Val Thr
            100                 105                 110

Val Ser Ser
        115

<210> SEQ ID NO 44
<211> LENGTH: 106
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 44

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Arg Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Asp Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Ser Cys Gln Gln Tyr Glu Asn Trp Pro Thr
                85                  90                  95

Phe Gly Gln Gly Thr Lys Val Glu Ile Lys
            100                 105

<210> SEQ ID NO 45
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Glu Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met His Trp Val Arg Gln Ala Pro Gly Gln Gly Leu Glu Trp Met
        35                  40                  45

Gly Ile Ile Asn Pro Ser Ser Gly Ser Thr Thr Tyr Ala Gln Lys Phe
50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Arg Ala Val Tyr Tyr Cys
                85                  90                  95

Ala Arg Gly Gln Gly Ser Ser Gly Trp Tyr Thr Phe Asp Tyr Trp Gly
            100                 105                 110

Gln Gly Thr Leu Val Thr Val Ser Ser
        115                 120

<210> SEQ ID NO 46
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Ala Ile Gln Leu Thr Gln Ser Pro Ser Ser Leu Ser Ala Ser Val Gly
1               5                   10                  15

Asp Arg Val Thr Ile Ser Cys Gln Ala Ser Gln Asp Ile Ser Asn Phe
            20                  25                  30
```

Leu Asn Trp Tyr Gln Gln Lys Pro Gly Lys Ala Pro Lys Leu Leu Ile
            35                  40                  45

Tyr Ala Ala Ser Lys Leu Gln Ser Gly Val Pro Ser Arg Phe Ser Gly
        50                  55                  60

Ser Gly Ser Gly Thr Asp Phe Ser Leu Thr Ile Asn Ser Leu Gln Pro
65                  70                  75                  80

Glu Asp Phe Ala Thr Tyr Tyr Cys Gln Gln Thr Asn Ser Phe Pro Leu
                85                  90                  95

Thr Phe Gly Gln Gly Thr Lys Val Glu Ile Lys
            100                 105

<210> SEQ ID NO 47
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Val Gly Gly Glu Val Val Asp Tyr Trp Gly Gln Gly
            100                 105                 110

Thr Leu Val Thr Val Ser Ser
        115

<210> SEQ ID NO 48
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Ser Tyr Glu Leu Met Gln Pro Pro Ser Val Ser Val Ala Pro Gly Gln
1               5                   10                  15

Thr Ala Arg Ile Thr Cys Gly Gly Lys Asn Ile Gly Arg Lys Ser Val
            20                  25                  30

His Trp Tyr Gln Gln Lys Pro Gly Gln Ala Pro Val Leu Val Val Tyr
        35                  40                  45

Asp Asp Arg Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Thr Asp His
                85                  90                  95

```
Val Val Phe Gly Gly Gly Thr Lys Val Thr Val Leu
            100                 105
```

<210> SEQ ID NO 49
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

```
Gln Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Tyr
            20                  25                  30

Tyr Met His Trp Val Arg Gln Ala Pro Gly Gln Gly Leu Glu Trp Val
        35                  40                  45

Gly Ile Ile Asn Pro Asn Gly Asp Lys Ala Gln Tyr Thr Gln Lys Leu
50                  55                  60

Lys Gly Arg Val Thr Met Thr Arg Asp Thr Ser Thr Asn Thr Val Tyr
65                  70                  75                  80

Met Glu Leu Ser Ser Leu Thr Ser Glu Asp Thr Ala Val Tyr Tyr Cys
                85                  90                  95

Thr Thr Asp His Asn Trp Arg Phe Asp Ser Trp Gly Gln Gly Thr Leu
            100                 105                 110

Val Thr Val Ser Ser
        115
```

<210> SEQ ID NO 50
<211> LENGTH: 103
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Thr Thr Phe Gly Gln
                85                  90                  95

Gly Thr Arg Leu Glu Ile Lys
            100
```

<210> SEQ ID NO 51
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Glu Val Gln Leu Val Gln Ser Gly Ala Glu Val Lys Lys Pro Gly Ala
1               5                   10                  15

Ser Val Lys Val Ser Cys Lys Ala Ser Gly Asn Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Ser Pro Ser Gly Asp Ser Thr Ser Tyr Ala Gln Lys Phe
    50                  55                  60

Gln Gly Arg Val Thr Met Thr Lys Asp Thr Ser Thr Ser Thr Val Ser
65                  70                  75                  80

Met Glu Leu Ser Ser Leu Arg Ser Glu Asp Thr Ala Val Tyr Tyr Cys
                85                  90                  95

Ala Arg Asp Gln Glu Gly Leu Arg Gly Ser Gly Tyr Tyr Gly Met Asp
            100                 105                 110

Val Trp Gly Gln Gly Thr Met Val Thr Val Ser Ser
        115                 120

<210> SEQ ID NO 52
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Ser Tyr Glu Leu Met Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Arg Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Val Val Phe Gly Gly Gly Thr Lys Leu Thr Val Leu
            100                 105

<210> SEQ ID NO 53
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Gln Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

```
Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Thr Asn Ser Asp Tyr Tyr Asp Ser Ser Gly Tyr Thr Asn Ala
            100                 105                 110

Phe Asp Ile Trp Gly Gln Gly Thr Met Val Thr Val Ser Ser
        115                 120                 125
```

<210> SEQ ID NO 54
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

```
Asp Ile Val Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Arg Ser
                20                  25                  30

Leu Asn Trp Tyr Gln Lys Lys Pro Gly Lys Ala Pro Asn Leu Leu Ile
            35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Met Pro Ile
                85                  90                  95

Ser Phe Gly Pro Gly Thr Lys Val Asp Ile Lys
            100                 105
```

<210> SEQ ID NO 55
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Gly Tyr Ser Gly Ser Tyr Phe Gly Lys Phe Asp Tyr Trp Gly Gln
            100                 105                 110
```

Gly Thr Leu Val Thr Val Ser Ser
        115                 120

<210> SEQ ID NO 56
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Gln Ala Gly Leu Thr Gln Pro Pro Ser Val Ser Gly Ala Pro Gly Gln
1               5                   10                  15

Arg Val Ser Ile Ser Cys Thr Gly Ser Asp Ser Asn Ile Gly Ala Pro
            20                  25                  30

Tyr Asp Val His Trp Tyr Gln Gln Leu Pro Gly Thr Ala Pro Arg Leu
        35                  40                  45

Leu Ile Tyr Ala Asn Thr Lys Arg Pro Ser Val Pro Asp Arg Phe
50                  55                  60

Ser Gly Trp Lys Ser Gly Thr Ser Ala Ser Leu Ala Ile Ser Gly Leu
65                  70                  75                  80

Gln Ser Glu Asp Glu Ala Ala Tyr Tyr Cys Ala Ala Trp Asp Asp Arg
                85                  90                  95

Leu Asn Ala Tyr Ile Phe Gly Ser Gly Thr Lys Leu Thr Val Leu
            100                 105                 110

<210> SEQ ID NO 57
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Asp Ser Ser Gly Asp Tyr Tyr Tyr Gly Met Asp Val
            100                 105                 110

Trp Gly Gln Gly Thr Thr Val Thr Val Ser Ser
        115                 120

<210> SEQ ID NO 58
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide -continued

<400> SEQUENCE: 58

Gln Pro Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Thr Asn
            20                  25                  30

Tyr Val Asn Trp Tyr Gln Gln Phe Pro Gly Thr Ala Pro Lys Gln Leu
            35                  40                  45

Ile Tyr Ser Asn Asn His Arg Pro Ser Gly Val Pro Asp Arg Phe Ser
50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Trp Val Phe Gly Val Gly Thr Lys Leu Thr Val Leu
            100                 105                 110

<210> SEQ ID NO 59
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Tyr Tyr Asp Ser Ser Gly Tyr Gly Val Gly Phe Asp Tyr
            100                 105                 110

Trp Gly Gln Gly Thr Leu Val Thr Val Ser Ser
        115                 120

<210> SEQ ID NO 60
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Gln Thr Val Val Thr Gln Pro Pro Ser Val Ser Ala Ala Pro Gly Gln
1               5                   10                  15

Lys Val Thr Ile Ser Cys Ser Gly Ser Ser Asn Ile Gly Asn Asn
            20                  25                  30

Tyr Val Ser Trp Tyr Gln Gln Leu Pro Gly Thr Ala Pro Lys Leu Leu
            35                  40                  45

Ile Tyr Asp Asn Asn Lys Arg Pro Ser Gly Ile Pro Asp Arg Phe Ser

```
                        50                  55                  60
Gly Ser Lys Ser Gly Thr Ser Ala Thr Leu Gly Ile Thr Gly Leu Gln
 65                  70                  75                  80

Thr Gly Asp Glu Ala Asp Tyr Tyr Cys Gly Thr Trp Asp Asn Ser Leu
                 85                  90                  95

Ser Ala Gly Val Phe Gly Gly Gly Thr Lys Leu Thr Val Leu
                100                 105                 110

<210> SEQ ID NO 61
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Glu Val Gln Leu Val Gln Ser Gly Val Glu Val Lys Lys Pro Gly Ala
 1               5                  10                  15

Thr Val Lys Ile Ser Cys Lys Val Ser Gly Tyr Thr Phe Thr Asp Tyr
                20                  25                  30

Tyr Met His Trp Val Arg Gln Ala Pro Gly Gln Gly Leu Glu Trp Met
             35                  40                  45

Gly Ile Ile Asn Pro Ser Gly Gly Ser Thr Ser Tyr Ala Gln Lys Phe
         50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Asp Arg Val Asp Ser Ser Ala Trp Ser Pro Gly Ala Asp Tyr
                100                 105                 110

Trp Gly Gln Gly Thr Leu Val Thr Val Ser Ser
            115                 120

<210> SEQ ID NO 62
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Gln Ser Val Leu Thr Gln Pro Pro Ser Val Ser Gly Ala Pro Gly Gln
 1               5                  10                  15

Arg Val Thr Ile Ser Cys Thr Gly Ser Ser Ser Asn Ile Gly Ala Gly
                20                  25                  30

Tyr Asp Val His Trp Tyr Gln Gln Leu Pro Gly Thr Ala Pro Lys Leu
             35                  40                  45

Leu Ile Tyr Asp Asn Asn Lys Arg Pro Ser Gly Ile Pro Asp Arg Phe
         50                  55                  60

Ser Gly Ser Lys Ser Gly Thr Ser Ala Thr Leu Gly Ile Thr Gly Leu
 65                  70                  75                  80

Gln Thr Gly Asp Glu Ala Asp Tyr Tyr Cys Gly Ser Trp Asp Ala Ser
                 85                  90                  95

Leu Ser Ala Ala Val Phe Gly Gly Gly Thr Lys Leu Thr Val Leu
                100                 105                 110
```

```
<210> SEQ ID NO 63
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Glu Val Gln Leu Val Gln Ser Gly Gly Glu Val Lys Lys Pro Gly Ala
1               5                   10                  15

Ser Val Lys Val Ser Cys Lys Ala Ser Gly Asn Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Ser Pro Ser Gly Asp Ser Thr Ser Tyr Ala Gln Lys Phe
    50                  55                  60

Gln Gly Arg Val Thr Met Thr Lys Asp Thr Ser Thr Ser Thr Val Ser
65                  70                  75                  80

Met Glu Leu Ser Ser Leu Arg Ser Glu Asp Thr Ala Val Tyr Tyr Cys
                85                  90                  95

Ala Arg Asp Gln Glu Gly Leu Arg Gly Ser Gly Tyr Tyr Gly Met Asp
            100                 105                 110

Val Trp Gly Gln Gly Thr Thr Val Thr Val Ser Ser
        115                 120

<210> SEQ ID NO 64
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Ser Tyr Glu Leu Met Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Val Val Phe Gly Gly Gly Thr Gln Leu Thr Val Leu
            100                 105

<210> SEQ ID NO 65
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Gln Ile Thr Leu Lys Glu Ser Gly Gly Gly Val Val Gln Pro Gly Arg
1               5                   10                  15
```

```
Ser Leu Arg Leu Ser Cys Ala Ala Ser Gly Phe Thr Phe Ser Thr Tyr
         20                  25                  30

Gly Met His Trp Val Arg Gln Ala Pro Gly Lys Gly Leu Glu Trp Val
         35                  40                  45

Ala Val Ile Leu Asn Asp Gly Ser Gln Ser His Tyr Ala Asp Ser Leu
 50                  55                  60

Lys Gly Arg Phe Thr Ile Ser Arg Asp Asn Ser Arg Asn Thr Leu Tyr
 65                  70                  75                  80

Leu Gln Met Asp Ser Leu Arg Val Glu Asp Thr Ala Met Tyr Tyr Cys
                 85                  90                  95

Ala Arg Asp Asp Arg Ala Ala Asn Ala Phe Asp Val Trp Gly Gln
             100                 105                 110

Gly Thr Met Val Thr Val Ser Ser
         115                 120

<210> SEQ ID NO 66
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Gln Ser Val Leu Thr Gln Pro Pro Ser Val Ser Ala Ala Pro Gly Gln
 1               5                  10                  15

Lys Val Thr Ile Ser Cys Ser Gly Ser Ser Ser Asn Ile Gly Asn Asn
             20                  25                  30

Tyr Val Ser Trp Tyr Gln Gln Leu Pro Gly Thr Ala Pro Lys Leu Leu
         35                  40                  45

Ile Tyr Asp Asn Asn Lys Arg Pro Ser Gly Ile Pro Asp Arg Phe Ser
 50                  55                  60

Gly Ser Lys Ser Gly Thr Ser Ala Thr Leu Gly Ile Thr Gly Leu Gln
 65                  70                  75                  80

Thr Gly Asp Glu Ala Asp Tyr Tyr Cys Gly Thr Trp Asp Ser Ser Leu
                 85                  90                  95

Ser Ala Trp Val Phe Gly Gly Gly Thr Lys Leu Thr Val Leu
             100                 105                 110

<210> SEQ ID NO 67
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Glu Val Gln Leu Val Gln Ser Gly Gly Glu Val Lys Lys Pro Gly Ala
 1               5                  10                  15

Ser Val Lys Val Ser Cys Lys Ala Ser Gly Asn Thr Phe Thr Ser Tyr
             20                  25                  30

Tyr Met His Trp Val Arg Gln Ala Pro Gly Gln Gly Leu Glu Trp Met
         35                  40                  45

Gly Ile Ile Ser Pro Ser Gly Asp Ser Thr Tyr Ala Gln Lys Phe
 50                  55                  60

Gln Gly Arg Val Thr Met Thr Lys Asp Thr Ser Thr Ser Thr Val Ser
 65                  70                  75                  80
```

```
Met Glu Leu Ser Ser Leu Arg Ser Glu Asp Thr Ala Val Tyr Tyr Cys
                85                  90                  95

Ala Arg Asp Gln Glu Gly Leu Arg Gly Ser Gly Tyr Tyr Gly Met Asp
            100                 105                 110

Val Trp Gly Gln Gly Thr Thr Val Thr Val Ser Ser
        115                 120
```

<210> SEQ ID NO 68
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

```
Ser Tyr Glu Leu Met Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Val Val Phe Gly Gly Gly Thr Gln Leu Thr Val Leu
            100                 105
```

<210> SEQ ID NO 69
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

```
Glu Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Leu His Trp Val Arg Gln Ala Pro Gly Gln Gly Leu Glu Trp Val
        35                  40                  45

Gly Leu Leu Asn Pro Ser Gly Ser Thr Asn Tyr Ala Gln Lys Phe
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ser Pro Asp Asp Tyr Tyr Gly Ser Gly Asn Tyr Asp Tyr
            100                 105                 110

Trp Gly Gln Gly Thr Leu Val Thr Val Ser Ser
        115                 120
```

<210> SEQ ID NO 70

<211> LENGTH: 110
<212> TYPE: PRT
<213> ORGANISM: Artificial Sequence
<220> FEATURE:
<223> OTHER INFORMATION: Description of Artificial Sequence: Synthetic
       polypeptide

<400> SEQUENCE: 70

Gln Pro Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln Tyr Pro Gly Lys Ala Pro Lys Leu
        35                  40                  45

Leu Ile Tyr Asp Val Asn Lys Arg Pro Ser Gly Val Ser Ile Arg Phe
    50                  55                  60

Ser Ala Ser Lys Ser Gly Asn Ala Ala Ser Leu Thr Leu Ser Gly Leu
65                  70                  75                  80

Gln Ala Glu Asp Glu Ala Asp Tyr Tyr Cys Ser Ser Tyr Ser Ser Arg
                85                  90                  95

Arg Gly Val Val Phe Gly Gly Gly Thr Lys Leu Thr Val Leu
            100                 105                 110

<210> SEQ ID NO 71
<211> LENGTH: 123
<212> TYPE: PRT
<213> ORGANISM: Artificial Sequence
<220> FEATURE:
<223> OTHER INFORMATION: Description of Artificial Sequence: Synthetic
       polypeptide

<400> SEQUENCE: 71

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Arg Tyr Ser Ser Ser Ala Ala Gly Tyr Gly Met Asp Val
            100                 105                 110

Trp Gly Gln Gly Thr Thr Val Thr Val Ser Ser
        115                 120

<210> SEQ ID NO 72
<211> LENGTH: 110
<212> TYPE: PRT
<213> ORGANISM: Artificial Sequence
<220> FEATURE:
<223> OTHER INFORMATION: Description of Artificial Sequence: Synthetic
       polypeptide

<400> SEQUENCE: 72

Gln Pro Val Leu Thr Gln Pro Ala Ser Val Ser Gly Ser Pro Gly Gln
1               5                   10                  15

Ser Ile Thr Ile Ser Cys Thr Gly Ile Asn Ser Asn Val Asp Gly Ser
                20                  25                  30

Asp Ala Val Ser Trp Tyr Gln Gln His Pro Gly Lys Ala Pro Lys Leu
            35                  40                  45

Ile Ala Phe Asp Val Thr Gln Arg Pro Ser Gly Val Pro Asp Arg Phe
        50                  55                  60

Ser Ala Ser Lys Ser Gly Lys Thr Ala Ser Leu Thr Ile Ser Gly Leu
65                  70                  75                  80

Gln Pro Glu Asp Glu Ala Asp Tyr Tyr Cys Ser Ser Tyr Thr Thr Ser
                85                  90                  95

Ser Thr Phe Val Phe Gly Thr Gly Thr Lys Val Thr Val Leu
            100                 105                 110

<210> SEQ ID NO 73
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Asp Trp Asn Tyr Ala Leu Asp Tyr Trp Gly Gln Gly Thr
            100                 105                 110

Leu Val Thr Val Ser Ser
        115

<210> SEQ ID NO 74
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Gln Pro Val Leu Thr Gln Pro Ala Ser Val Ser Gly Ser Pro Gly Gln
1               5                   10                  15

Ser Ile Thr Ile Ser Cys Thr Gly Thr Arg Ser Asp Val Gly Gly Tyr
                20                  25                  30

Ser Tyr Val Ser Trp Tyr Gln Gln His Pro Gly Lys Ala Pro Lys Leu
            35                  40                  45

Ile Tyr Asp Val Thr Lys Arg Pro Ser Gly Val Ser Asn Arg Phe Ser
        50                  55                  60

Gly Ser Lys Ser Gly Asn Thr Ala Ser Leu Thr Ile Ser Gly Leu Gln
65                  70                  75                  80

Ala Glu Asp Glu Ala Asp Tyr Tyr Cys Ser Ser Tyr Thr Ser Ser
                85                  90                  95

Thr Tyr Val Phe Gly Thr Gly Thr Lys Val Thr Val Leu
            100                 105

<210> SEQ ID NO 75
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Asp Leu Ala Met Arg Arg Gly Tyr Ser Tyr Gly Tyr Pro
            100                 105                 110

Gly Tyr Trp Gly Gln Gly Thr Leu Val Thr Val Ser Ser
        115                 120                 125

<210> SEQ ID NO 76
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Gln Ser Val Leu Thr Gln Pro Pro Ser Ala Ser Gly Ser Pro Gly Gln
1               5                   10                  15

Ser Leu Ala Ile Ser Cys Thr Gly Thr Ser Ser Asp Val Gly Gly Tyr
            20                  25                  30

Asn Tyr Val Ser Trp Tyr Gln His Pro Gly Lys Ala Pro Lys Leu
        35                  40                  45

Ile Ile Tyr Asp Val Asn Lys Arg Pro Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Phe Cys Ser Ser Tyr Ala Val Asn
                85                  90                  95

Asn Asn Ser Pro Tyr Phe Phe Gly Thr Gly Thr Lys Val Thr Val Leu
            100                 105                 110

<210> SEQ ID NO 77
<211> LENGTH: 118
<212> TYPE: PRT
<213> ORGANISM: Artificial Sequence
<220> FEATURE:

```
<223> OTHER INFORMATION: Description of Artificial Sequence: Synthetic
      polypeptide

<400> SEQUENCE: 77

Gln Val Gln Leu Val Gln Ser Gly Gly Gly Leu Ile Gln Pro Gly Gly
1               5                   10                  15

Ser Leu Arg Leu Ser Cys Ala Ala Ser Ala Phe Thr Val Ser Asn Phe
            20                  25                  30

Tyr Met Thr Trp Val Arg Gln Ala Pro Gly Lys Gly Leu Glu Trp Val
        35                  40                  45

Ser Val Ile Asp Ser Gly Gly Asn Thr Tyr Tyr Ala Asp Ser Val Arg
    50                  55                  60

Gly Arg Phe Thr Ile Ser Arg Asp Asn Ser Lys Asn Thr Leu Phe Leu
65                  70                  75                  80

Gln Met Asn Ser Leu Arg Ala Glu Asp Thr Ala Val Tyr Tyr Cys Ala
                85                  90                  95

Arg Asp Leu Gly Tyr Tyr Tyr Ala Met Asp Val Trp Gly Gln Gly Thr
            100                 105                 110

Thr Val Thr Val Ser Ser
        115

<210> SEQ ID NO 78
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Thr Ser
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Thr
                85                  90                  95

Phe Gly Gln Gly Thr Lys Leu Glu Ile Lys
            100                 105

<210> SEQ ID NO 79
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
```

```
                35                  40                  45
Gly Trp Ile Ser Ala Tyr Asn Gly Asn Thr Asn Tyr Ala Gln Lys Leu
 50                  55                  60

Gln Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Asp Leu Ala Tyr Ser Ser Gly Trp Leu Asp Tyr Trp Gly Gln
            100                 105                 110

Gly Thr Leu Val Thr Val Ser Ser
            115                 120

<210> SEQ ID NO 80
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Gln Ala Gly Leu Thr Gln Pro Ala Ser Val Ser Gly Ser Pro Gly Gln
 1               5                  10                  15

Ser Ile Thr Met Ser Cys Ile Val Ser Asn Ile Asp Ile Gly Gly Phe
                20                  25                  30

His Tyr Val Ser Trp Tyr Gln His Arg Pro Gly Glu Ala Pro Lys Leu
             35                  40                  45

Leu Ile Tyr Asp Val Asp Lys Arg Pro Pro Gly Val Ser Asn Arg Phe
 50                  55                  60

Ser Ala Ser Lys Ser Gly His Thr Ala Ser Leu Thr Ile Ser Gly Leu
 65                  70                  75                  80

His Pro Glu Asp Asp Ala Glu Tyr Tyr Cys Ser Ser Phe Thr Ser Arg
                85                  90                  95

Ser Val Leu Phe Gly Gly Gly Thr Lys Val Thr Val Leu
            100                 105

<210> SEQ ID NO 81
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asn Tyr
                20                  25                  30

Asp Ile Ser Trp Val Arg Gln Ala Pro Gly Gln Gly Leu Glu Trp Met
             35                  40                  45

Gly Trp Ile Ser Thr Tyr Asn Gly Asp Thr Ile Tyr Ala Gln Lys Leu
 50                  55                  60

Gln Asp Arg Val Thr Met Thr Thr Asp Thr Ser Thr Ser Thr Ala Tyr
 65                  70                  75                  80

Met Glu Val Arg Ser Leu Arg Ser Asp Asp Thr Ala Val Tyr Tyr Cys
                85                  90                  95

Ala Arg Gly Asn Asp Leu Asp Tyr Trp Gly Gln Gly Thr Leu Val Thr
```

Val Ser Ser
    115

<210> SEQ ID NO 82
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Gln Ser Val Leu Thr Gln Pro Ala Ser Val Ser Gly Ser Pro Gly Gln
1               5                   10                  15

Ser Ile Thr Ile Ser Cys Thr Glu Thr Ser Ser Asp Val Gly Thr Tyr
            20                  25                  30

Asn Tyr Val Ser Trp Tyr Gln Gln His Pro Gly Lys Ala Pro Gln Leu
        35                  40                  45

Ile Ile Phe Asp Val Ser Asn Arg Pro Ser Gly Val Ser Thr Arg Phe
    50                  55                  60

Ser Gly Ser Lys Ser Gly Asn Thr Ala Ser Leu Thr Ile Ser Gly Leu
65                  70                  75                  80

Gln Thr Glu Asp Glu Ala Asp Tyr Tyr Cys Ser Ser Tyr Ile Ala Thr
                85                  90                  95

Tyr Thr Pro Leu Tyr Val Phe Gly Thr Gly Thr Lys Leu Thr Val Leu
            100                 105                 110

<210> SEQ ID NO 83
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Glu Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met His Trp Val Arg Gln Ala Pro Gly Gln Gly Leu Glu Trp Met
        35                  40                  45

Gly Ile Ile Asn Pro Ser Asp Gly Asn Thr Ser Tyr Ala Gln Lys Phe
    50                  55                  60

Gln Gly Arg Val Thr Met Thr Lys Asp Thr Ser Thr Ser Thr Val Tyr
65                  70                  75                  80

Met Glu Leu Ser Ser Leu Arg Ser Asp Asp Thr Ala Val Tyr Tyr Cys
                85                  90                  95

Ala Arg Glu Ser Ser Ser Trp Glu Thr Tyr Phe Asp Tyr Trp Gly Gln
            100                 105                 110

Gly Thr Leu Val Thr Val Ser Ser
        115                 120

<210> SEQ ID NO 84
<211> LENGTH: 108
<212> TYPE: PRT
<213> ORGANISM: Artificial Sequence
<220> FEATURE:
<223> OTHER INFORMATION: Description of Artificial Sequence: Synthetic

```
            polypeptide

<400> SEQUENCE: 84

Ser Tyr Glu Leu Met Gln Pro Pro Ser Val Ser Val Ala Pro Gly Lys
1               5                   10                  15

Thr Ala Lys Ile Thr Cys Gly Gly Asp Asn Ile Gly Ile Lys Ser Val
            20                  25                  30

His Trp Tyr Gln Gln Lys Pro Gly Gln Ala Pro Ile Leu Val Ile His
        35                  40                  45

His Asp Arg Gly Arg Pro Ser Gly Ile Pro Glu Arg Leu Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Gly Thr Ser Asp His
                85                  90                  95

Val Val Phe Gly Gly Gly Thr Lys Leu Thr Val Leu
            100                 105

<210> SEQ ID NO 85
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Pro Glu Tyr Cys Ser Gly Gly Ser Cys Tyr Ser Ala
            100                 105                 110

Asp Ala Phe Asp Ile Trp Gly Gln Gly Thr Met Val Thr Val Ser Ser
        115                 120                 125

<210> SEQ ID NO 86
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45
```

Gly Lys Asn Asn Arg Pro Ser Gly Ile Pro Asp Arg Phe Ser Gly Ser
            50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

Pro Leu Val Phe Gly Thr Gly Thr Lys Leu Thr Val Leu
            100                 105

<210> SEQ ID NO 87
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Glu Val Gln Leu Val Gln Ser Gly Ala Glu Val Arg Lys Pro Gly Ala
1               5                   10                  15

Ser Val Lys Val Ser Cys Lys Pro Ser Gly Tyr Ile Phe Ser Ser Arg
            20                  25                  30

Tyr Met His Trp Val Arg Gln Ala Pro Gly Gln Gly Leu Glu Trp Met
        35                  40                  45

Gly Ile Val Asn Pro Ser Gly Ser Thr Lys Tyr Ala Gln Lys Phe
    50                  55                  60

Gln Gly Arg Ile Thr Met Thr Arg Asp Thr Ser Thr Arg Thr Phe Tyr
65                  70                  75                  80

Met Glu Leu Asn Ser Leu Arg Ser Glu Asp Thr Ala Val Tyr Tyr Cys
                85                  90                  95

Ala Arg His Thr Gly Asn His Gly Gly Trp Tyr Met Asp Gly Phe Asp
            100                 105                 110

Met Trp Gly Gln Gly Thr Met Val Thr Val Ser Ser
        115                 120

<210> SEQ ID NO 88
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Gln Ala Gly Leu Thr Gln Pro Pro Ser Val Ser Gly Ala Pro Gly Gln
1               5                   10                  15

Arg Val Thr Ile Ser Cys Ser Gly Ser Thr Ser Asn Ile Gly Ser Asn
            20                  25                  30

Ile Val Asn Trp Tyr Gln Gln Leu Pro Gly Thr Ala Pro Lys Leu Leu
        35                  40                  45

Ile Phe Asn Asn His His Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Gln
                85                  90                  95

Asn Ala Tyr Val Phe Gly Thr Gly Thr Lys Val Thr Val Leu
            100                 105                 110

<210> SEQ ID NO 89
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Glu Glu Gly Gly Arg Leu Gly Phe Asp Tyr Trp Gly Gln
            100                 105                 110

Gly Thr Leu Val Thr Val Ser Ser
        115                 120

<210> SEQ ID NO 90
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Asn Phe Met Leu Thr Gln Pro Pro Ser Val Ser Ala Ala Pro Gly Gln
1               5                   10                  15

Arg Val Thr Ile Ser Cys Ser Gly Arg Ser Thr Asn Ile Gly Lys Asn
            20                  25                  30

Asp Val Ser Trp Tyr Gln Gln Phe Pro Gly Ala Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Asn Gly Leu
                85                  90                  95

Gly Val Val Leu Phe Gly Gly Gly Thr Lys Leu Thr Val Leu
            100                 105                 110

<210> SEQ ID NO 91
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Leu Ala Tyr Ser Ser Gly Trp Leu Asp Tyr Trp Gly Gln
            100                 105                 110

Gly Thr Leu Val Thr Val Ser Ser
            115                 120

<210> SEQ ID NO 92
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Gln Pro Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Asp Lys Ala Pro Lys Leu
        35                  40                  45

Ile Ile Tyr Asp Val Ser Lys Arg Pro Ser Gly Val Ser Thr Arg Phe
    50                  55                  60

Ser Gly Ser Lys Ser Ala Tyr Thr Ala Ser Leu Thr Ile Ser Gly Leu
65                  70                  75                  80

Arg Ala Glu Asp Glu Ala Asp Tyr Tyr Cys Ser Ser Phe Thr Asn Asp
                85                  90                  95

Ser Pro Val Phe Gly Gly Gly Thr Gln Leu Thr Val Leu
            100                 105                 110

<210> SEQ ID NO 93
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Glu Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Ile His Trp Val Arg Gln Ala Pro Gly Gln Gly Leu Glu Trp Met
        35                  40                  45

Gly Val Ile Asn Pro Ser Gly Gly Ser Thr Thr Tyr Ala Glu Lys Phe
    50                  55                  60

```
Gln Gly Arg Ile Thr Met Thr Arg Asp Thr Ser Thr Lys Met Leu Phe
65                  70                  75                  80

Met Glu Leu Ser Ser Leu Arg Ser Asp Thr Ala Val Tyr Tyr Cys
                85                  90                  95

Ala Arg Ser Pro Gly Ala Ala Leu Phe Asp Tyr Trp Gly Gln Gly Thr
            100                 105                 110

Leu Val Thr Val Ser Ser
            115

<210> SEQ ID NO 94
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Gln Ser Val Val Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Val Pro Gly Thr Ala Pro Lys Leu Leu
        35                  40                  45

Ile Tyr Asp Asn Asn Glu Arg Pro Ser Gly Ile Pro Asp Arg Phe Ser
50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Gly Val Phe Gly Gly Gly Thr Lys Leu Thr Val Leu
            100                 105                 110

<210> SEQ ID NO 95
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ile Asp Tyr
            20                  25                  30

Ser Met His Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Leu Tyr Asp Ser Ser Val Arg Asp Ala Phe Asp Ile
            100                 105                 110

Trp Gly Gln Gly Thr Met Val Thr Val Ser Ser
            115                 120
```

<210> SEQ ID NO 96
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Gln Ser Val Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Ala Gly Ser
                85                  90                  95

Asn Asn Leu Val Phe Gly Gly Gly Thr Lys Val Thr Val Leu
            100                 105                 110

<210> SEQ ID NO 97
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

Glu Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met His Trp Val Arg Gln Ala Pro Gly Gln Gly Leu Glu Trp Met
        35                  40                  45

Gly Ile Ile Asn Pro Ser Asp Gly Asn Thr Ser Tyr Ala Gln Lys Phe
    50                  55                  60

Gln Gly Arg Val Thr Met Thr Lys Asp Thr Ser Thr Ser Thr Val Tyr
65                  70                  75                  80

Met Glu Leu Ser Ser Leu Arg Ser Asp Asp Thr Ala Val Tyr Tyr Cys
                85                  90                  95

Ala Arg Glu Ser Ser Ser Trp Glu Thr Tyr Phe Asp Tyr Trp Gly Gln
            100                 105                 110

Gly Thr Leu Val Thr Val Ser Ser
        115                 120

<210> SEQ ID NO 98
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Ser Tyr Glu Leu Met Gln Pro Pro Ser Val Ser Val Ala Pro Gly Lys

```
1               5                   10                  15
Thr Ala Arg Ile Thr Cys Gly Gly Asn Asn Ile Gly Ser Lys Ser Val
                20                  25                  30

His Trp Tyr Gln Gln Lys Pro Gly Gln Ala Pro Val Leu Val Val Tyr
                35                  40                  45

Asp Asp Ser Asp Arg Pro Ser Gly Ile Pro Glu Arg Phe Ser Gly Ser
                50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Val Val Phe Gly Gly Gly Thr Lys Leu Thr Val Leu
                100                 105
```

<210> SEQ ID NO 99
<211> LENGTH: 122
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 99

```
Gln Val Gln Leu Val Gln Ser Gly Gly Gly Leu Val Gln Ser Gly Gly
1               5                   10                  15

Ser Leu Arg Leu Ser Cys Ala Ala Ser Gly Phe Ser Phe Arg Ser His
                20                  25                  30

Trp Met His Trp Val Arg Gln Ala Pro Gly Lys Gly Leu Glu Trp Val
                35                  40                  45

Ala Ser Ile Ser Pro Asp Gly Thr Asp Lys Tyr Tyr Val Glu Ser Leu
                50                  55                  60

Gln Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gln Val Glu Gln Arg Gly Val Tyr Asp Met Asp Val Trp
                100                 105                 110

Gly Gln Gly Thr Thr Val Thr Val Ser Ser
        115                 120
```

<210> SEQ ID NO 100
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 100

```
Val Ile Trp Met Thr Gln Ser Pro Ser Ser Leu Ser Ala Ser Val Gly
1               5                   10                  15

Asp Arg Val Thr Ile Thr Cys Gln Ala Thr Gln Asp Ile Asn Asn Asn
                20                  25                  30

Leu Asn Trp Tyr Gln His Arg Pro Gly Glu Ala Pro Thr Leu Leu Ile
                35                  40                  45

Tyr Gly Ala Ser Thr Leu Gln Ser Gly Val Pro Ser Arg Phe Ser Gly
                50                  55                  60

Ser Gly Phe Gly Thr Asp Phe Thr Leu Thr Ile Ser Ser Leu Gln Pro
```

```
                           65                  70                  75                  80
Glu Asp Val Ala Thr Tyr Tyr Cys Gln Lys Tyr Asp Asp Pro Leu
                    85                  90                  95

Thr Phe Gly Gly Gly Thr Lys Val Glu Ile Lys
                    100                 105

<210> SEQ ID NO 101
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Gln Val Gln Leu Val Gln Ser Gly Ala Glu Val Lys Lys Pro Gly Ala
1               5                   10                  15

Ser Val Lys Val Ser Cys Gln Ala Ser Gly Tyr Thr Phe Thr Ser Tyr
                20                  25                  30

Asp Ile His Trp Val Arg Gln Val Pro Gly Gln Arg Leu Glu Trp Met
            35                  40                  45

Gly Ile Ile Asn Pro Ser Gly Gly Ser Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Ser Tyr Gly Pro Ser Asp Tyr Trp Gly Gln Gly
                100                 105                 110

Thr Leu Val Thr Val Ser Ser
        115

<210> SEQ ID NO 102
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Asp Val Val Met Thr Gln Ser Pro Ser Thr Leu Ser Ala Ser Val Gly
1               5                   10                  15

Asp Arg Val Thr Ile Thr Cys Arg Ala Ser Gln Arg Ile Ser Ser Trp
                20                  25                  30

Leu Ala Trp Tyr Gln Gln Lys Pro Gly Lys Ala Pro Lys Ser Leu Ile
            35                  40                  45

Tyr Ala Ala Ser Ser Leu Gln Ser Gly Val Pro Ser Lys Phe Ser Gly
        50                  55                  60

Gly Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ile Tyr Tyr Pro Pro
                85                  90                  95

Thr Phe Gly Gln Gly Thr Arg Leu Glu Ile Lys
                100                 105

<210> SEQ ID NO 103
<211> LENGTH: 119
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 103

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Ser Tyr
            20                  25                  30
Ala Met His Trp Val Arg His Ala Pro Gly Gln Arg Leu Glu Trp Met
        35                  40                  45
Gly Trp Ile Asn Ala Gly Asn Gly Asn Thr Lys Tyr Ser Gln Lys Phe
    50                  55                  60
Gln Gly Arg Val Thr Ile Thr Arg Asp Thr Ser Ala Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Asp Leu Asp Tyr Tyr Gly Met Asp Val Trp Gly Gln Gly
            100                 105                 110
Thr Thr Val Thr Val Ser Ser
        115
```

<210> SEQ ID NO 104
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

```
Gln Pro Val Leu Thr Gln Pro Pro Ser Ala Ser Gly Thr Pro Gly Gln
1               5                   10                  15
Arg Val Thr Ile Ser Cys Ser Gly Ser Ser Ser Asn Ile Gly Ser Asn
            20                  25                  30
Ile Val Asn Trp Tyr Gln Gln Leu Pro Gly Thr Ala Pro Lys Leu Leu
        35                  40                  45
Ile Tyr Ser Asn Asn Arg Arg Pro Ser Gly Val Pro Asp Arg Phe Ser
    50                  55                  60
Gly Ser Lys Ser Gly Ser Ser Ala Ser Leu Ala Ile Ser Gly Leu Gln
65                  70                  75                  80
Ser Glu Asp Glu Ala Asp Tyr Tyr Cys Ala Ala Trp Asp Ala Thr Leu
                85                  90                  95
Gly Gly Leu Tyr Val Phe Gly Thr Gly Thr Lys Val Thr Val Leu
            100                 105                 110
```

<210> SEQ ID NO 105
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

```
Glu Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Ser Tyr
            20                  25                  30
```

Tyr Met His Trp Val Arg Gln Ala Pro Gly Gln Gly Leu Glu Trp Met
            35                  40                  45

Gly Ile Ile Asn Pro Ser Asp Gly Asn Thr Ser Tyr Ala Gln Lys Phe
 50                  55                  60

Gln Gly Arg Val Thr Met Thr Lys Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Glu Ser Ser Ser Trp Glu Tyr Phe Asp Tyr Trp Gly Gln
                100                 105                 110

Gly Thr Leu Val Thr Val Ser Ser
            115                 120

<210> SEQ ID NO 106
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Gln Pro Val Leu Thr Gln Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Ile Tyr
            35                  40                  45

Tyr Asp Thr Asp Arg Pro Ser Gly Ile Pro Glu Arg Phe Ser Gly Ser
 50                  55                  60

Asn Ser Gly Asn Thr Ala Thr Leu Thr Ile Ser Arg Val Glu Ala Gly
 65                  70                  75                  80

Asp Glu Ala Asp Phe Tyr Cys Gln Val Trp Ser Ser Ser Asp His
                 85                  90                  95

Val Val Phe Gly Gly Gly Thr Lys Leu Thr Val Leu
                100                 105

<210> SEQ ID NO 107
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
            35                  40                  45

Ser Tyr Ile Ser Ser Ser Ser Ser Tyr Thr Asn Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

-continued

Ala Lys His Ser Ser Ser Trp Tyr Gly Asp Leu Asp Tyr Trp Gly Gln
            100                 105                 110

Gly Thr Leu Val Thr Val Ser Ser
        115                 120

<210> SEQ ID NO 108
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

Gln Ser Ala Leu Thr Gln Pro Pro Ser Val Ser Ala Ala Pro Gly Gln
1               5                   10                  15

Lys Val Thr Ile Ser Cys Ser Gly Ser Ser Asn Ile Ala Asn Asn
            20                  25                  30

Tyr Val Ser Trp Tyr Gln Gln Leu Pro Gly Thr Ala Pro Lys Leu Leu
            35                  40                  45

Ile Tyr Asp Asn Asn Lys Arg Pro Ser Gly Ile Pro Asp Arg Phe Ser
50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Gly Ser Leu
                85                  90                  95

Ser Ala Gly Val Phe Gly Gly Gly Thr Lys Leu Thr Val Leu
            100                 105                 110

<210> SEQ ID NO 109
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

Gln Met Gln Leu Val Gln Ser Gly Ala Glu Val Lys Lys Pro Gly Ser
1               5                   10                  15

Ser Val Lys Val Ser Cys Lys Ala Ser Gly Ala Thr Phe Ser Ser Tyr
            20                  25                  30

Ala Met Ser Trp Val Arg Gln Ala Pro Gly Gln Gly Leu Glu Trp Met
            35                  40                  45

Gly Ala Val Ile Pro Ile Phe Gly Thr Thr Asn Tyr Ala Pro Lys Phe
50                  55                  60

Glu Gly Arg Val Thr Ile Thr Ala Asp Glu Ser Thr Ser Thr Val Tyr
65                  70                  75                  80

Met Glu Leu Ser Ser Leu Thr Ser Glu Asp Thr Ala Val Tyr Tyr Cys
                85                  90                  95

Ala Arg Gln Ile Gly Glu Val Val Gly Gly Ile Met Glu Asp Tyr Trp
            100                 105                 110

Gly Gln Gly Thr Leu Val Thr Val Ser Ser
            115                 120

<210> SEQ ID NO 110
<211> LENGTH: 107
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 110

Asp Ile Val Met Thr Gln Ser Pro Ser Ser Leu Ser Pro Ser Ile Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr His Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Ser Ala Pro Leu
                85                  90                  95

Thr Phe Gly Gly Gly Thr Lys Val Glu Ile Lys
            100                 105

<210> SEQ ID NO 111
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Glu Val Gln Leu Val Glu Ser Gly Gly Gly Leu Ile Gln Pro Gly Gly
1               5                   10                  15

Ser Leu Arg Leu Ser Cys Ala Ala Ser Ala Phe Thr Val Ser Asn Phe
            20                  25                  30

Tyr Met Thr Trp Val Arg Gln Ala Pro Gly Lys Gly Leu Glu Trp Val
        35                  40                  45

Ser Val Ile Asp Ser Gly Gly Asn Thr Tyr Tyr Ala Asp Ser Val Arg
    50                  55                  60

Gly Arg Phe Thr Ile Ser Arg Asp Asn Ser Lys Asn Thr Leu Phe Leu
65                  70                  75                  80

Gln Met Asn Ser Leu Arg Ala Glu Asp Thr Ala Val Tyr Tyr Cys Ala
                85                  90                  95

Arg Asp Leu Gly Tyr Tyr Tyr Ala Met Asp Val Trp Gly Gln Gly Thr
            100                 105                 110

Thr Val Thr Val Ser Ser
        115

<210> SEQ ID NO 112
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Thr Ser
            20                  25                  30
```

```
Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Thr
                85                  90                  95

Phe Gly Gln Gly Thr Lys Leu Glu Ile Lys
            100                 105

<210> SEQ ID NO 113
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Asp Ile Gln Met Thr Gln Ser Pro Ser Ser Leu Ser Ala Ser Val Gly
1               5                   10                  15

Asp Arg Val Thr Ile Thr Cys Pro Ala Ser Gln Ser Ile Ser Thr Ser
            20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Thr
                85                  90                  95

Phe Gly Gln Gly Thr Lys Leu Glu Ile Lys
            100                 105

<210> SEQ ID NO 114
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

Asp Ile Gln Met Thr Gln Ser Pro Ser Ser Leu Ser Ala Ser Val Gly
1               5                   10                  15

Asp Arg Val Thr Ile Thr Cys Arg Ala Ser His Ser Ile Ser Thr Ser
            20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Thr
                85                  90                  95

Phe Gly Gln Gly Thr Lys Leu Glu Ile Lys
            100                 105
```

<210> SEQ ID NO 115
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

Asp Ile Gln Met Thr Gln Ser Pro Ser Ser Leu Ser Ala Ser Val Gly
1               5                   10                  15

Asp Arg Val Thr Ile Thr Cys Arg Ala Ser Pro Ser Ile Ser Thr Ser
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Thr
                85                  90                  95

Phe Gly Gln Gly Thr Lys Leu Glu Ile Lys
            100                 105

<210> SEQ ID NO 116
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Thr Ser Thr Ser
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Thr
                85                  90                  95

Phe Gly Gln Gly Thr Lys Leu Glu Ile Lys
            100                 105

<210> SEQ ID NO 117
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ser Ser Thr Ser

```
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Thr
                 85                  90                  95

Phe Gly Gln Gly Thr Lys Leu Glu Ile Lys
                100                 105

<210> SEQ ID NO 118
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Phe Ser Thr Ser
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Thr
                 85                  90                  95

Phe Gly Gln Gly Thr Lys Leu Glu Ile Lys
                100                 105

<210> SEQ ID NO 119
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Pro Ser Thr Ser
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Thr
                 85                  90                  95

Phe Gly Gln Gly Thr Lys Leu Glu Ile Lys
```

<210> SEQ ID NO 120
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ala Ser
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Thr
                85                  90                  95

Phe Gly Gln Gly Thr Lys Leu Glu Ile Lys
            100                 105

<210> SEQ ID NO 121
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Thr Thr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Thr
                85                  90                  95

Phe Gly Gln Gly Thr Lys Leu Glu Ile Lys
            100                 105

<210> SEQ ID NO 122
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Thr Ser
                20                  25                  30

Gln Asn Trp Tyr Gln Gln Lys Pro Gly Lys Ala Pro Lys Leu Leu Ile
         35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Thr
                 85                  90                  95

Phe Gly Gln Gly Thr Lys Leu Glu Ile Lys
            100                 105

<210> SEQ ID NO 123
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Thr Ser
                20                  25                  30

Leu Asn Trp Tyr Gln Gln Lys Pro Gly Lys Ala Pro Lys Leu Leu Ile
         35                  40                  45

Tyr Leu Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Thr
                 85                  90                  95

Phe Gly Gln Gly Thr Lys Leu Glu Ile Lys
            100                 105

<210> SEQ ID NO 124
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Asn Phe
                20                  25                  30

Tyr Met Thr Trp Val Arg Gln Ala Pro Gly Lys Gly Leu Glu Trp Val
         35                  40                  45

Ser Val Ile Asp Ser Gly Gly Asn Thr Tyr Tyr Ala Asp Ser Val Arg
 50                  55                  60

Gly Arg Phe Thr Ile Ser Arg Asp Asn Ser Lys Asn Thr Leu Phe Leu
65                   70                  75                  80

Gln Met Asn Ser Leu Arg Ala Glu Asp Thr Ala Val Tyr Tyr Cys Ala
                 85                  90                  95

```
Arg Asp Leu Gly Tyr Tyr Tyr Ala Met Asp Val Trp Gly Gln Gly Thr
            100                 105                 110

Thr Val Thr Val Ser Ser
        115

<210> SEQ ID NO 125
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

Glu Val Gln Leu Val Glu Ser Gly Gly Gly Leu Ile Gln Pro Gly Gly
1               5                   10                  15

Ser Leu Arg Leu Ser Cys Ala Ala Ser Ala Phe Thr Val Ser Asn Phe
            20                  25                  30

Ser Met Thr Trp Val Arg Gln Ala Pro Gly Lys Gly Leu Glu Trp Val
        35                  40                  45

Ser Val Ile Asp Ser Gly Gly Asn Thr Tyr Tyr Ala Asp Ser Val Arg
    50                  55                  60

Gly Arg Phe Thr Ile Ser Arg Asp Asn Ser Lys Asn Thr Leu Phe Leu
65                  70                  75                  80

Gln Met Asn Ser Leu Arg Ala Glu Asp Thr Ala Val Tyr Tyr Cys Ala
                85                  90                  95

Arg Asp Leu Gly Tyr Tyr Tyr Ala Met Asp Val Trp Gly Gln Gly Thr
            100                 105                 110

Thr Val Thr Val Ser Ser
        115

<210> SEQ ID NO 126
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

Glu Val Gln Leu Val Glu Ser Gly Gly Gly Leu Ile Gln Pro Gly Gly
1               5                   10                  15

Ser Leu Arg Leu Ser Cys Ala Ala Ser Ala Phe Thr Val Ser Asn Phe
            20                  25                  30

Gly Met Thr Trp Val Arg Gln Ala Pro Gly Lys Gly Leu Glu Trp Val
        35                  40                  45

Ser Val Ile Asp Ser Gly Gly Asn Thr Tyr Tyr Ala Asp Ser Val Arg
    50                  55                  60

Gly Arg Phe Thr Ile Ser Arg Asp Asn Ser Lys Asn Thr Leu Phe Leu
65                  70                  75                  80

Gln Met Asn Ser Leu Arg Ala Glu Asp Thr Ala Val Tyr Tyr Cys Ala
                85                  90                  95

Arg Asp Leu Gly Tyr Tyr Tyr Ala Met Asp Val Trp Gly Gln Gly Thr
            100                 105                 110

Thr Val Thr Val Ser Ser
        115

<210> SEQ ID NO 127
```

<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

Glu Val Gln Leu Val Glu Ser Gly Gly Gly Leu Ile Gln Pro Gly Gly
1               5                   10                  15

Ser Leu Arg Leu Ser Cys Ala Ala Ser Ala Phe Thr Val Ser Asn Phe
            20                  25                  30

Ala Met Thr Trp Val Arg Gln Ala Pro Gly Lys Gly Leu Glu Trp Val
        35                  40                  45

Ser Val Ile Asp Ser Gly Gly Asn Thr Tyr Tyr Ala Asp Ser Val Arg
    50                  55                  60

Gly Arg Phe Thr Ile Ser Arg Asp Asn Ser Lys Asn Thr Leu Phe Leu
65                  70                  75                  80

Gln Met Asn Ser Leu Arg Ala Glu Asp Thr Ala Val Tyr Tyr Cys Ala
                85                  90                  95

Arg Asp Leu Gly Tyr Tyr Tyr Ala Met Asp Val Trp Gly Gln Gly Thr
            100                 105                 110

Thr Val Thr Val Ser Ser
        115

<210> SEQ ID NO 128
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

Glu Val Gln Leu Val Glu Ser Gly Gly Gly Leu Ile Gln Pro Gly Gly
1               5                   10                  15

Ser Leu Arg Leu Ser Cys Ala Ala Ser Ala Phe Thr Val Ser Asn Phe
            20                  25                  30

Tyr Met Thr Trp Val Arg Gln Ala Pro Gly Lys Gly Leu Glu Trp Val
        35                  40                  45

Ser Val Ile Asp Ser Gly Gly Asn Thr Tyr Tyr Ala Asp Ser Val Arg
    50                  55                  60

Gly Arg Phe Thr Ile Ser Arg Asp Asn Ser Lys Asn Thr Leu Phe Leu
65                  70                  75                  80

Gln Met Asn Ser Leu Arg Ala Glu Asp Thr Ala Val Tyr Tyr Cys Ala
                85                  90                  95

Arg Ala Leu Gly Tyr Tyr Tyr Ala Met Asp Val Trp Gly Gln Gly Thr
            100                 105                 110

Thr Val Thr Val Ser Ser
        115

<210> SEQ ID NO 129
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

Glu Val Gln Leu Val Glu Ser Gly Gly Gly Leu Ile Gln Pro Gly Gly
1               5                   10                  15

Ser Leu Arg Leu Ser Cys Ala Ala Ser Ala Phe Thr Val Ser Asn Phe
            20                  25                  30

Tyr Met Thr Trp Val Arg Gln Ala Pro Gly Lys Gly Leu Glu Trp Val
            35                  40                  45

Ser Val Ile Asp Ser Gly Gly Asn Thr Tyr Tyr Ala Asp Ser Val Arg
        50                  55                  60

Gly Arg Phe Thr Ile Ser Arg Asp Asn Ser Lys Asn Thr Leu Phe Leu
65                  70                  75                  80

Gln Met Asn Ser Leu Arg Ala Glu Asp Thr Ala Val Tyr Tyr Cys Ala
            85                  90                  95

Arg Ser Leu Gly Tyr Tyr Tyr Ala Met Asp Val Trp Gly Gln Gly Thr
            100                 105                 110

Thr Val Thr Val Ser Ser
            115

<210> SEQ ID NO 130
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Glu Val Gln Leu Val Glu Ser Gly Gly Gly Leu Ile Gln Pro Gly Gly
1               5                   10                  15

Ser Leu Arg Leu Ser Cys Ala Ala Ser Ala Phe Thr Val Ser Asn Phe
            20                  25                  30

Tyr Met Thr Trp Val Arg Gln Ala Pro Gly Lys Gly Leu Glu Trp Val
            35                  40                  45

Ser Val Ile Asp Ser Gly Gly Asn Thr Tyr Tyr Ala Asp Ser Val Arg
        50                  55                  60

Gly Arg Phe Thr Ile Ser Arg Asp Asn Ser Lys Asn Thr Leu Phe Leu
65                  70                  75                  80

Gln Met Asn Ser Leu Arg Ala Glu Asp Thr Ala Val Tyr Tyr Cys Ala
            85                  90                  95

Arg Asp Leu Gly Tyr Tyr Tyr Ala Leu Asp Val Trp Gly Gln Gly Thr
            100                 105                 110

Thr Val Thr Val Ser Ser
            115

<210> SEQ ID NO 131
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 131

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Thr Thr
            20                  25                  30

Gln Asn Trp Tyr Gln Gln Lys Pro Gly Lys Ala Pro Lys Leu Leu Ile
            35                  40                  45

```
Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Thr
                85                  90                  95

Phe Gly Gln Gly Thr Lys Leu Glu Ile Lys
                100                 105

<210> SEQ ID NO 132
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 132

Glu Val Gln Leu Val Glu Ser Gly Gly Gly Leu Ile Gln Pro Gly Gly
1               5                   10                  15

Ser Leu Arg Leu Ser Cys Ala Ala Ser Ala Phe Thr Val Ser Asn Phe
            20                  25                  30

Tyr Met Thr Trp Val Arg Gln Ala Pro Gly Lys Gly Leu Glu Trp Val
        35                  40                  45

Ser Val Ile Asp Ser Gly Gly Asn Thr Tyr Tyr Ala Asp Ser Val Arg
    50                  55                  60

Gly Arg Phe Thr Ile Ser Arg Asp Asn Ser Lys Asn Thr Leu Phe Leu
65                  70                  75                  80

Gln Met Asn Ser Leu Arg Ala Glu Asp Thr Ala Val Tyr Tyr Cys Ala
                85                  90                  95

Arg Ser Leu Gly Tyr Tyr Tyr Ala Leu Asp Val Trp Gly Gln Gly Thr
                100                 105                 110

Thr Val Thr Val Ser Ser
        115

<210> SEQ ID NO 133
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 133

Asp Ile Gln Met Thr Gln Ser Pro Ser Ser Leu Ser Ala Ser Val Gly
1               5                   10                  15

Asp Arg Val Thr Ile Thr Cys Arg Ala Ser Pro Ser Ile Ser Thr Ser
            20                  25                  30

Leu Asn Trp Tyr Gln Gln Lys Pro Gly Lys Ala Pro Lys Leu Leu Ile
        35                  40                  45

Tyr Leu Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Thr
                85                  90                  95

Phe Gly Gln Gly Thr Lys Leu Glu Ile Lys
                100                 105
```

```
<210> SEQ ID NO 134
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134

Asp Ile Gln Met Thr Gln Ser Pro Ser Ser Leu Ser Ala Ser Val Gly
1               5                   10                  15

Asp Arg Val Thr Ile Thr Cys Arg Ala Ser Pro Ser Ile Ser Ala Ser
            20                  25                  30

Leu Asn Trp Tyr Gln Gln Lys Pro Gly Lys Ala Pro Lys Leu Leu Ile
        35                  40                  45

Tyr Leu Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Thr
                85                  90                  95

Phe Gly Gln Gly Thr Lys Leu Glu Ile Lys
            100                 105

<210> SEQ ID NO 135
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

Glu Val Gln Leu Val Glu Ser Gly Gly Gly Leu Ile Gln Pro Gly Gly
1               5                   10                  15

Ser Leu Arg Leu Ser Cys Ala Ala Ser Ala Phe Thr Val Ser Asn Phe
            20                  25                  30

Tyr Met Thr Trp Val Arg Gln Ala Pro Gly Lys Gly Leu Glu Trp Val
        35                  40                  45

Ser Val Ile Asp Ser Gly Gly Asn Thr Tyr Tyr Ala Asp Ser Val Arg
50                  55                  60

Gly Arg Phe Thr Ile Ser Arg Asp Asn Ser Lys Asn Thr Leu Phe Leu
65                  70                  75                  80

Gln Met Asn Ser Leu Arg Ala Glu Asp Thr Ala Val Tyr Tyr Cys Ala
                85                  90                  95

Arg Ala Leu Gly Tyr Tyr Tyr Ala Leu Asp Val Trp Gly Gln Gly Thr
            100                 105                 110

Thr Val Thr Val Ser Ser
        115

<210> SEQ ID NO 136
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 136

Asp Ile Gln Met Thr Gln Ser Pro Ser Ser Leu Ser Ala Ser Val Gly
```

```
                1               5                  10                 15
Asp Arg Val Thr Ile Thr Cys Arg Ala Ser Gln Ser Ile Ser Ala Ser
                20                 25                 30

Leu Asn Trp Tyr Gln Gln Lys Pro Gly Lys Ala Pro Lys Leu Leu Ile
        35                 40                 45

Tyr Leu Ala Ser Ser Leu Gln Ser Gly Val Pro Ser Arg Phe Ser Gly
        50                 55                 60

Ser Gly Ser Gly Thr Asp Phe Thr Leu Thr Ile Ser Ser Leu Gln Pro
65                 70                 75                 80

Glu Asp Phe Ala Thr Tyr Tyr Cys Gln Gln Ser Tyr Ser Thr Pro Thr
                85                 90                 95

Phe Gly Gln Gly Thr Lys Leu Glu Ile Lys
                100                105
```

<210> SEQ ID NO 137
<211> LENGTH: 106
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 137

```
Asp Ile Gln Met Thr Gln Ser Pro Ser Ser Leu Ser Ala Ser Val Gly
1               5                  10                 15

Asp Arg Val Thr Ile Thr Cys Arg Ala Ser Gln Ser Thr Ser Ala Ser
                20                 25                 30

Leu Asn Trp Tyr Gln Gln Lys Pro Gly Lys Ala Pro Lys Leu Leu Ile
        35                 40                 45

Tyr Leu Ala Ser Ser Leu Gln Ser Gly Val Pro Ser Arg Phe Ser Gly
        50                 55                 60

Ser Gly Ser Gly Thr Asp Phe Thr Leu Thr Ile Ser Ser Leu Gln Pro
65                 70                 75                 80

Glu Asp Phe Ala Thr Tyr Tyr Cys Gln Gln Ser Tyr Ser Thr Pro Thr
                85                 90                 95

Phe Gly Gln Gly Thr Lys Leu Glu Ile Lys
                100                105
```

<210> SEQ ID NO 138
<211> LENGTH: 106
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 138

```
Asp Ile Gln Met Thr Gln Ser Pro Ser Ser Leu Ser Ala Ser Val Gly
1               5                  10                 15

Asp Arg Val Thr Ile Thr Cys Arg Ala Ser Gln Ser Pro Ser Thr Ser
                20                 25                 30

Leu Asn Trp Tyr Gln Gln Lys Pro Gly Lys Ala Pro Lys Leu Leu Ile
        35                 40                 45

Tyr Leu Ala Ser Ser Leu Gln Ser Gly Val Pro Ser Arg Phe Ser Gly
        50                 55                 60

Ser Gly Ser Gly Thr Asp Phe Thr Leu Thr Ile Ser Ser Leu Gln Pro
65                 70                 75                 80

Glu Asp Phe Ala Thr Tyr Tyr Cys Gln Gln Ser Tyr Ser Thr Pro Thr
```

```
                85                  90                  95

Phe Gly Gln Gly Thr Lys Leu Glu Ile Lys
            100                 105

<210> SEQ ID NO 139
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Glu Val Gln Leu Val Glu Ser Gly Gly Gly Leu Ile Gln Pro Gly Gly
1               5                   10                  15

Ser Leu Arg Leu Ser Cys Ala Ala Ser Ala Phe Thr Val Ser Asn Phe
            20                  25                  30

Ala Met Thr Trp Val Arg Gln Ala Pro Gly Lys Gly Leu Glu Trp Val
        35                  40                  45

Ser Val Ile Asp Ser Gly Gly Asn Thr Tyr Tyr Ala Asp Ser Val Arg
    50                  55                  60

Gly Arg Phe Thr Ile Ser Arg Asp Asn Ser Lys Asn Thr Leu Phe Leu
65                  70                  75                  80

Gln Met Asn Ser Leu Arg Ala Glu Asp Thr Ala Val Tyr Tyr Cys Ala
                85                  90                  95

Arg Ser Leu Gly Tyr Tyr Tyr Ala Leu Asp Val Trp Gly Gln Gly Thr
            100                 105                 110

Thr Val Thr Val Ser Ser
        115

<210> SEQ ID NO 140
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Pro Ser Ala Ser
            20                  25                  30

Leu Asn Trp Tyr Gln Gln Lys Pro Gly Lys Ala Pro Lys Leu Leu Ile
        35                  40                  45

Tyr Leu Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Thr
                85                  90                  95

Phe Gly Gln Gly Thr Lys Leu Glu Ile Lys
            100                 105

<210> SEQ ID NO 141
<211> LENGTH: 106
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 141

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ser Ser Thr Ser
            20                  25                  30

Leu Asn Trp Tyr Gln Gln Lys Pro Gly Lys Ala Pro Lys Leu Leu Ile
        35                  40                  45

Tyr Leu Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Thr
                85                  90                  95

Phe Gly Gln Gly Thr Lys Leu Glu Ile Lys
            100                 105

<210> SEQ ID NO 142
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 142

Glu Val Gln Leu Val Glu Ser Gly Gly Gly Leu Ile Gln Pro Gly Gly
1               5                   10                  15

Ser Leu Arg Leu Ser Cys Ala Ala Ser Ala Phe Thr Val Ser Asn Phe
            20                  25                  30

Ala Met Thr Trp Val Arg Gln Ala Pro Gly Lys Gly Leu Glu Trp Val
        35                  40                  45

Ser Val Ile Asp Ser Gly Gly Asn Thr Tyr Tyr Ala Asp Ser Val Arg
    50                  55                  60

Gly Arg Phe Thr Ile Ser Arg Asp Asn Ser Lys Asn Thr Leu Phe Leu
65                  70                  75                  80

Gln Met Asn Ser Leu Arg Ala Glu Asp Thr Ala Val Tyr Tyr Cys Ala
                85                  90                  95

Arg Asp Leu Gly Tyr Tyr Ala Leu Asp Val Trp Gly Gln Gly Thr
            100                 105                 110

Thr Val Thr Val Ser Ser
        115

<210> SEQ ID NO 143
<211> LENGTH: 5
<212> TYPE: PRT
<213> ORGANISM: Artificial Sequence
<220> FEATURE:
<223> OTHER INFORMATION: Description of Artificial Sequence: Synthetic
      Hinge region sequence

<400> SEQUENCE: 143

Cys Pro Ser Cys Pro
1               5

<210> SEQ ID NO 144
<211> LENGTH: 5
<212> TYPE: PRT
<213> ORGANISM: Artificial Sequence

```
<220> FEATURE:
<223> OTHER INFORMATION: Description of Artificial Sequence: Synthetic
      Hinge region sequence

<400> SEQUENCE: 144

Cys Pro Pro Cys Pro
1               5
```